(12) United States Patent
Fischer et al.

(10) Patent No.: US 7,109,394 B2
(45) Date of Patent: *Sep. 19, 2006

(54) METHODS FOR MODULATING FLORAL ORGAN IDENTITY, MODULATING FLORAL ORGAN NUMBER, INCREASING OF MERISTEM SIZE, AND DELAYING FLOWERING TIME

(75) Inventors: Robert Fischer, El Cerrito, CA (US); Yeonhee Choi, Emeryville, CA (US); Mike Hannon, Livermore, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/840,743

(22) Filed: Apr. 23, 2001

(65) Prior Publication Data

US 2003/0135890 A1 Jul. 17, 2003

Related U.S. Application Data

(63) Continuation-in-part of application No. 09/553,690, filed on Apr. 21, 2000, now Pat. No. 6,476,296.

(51) Int. Cl.
*C12N 15/82* (2006.01)
(52) U.S. Cl. .................. 800/290; 800/287; 800/285
(58) Field of Classification Search ............ 800/278, 800/290, 298, 287; 435/468, 419; 530/23.6
See application file for complete search history.

(56) References Cited

U.S. PATENT DOCUMENTS 6,476,296 B1 * 11/2002 Fischer et al. ............. 800/290

OTHER PUBLICATIONS

Lazar et al, 1988, Mol. Cell. Biol. 8: 1247-1252.*
Hill et al, 1998, Biochem. Biophys. Res. Comm. 244:573-577.*
Lin et al, May 1, 2000, Sptrembl Accession Nos. Q9SR66 and Q9SJQ6.*
Bevan et al, Jun. 1, 1998, GenBank Accession No. O49498.*
Bevan et al, Apr. 20, 2000, Accession Nos. T48452, T48453, and 48454.*
Bevan et al, Apr. 23, 1999, GenBank Accession No. T05430.*
Asada et al, 2001, EMBL Accession No. Q94LX6.*
Rounsley et al, 1997, GenBank Accession Nos. B60854 and B28303.*
Duggleby, 1997, Gene 190:245-249.*
Roldán-Arjona et al, 2000, Plant Mol. Biol. 44:43-52.*
White et al, 1999, GenBank Accession No. AE002073.*
Smith et al, 1997, GenBank Accession No. AE000855.*
Bult et al, 2001, GenBank Accession No. Q58030.*
Choi et al, 2002, Cell 110: 1-20.*
Leyser et al, 1992, Devel. 116:397-403.*
Thomas et al, 2001, Plant J. 25:417-425.*
Xiao et al, 2003, Devel. Cell 5:891-901.*
Chuang et al, 2000, Proc. Natl. Acad. Sci. 97:4985-4990.*
Akama, et al. "Efficient Transformation of *Arabidopsis thaliana*; Comparison of the Efficiencies with Various Organs, Plant Ecotypes and *Agrobacterium* Strains" *Plant Cell Reports* (1992) vol. 12, pp. 7-11.
Bevan, et al. GenBank Accession No. AL1602875, Mar. 31, 2000.
Bevan, et al. GenBank Accession No. AL162972, Apr. 3, 2000.
Bevan, et al. Accession No. T48452, *Protein Sequence Database* Apr. 20, 2000.
Bevan, et al. Accession No. T48453, *Protein Sequence Database* Apr. 20, 2000.
Bevan, et al. Accession No. T48454, *Protein Sequence Database* Apr. 20, 2000.
Bork, et al. Accession No. Y10157, Jul. 1, 1998.
Bult, et al. Accession No. Q58030, Nov. 1, 1997.
Rounsley, et al. GenBank Accession No. B60854, 1997.
Rounsley, et al. GenBank Accession No. B28303, 1997.
Scharer and Jiricny, "Recent Progress in the Biology, Chemistry and Structural Biology of DNA Glycosylases" *BioEssays* (2001) vol. 23, pp. 270-281.
Smith, et al. Accession No. AE000855 Nov. 15, 1997.
Smith, et al. Accession No. AE000666 Nov. 15, 1997.
White, et al. Accession No. AE002073 Nov. 22, 1999.
White, et al. Accession No. AE000513 Nov. 22, 1999.

* cited by examiner

*Primary Examiner*—Anne Kubelik
(74) *Attorney, Agent, or Firm*—Townsend and Townsend and Crew LLP

(57) ABSTRACT

This invention is directed to plant genetic engineering. In particular, it relates to DEMETER (DMT) nucleic acids and polypeptides that control, for example, seed (and in particular endosperm, embryo and seed coat) development, flowering time, chromosomal DNA methylation and transcription in plants.

8 Claims, No Drawings

SEQUENCE LISTING

<160> NUMBER OF SEQ ID NOS: 119

<210> SEQ ID NO 1
<211> LENGTH: 12785
<212> TYPE: DNA
<213> ORGANISM: Arabidopsis thaliana
<220> FEATURE:
<223> OTHER INFORMATION: DEMETER (DMT) genomic sequence

<400> SEQUENCE: 1

-continued

```
aagcttaaag ctaccaacat cgaatttagt aaaagaccca tgatttgaaa ttggaattgt      60
cggcaaaatc gagaagatat agagccgaca cgggaacagt gaaaaccaca aagcgcgtaa     120
gaatgaaaca gtgggagaag gaagagagaa tcttaccgat cattcgaggg aaaagatggg    180
aatcagagaa aaatctggaa aaaagaaat taagagaaag agagagaaga aagtgaggag     240
gaagatgcag tgaagactgc tatagccaca tcccacatgg tgtgatgaga gagagagaga    300
gagaggttaa agcagcaaat tgtggagaga taaagagaga gagagactga gcgagtcaag    360
ttcgtcgtcg tgtttaaaag aaagaatcct atatttgcct ttttctttac tactttattt    420
tcagactatt tgcttatttt gcctcaaact tttttgattg tcacttttcg atcctaaagt    480
gtttgacaat ttacctgcct ttttctccaa gaaaaatcag aacagaccac agcaaattta    540
tgtattttct attaaaaaag aaagaaagaa ttcatattac ttatagaatt aaaagctaag    600
cagttgaaaa cgtgaaagca gaatttctaa aaaaaatagt aaactgctac aaacttattt    660
atgtgtatat aacatatcta taaagaaact caaatatatg ataaatcatt ttaacaaaat    720
ttctatgaaa ttataataaa aaagtcact tttgacactt aaaaggttga caataaccgt     780
ctctccaaaa aaaatcaaa acatttataa tttctaaaac tatggtgtaa ttttgctgaa     840
atcaaaaaga aagaaggat ttctatatca taagtttcat tattgtatca aactttcaaa    900
tttcatgtaa tttgaaagga aaaaaattaa gatataatgt tgttttttgtt cttatgtta   960 cattttcatg gaatatatat tcataacaaa aaatgtattt taatatgatg agagattacc   1020
atccaaaagg tcgaacttat ataaaacaag ttaataacta acaatacat gtgatcacaa    1080 tcaatgacag ttttgatctt aaaatagaaa tgattgagca aacctcaaaa atgtcttctt   1140
aggatcacaa aatctttcct ttagcttatt aaagccggga gttcaactct ctctcccttg    1200
tagacttttt gttttcaaat ctttttcttt caaaaaatca ataattagtt aatgggcata   1260
atatttggtt ttaattaagt ccatagattt tttaggacca tctctaatca cgacaaatat   1320
cctaaattgt aacacattta aaacttaaaa gtattgcatt cacaatcctt aaaatatata   1380
tatatatata tatatatata tatatatata tatgaaag ttatatagaa acgataactc     1440
cttactcaac aattagccca aaaaaacatc cataatgcat ttaaactagg aattttaaca   1500
aactcaaata ggttggtagt taaaaaaaaa caaatagtag atgtacatac gtacctttaa    1560
aaatatatac tcatatcgaa agttttaaat tttgcgaaat taaatacatt tatctatcaa   1620
ttaaaataca tttaataatg cataattctg taatatctat ctttaatttc catatagaac   1680
caaaacaaaa taaacatatc aaatagtttt aacttaacaa aaacgttagg gaaaagttga   1740
cctaactagc ttgattgacg ttgaacttgt caatgcgaaa gcgatatttc caatatatac   1800
tacatgtagt attatttata tggaagtttc taaaaaggtg ttgagtggat tgttacttgt   1860
tggaggatgc tatttttttcc ttcttgccat aatattttac gagtatggga taactacata   1920
ctcatgatta tgaaacgctc actttatttg aaaaacctcc taatacacca aatatgtcac   1980
tagattccaa aacgtagacc aattgtatct aatctcaaat tctcaatcaa agtattaatt   2040
taccgatggt aagaaaagtt aaccgatata attatcaaaa gaaagaataa gtcaacagat   2100
tcttaatctc tttattttgg tatatgaaca tttgtacaaa aatctcaaaa gatatgtaac   2160
tgtttaaaat ataaattcac tgagattaat tcttcagact cgtgttagct ataataatgt   2220
caagagttct tcttgtttca aggaaaaacc ttaaagatat gtatattttc tgtaattatg   2280
atgatataat ttgctattca ttgtcacaaa cattacttta aaaaatcgta ttttcattac   2340
```

```
tacaatgttg actaagaaca aaaatacatt gattattgat atatcgtcaa ctgaattttc    2400
ttccgaggga tataattctc aaacatagca agaatctcat aataatgttt cgtgactacc    2460
tttagacgaa attttttaa gattcgtaac gtgacttatg gtctcttgct gtggggtca     2520 atgcgaataa atctaaatgt atgggagtca ataaaatac caagaaaaat aaaggagcag    2580
cacccaataa actatatggg accagaaatc ctttcattgg tttaaaatag gattatcccg   2640
aaagatgaag gactaaattg aaactgattg ggggtaggaa gagatccgtc acaatcatta   2700
atggcttcca cgcggaaact tgtcgtttat acaatttcat taactttcgg gtcgggttta   2760
tattccaaat gggtcaaata atattagttt aatacactaa cggagtaatt aattggtgac   2820 tacaattta tcagtttggt gcaattagaa acgaacatag tcgtaaaata cgagttcggt    2880
gttatacctt tatttacgtt aaaaaaatac gagaattttg tgtcaaattt caaattaatt   2940
tcatgaatat atggaaatta ttagatactc tagcgaaaat agtgattatg agcgttttac   3000
aaaaaatcga ttttagcatt gaacttcctt tatgtaattc ggtcaaatgt tggcatgaag   3060
aagcaagttt gcaacattaa atttcattta aaaatcgtgt tgacatactt taaaatctaa   3120
atataggaag aagaccaaaa cattaaattt agtaagattc taatgaacat ttataagtta   3180
taacttataa ccaacaaaag ttgggtttag cgttgttgct ttatctgaaa acttgcaaac   3240
taaaccattt aataggact aatgacaatt aacaacaaaa tacacttaag caacaacgtc    3300
ctcgtgaata taatttgggc ctcaggccca tattgctaac gccaactgat atttcacttt   3360
attccttctt catctcacca cactctctct ctatctctat ctctaacggc atagctgact   3420
cagtgttctc cggcattgac tcgcctgaga atcagaaagc ttagatcggt gagcttttag   3480
ctccattttc tgtttatta catattattt ccttttttc tctctcccctt ttttatctgg    3540 aatttgttct gctaaatttt ccagctgtta cattttccga tcacgagaag aatcactggg   3600
tttttatgtt aatcaataca tgttcctgtt ttctgatcat aaatctcagc tattaacacc   3660
tgattttgat tctgcgtaat aaaaacctct gatttgcttt tatcttcact ttccccataa   3720
acattgctta ctttattcgc tcttctttta ccgtttccag ctaaaaaatt cttcgctatt   3780
caatgtgttt ctcgttttgt tgatgagaaa aatatctgac aaaaaatcat ttattgcatt   3840
ttatggtgca gattcttagt taatgtcgcc ttctctaacc aagtcagatt aaaaaggagt   3900
gttcgtccat gttgctttgt tttggtgttt ggagagagtt ttcggagagt taggtgagtg   3960
ttatttgggg tgaggtagtg ataaggtttg aaggggagt gattcatcaa gtgtgttatg    4020
aattcgaggg ctgatccggg ggatagatat tttcgagttc ctttggagaa tcaaactcaa   4080
caagagttca tgggttcttg gattccattt acacccaaaa aacctagatc aagtctgatg   4140
gtagatgaga gagtgataaa ccaggatcta aatgggtttc caggtggtga atttgtagac   4200 agggattct gcaacactgg tgtggatcat aatgggtttt tgatcatgg tgctcatcag    4260 ggcgttacca acttaagtat gatgatcaat agcttagcgg gatcacatgc acaagcttgg   4320
agtaatagtg agagagatct tttgggcagg agtgaggtga cttctccttt agcaccagtt   4380
atcagaaaca ccaccggtaa tgtagagccg gtcaatggaa attttacttc agatgtgggt   4440
atggtaaatg gtcctttcac ccagagtggc acttctcaag ctggctataa tgagtttgaa   4500
ttggatgact tgttgaatcc tgatcagatg cccttctcct tcacaagctt gctgagtggt   4560
ggggatagct tattcaaggt tcgtcaatgt gagtgatcaa atctatttc agtttttttt    4620 tttcccttc ttccgttctt gcagtactta gagtagaaca tgaattagaa tatcttaaga    4680
aagtcatggt tttgaacaga tggacctcca gcgtgtaaca agcctcttta caatttgaat   4740
```

-continued

```
tcaccaatta gaagagaagc agttgggtca gtctgtgaaa gttcgtttca atatgtaccg    4800
tcaacgccca gtctgttcag aacaggtgaa aagactggat tccttgaaca gatagttaca    4860
actactggac atgaaatccc agagccgaaa tctgacaaaa gtatgcagag cattatggac    4920
tcgtctgctg ttaatgcgac ggaagctact gaacaaaatg atggcagcag acaagatgtt    4980
ctggagttcg accttaacaa aactcctcag cagaaaccct ccaaaaggaa aaggaagttc    5040
atgcccaagg tggtcgtgga aggcaaacct aaaagaaagc cacgcaaacc tgcagaactt    5100
cccaaagtgg tcgtggaagg caaacctaaa aggaagccac gcaaagctgc aactcaggaa    5160
aaagtgaaat ctaaagaaac cgggagtgcc aaaaagaaaa atttgaaaga atcagcaact    5220
aaaaagccag ccaatgttgg agatatgagc aacaaaagcc ctgaagtcac actcaaaagt    5280
tgcagaaaag ctttgaattt tgacttggag aatcctggag atgcgaggca aggtgactct    5340
gagtctgaaa ttgtccagaa cagtagtggc gcaaactcgt tttctgagat cagagatgcc    5400
attggtggaa ctaatggtag tttcctggat tcagtgtcac aaatagacaa gaccaatgga    5460 ttggggcta tgaaccagcc acttgaagtg tcaatgggaa accagccaga taaactatct    5520
acaggagcga aactggccag agaccaacaa cctgatttat tgactagaaa ccagcaatgc    5580
cagttcccag tggcaaccca gaacacccag ttcccaatgg aaaaccaaca agcttggctt    5640
cagatgaaaa accaacttat tggctttcca tttggtaacc agcaacctcg catgaccata    5700
agaaaccagc agccttgctt ggccatgggt aatcaacaac ctatgtatct gataggaact    5760
ccacggcctg cattagtaag tggaaaccag caactaggag gtccccaagg aaacaagcgg    5820
cctatatttt tgaatcacca gacttgttta cctgctggaa atcagctata tggatcacct    5880
acagacatgc atcaacttgt tatgtcaacc ggagggcaac aacatggact actgataaaa    5940
aaccagcaac ctggatcatt aataagaggc cagcagcctt gcgtaccttt gattgaccag    6000
caacctgcaa ctccaaaagg ttttactcac ttgaatcaga tggtagctac cagcatgtca    6060
tcgcctgggc ttcgacctca ttctcagtca caagttccta caacatatct acatgtggaa    6120
tctgttccca ggattttgaa tgggactaca ggtacatgcc agagaagcag ggctcctgca    6180
tacgattctt tacagcaaga tatccatcaa ggaaataagt acatactttc tcatgagata    6240
tccaatggta atgggtgcaa gaaagcgtta cctcaaaact cttctctgcc aactccaatt    6300
atggctaaac ttgaggaagc caggggctcg aagagacagt atcatcgtgc aatgggacag    6360
acggaaaagc atgatctaaa cttagctcaa cagattgctc aatcacaaga tgtggagaga    6420
cataacagca gcacgtgtgt ggaatatta gatgctgcaa agaaaacgaa atccagaaa    6480 gtagtccaag aaaatttgca tggcatgcca cctgaggtta tagaaatcga ggatgatcca    6540
actgatgggg caagaaaagg taaaaatact gccagcatca gtaaaggtgc atctaaagga    6600
aactcgtctc cagttaaaaa gacagcagaa aaggagaaat gtattgtccc aaaaacgcct    6660
gcaaaaaagg gtcgagcagg tagaaaaaaa tcagtacctc cgcctgctca tgcctcagag    6720
atccagcttt ggcaacctac tcctccaaag acacctttat caagaagcaa gcctaaagga    6780
aaagggagaa agtccataca agattcagga aaagcaagag gtaactaatg tattctacaa    6840
tctctgtgat ataattttga gattttagta actgatgtgt ccaaaccagc tccttatcac    6900
tgttggtgcg ttgtataggt ccatcaggag aacttctgtg tcaggattct attgcggaaa    6960
taatttacag gatgcaaaat ctgtatctag gagacaaaga aagagaacaa gagcaaaatg    7020
caatggtctt gtacaaagga gatggtgcac ttgttcccta tgagagcaag aagcgaaaac    7080
```

```
caagacccaa agttgacatt gacgatgaaa caactcgcat atggaactta ctgatgggga   7140
aaggagatga aaagaaggg gatgaagaga aggataaaaa gaaagagaag tggtgggaag   7200
aagaaagaag agtcttccga ggaagggctg attccttcat cgctcgcatg cacctggtac   7260
aaggtgaaga tccacttctc ttctcaactc cattttatt cacacaaatt agtagaatac   7320
tcaaaaatga tgttttgttt gcaaaatttt aaaattcact agttaaccat gtcaaataat   7380
attcataatg catcttgtga agaacaggtg tgcatttatg gtgacagctg aatggtttat   7440
gtgcctatta tttcttttac tgctatagat gaccaattga acttaaacgt ttacaggaga   7500
tagacgtttt tcgccatgga agggatcggt ggttgattcg gtcattggag ttttccttac   7560
acagaatgtc tcggatcacc tttcaaggta tatgagttgc cttaataaat tgagttccaa   7620
aacatagaaa ttaacccatg gtggttttac aatgcagctc tgcgttcatg tctctagctg   7680
ctcgattccc tccaaaatta agcagcagcc gagaagatga aggaatgtt agaagcgtag   7740
ttgttgaaga tccagaagga tgcattctga acttaaatga aattccttcg tggcaggaaa   7800
aggttcaaca tccatctgac atggaagttt ctggggttga tagtggatca aaagagcagc   7860
taagggactg ttcaaactct ggaattgaaa gatttaattt cttagagaag agtattcaaa   7920
atttagaaga ggaagtatta tcatcacaag attcttttga tccggcgata tttcagtcgt   7980
gtgggagagt tggatcctgt tcatgttcca aatcagacgc agagtttcct acaaccaggt   8040
gtgaaacaaa aactgtcagt ggaacatcac aatcagtgca aactgggagc ccaaacttgt   8100
ctgatgaaat ttgtcttcaa gggaatgaga gaccgcatct atatgaagga tctggtgatg   8160
ttcagaaaca agaaactaca aatgtcgctc agaagaaacc tgatcttgaa aaaacaatga   8220
attggaaaga ctctgtctgt tttggtcagc caagaaatga tactaattgg caaacaactc   8280
cttccagcag ctatgagcag tgtgcgactc gacagccaca tgtactagac atagaggatt   8340
ttggaatgca gggtgaaggc cttggttatt cttggatgtc catctcacca agagttgaca   8400
gagtaaagaa caaaaatgta ccacgcaggt ttttcagaca aggtggaagt gttccaagag   8460
aattcacagg tcagatcata ccatcaacgc ctcatgaatt accaggaatg ggattgtccg   8520
gttcctcaag cgccgtccaa gaacaccagg acgatacccca acataatcaa caagatgaga   8580
tgaataaagc atcccattta caaaaaacat ttttggatct gctcaactcc tctgaagaat   8640
gccttacaag acagtccagt accaaacaga acatcacgga tggctgtcta ccgagagata   8700
gaactgctga agacgtggtt gatccgctca gtaacaattc aagcttacag aacatattgg   8760
tcgaatcaaa ttccagcaat aaagagcaga cggcagttga atacaaggag acaaatgcca   8820
ctatttttacg agagatgaaa gggacgcttg ctgatgggaa aaagcctaca agccagtggg   8880
atagtctcag aaaagatgtg gagggaatg aaggagaca ggaacgaaac aaaaacaata   8940
tggattccat agactatgaa gcaataagac gtgctagtat cagcgagatt tctgaggcta   9000
tcaaggaaag agggatgaat aacatgttgg ccgtacgaat taaggtaaat ctactaattt   9060
cagttgagac cctcatcaaa tctgtcagaa ggcttgaaca tcagtaaatt atgtaaccat   9120
atttacaaca ttgcaggatt tcctagaacg gatagtaaaa gatcatggtg gtatcgacct   9180
tgaatggttg agagaatctc ctcctgataa agccaagtgg gtaaatcaca tttttagtga   9240
ctgcaacact agcacgatcg atttactcaa caattacgtc aaactgagta ttaacaagtt   9300
gctcatgaac atttcacagg gactatctct tgagcataag aggtctgggt ttgaaaagtg   9360
ttgaatgcgt gcgactctta acactccaca atcttgcttt ccctgtgagt cagactattc   9420
cattatctac taaaaactta gaataactcc ggctaactaa gctggaactt gtattgatga   9480
```

```
tatgaaggtt gacacgaatg ttggaaggat agcagttagg atgggatggg tgcctctaca    9540
accoctacct gaatcacttc agttacacct cctggagctg taagtttctt tttgtttgtc    9600
atctaaacaa cgaaattttt atgcaagtca taaccatgct gtgttttcac agatacccag    9660
tgctcgagtc catccaaaaa tttctttggc caagactttg caaactcgat caacgaacac    9720
tgtatgctca taaactctaa caaatcatct gtctgaaaaa ccaatatttc tttggtagaa    9780
ttctattgtc attactcatt actaacagcg aaattaatta acgttctttt tcttactcag    9840
gtatgaatta cactaccaac tgattacgtt tggaaaggta ttattgctct aagctttgaa    9900
tttatcatat ggtaatttca agcattgtag gcacctgatc aattatgtgt ctaaatcatg    9960
tgaattcatg tcaggtattt tgcacaaaga gtagaccaaa ttgtaatgca tgtccaatga   10020
gaggagagtg cagacacttt gccagtgctt atgctaggta agcaagcttt catgtactta   10080
tatgcaataa ttaaagataa aatttaggat tatgggtaag ttacaaaaaa ttaggctcag   10140
tttcatggta gctagctgga aatagtatta caagaacaac ataaagatca aagacagaat   10200
catggatcca tatgcactat cattttagct cttgtaatcc atacatgaac actatatgcc   10260
aaagtaggga tttcaaatat gagattcgat gactgatgcc attgtaacag tgcaagactt   10320
gctttaccgg caccagagga gaggagctta acaagtgcaa ctattccggt ccctcccgag   10380
tcctatcctc ctgtagccat cccgatgata gaactacctc ttccgttgga gaaatcccta   10440
gcaagtggag caccatcgaa tagagaaaac tgtgaaccaa taattgaaga gccggcctcg   10500
cccgggcaag agtgcactga ataaccgag agtgatattg aagatgctta ctacaatgag   10560
gaccctgacg agatcccaac aataaaactc aacattgaac agtttggaat gactctacgg   10620
gaacacatga aagaaacat ggagctccaa gaaggtgaca tgtccaaggc tttggttgct   10680
ttgcatccaa caactacttc tattccaact cccaaactaa agaacattag ccgtctcagg   10740
acagagcacc aagtgtaagc taatatctcc tcctatattt tatcttccat ataaattttg   10800
gggaaaaaat cgctctccat ctggttttag aacatgcggg tcagccaggg ttatggcatt   10860
tttatatatt tcaccgatcg gcccgagctg gctctggttg actcgtatgc caccctgcat   10920
tgaacaaacc agtaggagac aagcaagcaa aacgttttaa gataaggtct atggtaaaat   10980
gacaaggtaa ctgataaatg tgtcgtctat ttgcaggtac gagctcccag attcacatcg   11040
tctccttgat ggtgtaagtc aattttttaac tctctctata ctcgagttgt ttcacttgag   11100
caacactgtt taaagtcct catttgataa aataacagat ggataaaaga gaaccagatg   11160
atccaagtcc ttatctctta gctatatgga caccaggtga gaataaaact gcaatgtttc   11220
attcatgtgt ctacagtatc aaagaaagta cagctagagc taaaaagcat ttgaaataga   11280
gtcggttaaa tatgaaagtt tgaatctgta aatgaaagcc ggaacgtagc attggtggat   11340
gttatatgta aattagtttt tgagattggt ctaatgtagt tgtttgactg ccaggtgaaa   11400
cagcgaattc ggcacaaccg cctgaacaga agtgtggagg gaaagcgtct ggcaaaatgt   11460
gctttgacga gacttgttct gagtgtaaca gtctgaggga agcaaactca cagacagttc   11520
gaggaactct tctggtgaga ttatcttgat ctttttgtgtt gctcatgaaa aggagaagtg   11580
agaatacaag tttgctaata tcattttttc gtcattcaca gataccttgt cggactgcca   11640
tgagaggaag ttttccgctc aacgggacat atttccaagt caacgaggtt agatgaaata   11700
aaactcaaac agacagacga aacattattt ctgtttagtg ttggttcttt atcctccttg   11760
ccattttta tcttgcagtt atttgcagac cacgagtcca gtctcaaacc catcgatgtt   11820
```

-continued

```
cctagagatt ggatatggga tctcccaaga aggactgttt acttcggaac atcagtaaca    11880
tcaatattca gaggtaaaaa cattcgtaat agagttagtt aatcaaatgt ccaaaacaca    11940
agaaagcttc accgtccaat acacaagaaa gcttcacctt ctctttgcca aaaaagatct    12000
tagaatgttt tgctgaattt gtgcaggtct ttcaacggag cagatacagt tctgcttttg    12060
gaaaggtaaa cgttaacttt cgacccagag aaatccggaa aatctattgc tttgttctga    12120
tcaatacgtt aaacatatac acacacactt tacacttagg accaatactg ttctgatctg    12180
tgatagaaac tggtaaacat ctaacaatta tgattgcagg attcgtatgt gtccgtggat    12240
tcgaacagaa gacaagagca ccgcgtccat taatggcaag gttgcatttt cctgcgagca    12300
aattgaagaa caacaaaacc taaagatgac tggaagaaag caaacgcatt gcttctctgc    12360
tctcctctat ttaaagccag gaaaagtccc atttagacat aataacagga atccaaatag    12420 gctatttttct ctttctttct tatttcattc atagagcaga agcgacacaa aaaagttttt    12480
tgggttattt attttctctc taacaaattt gtagcgtttt gggtcttttt ctggctgtca    12540
ctagcgtggc aaatccaatg tccgcgcaca cttaggcgca ttgtcaataa attctccggc    12600
caccggagtg ttacgatctt ttccaacggc ggctaatgcg atatttccgg taacacatat    12660
tccttattct atgttggttt tgtgtacggc gtgggcctta ctagacaatg atcatcaata    12720
aaactaacac aaagttgaat gctacaaagt agaaagtgaa gaaaaaataa tatagacatt    12780
gccga                                                                12785
```

<210> SEQ ID NO 2
<211> LENGTH: 1729
<212> TYPE: PRT
<213> ORGANISM: Arabidopsis thaliana
<220> FEATURE:
<223> OTHER INFORMATION: DEMETER (DMT)

<400> SEQUENCE: 2

```
Met Gln Ser Ile Met Asp Ser Ser Ala Val Asn Ala Thr Glu Ala Thr
  1               5                  10                  15

Glu Gln Asn Asp Gly Ser Arg Gln Asp Val Leu Glu Phe Asp Leu Asn
                 20                  25                  30

Lys Thr Pro Gln Gln Lys Pro Ser Lys Arg Lys Arg Lys Phe Met Pro
             35                  40                  45

Lys Val Val Glu Gly Lys Pro Arg Lys Pro Arg Lys Pro Ala
         50                  55                  60

Glu Leu Pro Lys Val Val Glu Gly Lys Pro Lys Arg Lys Pro Arg
 65                  70                  75                  80

Lys Ala Ala Thr Gln Glu Lys Val Lys Ser Lys Glu Thr Gly Ser Ala
                 85                  90                  95

Lys Lys Lys Asn Leu Lys Glu Ser Ala Thr Lys Lys Pro Ala Asn Val
            100                 105                 110

Gly Asp Met Ser Asn Lys Ser Pro Glu Val Thr Leu Lys Ser Cys Arg
        115                 120                 125

Lys Ala Leu Asn Phe Asp Leu Glu Asn Pro Gly Asp Ala Arg Gln Gly
    130                 135                 140

Asp Ser Glu Ser Glu Ile Val Gln Asn Ser Ser Gly Ala Asn Ser Phe
145                 150                 155                 160

Ser Glu Ile Arg Asp Ala Ile Gly Gly Thr Asn Gly Ser Phe Leu Asp
                165                 170                 175

Ser Val Ser Gln Ile Asp Lys Thr Asn Gly Leu Gly Ala Met Asn Gln
            180                 185                 190
```

-continued

```
Pro Leu Glu Val Ser Met Gly Asn Gln Pro Asp Lys Leu Ser Thr Gly
        195                 200                 205
Ala Lys Leu Ala Arg Asp Gln Gln Pro Asp Leu Leu Thr Arg Asn Gln
    210                 215                 220
Gln Cys Gln Phe Pro Val Ala Thr Gln Asn Thr Gln Phe Pro Met Glu
225                 230                 235                 240
Asn Gln Gln Ala Trp Leu Gln Met Lys Asn Gln Leu Ile Gly Phe Pro
                245                 250                 255
Phe Gly Asn Gln Gln Pro Arg Met Thr Ile Arg Asn Gln Gln Pro Cys
            260                 265                 270
Leu Ala Met Gly Asn Gln Gln Pro Met Tyr Leu Ile Gly Thr Pro Arg
        275                 280                 285
Pro Ala Leu Val Ser Gly Asn Gln Gln Leu Gly Gly Pro Gln Gly Asn
    290                 295                 300
Lys Arg Pro Ile Phe Leu Asn His Gln Thr Cys Leu Pro Ala Gly Asn
305                 310                 315                 320
Gln Leu Tyr Gly Ser Pro Thr Asp Met His Gln Leu Val Met Ser Thr
                325                 330                 335
Gly Gly Gln Gln His Gly Leu Leu Ile Lys Asn Gln Gln Pro Gly Ser
            340                 345                 350
Leu Ile Arg Gly Gln Gln Pro Cys Val Pro Leu Ile Asp Gln Gln Pro
        355                 360                 365
Ala Thr Pro Lys Gly Phe Thr His Leu Asn Gln Met Val Ala Thr Ser
    370                 375                 380
Met Ser Ser Pro Gly Leu Arg Pro His Ser Gln Ser Gln Val Pro Thr
385                 390                 395                 400
Thr Tyr Leu His Val Glu Ser Val Ser Arg Ile Leu Asn Gly Thr Thr
                405                 410                 415
Gly Thr Cys Gln Arg Ser Arg Ala Pro Ala Tyr Asp Ser Leu Gln Gln
            420                 425                 430
Asp Ile His Gln Gly Asn Lys Tyr Ile Leu Ser His Glu Ile Ser Asn
        435                 440                 445
Gly Asn Gly Cys Lys Lys Ala Leu Pro Gln Asn Ser Ser Leu Pro Thr
    450                 455                 460
Pro Ile Met Ala Lys Leu Glu Glu Ala Arg Gly Ser Lys Arg Gln Tyr
465                 470                 475                 480
His Arg Ala Met Gly Gln Thr Glu Lys His Asp Leu Asn Leu Ala Gln
                485                 490                 495
Gln Ile Ala Gln Ser Gln Asp Val Glu Arg His Asn Ser Ser Thr Cys
            500                 505                 510
Val Glu Tyr Leu Asp Ala Ala Lys Thr Lys Ile Gln Lys Val Val
        515                 520                 525
Gln Glu Asn Leu His Gly Met Pro Pro Glu Val Ile Glu Ile Glu Asp
    530                 535                 540
Asp Pro Thr Asp Gly Ala Arg Lys Gly Lys Asn Thr Ala Ser Ile Ser
545                 550                 555                 560
Lys Gly Ala Ser Lys Gly Asn Ser Ser Pro Val Lys Lys Thr Ala Glu
                565                 570                 575
Lys Glu Lys Cys Ile Val Pro Lys Thr Pro Ala Lys Lys Gly Arg Ala
            580                 585                 590
Gly Arg Lys Lys Ser Val Pro Pro Ala His Ala Ser Glu Ile Gln
        595                 600                 605
```

```
Leu Trp Gln Pro Thr Pro Pro Lys Thr Pro Leu Ser Arg Ser Lys Pro
    610                 615                 620

Lys Gly Lys Gly Arg Lys Ser Ile Gln Asp Ser Gly Lys Ala Arg Gly
625                 630                 635                 640

Pro Ser Gly Glu Leu Leu Cys Gln Asp Ser Ile Ala Glu Ile Ile Tyr
                645                 650                 655

Arg Met Gln Asn Leu Tyr Leu Gly Asp Lys Glu Arg Glu Gln Glu Gln
            660                 665                 670

Asn Ala Met Val Leu Tyr Lys Gly Asp Gly Ala Leu Val Pro Tyr Glu
        675                 680                 685

Ser Lys Lys Arg Lys Pro Arg Pro Lys Val Asp Ile Asp Asp Glu Thr
    690                 695                 700

Thr Arg Ile Trp Asn Leu Leu Met Gly Lys Gly Asp Glu Lys Glu Gly
705                 710                 715                 720

Asp Glu Glu Lys Asp Lys Lys Glu Lys Trp Trp Glu Glu Glu Arg
                725                 730                 735

Arg Val Phe Arg Gly Arg Ala Asp Ser Phe Ile Ala Arg Met His Leu
            740                 745                 750

Val Gln Gly Asp Arg Arg Phe Ser Pro Trp Lys Gly Ser Val Val Asp
        755                 760                 765

Ser Val Ile Gly Val Phe Leu Thr Gln Asn Val Ser Asp His Leu Ser
    770                 775                 780

Ser Ser Ala Phe Met Ser Leu Ala Ala Arg Phe Pro Pro Lys Leu Ser
785                 790                 795                 800

Ser Ser Arg Glu Asp Glu Arg Asn Val Arg Ser Val Val Val Glu Asp
                805                 810                 815

Pro Glu Gly Cys Ile Leu Asn Leu Asn Glu Ile Pro Ser Trp Gln Glu
            820                 825                 830

Lys Val Gln His Pro Ser Asp Met Glu Val Ser Gly Val Asp Ser Gly
        835                 840                 845

Ser Lys Glu Gln Leu Arg Asp Cys Ser Asn Ser Gly Ile Glu Arg Phe
    850                 855                 860

Asn Phe Leu Glu Lys Ser Ile Gln Asn Leu Glu Glu Val Leu Ser
865                 870                 875                 880

Ser Gln Asp Ser Phe Asp Pro Ala Ile Phe Gln Ser Cys Gly Arg Val
                885                 890                 895

Gly Ser Cys Ser Cys Ser Lys Ser Asp Ala Glu Phe Pro Thr Thr Arg
            900                 905                 910

Cys Glu Thr Lys Thr Val Ser Gly Thr Ser Gln Ser Val Gln Thr Gly
        915                 920                 925

Ser Pro Asn Leu Ser Asp Glu Ile Cys Leu Gln Gly Asn Glu Arg Pro
    930                 935                 940

His Leu Tyr Glu Gly Ser Gly Asp Val Gln Lys Gln Glu Thr Thr Asn
945                 950                 955                 960

Val Ala Gln Lys Lys Pro Asp Leu Glu Lys Thr Met Asn Trp Lys Asp
                965                 970                 975

Ser Val Cys Phe Gly Gln Pro Arg Asn Asp Thr Asn Trp Gln Thr Thr
            980                 985                 990

Pro Ser Ser Ser Tyr Glu Gln Cys Ala Thr Arg Gln Pro His Val Leu
        995                 1000                1005

Asp Ile Glu Asp Phe Gly Met Gln Gly Glu Gly Leu Gly Tyr Ser Trp
    1010                1015                1020

Met Ser Ile Ser Pro Arg Val Asp Arg Val Lys Asn Lys Asn Val Pro
```

```
                1025                1030                1035                1040
Arg Arg Phe Phe Arg Gln Gly Gly Ser Val Pro Arg Glu Phe Thr Gly
            1045                1050                1055
Gln Ile Ile Pro Ser Thr Pro His Glu Leu Pro Gly Met Gly Leu Ser
            1060                1065                1070
Gly Ser Ser Ser Ala Val Gln Glu His Gln Asp Asp Thr Gln His Asn
            1075                1080                1085
Gln Gln Asp Glu Met Asn Lys Ala Ser His Leu Gln Lys Thr Phe Leu
    1090                1095                1100
Asp Leu Leu Asn Ser Ser Glu Glu Cys Leu Thr Arg Gln Ser Ser Thr
1105                1110                1115                1120
Lys Gln Asn Ile Thr Asp Gly Cys Leu Pro Arg Asp Arg Thr Ala Glu
            1125                1130                1135
Asp Val Val Asp Pro Leu Ser Asn Asn Ser Ser Leu Gln Asn Ile Leu
            1140                1145                1150
Val Glu Ser Asn Ser Ser Asn Lys Glu Gln Thr Ala Val Glu Tyr Lys
            1155                1160                1165
Glu Thr Asn Ala Thr Ile Leu Arg Glu Met Lys Gly Thr Leu Ala Asp
    1170                1175                1180
Gly Lys Lys Pro Thr Ser Gln Trp Asp Ser Leu Arg Lys Asp Val Glu
1185                1190                1195                1200
Gly Asn Glu Gly Arg Gln Glu Arg Asn Lys Asn Asn Met Asp Ser Ile
            1205                1210                1215
Asp Tyr Glu Ala Ile Arg Arg Ala Ser Ile Ser Glu Ile Ser Glu Ala
            1220                1225                1230
Ile Lys Glu Arg Gly Met Asn Asn Met Leu Ala Val Arg Ile Lys Asp
            1235                1240                1245
Phe Leu Glu Arg Ile Val Lys Asp His Gly Gly Ile Asp Leu Glu Trp
            1250                1255                1260
Leu Arg Glu Ser Pro Pro Asp Lys Ala Lys Asp Tyr Leu Leu Ser Ile
1265                1270                1275                1280
Arg Gly Leu Gly Leu Lys Ser Val Glu Cys Val Arg Leu Leu Thr Leu
            1285                1290                1295
His Asn Leu Ala Phe Pro Val Asp Thr Asn Val Gly Arg Ile Ala Val
            1300                1305                1310
Arg Met Gly Trp Val Pro Leu Gln Pro Leu Pro Glu Ser Leu Gln Leu
            1315                1320                1325
His Leu Leu Glu Leu Tyr Pro Val Leu Glu Ser Ile Gln Lys Phe Leu
    1330                1335                1340
Trp Pro Arg Leu Cys Lys Leu Asp Gln Arg Thr Leu Tyr Glu Leu His
1345                1350                1355                1360
Tyr Gln Leu Ile Thr Phe Gly Lys Val Phe Cys Thr Lys Ser Arg Pro
            1365                1370                1375
Asn Cys Asn Ala Cys Pro Met Arg Gly Glu Cys Arg His Phe Ala Ser
            1380                1385                1390
Ala Tyr Ala Ser Ala Arg Leu Ala Leu Pro Ala Pro Glu Glu Arg Ser
            1395                1400                1405
Leu Thr Ser Ala Thr Ile Pro Val Pro Pro Glu Ser Phe Pro Pro Val
    1410                1415                1420
Ala Ile Pro Met Ile Glu Leu Pro Leu Pro Leu Glu Lys Ser Leu Ala
1425                1430                1435                1440
Ser Gly Ala Pro Ser Asn Arg Glu Asn Cys Glu Pro Ile Ile Glu Glu
            1445                1450                1455
```

-continued

```
Pro Ala Ser Pro Gly Gln Glu Cys Thr Glu Ile Thr Glu Ser Asp Ile
        1460                1465                1470
Glu Asp Ala Tyr Tyr Asn Glu Asp Pro Asp Glu Ile Pro Thr Ile Lys
    1475                1480                1485
Leu Asn Ile Glu Gln Phe Gly Met Thr Leu Arg Glu His Met Glu Arg
1490                1495                1500
Asn Met Glu Leu Gln Glu Gly Asp Met Ser Lys Ala Leu Val Ala Leu
1505                1510                1515                1520
His Pro Thr Thr Thr Ser Ile Pro Thr Pro Lys Leu Lys Asn Ile Ser
        1525                1530                1535
Arg Leu Arg Thr Glu His Gln Val Tyr Glu Leu Pro Asp Ser His Arg
    1540                1545                1550
Leu Leu Asp Gly Met Asp Lys Arg Glu Pro Asp Asp Pro Ser Pro Tyr
1555                1560                1565
Leu Leu Ala Ile Trp Thr Pro Gly Glu Thr Ala Asn Ser Ala Gln Pro
    1570                1575                1580
Pro Glu Gln Lys Cys Gly Gly Lys Ala Ser Gly Lys Met Cys Phe Asp
1585                1590                1595                1600
Glu Thr Cys Ser Glu Cys Asn Ser Leu Arg Glu Ala Asn Ser Gln Thr
        1605                1610                1615
Val Arg Gly Thr Leu Leu Ile Pro Cys Arg Thr Ala Met Arg Gly Ser
    1620                1625                1630
Phe Pro Leu Asn Gly Thr Tyr Phe Gln Val Asn Glu Leu Phe Ala Asp
    1635                1640                1645
His Glu Ser Ser Leu Lys Pro Ile Asp Val Pro Arg Asp Trp Ile Trp
1650                1655                1660
Asp Leu Pro Arg Arg Thr Val Tyr Phe Gly Thr Ser Val Thr Ser Ile
1665                1670                1675                1680
Phe Arg Gly Leu Ser Thr Glu Gln Ile Gln Phe Cys Phe Trp Lys Gly
        1685                1690                1695
Phe Val Cys Val Arg Gly Phe Glu Gln Lys Thr Arg Ala Pro Arg Pro
    1700                1705                1710
Leu Met Ala Arg Leu His Phe Pro Ala Ser Lys Leu Lys Asn Asn Lys
        1715                1720                1725
Thr
```

<210> SEQ ID NO 3
<211> LENGTH: 3424
<212> TYPE: DNA
<213> ORGANISM: Arabidopsis thaliana
<220> FEATURE:
<223> OTHER INFORMATION: DMT 5' flanking sequence

<400> SEQUENCE: 3

```
aagcttaaag ctaccaacat cgaatttagt aaaagaccca tgatttgaaa ttggaattgt    60
cggcaaaatc gagaagatat agagccgaca cgggaacagt gaaaaccaca agcgcgtaa   120
gaatgaaaca gtgggagaag gaagagagaa tcttaccgat cattcgaggg aaaagatggg   180
aatcagagaa aaatctggaa aaaagaaat taagagaaag agagagaaga aagtgaggag   240
gaagatgcag tgaagactgc tatagccaca tcccacatgg tgtgatgaga gagagagaga   300
gagaggttaa agcagcaaat tgtggagaga taaagagaga gagagactga gcgagtcaag   360
ttcgtcgtcg tgtttaaaag aaagaatcct atatttgcct ttttctttac tactttattt   420
tcagactatt tgcttatttt gcctcaaact tttttgattg tcacttttcg atcctaaagt   480
```

```
gtttgacaat ttacctgcct ttttctccaa gaaaaatcag aacagaccac agcaaattta    540
tgtattttct attaaaaaag aaagaaagaa ttcatattac ttatagaatt aaaagctaag    600
cagttgaaaa cgtgaaagca gaatttctaa aaaaaatagt aaactgctac aaacttattt    660
atgtgtatat aacatatcta taaagaaact caaatatatg ataaatcatt ttaacaaaat    720
ttctatgaaa ttataataaa aaaagtcact tttgacactt aaaaggttga caataaccgt    780
ctctccaaaa aaaatcaaa acatttataa tttctaaaac tatggtgtaa ttttgctgaa    840
atcaaaaaga aagaaggat ttctatatca taagtttcat tattgtatca aactttcaaa    900
tttcatgtaa tttgaaagga aaaaaattaa gatataatgt tgttttttgtt tcttatgtta    960 cattttcatg gaatatatat tcataacaaa aaatgtattt taatatgatg agagattacc   1020
atccaaaagg tcgaacttat ataaaacaag ttaataacta acaatacat gtgatcacaa    1080 tcaatgacag ttttgatctt aaaatagaaa tgattgagca acctcaaaa atgtcttctt    1140 aggatcacaa aatctttcct ttagcttatt aaagccggga gttcaactct ctctcccttg   1200 tagactttt gttttcaaat cttttttcttt caaaaaatca ataattagtt aatgggcata   1260
atatttggtt ttaattaagt ccatagattt tttaggacca tctctaatca cgacaaatat   1320
cctaaattgt aacacattta aaacttaaaa gtattgcatt cacaatccct aaaatatata   1380
tatatatata tatatatata tatatatata tatatgaaag ttatatagaa acgataactc   1440
cttactcaac aattagccca aaaaaacatc cataatgcat ttaaactagg aattttaaca   1500
aactcaaata ggttggtagt taaaaaaaaa caaatagtag atgtacatac gtacctttaa   1560
aaatatatac tcatatcgaa agttttaaat tttgcgaaat taaatacatt tatctatcaa   1620
ttaaaataca tttaataatg cataattctg taatatctat cttttaatttc catatagaac   1680 caaaacaaaa taaacatatc aaatagtttt aacttaacaa aaacgttagg gaaaagttga   1740
cctaactagc ttgattgacg ttgaacttgt caatgcgaaa gcgatatttc caatatatac   1800
tacatgtagt attatttata tggaagtttc taaaaaggtg ttgagtggat tgttacttgt   1860
tggaggatgc tatttttttcc ttcttgccat aatattttac gagtatggga taactacata   1920
ctcatgatta tgaaacgctc actttatttg aaaaacctcc taatacacca aatatgtcac   1980
tagattccaa aacgtagacc aattgtatct aatctcaaat tctcaatcaa agtattaatt   2040
taccgatggt aagaaaagtt aaccgatata attatcaaaa gaaagaataa gtcaacagat   2100
tcttaatctc tttattttgg tatatgaaca tttgtacaaa aatctcaaaa gatatgtaac   2160
tgtttaaaat ataaattcac tgagattaat tcttcagact cgtgttagct ataataatgt   2220
caagagttct tcttgtttca aggaaaaacc ttaaagatat gtatattttc tgtaattatg   2280
atgatataat ttgctattca ttgtcacaaa cattacttta aaaaatcgta ttttcattac   2340
tacaatgttg actaagaaca aaaatacatt gattattgat atatcgtcaa ctgaattttc   2400
ttccgaggga tataattctc aaacatagca agaatctcat aataatgttt cgtgactacc   2460
tttagacgaa attttttttaa gattcgtaac gtgacttatg gtctcttgct gtggggggtca   2520 atgcgaataa atctaaatgt atgggagtca ataaaaatac caagaaaaat aaaggagcag   2580
cacccaataa actatatggg accagaaatc ctttcattgg tttaaaatag gattatcccg   2640
aaagatgaag gactaaattg aaactgattg ggggtaggaa gagatccgtc acaatcatta   2700
atggcttcca cgcggaaact tgtcgtttat acaatttcat taactttcgg gtcgggttta   2760
tattccaaat gggtcaaata atattagttt aatacactaa cggagtaatt aattggtgac   2820
```

-continued

```
tacaatttta tcagtttggt gcaattagaa acgaacatag tcgtaaaata cgagttcggt    2880
gttataccct tatttacgtt aaaaaaatac gagaattttg tgtcaaattt caaattaatt    2940
tcatgaatat atggaaatta ttagatactc tagcgaaaat agtgattatg agcgttttac    3000
aaaaatacga ttttagcatt gaacttcctt tatgtaattc ggtcaaatgt tggcatgaag    3060
aagcaagttt gcaacattaa atttcattta aaaatcgtgt tgacatactt aaaatctaa     3120 atataggaag aagaccaaaa cattaaattt agtaagattc taatgaacat ttataagtta    3180
taacttataa ccaacaaaag ttgggtttag cgttgttgct ttatctgaaa acttgcaaac    3240
taaaccattt taataggact aatgacaatt aacaacaaaa tacacttaag caacaacgtc    3300
ctcgtgaata taatttgggc ctcaggccca tattgctaac gccaactgat atttcacttt    3360
attccttctt catctcacca cactctctct ctatctctat ctctaacggc atagctgact    3420
cagt                                                                 3424
```

<210> SEQ ID NO 4
<211> LENGTH: 205
<212> TYPE: DNA
<213> ORGANISM: Arabidopsis thaliana
<220> FEATURE:
<223> OTHER INFORMATION: DMT 3' flanking sequence

<400> SEQUENCE: 4

```
agatgactgg aagaaagcaa acgcattgct tctctgctct cctctattta aagccaggaa     60
aagtcccatt tagacataat aacaggaatc caaataggct attttctctt tctttcttat    120
ttcattcata gagcagaagc gacacaaaaa agttttttgg gttatttatt ttctctctaa    180
caaaaaaaaa aaaaaaaaac tcgag                                          205
```

<210> SEQ ID NO 5
<211> LENGTH: 6873
<212> TYPE: DNA
<213> ORGANISM: Arabidopsis thaliana
<220> FEATURE:
<223> OTHER INFORMATION: DMT cDNA

<400> SEQUENCE: 5

```
gttctccggc attgactcgc ctgagaatca gaaagcttag atcggtgagc ttttagctcc     60
attttctgtt tatttacata ttatttcctt tttttctctc tccctttttt atctggaatt    120
tgttctgcta aattttccag ctgttacatt ttccgatcac gagaagaatc actgggtttt    180
tatgttaatc aatacatgtt cctgttttct gatcataaat ctcagctatt aacacctgat    240
tttgattctg cgtaataaaa acctctgatt tgcttttatc ttcactttcc ccataaacat    300
tgcttacttt attcgctctt cttttaccgt ttccagctaa aaaattcttc gctattcaat    360
gtgtttctcg ttttgttgat gagaaaaata tctgacaaaa aatcatttat tgcattttat    420
ggtgcagatt cttagttaat gtcgccttct ctaaccaagt cagattaaaa aggagtgttc    480
gtccatgttg ctttgttttg gtgtttggag agagttttcg gagagttagg tgagtgttat    540
ttggggtgag gtagtgataa ggtttgaagg gggagtgatt catcaagtgt gttatgaatt    600
cgagggctga tccgggggat agatattttc gagttccttt ggagaatcaa actcaacaag    660
agttcatggg ttcttggatt ccatttacac ccaaaaaacc tagatcaagt ctgatggtag    720
atgagagagt gataaaccag gatctaaatg ggtttccagg tggtgaattt gtagacaggg    780
gattctgcaa cactggtgtg gatcataatg ggttttttga tcatggtgct catcagggcg    840
ttaccaactt aagtatgatg atcaatagct tagcgggatc acatgcacaa gcttggagta    900
```

```
atagtgagag agatcttttg ggcaggagtg aggtgacttc tcctttagca ccagttatca    960
gaaacaccac cggtaatgta gagccggtca atggaaattt tacttcagat gtgggtatgg   1020
taaatggtcc tttcacccag agtggcactt ctcaagctgg ctataatgag tttgaattgg   1080
atgacttgtt gaatcctgat cagatgccct tctccttcac aagcttgctg agtggtgggg   1140
atagcttatt caaggttcgt caatgtgagt gatcaaatct attttcagtt ttttttttc    1200
cctttcttcc gttcttgcag tacttagagt agaacatgaa ttagaatatc ttaagaaagt   1260
catggttttg aacagatgga cctccagcgt gtaacaagcc tctttacaat ttgaattcac   1320
caattagaag agaagcagtt gggtcagtct gtgaaagttc gtttcaatat gtaccgtcaa   1380
cgcccagtct gttcagaaca ggtgaaaaga ctggattcct tgaacagata gttacaacta   1440
ctggacatga atcccagag ccgaaatctg acaaagtat gcagagcatt atggactcgt     1500
ctgctgttaa tgcgacggaa gctactgaac aaaatgatgg cagcagacaa gatgttctgg   1560
agttcgacct taacaaaact cctcagcaga aaccctccaa aaggaaaagg aagttcatgc   1620
ccaaggtggt cgtggaaggc aaacctaaaa gaaagccacg caaacctgca gaacttccca   1680
aagtggtcgt ggaaggcaaa cctaaaagga agccacgcaa agctgcaact caggaaaaag   1740
tgaaatctaa agaaaccggg agtgccaaaa agaaaaattt gaaagaatca gcaactaaaa   1800
agccagccaa tgttggagat atgagcaaca aaagccctga agtcacactc aaaagttgca   1860
gaaaagcttt gaattttgac ttggagaatc ctggagatgc gaggcaaggt gactctgagt   1920
ctgaaattgt ccagaacagt agtggcgcaa actcgttttc tgagatcaga gatgccattg   1980
gtggaactaa tggtagtttc ctggattcag tgtcacaaat agacaagacc aatggattgg   2040
gggctatgaa ccagccactt gaagtgtcaa tgggaaacca gccagataaa ctatctacag   2100
gagcgaaact ggccagagac caacaacctg atttattgac tagaaaccag caatgccagt   2160
tcccagtggc aacccagaac acccagttcc caatggaaaa ccaacaagct tggcttcaga   2220
tgaaaaacca acttattggc tttccatttg gtaaccagca acctcgcatg accataagaa   2280
accagcagcc ttgcttggcc atgggtaatc aacaacctat gtatctgata ggaactccac   2340
ggcctgcatt agtaagtgga accagcaac taggaggtcc ccaaggaaac aagcggccta   2400
tattttgaa tcaccagact tgtttacctg ctggaaatca gctatatgga tcacctacag   2460
acatgcatca acttgttatg tcaaccggag ggcaacaaca tggactactg ataaaaaacc   2520
agcaacctgg atcattaata agaggccagc agccttgcgt acctttgatt gaccagcaac   2580
ctgcaactcc aaaaggtttt actcacttga atcagatggt agctaccagc atgtcatcgc   2640
ctgggcttcg acctcattct cagtcacaag ttcctacaac atatctacat gtggaatctg   2700
tttccaggat tttgaatggg actacaggta catgccagag aagcagggct cctgcatacg   2760
attctttaca gcaagatatc catcaaggaa ataagtacat acttctctcat gagatatcca   2820
atggtaatgg gtgcaagaaa gcgttacctc aaaactcttc tctgccaact ccaattatgg   2880
ctaaacttga ggaagccagg ggctcgaaga gacagtatca tcgtgcaatg ggacagacgg   2940
aaaagcatga tctaaactta gctcaacaga ttgctcaatc acaagatgtg gagagacata   3000
acagcagcac gtgtgtggaa tatttagatg ctgcaaagaa aacgaaaatc cagaaagtag   3060
tccaagaaaa tttgcatggc atgccacctg aggttataga aatcgaggat gatccaactg   3120
atggggcaag aaaaggtaaa aatactgcca gcatcagtaa aggtgcatct aaaggaaact   3180
cgtctccagt taaaaagaca gcagaaaagg agaaatgtat tgtcccaaaa acgcctgcaa   3240
```

```
aaaagggtcg agcaggtaga aaaaaatcag tacctccgcc tgctcatgcc tcagagatcc    3300
agctttggca acctactcct ccaaagacac ctttatcaag aagcaagcct aaaggaaaag    3360
ggagaaagtc catacaagat tcaggaaaag caagaggtcc atcaggagaa cttctgtgtc    3420
aggattctat tgcggaaata atttacagga tgcaaaatct gtatctagga gacaaagaaa    3480
gagaacaaga gcaaaatgca atggtcttgt acaaggaga tggtgcactt gttccctatg    3540
agagcaagaa gcgaaaacca agacccaaag ttgacattga cgatgaaaca actcgcatat    3600
ggaacttact gatggggaaa ggagatgaaa agaagggga tgaagagaag gataaaaaga    3660
aagagaagtg gtgggaagaa gaaagaagag tcttccgagg aagggctgat tccttcatcg    3720
ctcgcatgca cctggtacaa ggagatagac gttttcgcc atggaaggga tcggtggttg    3780
attcggtcat tggagttttc cttacacaga atgtctcgga tcacctttca agctctgcgt    3840
tcatgtctct agctgctcga ttccctccaa aattaagcag cagccgagaa gatgaaagga    3900
atgttagaag cgtagttgtt gaagatccag aaggatgcat tctgaactta aatgaaattc    3960
cttcgtggca ggaaaaggtt caacatccat ctgacatgga agtttctggg gttgatagtg    4020
gatcaaaaga gcagctaagg gactgttcaa actctggaat tgaaagattt aatttcttag    4080
agaagagtat tcaaaattta gaagaggaag tattatcatc acaagattct tttgatccgg    4140
cgatatttca gtcgtgtggg agagttggat cctgttcatg ttccaaatca gacgcagagt    4200
ttcctacaac caggtgtgaa acaaaaactg tcagtggaac atcacaatca gtgcaaactg    4260
ggagcccaaa cttgtctgat gaaatttgtc ttcaagggaa tgagagaccg catctatatg    4320
aaggatctgg tgatgttcag aaacaagaaa ctacaaatgt cgctcagaag aaacctgatc    4380
ttgaaaaaac aatgaattgg aaagactctg tctgttttgg tcagccaaga aatgatacta    4440
attggcaaac aactccttcc agcagctatg agcagtgtgc gactcgacag ccacatgtac    4500
tagacataga ggattttgga atgcaaggtg aaggccttgg ttattcttgg atgtccatct    4560
caccaagagt tgacagagta aagaacaaaa atgtaccacg caggttttc agacaaggtg    4620 gaagtgttcc aagagaattc acaggtcaga tcataccatc aacgcctcat gaattaccag    4680
gaatgggatt gtccggttcc tcaagcgccg tccaagaaca ccaggacgat acccaacata    4740
atcaacaaga tgagatgaat aaagcatccc atttacaaaa aacatttttg gatctgctca    4800
actcctctga agaatgcctt acaagacagt ccagtaccaa acagaacatc acggatggct    4860
gtctaccgag agatagaact gctgaagacg tggttgatcc gctcagtaac aattcaagct    4920
tacagaacat attggtcgaa tcaaattcca gcaataaaga gcagacggca gttgaataca    4980
aggagacaaa tgccactatt ttacgagaga tgaaagggac gcttgctgat gggaaaaagc    5040
ctacaagcca gtgggatagt ctcagaaaag atgtggaggg aatgaagggg agacaggaac    5100
gaaacaaaaa caatatggat tccatagact atgaagcaat aagacgtgct agtatcagcg    5160
agatttctga ggctatcaag gaaagaggga tgaataacat gttggccgta cgaattaagg    5220
atttcctaga acggatagtt aaagatcatg gtggtatcga ccttgaatgg ttgagagaat    5280
ctcctcctga taaagccaag gactatctct tgagcataag aggtctgggt ttgaaaagtg    5340
ttgaatgcgt gcgactctta acactccaca atcttgcttt ccctgttgac acgaatgttg    5400
gaaggatagc agttaggatg ggatgggtgc ctctacaacc cctacctgaa tcacttcagt    5460
tacacctcct ggagctatac ccagtgctcg agtccatcca aaaatttctt tggccaagac    5520
tttgcaaact cgatcaacga acactgtatg aattacacta ccaactgatt acgtttggaa    5580
aggtattttg cacaaagagt agaccaaatt gtaatgcatg tccaatgaga ggagagtgca    5640
```

```
gacactttgc cagtgcttat gctagtgcaa gacttgcttt accggcacca gaggagagga      5700
gcttaacaag tgcaactatt ccggtccctc ccgagtcctt tcctcctgta gccatcccga      5760
tgatagaact acctcttccg ttggagaaat ccctagcaag tggagcacca tcgaatagag      5820
aaaactgtga accaataatt gaagagccgg cctcgcccgg gcaagagtgc actgaaataa      5880
ccgagagtga tattgaagat gcttactaca atgaggaccc tgacgagatc caacaataa       5940 aactcaacat tgaacagttt ggaatgactc tacgggaaca catggaaaga aacatggagc      6000
tccaagaagg tgacatgtcc aaggcttttgg ttgctttgca tccaacaact acttctattc     6060
caactcccaa actaaagaac attagccgtc tcaggacaga gcaccaagtg tacgagctcc      6120
cagattcaca tcgtctcctt gatggtatgg ataaaagaga accagatgat ccaagtcctt      6180
atctcttagc tatatggaca ccaggtgaaa cagcgaattc ggcacaaccg cctgaacaga      6240
agtgtggagg gaaagcgtct ggcaaaatgt gctttgacga acttgttct gagtgtaaca       6300 gtctgaggga agcaaactca cagacagttc gaggaactct tctgatacct tgtcggactg      6360
ccatgagagg aagtttttccg ctcaacggga catatttcca agtcaacgag ttatttgcag     6420
accacgagtc cagtctcaaa cccatcgatg ttcctagaga ttggatatgg gatctcccaa      6480
gaaggactgt ttacttcgga acatcagtaa catcaatatt cagaggtctt tcaacggagc      6540
agatacagtt ctgcttttgg aaaggattcg tatgtgtccg tggattcgaa cagaagacaa      6600
gagcaccgcg tccattaatg gcaaggttgc attttcctgc gagcaaattg aagaacaaca      6660
aaacctaaag atgactggaa gaaagcaaac gcattgcttc tctgctctcc tctatttaaa      6720
gccaggaaaa gtcccattta gacataataa caggaatcca aataggctat tttctctttc      6780
tttcttattt cattcataga gcagaagcga cacaaaaaag ttttttgggt tatttatttt      6840
ctctctaaca aaaaaaaaa aaaaaactc gag                                     6873
```

<210> SEQ ID NO 6
<211> LENGTH: 1478
<212> TYPE: DNA
<213> ORGANISM: Arabidopsis thaliana
<220> FEATURE:
<223> OTHER INFORMATION: DMT 5' untranslated region

<400> SEQUENCE: 6

```
gttctccggc attgactcgc ctgagaatca gaaagcttag atcggtgagc ttttagctcc        60
attttctgtt tatttacata ttatttcctt tttttctctc tcccttttt atctggaatt       120 tgttctgcta aattttccag ctgttacatt ttccgatcac gagaagaatc actgggtttt      180
tatgttaatc aatacatgtt cctgttttct gatcataaat ctcagctatt aacacctgat      240
tttgattctg cgtaataaaa acctctgatt tgcttttatc ttcactttcc ccataaacat      300
tgcttacttt attcgctctt cttttaccgt ttccagctaa aaaattcttc gctattcaat      360
gtgtttctcg ttttgttgat gagaaaaata tctgacaaaa aatcatttat tgcattttat      420
ggtgcagatt cttagttaat gtcgccttct ctaaccaagt cagattaaaa aggagtgttc      480
gtccatgttg ctttgttttg gtgtttggag agagttttcg gagagttagg tgagtgttat      540
ttggggtgag gtagtgataa ggtttgaagg gggagtgatt catcaagtgt gttatgaatt      600
cgagggctga tccgggggat agatattttc gagttccttt ggagaatcaa actcaacaag      660
agttcatggg ttcttggatt ccatttacac ccaaaaaacc tagatcaagt ctgatggtag      720
atgagagagt gataaaccag gatctaaatg ggtttccagg tggtgaattt gtagacaggg      780
```

-continued

| | |
|---|---|
| gattctgcaa cactggtgtg gatcataatg gggtttttga tcatggtgct catcagggcg | 840 |
| ttaccaactt aagtatgatg atcaatagct tagcgggatc acatgcacaa gcttggagta | 900 |
| atagtgagag agatcttttg ggcaggagtg aggtgacttc tcctttagca ccagttatca | 960 |
| gaaacaccac cggtaatgta gagccggtca atggaaattt tacttcagat gtgggtatgg | 1020 |
| taaatggtcc tttcacccag agtggcactt ctcaagctgg ctataatgag tttgaattgg | 1080 |
| atgacttgtt gaatcctgat cagatgccct tctccttcac aagcttgctg agtggtgggg | 1140 |
| atagcttatt caaggttcgt caatgtgagt gatcaaatct attttcagtt tttttttttc | 1200 |
| cctttcttcc gttcttgcag tacttagagt agaacatgaa ttagaatatc ttaagaaagt | 1260 |
| catggttttg aacagatgga cctccagcgt gtaacaagcc tctttacaat ttgaattcac | 1320 |
| caattagaag agaagcagtt gggtcagtct gtgaaagttc gtttcaatat gtaccgtcaa | 1380 |
| cgcccagtct gttcagaaca ggtgaaaaga ctggattcct tgaacagata gttacaacta | 1440 |
| ctggacatga aatcccagag ccgaaatctg acaaaagt | 1478 |

<210> SEQ ID NO 7
<211> LENGTH: 10620
<212> TYPE: DNA
<213> ORGANISM: Arabidopsis thaliana
<220> FEATURE:
<223> OTHER INFORMATION: DMT1 (1DMT5) gene sequence from BAC T32M21

<400> SEQUENCE: 7

| | |
|---|---|
| tcactagatt ccaaaacgta gaccaattgt atctaatctc aaattctcaa tcaaagtatt | 60 |
| aatttaccga tggtaagaaa agttaaccga tataattatc aaaagaaaga ataagtcaac | 120 |
| agattcttaa tctctttatt ttggtatatg aacatttgta caaaaatctc aaagatatg | 180 |
| taactgttta aaatataaat tcactgagat taattcttca gactcgtgtt agctataata | 240 |
| atgtcaagag ttcttcttgt ttcaaggaaa aaccttaaag atatgtatat tttctgtaat | 300 |
| tatgatgata taatttgcta ttcattgtca caaacattac tttaaaaaat cgtattttca | 360 |
| ttactacaat gttgactaag aacaaaaata cattgattat tgatatatcg tcaactgaat | 420 |
| tttcttccga gggatataat tctcaaacat agcaagaatc tcataataat gtttcgtgac | 480 |
| tacctttaga cgaaattttt ttaagattcg taacgtgact tatggtctct tgctgtgggg | 540 |
| gtcaatgcga ataaatctaa atgtatggga gtcaaataaa ataccaagaa aaataaagga | 600 |
| gcagcaccca ataaactata tgggaccaga aatccttttca ttggtttaaa ataggattat | 660 |
| cccgaaagat gaaggactaa attgaaactg attgggggta ggaagagatc cgtcacaatc | 720 |
| attaatggct tccacgcgga aacttgtcgt ttatacaatt tcattaactt tcgggtcggg | 780 |
| tttatattcc aaatgggtca aataatatta gtttaataca ctaacggagt aattaattgg | 840 |
| tgactacaat tttatcagtt tggtgcaatt agaaacgaac atagtcgtaa aatacgagtt | 900 |
| cggtgttata cctttatttta cgttaaaaaa atacgagaat tttgtgtcaa atttcaaatt | 960 |
| aatttcatga atatatggaa attattagat actctagcga aaatagtgat tatgagcgtt | 1020 |
| ttacaaaaat acgattttag cattgaactt cctttatgta attcggtcaa atgttggcat | 1080 |
| gaagaagcaa gtttgcaaca ttaaatttca tttaaaaatc gtgttgacat acttttaaaat | 1140 |
| ctaaatatag gaagaagacc aaaacattaa atttagtaag attctaatga acatttataa | 1200 |
| gttataactt ataaccaaca aaagttgggt ttagcgttgt tgctttatct gaaaacttgc | 1260 |
| aaactaaacc attttaatag gactaatgac aattaacaac aaaatacact taagcaacaa | 1320 |
| cgtcctcgtg aatataattt gggcctcagg cccatattgc taacgccaac tgatatttca | 1380 |

-continued

```
ctttattcct tcttcatctc accacactct ctctctatct ctatctctaa cggcatagct  1440
gactcagtgt tctccggcat tgactcgcct gagaatcaga aagcttagat cggtgagctt  1500
ttagctccat tttctgttta tttacatatt atttcctttt tttctctctc ccttttttat  1560
ctggaatttg ttctgctaaa ttttccagct gttacatttt ccgatcacga gaagaatcac  1620
tgggttttta tgttaatcaa tacatgttcc tgttttctga tcataaatct cagctattaa  1680
cacctgattt tgattctgcg taataaaaac ctctgatttg cttttatctt cactttcccc  1740
ataaacattg cttactttat tcgctcttct tttaccgttt ccagctaaaa aattcttcgc  1800
tattcaatgt gtttctcgtt ttgttgatga gaaaaatatc tgacaaaaaa tcatttattg  1860
cattttatgg tgcagattct tagttaatgt cgccttctct aaccaagtca gattaaaaag  1920
gagtgttcgt ccatgttgct ttgttttggt gtttggagag agttttcgga gagttaggtg  1980
agtgttattt ggggtgaggt agtgataagg tttgaagggg gagtgattca tcaagtgtgt  2040
tatgaattcg agggctgatc cgggggatag atattttcga gttcctttgg agaatcaaac  2100
tcaacaagag ttcatggggtt cttggattcc atttacaccc aaaaaaccta gatcaagtct  2160
gatggtagat gagagagtga taaaccagga tctaaatggg tttccaggtg gtgaatttgt  2220
agacagggga ttctgcaaca ctggtgtgga tcataatggg gttttttgatc atggtgctca  2280
tcaggcgtt accaacttaa gtatgatgat caatagctta gcgggatcac atgcacaagc  2340
ttggagtaat agtgagagag atcttttggg caggagtgag gtgacttctc ctttagcacc  2400
agttatcaga aacaccaccg gtaatgtaga gccggtcaat ggaaattta cttcagatgt  2460
gggtatggta aatggtcctt tcacccagag tggcacttct caagctggct ataatgagtt  2520
tgaattggat gacttgttga atcctgatca gatgcccttc tccttcacaa gcttgctgag  2580
tggtggggat agcttattca aggttcgtca atgtgagtga tcaaatctat tttcagtttt  2640
tttttttccc tttcttccgt tcttgcagta cttagagtag aacatgaatt agaatatctt  2700
aagaaagtca tggttttgaa cagatggacc tccagcgtgt aacaagcctc tttacaattt  2760
gaattcacca attagaagag aagcagttgg gtcagtctgt gaaagttcgt ttcaatatgt  2820
accgtcaacg cccagtctgt tcagaacagg tgaaaagact ggattccttg aacagatagt  2880
tacaactact ggacatgaaa tcccagagcc gaaatctgac aaaagtatgc agagcattat  2940
ggactcgtct gctgttaatg cgacggaagc tactgaacaa aatgatggca gcagacaaga  3000
tgttctggag ttcgaccctta acaaaactcc tcagcagaaa ccctccaaaa ggaaaaggaa  3060
gttcatgccc aaggtggtcg tggaaggcaa acctaaaaga aagccacgca aacctgcaga  3120
acttcccaaa gtggtcgtgg aaggcaaacc taaaaggaag ccacgcaaag ctgcaactca  3180
ggaaaaagtg aaatctaaag aaaccgggag tgccaaaaag aaaaatttga aagaatcagc  3240
aactaaaaag ccagccaatg ttggagatat gagcaacaaa agccctgaag tcacactcaa  3300
aagttgcaga aaagctttga attttgactt ggagaatcct ggagatgcga ggcaaggtga  3360
ctctgagtct gaaattgtcc agaacagtag tggcgcaaac tcgttttctg agatcagaga  3420
tgccattggt ggaactaatg gtagtttcct ggattcagtg tcacaaatag acaagaccaa  3480
tggattgggg gctatgaacc agccacttga agtgtcaatg ggaaaccagc cagataaact  3540
atctacagga gcgaaactgg ccagagacca acaacctgat ttattgacta gaaaccagca  3600
atgccagttc ccagtggcaa cccagaacac ccagttccca atggaaaacc aacaagcttg  3660
gcttcagatg aaaaaccaac ttattggctt tccatttggt aaccagcaac ctcgcatgac  3720
```

```
cataagaaac cagcagcctt gcttggccat gggtaatcaa caacctatgt atctgatagg    3780
aactccacgg cctgcattag taagtggaaa ccagcaacta ggaggtcccc aaggaaacaa    3840
gcggcctata ttttgaatc accagacttg tttacctgct ggaaatcagc tatatggatc    3900
acctacagac atgcatcaac ttgttatgtc aaccggaggg caacaacatg gactactgat    3960
aaaaaaccag caacctggat cattaataag aggccagcag ccttgcgtac ctttgattga    4020
ccagcaacct gcaactccaa aaggttttac tcacttgaat cagatggtag ctaccagcat    4080
gtcatcgcct gggcttcgac ctcattctca gtcacaagtt cctacaacat atctacatgt    4140
ggaatctgtt tccaggattt tgaatgggac tacaggtaca tgccagagaa gcagggctcc    4200
tgcatacgat tctttacagc aagatatcca tcaaggaaat aagtacatac tttctcatga    4260
gatatccaat ggtaatgggt gcaagaaagc gttacctcaa aactcttctc tgccaactcc    4320
aattatggct aaacttgagg aagccagggg ctcgaagaga cagtatcatc gtgcaatggg    4380
acagacggaa aagcatgatc taaacttagc tcaacagatt gctcaatcac aagatgtgga    4440
gagacataac agcagcacgt gtgtggaata tttagatgct gcaagaaaaa cgaaaatcca    4500
gaaagtagtc caagaaaatt tgcatggcat gccacctgag gttatagaaa tcgaggatga    4560
tccaactgat ggggcaagaa aaggtaaaaa tactgccagc atcagtaaag gtgcatctaa    4620
aggaaactcg tctccagtta aaaagacagc agaaaaggag aaatgtattg tcccaaaaac    4680
gcctgcaaaa aagggtcgag caggtagaaa aaaatcagta cctccgcctg ctcatgcctc    4740
agagatccag ctttggcaac ctactcctcc aaagacacct ttatcaagaa gcaagcctaa    4800
aggaaaaggg agaaagtcca tacaagattc aggaaaagca agaggtaact aatgtattct    4860
acaatctctg tgatataatt ttgagatttt agtaactgat gtgtccaaac cagctcctta    4920
tcactgttgg tgcgttgtat aggtccatca ggagaacttc tgtgtcagga ttctattgcg    4980
gaaataattt acaggatgca aaatctgtat ctaggagaca aagaaagaga acaagagcaa    5040
aatgcaatgg tcttgtacaa aggagatggt gcacttgttc cctatgagag caagaagcga    5100
aaaccaagac ccaaagttga cattgacgat gaaacaactc gcatatggaa cttactgatg    5160 gggaaggag atgaaaaaga aggggatgaa gagaaggata aaaagaaaga gaagtggtgg    5220
gaagaagaaa gaagagtctt ccgaggaagg gctgattcct tcatcgctcg catgcacctg    5280
gtacaaggtg aagatccact tctcttctca actccatttt tattcacaca aattagtaga    5340
atactcaaaa atgatgtttt gtttgcaaaa ttttaaaatt cactagttaa ccatgtcaaa    5400
taatattcat aatgcatctt gtgaagaaca ggtgtgcatt tatggtgaca gctgaatggt    5460
ttatgtgcct attatttctt ttactgctat agatgaccaa ttgaacttaa acgtttacag    5520
gagatagacg tttttcgcca tggaagggat cggtggttga ttcggtcatt ggagttttcc    5580
ttacacagaa tgtctcggat cacctttcaa ggtatatgag ttgccttaat aaattgagtt    5640
ccaaaacata gaaattaacc catggtggtt ttacaatgca gctctgcgtt catgtctcta    5700
gctgctcgat tccctccaaa attaagcagc agccgagaag atgaaaggaa tgttagaagc    5760
gtagttgttg aagatccaga aggatgcatt ctgaacttaa atgaaattcc ttcgtggcag    5820
gaaaaggttc aacatccatc tgacatggaa gtttctgggg ttgatagtgg atcaaaagag    5880
cagctaaggg actgttcaaa ctctggaatt gaaagattta atttcttaga gaagagtatt    5940
caaaatttag aagaggaagt attatcatca caagattctt ttgatccggc gatatttcag    6000
tcgtgtggga gagttggatc ctgttcatgt tccaaatcag acgcagagtt tcctacaacc    6060
aggtgtgaaa caaaaactgt cagtggaaca tcacaatcag tgcaaactgg gagcccaaac    6120
```

-continued

```
ttgtctgatg aaatttgtct tcaagggaat gagagaccgc atctatatga aggatctggt    6180
gatgttcaga aacaagaaac tacaaatgtc gctcagaaga aacctgatct tgaaaaaaca    6240
atgaattgga aagactctgt ctgttttggt cagccaagaa atgatactaa ttggcaaaca    6300
actccttcca gcagctatga gcagtgtgcg actcgacagc cacatgtact agacatagag    6360
gattttggaa tgcaaggtga aggccttggt tattcttgga tgtccatctc accaagagtt    6420
gacagagtaa agaacaaaaa tgtaccacgc aggttttttca gacaaggtgg aagtgttcca    6480
agagaattca caggtcagat cataccatca acgcctcatg aattaccagg aatgggattg    6540
tccggttcct caagcgccgt ccaagaacac caggacgata cccaacataa tcaacaagat    6600
gagatgaata aagcatccca tttacaaaaa acattttttgg atctgctcaa ctcctctgaa    6660
gaatgcctta caagacagtc cagtaccaaa cagaacatca cggatggctg tctaccgaga    6720
gataaaactg ctgaagacgt ggttgatccg ctcagtaaca attcaagctt acagaacata    6780
ttggtcgaat caaattccag caataaagag cagacggcag ttgaatacaa ggagacaaat    6840
gccactattt tacgagagat gaaagggacg cttgctgatg ggaaaaagcc tacaagccag    6900
tgggatagtc tcagaaaaga tgtggagggg aatgaaggga gacaggaacg aaacaaaaac    6960
aatatggatt ccatagacta tgaagcaata agacgtgcta gtatcagcga gatttctgag    7020
gctatcaagg aaagagggat gaataacatg ttggccgtac gaattaaggt aaatctacta    7080
atttcagttg agaccctcat caaatctgtc agaaggcttg aacatcagta aattatgtaa    7140
ccatatttac aacattgcag gatttcctag aacggatagt taaagatcat ggtggtatcg    7200
accttgaatg gttgagagaa tctcctcctg ataaagccaa gtgggtaaat cacattttta    7260
gtgactgcaa cactagcacg atcgatttac tcaacaatta cgtcaaactg agtattaaca    7320
agttgctcat gaacatttca cagggactat ctcttgagca taagaggtct gggtttgaaa    7380
agtgttgaat gcgtgcgact cttaacactc cacaatcttg cttttccctgt gagtcagact    7440
attccattat ctactaaaaa cttagaataa ctccggctaa ctaagctgga acttgtattg    7500
atgatatgaa ggttgacacg aatgttggaa ggatagcagt taggatggga tgggtgcctc    7560
tacaaccccct acctgaatca cttcagttac acctcctgga gctgtaagtt tcttttttgtt    7620
tgtcatctaa acaacgaaat ttttatgcaa gtcataacca tgctgtgttt tcacagatac    7680
ccagtgctcg agtccatcca aaaatttctt tggccaagac tttgcaaact cgatcaacga    7740
acactgtatg ctcataaact ctaacaaatc atctgtctga aaaccaata tttcttttggt    7800
agaattctat tgtcattact cattactaac agcgaaatta attaacgttc ttttttcttac    7860
tcaggtatga attacactac caactgatta cgtttggaaa ggtattattg ctctaagctt    7920
tgaatttatc atatggtaat ttcaagcatt gtaggcacct gatcaattat gtgtctaaat    7980
catgtgaatt catgtcaggt attttgcaca aagagtagac caaattgtaa tgcatgtcca    8040
atgagaggag agtgcagaca cttttgccagt gcttatgcta ggtaagcaag ctttcatgta    8100
cttatatgca ataattaaag ataaaattta ggattatggg taagtaacaa aaaattaggc    8160
tcagtttcat ggtagctagc tggaaatagt attacaagaa caacataaag atcaaagaca    8220
gaatcatgga tccatatgca ctatcatttt agctcttgta atccatacat gaacactata    8280
tgccaaagta gggatttcaa atatgagatt cgatgactga tgccattgta acagtgcaag    8340
acttgcttta ccggcaccag aggagaggag cttaacaagt gcaactattc cggtccctcc    8400
cgagtcctat cctcctgtag ccatcccgat gatagaacta cctcttccgt tggagaaatc    8460
```

-continued

```
cctagcaagt ggagcaccat cgaatagaga aaactgtgaa ccaataattg aagagccggc    8520
ctcgcccggg caagagtgca ctgaaataac cgagagtgat attgaagatg cttactacaa    8580
tgaggaccct gacgagatcc caacaataaa actcaacatt gaacagtttg gaatgactct    8640
acgggaacac atggaaagaa acatggagct ccaagaaggt gacatgtcca aggctttggt    8700
tgctttgcat ccaacaacta cttctattcc aactcccaaa ctaaagaaca ttagccgtct    8760
caggacagag caccaagtgt aagctaatat ctcctcctat attttatctt ccatataaat    8820
tttggggaaa aaatcgctct ccatctggtt ttagaacatg cgggtcagcc agggttatgg    8880
cattttata tatttcaccg atcggcccga gctggctctg gttgactcgt atgccaccct    8940
gcattgaaca aaccagtagg agacaagcaa gcaaaacgtt ttaagataag gtctatggta    9000
aaatgacaag gtaactgata aatgtgtcgt ctatttgcag gtacgagctc ccagattcac    9060
atcgtctcct tgatggtgta agtcaatttt taactctctc tatactcgag ttgtttcact    9120
tgagcaacac tgtttaaaag tcctcatttg ataaaataac agatggataa aagagaacca    9180
gatgatccaa gtccttatct cttagctata tggacaccag gtgagaataa aactgcaatg    9240
tttcattcat gtgtctacag tatcaaagaa agtacagcta gagctaaaaa gcatttgaaa    9300
tagagtcggt taaatatgaa agtttgaatc tgtaaatgaa agccggaacg tagcattggt    9360
ggatgttata tgtaaattag ttttttgagat tggtctaatg tagttgtttg actgccaggt    9420
gaaacagcga attcggcaca accgcctgaa cagaagtgtg gagggaaagc gtctggcaaa    9480
atgtgctttg acgagacttg ttctgagtgt aacagtctga gggaagcaaa ctcacagaca    9540
gttcgaggaa ctcttctggt gagattatct tgatcttttg tgttgctcat gaaaaggaga    9600
agtgagaata caagtttgct aatatcattt tttcgtcatt cacagatacc ttgtcggact    9660
gccatgagag gaagttttcc gctcaacggg acatatttcc aagtcaacga ggttagatga    9720
aataaaactc aaacagacag acgaaacatt atttctgttt agtgttggtt ctttatcctc    9780
cttgccatt ttta tcttgc agttatttgc agaccacgag tccagtctca aacccatcga    9840
tgttcctaga gattggatat gggatctccc aagaaggact gtttacttcg gaacatcagt    9900
aacatcaata ttcagaggta aaaacattcg taatagagtt agttaatcaa atgtccaaaa    9960
cacaagaaag cttcaccgtc caatacacaa gaaagcttca ccttctcttt gccaaaaaag   10020
atcttagaat gttttgctga atttgtgcag gtctttcaac ggagcagata cagttctgct   10080
tttgaaagg taaacgttaa ctttcgaccc agagaaatcc ggaaaatcta ttgctttgtt   10140
ctgatcaata cgttaaacat atacacacac actttacact taggaccaat actgttctga   10200
tctgtgatag aaactggtaa acatctaaca attatgattg caggattcgt atgtgtccgt   10260
ggattcgaac agaagacaag agcaccgcgt ccattaatgg caaggttgca ttttcctgcg   10320
agcaaattga agaacaacaa aacctaaaga tgactggaag aaagcaaacg cattgcttct   10380
ctgctctcct ctatttaaag ccaggaaaag tcccatttag acataataac aggaatccaa   10440
ataggctatt ttctctttct ttcttatttc attcatagag cagaagcgac acaaaaaagt   10500
ttttggggtt atttattttc tctctaacaa atttgtagcg ttttgggtct ttttctggct   10560
gtcactagcg tggcaaatcc aatgtctgcg cacacttagg cgcattgtca ataaaatttc   10620
```

<210> SEQ ID NO 8
<211> LENGTH: 1413
<212> TYPE: PRT
<213> ORGANISM: Arabidopsis thaliana
<220> FEATURE:
<223> OTHER INFORMATION: DMT2 (1DMT2)

```
<400> SEQUENCE: 8

Met Glu Lys Gln Arg Arg Glu Glu Ser Ser Phe Gln Gln Pro Pro Trp
 1               5                  10                  15

Ile Pro Gln Thr Pro Met Lys Pro Phe Ser Pro Ile Cys Pro Tyr Thr
             20                  25                  30

Val Glu Asp Gln Tyr His Ser Ser Gln Leu Glu Glu Arg Arg Phe Val
         35                  40                  45

Gly Asn Lys Asp Met Ser Gly Leu Asp His Leu Ser Phe Gly Asp Leu
     50                  55                  60

Leu Ala Leu Ala Asn Thr Ala Ser Leu Ile Phe Ser Gly Gln Thr Pro
65                  70                  75                  80

Ile Pro Thr Arg Asn Thr Glu Val Met Gln Lys Gly Thr Glu Glu Val
                 85                  90                  95

Glu Ser Leu Ser Ser Val Ser Asn Asn Val Ala Glu Gln Ile Leu Lys
            100                 105                 110

Thr Pro Glu Lys Pro Lys Arg Lys His Arg Pro Lys Val Arg Arg
        115                 120                 125

Glu Ala Lys Pro Lys Arg Glu Pro Lys Pro Arg Ala Pro Arg Lys Ser
130                 135                 140

Val Val Thr Asp Gly Gln Glu Ser Lys Thr Pro Lys Arg Lys Tyr Val
145                 150                 155                 160

Arg Lys Lys Val Glu Val Ser Lys Asp Gln Asp Ala Thr Pro Val Glu
                165                 170                 175

Ser Ser Ala Ala Val Glu Thr Ser Thr Arg Pro Lys Arg Leu Cys Arg
            180                 185                 190

Arg Val Leu Asp Phe Glu Ala Glu Asn Gly Glu Asn Gln Thr Asn Gly
        195                 200                 205

Asp Ile Arg Glu Ala Gly Glu Met Glu Ser Ala Leu Gln Glu Lys Gln
    210                 215                 220

Leu Asp Ser Gly Asn Gln Glu Leu Lys Asp Cys Leu Leu Ser Ala Pro
225                 230                 235                 240

Ser Thr Pro Lys Arg Lys Arg Ser Gln Gly Lys Arg Lys Gly Val Gln
                245                 250                 255

Pro Lys Lys Asn Gly Ser Asn Leu Glu Glu Val Asp Ile Ser Met Ala
            260                 265                 270

Gln Ala Ala Lys Arg Arg Gln Gly Pro Thr Cys Cys Asp Met Asn Leu
        275                 280                 285

Ser Gly Ile Gln Tyr Asp Glu Gln Cys Asp Tyr Gln Lys Met His Trp
    290                 295                 300

Leu Tyr Ser Pro Asn Leu Gln Gln Gly Gly Met Arg Tyr Asp Ala Ile
305                 310                 315                 320

Cys Ser Lys Val Phe Ser Gly Gln Gln His Asn Tyr Val Ser Ala Phe
                325                 330                 335

His Ala Thr Cys Tyr Ser Ser Thr Ser Gln Leu Ser Ala Asn Arg Val
            340                 345                 350

Leu Thr Val Glu Glu Arg Arg Glu Gly Ile Phe Gln Gly Arg Gln Glu
        355                 360                 365

Ser Glu Leu Asn Val Leu Ser Asp Lys Ile Asp Thr Pro Ile Lys Lys
    370                 375                 380

Lys Thr Thr Gly His Ala Arg Phe Arg Asn Leu Ser Ser Met Asn Lys
385                 390                 395                 400

Leu Val Glu Val Pro Glu His Leu Thr Ser Gly Tyr Cys Ser Lys Pro
```

-continued

```
                405                 410                 415
Gln Gln Asn Asn Lys Ile Leu Val Asp Thr Arg Val Thr Val Ser Lys
            420                 425                 430
Lys Lys Pro Thr Lys Ser Glu Lys Ser Gln Thr Lys Gln Lys Asn Leu
            435                 440                 445
Leu Pro Asn Leu Cys Arg Phe Pro Ser Phe Thr Gly Leu Ser Pro
            450                 455                 460
Asp Glu Leu Trp Lys Arg Arg Asn Ser Ile Glu Thr Ile Ser Glu Leu
465                 470                 475                 480
Leu Arg Leu Leu Asp Ile Asn Arg Glu His Ser Glu Thr Ala Leu Val
                485                 490                 495
Pro Tyr Thr Met Asn Ser Gln Ile Val Leu Phe Gly Gly Ala Gly
                500                 505                 510
Ala Ile Val Pro Val Thr Pro Val Lys Lys Pro Arg Pro Arg Pro Lys
                515                 520                 525
Val Asp Leu Asp Asp Glu Thr Asp Arg Val Trp Lys Leu Leu Leu Glu
                530                 535                 540
Asn Ile Asn Ser Glu Gly Val Asp Gly Ser Asp Glu Gln Lys Ala Lys
545                 550                 555                 560
Trp Trp Glu Glu Glu Arg Asn Val Phe Arg Gly Arg Ala Asp Ser Phe
                565                 570                 575
Ile Ala Arg Met His Leu Val Gln Gly Asp Arg Arg Phe Thr Pro Trp
                580                 585                 590
Lys Gly Ser Val Val Asp Ser Val Gly Val Phe Leu Thr Gln Asn
                595                 600                 605
Val Ser Asp His Leu Ser Ser Ser Ala Phe Met Ser Leu Ala Ser Gln
                610                 615                 620
Phe Pro Val Pro Phe Val Pro Ser Ser Asn Phe Asp Ala Gly Thr Ser
625                 630                 635                 640
Ser Met Pro Ser Ile Gln Ile Thr Tyr Leu Asp Ser Glu Glu Thr Met
                645                 650                 655
Ser Ser Pro Pro Asp His Asn His Ser Ser Val Thr Leu Lys Asn Thr
                660                 665                 670
Gln Pro Asp Glu Glu Lys Asp Tyr Val Pro Ser Asn Glu Thr Ser Arg
                675                 680                 685
Ser Ser Ser Glu Ile Ala Ile Ser Ala His Glu Ser Val Asp Lys Thr
                690                 695                 700
Thr Asp Ser Lys Glu Tyr Val Asp Ser Asp Arg Lys Gly Ser Ser Val
705                 710                 715                 720
Glu Val Asp Lys Thr Asp Glu Lys Cys Arg Val Leu Asn Leu Phe Pro
                725                 730                 735
Ser Glu Asp Ser Ala Leu Thr Cys Gln His Ser Met Val Ser Asp Ala
                740                 745                 750
Pro Gln Asn Thr Glu Arg Ala Gly Ser Ser Glu Ile Asp Leu Glu
                755                 760                 765
Gly Glu Tyr Arg Thr Ser Phe Met Lys Leu Leu Gln Gly Val Gln Val
                770                 775                 780
Ser Leu Glu Asp Ser Asn Gln Val Ser Pro Asn Met Ser Pro Gly Asp
785                 790                 795                 800
Cys Ser Ser Glu Ile Lys Gly Phe Gln Ser Met Lys Glu Pro Thr Lys
                805                 810                 815
Ser Ser Val Asp Ser Ser Glu Pro Gly Cys Cys Ser Gln Gln Asp Gly
                820                 825                 830
```

-continued

```
Asp Val Leu Ser Cys Gln Lys Pro Thr Leu Lys Glu Lys Gly Lys Lys
            835                 840                 845

Val Leu Lys Glu Glu Lys Lys Ala Phe Asp Trp Asp Cys Leu Arg Arg
    850                 855                 860

Glu Ala Gln Ala Arg Ala Gly Ile Arg Glu Lys Thr Arg Ser Thr Met
865                 870                 875                 880

Asp Thr Val Asp Trp Lys Ala Ile Arg Ala Asp Val Lys Glu Val
                885                 890                 895

Ala Glu Thr Ile Lys Ser Arg Gly Met Asn His Lys Leu Ala Glu Arg
            900                 905                 910

Ile Gln Tyr Leu Thr Leu Asn Met Lys Ile Met Gln Gly Phe Leu Asp
        915                 920                 925

Arg Leu Val Asn Asp His Gly Ser Ile Asp Leu Glu Trp Leu Arg Asp
    930                 935                 940

Val Pro Pro Asp Lys Ala Lys Glu Tyr Leu Leu Ser Phe Asn Gly Leu
945                 950                 955                 960

Gly Leu Lys Ser Val Glu Cys Val Arg Leu Leu Thr Leu His Leu
            965                 970                 975

Ala Phe Pro Val Asp Thr Asn Val Gly Arg Ile Ala Val Arg Leu Gly
        980                 985                 990

Trp Val Pro Leu Gln Pro Leu Pro Glu Ser Leu Gln Leu His Leu Leu
    995                 1000                1005

Glu Met Tyr Pro Met Leu Glu Ser Ile Gln Lys Tyr Leu Trp Pro Arg
    1010                1015                1020

Leu Cys Lys Leu Asp Gln Lys Thr Leu Tyr Glu Leu His Tyr Gln Met
1025                1030                1035                1040

Ile Thr Phe Gly Lys Val Phe Cys Thr Lys Ser Lys Pro Asn Cys Asn
            1045                1050                1055

Ala Cys Pro Met Lys Gly Glu Cys Arg His Phe Ala Ser Ala Phe Ala
        1060                1065                1070

Arg Lys Phe Ser Asn Ile His Leu Phe Tyr Ser Ala Arg Leu Ala Leu
    1075                1080                1085

Pro Ser Thr Glu Lys Gly Met Gly Thr Pro Asp Lys Asn Pro Leu Pro
    1090                1095                1100

Leu His Leu Pro Glu Pro Phe Gln Arg Glu Gln Gly Ser Glu Val Val
1105                1110                1115                1120

Gln His Ser Glu Pro Ala Lys Lys Val Thr Cys Cys Glu Pro Ile Ile
            1125                1130                1135

Glu Glu Pro Ala Ser Pro Glu Pro Glu Thr Ala Glu Val Ser Ile Ala
        1140                1145                1150

Asp Ile Glu Glu Ala Phe Phe Glu Asp Pro Glu Glu Ile Pro Thr Ile
    1155                1160                1165

Arg Leu Asn Met Asp Ala Phe Thr Ser Asn Leu Lys Lys Ile Met Glu
    1170                1175                1180

His Asn Lys Glu Leu Gln Asp Gly Asn Met Ser Ser Ala Leu Val Ala
1185                1190                1195                1200

Leu Thr Ala Glu Thr Ala Ser Leu Pro Met Pro Lys Leu Lys Asn Ile
            1205                1210                1215

Ser Gln Leu Arg Thr Glu His Arg Val Tyr Glu Leu Pro Asp Glu His
        1220                1225                1230

Pro Leu Leu Ala Gln Leu Glu Lys Arg Glu Pro Asp Asp Pro Cys Ser
    1235                1240                1245
```

```
Tyr Leu Leu Ala Ile Trp Thr Pro Gly Glu Thr Ala Asp Ser Ile Gln
    1250                1255                1260

Pro Ser Val Ser Thr Cys Ile Phe Gln Ala Asn Gly Met Leu Cys Asp
1265                1270                1275                1280

Glu Glu Thr Cys Phe Ser Cys Asn Ser Ile Lys Glu Thr Arg Ser Gln
                1285                1290                1295

Ile Val Arg Gly Thr Ile Leu Ile Pro Cys Arg Thr Ala Met Arg Gly
            1300                1305                1310

Ser Phe Pro Leu Asn Gly Thr Tyr Phe Gln Val Asn Glu Val Phe Ala
        1315                1320                1325

Asp His Ala Ser Ser Leu Asn Pro Ile Asn Val Pro Arg Glu Leu Ile
    1330                1335                1340

Trp Glu Leu Pro Arg Arg Thr Val Tyr Phe Gly Thr Ser Val Pro Thr
1345                1350                1355                1360

Ile Phe Lys Gly Leu Ser Thr Glu Lys Ile Gln Ala Cys Phe Trp Lys
                1365                1370                1375

Gly Tyr Val Cys Val Arg Gly Phe Asp Arg Lys Thr Arg Gly Pro Lys
            1380                1385                1390

Pro Leu Ile Ala Arg Leu His Phe Pro Ala Ser Lys Leu Lys Gly Gln
        1395                1400                1405

Gln Ala Asn Leu Ala
    1410

<210> SEQ ID NO 9
<211> LENGTH: 480
<212> TYPE: PRT
<213> ORGANISM: Arabidopsis thaliana
<220> FEATURE:
<223> OTHER INFORMATION: DMT2 (1DMT2) novel amino terminus

<400> SEQUENCE: 9

Met Glu Lys Gln Arg Arg Glu Glu Ser Ser Phe Gln Gln Pro Pro Trp
1               5                   10                  15

Ile Pro Gln Thr Pro Met Lys Pro Phe Ser Pro Ile Cys Pro Tyr Thr
            20                  25                  30

Val Glu Asp Gln Tyr His Ser Ser Gln Leu Glu Glu Arg Arg Phe Val
        35                  40                  45

Gly Asn Lys Asp Met Ser Gly Leu Asp His Leu Ser Phe Gly Asp Leu
    50                  55                  60

Leu Ala Leu Ala Asn Thr Ala Ser Leu Ile Phe Ser Gly Gln Thr Pro
65                  70                  75                  80

Ile Pro Thr Arg Asn Thr Glu Val Met Gln Lys Gly Thr Glu Glu Val
                85                  90                  95

Glu Ser Leu Ser Ser Val Ser Asn Asn Val Ala Glu Gln Ile Leu Lys
            100                 105                 110

Thr Pro Glu Lys Pro Lys Arg Lys Lys His Arg Pro Lys Val Arg Arg
        115                 120                 125

Glu Ala Lys Pro Lys Arg Glu Pro Lys Pro Arg Ala Pro Arg Lys Ser
    130                 135                 140

Val Val Thr Asp Gly Gln Glu Ser Lys Thr Pro Lys Arg Lys Tyr Val
145                 150                 155                 160

Arg Lys Lys Val Glu Val Ser Lys Asp Gln Asp Ala Thr Pro Val Glu
                165                 170                 175

Ser Ser Ala Ala Val Glu Thr Ser Thr Arg Pro Lys Arg Leu Cys Arg
            180                 185                 190
```

```
Arg Val Leu Asp Phe Glu Ala Glu Asn Gly Glu Asn Gln Thr Asn Gly
            195                 200                 205

Asp Ile Arg Glu Ala Gly Glu Met Glu Ser Ala Leu Gln Glu Lys Gln
        210                 215                 220

Leu Asp Ser Gly Asn Gln Glu Leu Lys Asp Cys Leu Leu Ser Ala Pro
225                 230                 235                 240

Ser Thr Pro Lys Arg Lys Arg Ser Gln Gly Lys Arg Lys Gly Val Gln
                245                 250                 255

Pro Lys Lys Asn Gly Ser Asn Leu Glu Glu Val Asp Ile Ser Met Ala
            260                 265                 270

Gln Ala Ala Lys Arg Arg Gln Gly Pro Thr Cys Cys Asp Met Asn Leu
        275                 280                 285

Ser Gly Ile Gln Tyr Asp Glu Gln Cys Asp Tyr Gln Lys Met His Trp
290                 295                 300

Leu Tyr Ser Pro Asn Leu Gln Gln Gly Gly Met Arg Tyr Asp Ala Ile
305                 310                 315                 320

Cys Ser Lys Val Phe Ser Gly Gln Gln His Asn Tyr Val Ser Ala Phe
                325                 330                 335

His Ala Thr Cys Tyr Ser Ser Thr Ser Gln Leu Ser Ala Asn Arg Val
            340                 345                 350

Leu Thr Val Glu Glu Arg Arg Glu Gly Ile Phe Gln Gly Arg Gln Glu
        355                 360                 365

Ser Glu Leu Asn Val Leu Ser Asp Lys Ile Asp Thr Pro Ile Lys Lys
370                 375                 380

Lys Thr Thr Gly His Ala Arg Phe Arg Asn Leu Ser Ser Met Asn Lys
385                 390                 395                 400

Leu Val Glu Val Pro Glu His Leu Thr Ser Gly Tyr Cys Ser Lys Pro
                405                 410                 415

Gln Gln Asn Asn Lys Ile Leu Val Asp Thr Arg Val Thr Val Ser Lys
            420                 425                 430

Lys Lys Pro Thr Lys Ser Glu Lys Ser Gln Thr Lys Gln Lys Asn Leu
        435                 440                 445

Leu Pro Asn Leu Cys Arg Phe Pro Pro Ser Phe Thr Gly Leu Ser Pro
450                 455                 460

Asp Glu Leu Trp Lys Arg Arg Asn Ser Ile Glu Thr Ile Ser Glu Leu
465                 470                 475                 480

<210> SEQ ID NO 10
<211> LENGTH: 8880
<212> TYPE: DNA
<213> ORGANISM: Arabidopsis thaliana
<220> FEATURE:
<223> OTHER INFORMATION: DMT2 (1DMT2) sequence from BAC F1011

<400> SEQUENCE: 10
tcgctgagcc tgggtttctt catcggacct ggatctctgg atctatcaaa cggtctacga      60
ggattctcca ttccaaagaa ctatacaata caagaggtac gcaaataatg ccctaaatta     120
aacctaatcg gcaaaaatcg attgcagtga caacaaatcc tcgttagagg ggaattcaga     180
gcattacaac aatcagtaac cctaagttac aatctaaaaa ttgagatgca taacgcgatt     240
ctgcgaagaa gacggagaag atagaaggaa tgcttcgaat tcggcaaaaa tgtcagagag     300
tttggacaat ctccgatcaa ttagggttgt gaattgggga ttttatggag acgagacaaa     360
aaaaagttga agatcggagc tggttccaaa aatatttagg cccatttaat gacccacatt     420
ccatgtataa taggcccatc atctaatatt tgacaacaat agaattcttt ggtccggttg     480
```

-continued

```
aactatctga tttaaaccaa gttaagtgag atcctccaca tatcgaacca gatcttgatt      540
caggtaacca aaagctaacc gtaaattcag atataaacca aacgaaggga acagagagtt      600
tacacagcta cgggtctgtt ttttgtgaca agtgtttgat acaaatttaa gacgaaacta      660
aaatgggatt tagaaacctt gtacaactct aggactgtta actttacgtt ttcactttct      720
tacattaact agattggaac agtgtgctct ctcactctta accataagct tgtatttgtt      780
tgcttgccaa cggattaggc gaggttagct tgttgtccct tcagtttgct cgccgggaag      840
tgcaatcttg caatcaaagg cttcggtccc ctcgtctttc gatcaaatcc acgtacacat      900
acgtacccta cataatatca aaagataagt tatgtttcag aacaagaaga aactgcttaa      960
tacaaaatgt acctttccaa aagcaagcct gtatcttctc agttgataaa cctgagaaaa     1020
atagagctca agtggttaga caactttct tttatataaa caatcgcatc acaatccaat      1080
aaagaaaatc ttatacccttt gaatatcgta ggaacagagg taccaaaata gaccgttctt     1140
cgaggtaatt cccatatcaa ttcccttggg acattgattg gtttaggct ggatgcatga      1200 tccgcaaaca cctgtatcaa tagaatacat cacaagtttc aatgcaaata attaaaatga     1260
aagagttgga gttattggag ttcaagtctt acctcattta cttgaaagta cgttccattt     1320
agaggaaaac taccctcat cgctgttcta caaggaatct gtacaattta caacatatta      1380
atctgtagaa aacataagtg tagtaagccg cataaggaga ttgatgcaac tacttaccaa     1440
aattgtccct ctcacaattt gagatctagt ctccttgatg ctgttgcagg agaaacaagt     1500
ctcctcgtca caaagcatac catttgcttg gaatatgcac gtactaacag acggttgaat     1560
agaatcagcc gtctcacctg ttgaataaca catcgattaa agataccgat ttgatttcat     1620
gattaaaaga tatgcaaatc attaaattac ctggcgtcca tatagcaagc aaataagaac     1680
atggatcatc aggttctctc tttttccaact gccacaagaa atcacaaaca gctagtcaga     1740
ttttacaata tagacagcac tctatacggc atgtgtcctt atccagttag ctcacatacc     1800
tgagctagaa gaggatgctc gtctggaagt tcgtaactgc aagatacggg aaaagaaaca     1860
agttatggca tagcctgtaa ttattgggaa gtttgtctgc tttccaactt acgagttcat     1920
gcttggtcaa tcacttaaat attctactct gttcaagctt taataatttt gaaaaatgtg     1980
tttctgattt cattttttaac ctaagaacga agaaaaacag agaaaaatgg attcttacac     2040
tcggtgttct gtccttaact ggctgatatt cttgagctta ggcattggaa gagaagcagt     2100
ttcagcagta agtgcaacta aagcgctgga catgttccg tcttgaagtt ccttgttgtg      2160
ttccattatc ttcttcaagt tactggtaaa tgcatccatg tttagcctga tggtaggaat     2220
ttcttctgga tcctcaaaaa acgcctcctc tatgtcagct attgatactt ctgcggtttc     2280
tggctccggt gaagcaggct cttcgatgat tggttcacaa catgtgacct tttttgctgg     2340
ttctgagtgc tgtactactt cagacccttg ctctctctgg aatggctctg gcaggtgtag     2400
aggcaaaggg ttttttatcag gtgtccccat acctttctct gtacttggta aagcaagcct     2460
tgcactgtaa aacaaatgaa tgttactaaa ttttctgtaa tgatgattca gagcttcgtt     2520
tagatacaga ccaattctca tttaactggg ttatatttta acaaggactt tcctcataga     2580
gtcatagtgg tactaaaggt ttaagagaac atgttgtagc accttgcaaa cgcactggca     2640
aaatgtctgc attctccttt catcggacat gcattgcaat taggtttgct ctttgtgcaa     2700
aagacctgat acaataatca agcagattac aaacctcatc atgtgagctg attttgacat     2760
acgtatatat gtatttcttt aatacatacc tttccaaaag taatcatctg gtagtgcaac     2820
```

```
tcatacctgt gagataatag ggtattaaac taatgaataa gtgtattaga ctgaggcatg    2880
aaaaaaaaaa agttagtgat aaacatcatt cttacaatgt ttttggtcg agtttgcaga     2940 gacgggcca aagatacttt tgaatagatt caagcatagg ataccagac aaaccaaacc     3000 tcagatgtat taagtaacaa attacaattt ccaagtagga ccattttgaa aagtgcttac    3060
atttccagaa gatgcaactg aagtgactct gggagcggct gaaggggcac ccatccaagt    3120
ctgacggcta tgcgcccaac atttgtatca acctgtcaat aaattaagtt catgcatcat    3180
ataattcact ttttataggg acagaaacaa aagtttgatc cttgcttact ggaaaggcaa    3240
gatggtgaag tgttagaagc cgcacacact ccacactttt cagtcccaat ccgttaaagc    3300
tcagaagata ttctctgcag ggttttgtaa tatacgagag tacataattc attattaagt    3360
cactaaaact gccaaagtag taatctttgt ataggttaat aaagaagaaa taaatgctt    3420 cgtctttcaa acttactttg ctttatctgg tggaacatct ctcaaccatt caagatcgat    3480
acttccatgg tcatttacca gtcgatcaag gaagccctgc atgattttca tgttcagagt    3540
caaatactta aaatgaatgt tatcacgaaa tttagccact aaatttttac ctgtatacgt    3600
tctgcaagtt tatggttcat cccgcgactc ttgattgttt cagcaacttc cttaacatct    3660
gctgctcgta ttgccttcca atccacggtg tccattgtac ttcttgtttt ttctctaatt    3720
cctgctctag cttgggcttc tcttcttaaa caatcccagt caaacgcttt ttttcctcc     3780 ttcaaaacct ttttcccttt ttctttaag gtaggtttct gacaactcaa acatcccca    3840 tcttgctgag agcaacaacc aggttcacta ctatcaacag aggattttgt gggctctttc    3900
attgactgga aacccttaat ttctgagcta caatcacccg gagacatatt tggtgatact    3960
tgattggaat cttctagaga gacttgtacc ccctgtagga gcttcataaa ggaagtacga    4020
tactctcctt ctaagtcgat ctctgagctt gatcctgctc tctctgtatt tgaggagca    4080 tcagacacca tcgaatgttg acatgtaagt gcagaatctt cagatggaaa caggttcagg    4140
acacgacact tctcatccgt cttatcaacc tctacacttg agccttttcg atctgaatca    4200
acatactcct ttgaatccgt ggttttgtca actgattcat gggctgagat ggcaatctca    4260
ctactgcttc tggaggtttc attgctaggt acataatcct tctcctcatc aggctgtgta    4320
tttttcaaag taacgaaact gtgattgtga tcgggtgggc ttgacatcgt ttcctctgag    4380
tccaagtacg ttatttgaat agaaggcatc gagcttgttc cagcgtcaaa gttactgctc    4440
ggtacaaaag ggacagggaa ctgggaagcc aacgacatga aagccgaact acaaggagta    4500
aaaaacatca aagcaagtta gttttgtgac ttttttgctgt cttggattta gtttgacata    4560
gaattatgta agagcttgta ccttgagaga tggtctgaaa catttgagt gagaaatact     4620 ccaacaacag aatccacgac ggatcccttc caaggcgtaa aacgtcgatc ccctgttaga    4680
aaccaaagac cataacaaga agcagtagct gagacatact aattgaaacc atgtggttag    4740
aacagaaaca cataaaagga caagtgtggt gtataacctt gtacaaggtg catccttgca    4800
ataaatgagt cagctcgtcc tcgaaacaca ttacgttctt cctcccacca tttcgccttc    4860
tgctcgtctt atccgtcaac accttcgcta ttaatattct ccaatagcag tttccacact    4920
ctgtctgtct catcgtctag atcaacctt ggtcgtgggc gtggttttt aacaggagtt     4980 acaggcacaa ttgctccagc gccaccacca aagagtacaa tctggctatt cattgtgtaa    5040
ggaacgagag cagtttcaga atgctccctg ttgatgtcta atagacgcaa tagctcactg    5100
attgtttcga tcgagttacg tcgtttccaa agttcatctg gagaaagacc tgcaggaatc    5160
aaacatcatc attatcaaga aatagtctgc atttaacaga ttcaaaaaaa caagaaata    5220
```

```
tagttctgta tctattcatt accagtaaat gaaggtggaa acggcaaag attcggaaga      5280 agattttcct gtttggtttg tgatttctca gacttggttg gcttcttttt gctcacagtc     5340
acccgcgtat caacaagaat cttattattt tgctgtggct tgctacaata tcctgaggtt     5400
aaatgctcag gaacttccac aagtttattc attgaagaca aattccggaa tcgagcatgg     5460
cctgttgttt tcttcttgat cggcgtgtct atcttatccg agagaacatt tagctcagac     5520
tcttgccttc cttgaaagat accttctcgt cttcttcaa cggttaggac tctattagca     5580
ctgagctgag atgtggaact gtagcacgta gcgtgaaagg cagaaacata attgtgctgt     5640
tgtccagaga atactttgct gcaaatggca tcatatctca tccctccctg ttgcaagttt     5700
ggggaataca accaatgcat tttctggtag tcacattgct catcatactg aatccctgat     5760
agattcatgt cgcaacaagt tggtccttgt cttctctttg cagcttgcgc catcgaaata     5820
tcgacttctt ctagattact gccattttc tttggttgaa ctccctttct tttaccttgg      5880
ctgcgctttc tcttgggcgt gctaggagcc gaaagaaggc aatcttttaa ctcttgattc     5940
ccagaatcta actgcttctc ttgaagagct gattccatct cacctgcttc tctaatgtca     6000
ccgttggtct ggttttctcc attttcggct tcaaaatcca agactcgtct acagagcctc     6060
ttaggacgag ttgaagtttc aacagctgct gatgattcaa ccggagtagc gtcttgatcc     6120
ttactgactt caaccttctt ccgcacatat ttcctctttg tgttttgct ttcttgacca      6180 tcggtgacaa cagacttcct cggagctcgt ggtttaggct ccctcttggg tttagcttct     6240
ctacgaacct ttggccgatg cttcttcctc ttaggttttt caggagtctt gaggatctgt     6300
tcagcaacat tgttactcac tgagctcaaa ctctccactt cttcagtacc tttttgcata     6360
acctctgtgt ttcctacatt gagaatcaca tctttctcag tccaactcaa acagaatcaa     6420
aatttgacaa agcgatttca tttctcatga gaccagaatc aaaatcccct cttacttgta     6480
ggtattggag tctgaccaga gaatatgagg gatgcagtgt tagctagagc aagcaaatcc     6540
ccaaaagaca agtgatcaag accactcata tccttgttcc caacaaatct cctgcatgca     6600
tcaataccct acttaaccaa ttacccatca ctactctttg aaatttctca actttagaac     6660
aaaaaagcac aaacctttcc tccaattgac tgctatgata ttgatcctcc accgtgtatg     6720
ggcagatcgg tgaaaatggc ttcatgggtg tctgaggaat ccatggaggt tgttgaaagc     6780
tgctttcttc tctcctctgt ttctccattt ctgactctat ttttactttt cttcactctt     6840
acttaaatca gaaccatttg agaaaaagct tggaactttc tattttttcc actgcaaaaa     6900
gttcaataat ttcttcaata aaagagatca ccaattttt ttaaaaatca cgattttata      6960
aaatgatcag atccacttt ttctgggggtt ttagagaaag agagatctcc ggaagtcatt     7020
gattttgggt gagtggcgac atgaacgatt aatccgttcg ttaggtgaaa gagagacttt     7080
ttagattcac aacaaaatgt aaaaaaaagt aagaaaaaaa caaaattcat taccagtaga     7140
atcaatggtt atggtggtga tggagagagt tagttcggtg gtagctatga gaggataaga     7200
tcactgatgc ttcgtttctt ctcttggaat cgatgaagtt aaagagtaat atagaaaag     7260 cttttttggc ctaacgtata aagaagagga tataacatgt gttgttgtgt gtttcactat     7320
ttttcataac cgtttgttta tgtagggcga agttcgtttt ggttggcggg aaagttta     7380 cggaatttta ttttaaaaat aatgattctt ttctacaaaa tctcctagac tatgggaaag     7440
atgatttaaa aagttaataa tattgtcgtt gttatcgtca tcgtcatcat cgtctttct     7500 gttatcttt tctctttaaa atttcgtatt ttttctcgtt tacgtaacta tttaaaatta     7560
```

-continued

```
tatgaactaa ctaattttat aattaataga aattataaaa taatcttaat tttgctttag    7620
atataaaata attagaactt tatttataaa tttatcatca aattatgatt taaacaaata    7680
acatgttatg taatccacgt ttataatttt gatcaataat atattatttt gctaattttt    7740
acgtaatctc ataaatttac acgttttcgt ttacatatgc agaagttaaa tgattcgttt    7800
tagaattatt attttccact gatatgggag ctagtgtagt agagtgatta ttaggctagt    7860
tgcccaacga gtctttcgtt tttgatcatt ccaaatgttt tagtctagta cgataggagt    7920
caaaatactg caccatatgt gtgaaactgt gaatgtgtgt gaaaaaaaga gtaattagtg    7980
tgctaacctt tgatttcctg tcatgcaaga aaccttcaaa gagacgtaca tgagaaatga    8040
gtattgtaaa tcatttattt catggacttg gttggaatct tagtgaatcg ttgttgtcaa    8100
tcttaacaac ttgttggatt ggttatgagc ctatgactta tgacttatga gtgagtcaat    8160
ggtggtcata acctaatgat tgggttatga gcaaagaaat ttggaatttg taaaaaaaaa    8220
aaaaaaaatc aagagctttt ttgtgtggac atatctatcc tagaaactga gacgaataat    8280
agtggataaa aagttgggaa cggattattc gaatgtttaa aactattatt gaaaacaata    8340
caactaaata tggtacaaaa gtaaacgaat tcgtatagct aaacctaatt caaattacga    8400
agctaatcca tacttggatc ctaaacgctt ttacttttac ttacggtttc tttttcaaaa    8460 aagttttttac aaatttgggt ttgtcttatg aagattatgg cagaagagac tgatcaaaag    8520
tgaatgccta attcggttta atccattcaa gtttatctta aacaatgaaa ctgaccatga    8580
aagtgaattc aaagaccaaa tcaaagaaaa attaaactga tttagttgta atattggtat    8640
tgaattaaac tataaataga aataaccaaa catataacca caaagaaga ctatttatat    8700 aaatatatga gttggaagtc attttttggac tattatataa gatctaatta tcacacgacg    8760
tgtggatgta tggttagcag agttgtgttc agagagttcg ataaagccat cactccaaac    8820
atacaaaata tccatacatt gatccaccaa tataaccggc tgtgtgccaa gcaaagtgaa    8880
```

<210> SEQ ID NO 11
<211> LENGTH: 1332
<212> TYPE: PRT
<213> ORGANISM: Arabidopsis thaliana
<220> FEATURE:
<223> OTHER INFORMATION: DMT3 (1DMT3)

<400> SEQUENCE: 11

```
Met Glu Val Glu Gly Glu Val Arg Glu Lys Glu Ala Arg Val Lys Gly
  1               5                  10                  15

Arg Gln Pro Glu Thr Glu Val Leu His Gly Leu Pro Gln Glu Gln Ser
                 20                  25                  30

Ile Phe Asn Asn Met Gln His Asn His Gln Pro Asp Ser Asp Arg Arg
             35                  40                  45

Arg Leu Ser Leu Glu Asn Leu Pro Gly Leu Tyr Asn Met Ser Cys Thr
         50                  55                  60

Gln Leu Leu Ala Leu Ala Asn Ala Thr Val Ala Thr Gly Ser Ser Ile
 65                  70                  75                  80

Gly Ala Ser Ser Ser Ser Leu Ser Ser Gln His Pro Thr Asp Ser Trp
                 85                  90                  95

Ile Asn Ser Trp Lys Met Asp Ser Asn Pro Trp Thr Leu Ser Lys Met
                100                 105                 110

Gln Lys Gln Gln Tyr Asp Val Ser Thr Pro Gln Lys Phe Leu Cys Asp
            115                 120                 125

Leu Asn Leu Thr Pro Glu Glu Leu Val Ser Thr Ser Thr Gln Arg Thr
```

-continued

```
            130                 135                 140
Glu Pro Glu Ser Pro Gln Ile Thr Leu Lys Thr Pro Gly Lys Ser Leu
145                 150                 155                 160

Ser Glu Thr Asp His Glu Pro His Asp Arg Ile Lys Lys Ser Val Leu
                165                 170                 175

Gly Thr Gly Ser Pro Ala Ala Val Lys Lys Arg Lys Ile Ala Arg Asn
            180                 185                 190

Asp Glu Lys Ser Gln Leu Glu Thr Pro Thr Leu Lys Arg Lys Lys Ile
            195                 200                 205

Arg Pro Lys Val Val Arg Glu Gly Lys Thr Lys Lys Ala Ser Ser Lys
    210                 215                 220

Ala Gly Ile Lys Lys Ser Ser Ile Ala Ala Thr Ala Thr Lys Thr Ser
225                 230                 235                 240

Glu Glu Ser Asn Tyr Val Arg Pro Lys Arg Leu Thr Arg Arg Ser Ile
                245                 250                 255

Arg Phe Asp Phe Asp Leu Gln Glu Glu Asp Glu Glu Phe Cys Gly Ile
            260                 265                 270

Asp Phe Thr Ser Ala Gly His Val Glu Gly Ser Ser Gly Glu Glu Asn
            275                 280                 285

Leu Thr Asp Thr Thr Leu Gly Met Phe Gly His Val Pro Lys Gly Arg
    290                 295                 300

Arg Gly Gln Arg Arg Ser Asn Gly Phe Lys Lys Thr Asp Asn Asp Cys
305                 310                 315                 320

Leu Ser Ser Met Leu Ser Leu Val Asn Thr Gly Pro Gly Ser Phe Met
                325                 330                 335

Glu Ser Glu Glu Asp Arg Pro Ser Asp Ser Gln Ile Ser Leu Gly Arg
            340                 345                 350

Gln Arg Ser Ile Met Ala Thr Arg Pro Arg Asn Phe Arg Ser Leu Lys
            355                 360                 365

Lys Leu Leu Gln Arg Ile Ile Pro Ser Lys Arg Asp Arg Lys Gly Cys
    370                 375                 380

Lys Leu Pro Arg Gly Leu Pro Lys Leu Thr Val Ala Ser Lys Leu Gln
385                 390                 395                 400

Leu Lys Val Phe Arg Lys Lys Arg Ser Gln Arg Asn Arg Val Ala Ser
                405                 410                 415

Gln Phe Asn Ala Arg Ile Leu Asp Leu Gln Trp Arg Arg Gln Asn Pro
            420                 425                 430

Thr Gly Thr Ser Leu Ala Asp Ile Trp Glu Arg Ser Leu Thr Ile Asp
            435                 440                 445

Ala Ile Thr Lys Leu Phe Glu Glu Leu Asp Ile Asn Lys Glu Gly Leu
    450                 455                 460

Cys Leu Pro His Asn Arg Glu Thr Ala Leu Ile Leu Tyr Lys Lys Ser
465                 470                 475                 480

Tyr Glu Glu Gln Lys Ala Ile Val Lys Tyr Ser Lys Lys Gln Lys Pro
                485                 490                 495

Lys Val Gln Leu Asp Pro Glu Thr Ser Arg Val Trp Lys Leu Leu Met
            500                 505                 510

Ser Ser Ile Asp Cys Asp Gly Val Asp Gly Ser Asp Glu Glu Lys Arg
            515                 520                 525

Lys Trp Trp Glu Glu Glu Arg Asn Met Phe His Gly Arg Ala Asn Ser
    530                 535                 540

Phe Ile Ala Arg Met Arg Val Val Gln Gly Asn Arg Thr Phe Ser Pro
545                 550                 555                 560
```

```
-continued

Trp Lys Gly Ser Val Val Asp Ser Val Gly Val Phe Leu Thr Gln
            565                 570                 575

Asn Val Ala Asp His Ser Ser Ser Ala Tyr Met Asp Leu Ala Ala
            580                 585                 590

Glu Phe Pro Val Glu Trp Asn Phe Asn Lys Gly Ser Cys His Glu Glu
            595                 600                 605

Trp Gly Ser Ser Val Thr Gln Glu Thr Ile Leu Asn Leu Asp Pro Arg
    610                 615                 620

Thr Gly Val Ser Thr Pro Arg Ile Arg Asn Pro Thr Arg Val Ile Ile
625                 630                 635                 640

Glu Glu Ile Asp Asp Glu Asn Asp Ile Asp Ala Val Cys Ser Gln
            645                 650                 655

Glu Ser Ser Lys Thr Ser Asp Ser Ser Ile Thr Ser Ala Asp Gln Ser
            660                 665                 670

Lys Thr Met Leu Leu Asp Pro Phe Asn Thr Val Leu Met Asn Glu Gln
    675                 680                 685

Val Asp Ser Gln Met Val Lys Gly Lys Gly His Ile Pro Tyr Thr Asp
    690                 695                 700

Asp Leu Asn Asp Leu Ser Gln Gly Ile Ser Met Val Ser Ser Ala Ser
705                 710                 715                 720

Thr His Cys Glu Leu Asn Leu Asn Glu Val Pro Pro Glu Val Glu Leu
            725                 730                 735

Cys Ser His Gln Gln Asp Pro Glu Ser Thr Ile Gln Thr Gln Asp Gln
            740                 745                 750

Gln Glu Ser Thr Arg Thr Glu Asp Val Lys Lys Asn Arg Lys Lys Pro
            755                 760                 765

Thr Thr Ser Lys Pro Lys Lys Ser Lys Glu Ser Ala Lys Ser Thr
    770                 775                 780

Gln Lys Lys Ser Val Asp Trp Asp Ser Leu Arg Lys Glu Ala Glu Ser
785                 790                 795                 800

Gly Gly Arg Lys Arg Glu Arg Thr Glu Arg Thr Met Asp Thr Val Asp
            805                 810                 815

Trp Asp Ala Leu Arg Cys Thr Asp Val His Lys Ile Ala Asn Ile Ile
            820                 825                 830

Ile Lys Arg Gly Met Asn Asn Met Leu Ala Glu Arg Ile Lys Ala Phe
    835                 840                 845

Leu Asn Arg Leu Val Lys Lys His Gly Ser Ile Asp Leu Glu Trp Leu
    850                 855                 860

Arg Asp Val Pro Pro Asp Lys Ala Lys Glu Tyr Leu Leu Ser Ile Asn
865                 870                 875                 880

Gly Leu Gly Leu Lys Ser Val Glu Cys Val Arg Leu Leu Ser Leu His
            885                 890                 895

Gln Ile Ala Phe Pro Val Asp Thr Asn Val Gly Arg Ile Ala Val Arg
            900                 905                 910

Leu Gly Trp Val Pro Leu Gln Pro Leu Pro Asp Glu Leu Gln Met His
    915                 920                 925

Leu Leu Glu Leu Tyr Pro Val Leu Glu Ser Val Gln Lys Tyr Leu Trp
    930                 935                 940

Pro Arg Leu Cys Lys Leu Asp Gln Lys Thr Leu Tyr Glu Leu His Tyr
945                 950                 955                 960

His Met Ile Thr Phe Gly Lys Val Phe Cys Thr Lys Val Lys Pro Asn
            965                 970                 975
```

```
Cys Asn Ala Cys Pro Met Lys Ala Glu Cys Arg His Tyr Ser Ser Ala
                980                 985                 990

Arg Ala Ser Ala Arg Leu Ala Leu Pro Glu Pro Glu Glu Ser Asp Arg
            995                1000                1005

Thr Ser Val Met Ile His Glu Arg Arg Ser Lys Arg Lys Pro Val Val
    1010                1015                1020

Val Asn Phe Arg Pro Ser Leu Phe Leu Tyr Gln Glu Lys Glu Gln Glu
1025                1030                1035                1040

Ala Gln Arg Ser Gln Asn Cys Glu Pro Ile Ile Glu Glu Pro Ala Ser
            1045                1050                1055

Pro Glu Pro Glu Tyr Ile Glu His Asp Ile Glu Asp Tyr Pro Arg Asp
            1060                1065                1070

Lys Asn Asn Val Gly Thr Ser Glu Asp Pro Trp Glu Asn Lys Asp Val
            1075                1080                1085

Ile Pro Thr Ile Ile Leu Asn Lys Glu Ala Gly Thr Ser His Asp Leu
    1090                1095                1100

Val Val Asn Lys Glu Ala Gly Thr Ser His Asp Leu Val Val Leu Ser
1105                1110                1115                1120

Thr Tyr Ala Ala Ala Ile Pro Arg Arg Lys Leu Lys Ile Lys Glu Lys
            1125                1130                1135

Leu Arg Thr Glu His His Val Phe Glu Leu Pro Asp His His Ser Ile
            1140                1145                1150

Leu Glu Gly Phe Glu Arg Arg Glu Ala Glu Asp Ile Val Pro Tyr Leu
            1155                1160                1165

Leu Ala Ile Trp Thr Pro Gly Glu Thr Val Asn Ser Ile Gln Pro Pro
    1170                1175                1180

Lys Gln Arg Cys Ala Leu Phe Glu Ser Asn Asn Thr Leu Cys Asn Glu
1185                1190                1195                1200

Asn Lys Cys Phe Gln Cys Asn Lys Thr Arg Glu Glu Glu Ser Gln Thr
            1205                1210                1215

Val Arg Gly Thr Ile Leu Ile Pro Cys Arg Thr Ala Met Arg Gly Gly
            1220                1225                1230

Phe Pro Leu Asn Gly Thr Tyr Phe Gln Thr Asn Glu Val Phe Ala Asp
            1235                1240                1245

His Asp Ser Ser Ile Asn Pro Ile Asp Val Pro Thr Glu Leu Ile Trp
    1250                1255                1260

Asp Leu Lys Arg Arg Val Ala Tyr Leu Gly Ser Ser Val Ser Ser Ile
1265                1270                1275                1280

Cys Lys Gly Leu Ser Val Glu Ala Ile Lys Tyr Asn Phe Gln Glu Gly
            1285                1290                1295

Tyr Val Cys Val Arg Gly Phe Asp Arg Glu Asn Arg Lys Pro Lys Ser
            1300                1305                1310

Leu Val Lys Arg Leu His Cys Ser His Val Ala Ile Arg Thr Lys Glu
        1315                1320                1325

Lys Thr Glu Glu
    1330

<210> SEQ ID NO 12
<211> LENGTH: 375
<212> TYPE: PRT
<213> ORGANISM: Arabidopsis thaliana
<220> FEATURE:
<223> OTHER INFORMATION: DMT3 (1DMT3) novel amino terminus

<400> SEQUENCE: 12
```

```
Met Glu Val Glu Gly Glu Val Arg Lys Glu Ala Arg Val Lys Gly
  1               5                  10                  15

Arg Gln Pro Glu Thr Glu Val Leu His Gly Leu Pro Gln Glu Gln Ser
                 20                  25                  30

Ile Phe Asn Asn Met Gln His Asn His Gln Pro Asp Ser Asp Arg Arg
             35                  40                  45

Arg Leu Ser Leu Glu Asn Leu Pro Gly Leu Tyr Asn Met Ser Cys Thr
         50                  55                  60

Gln Leu Leu Ala Leu Ala Asn Ala Thr Val Ala Thr Gly Ser Ser Ile
 65                  70                  75                  80

Gly Ala Ser Ser Ser Ser Leu Ser Ser Gln His Pro Thr Asp Ser Trp
                 85                  90                  95

Ile Asn Ser Trp Lys Met Asp Ser Asn Pro Trp Thr Leu Ser Lys Met
            100                 105                 110

Gln Lys Gln Gln Tyr Asp Val Ser Thr Pro Gln Lys Phe Leu Cys Asp
            115                 120                 125

Leu Asn Leu Thr Pro Glu Glu Leu Val Ser Thr Ser Thr Gln Arg Thr
            130                 135                 140

Glu Pro Glu Ser Pro Gln Ile Thr Leu Lys Thr Pro Gly Lys Ser Leu
145                 150                 155                 160

Ser Glu Thr Asp His Glu Pro His Asp Arg Ile Lys Lys Ser Val Leu
                165                 170                 175

Gly Thr Gly Ser Pro Ala Ala Val Lys Lys Arg Lys Ile Ala Arg Asn
                180                 185                 190

Asp Glu Lys Ser Gln Leu Glu Thr Pro Thr Leu Lys Arg Lys Lys Ile
            195                 200                 205

Arg Pro Lys Val Val Arg Glu Gly Lys Thr Lys Lys Ala Ser Ser Lys
210                 215                 220

Ala Gly Ile Lys Lys Ser Ser Ile Ala Ala Thr Ala Lys Thr Ser
225                 230                 235                 240

Glu Glu Ser Asn Tyr Val Arg Pro Lys Arg Leu Thr Arg Arg Ser Ile
                245                 250                 255

Arg Phe Asp Phe Asp Leu Gln Glu Glu Asp Glu Phe Cys Gly Ile
            260                 265                 270

Asp Phe Thr Ser Ala Gly His Val Glu Gly Ser Ser Gly Glu Glu Asn
            275                 280                 285

Leu Thr Asp Thr Thr Leu Gly Met Phe Gly His Val Pro Lys Gly Arg
            290                 295                 300

Arg Gly Gln Arg Arg Ser Asn Gly Phe Lys Lys Thr Asp Asn Asp Cys
305                 310                 315                 320

Leu Ser Ser Met Leu Ser Leu Val Asn Thr Gly Pro Gly Ser Phe Met
                325                 330                 335

Glu Ser Glu Glu Asp Arg Pro Ser Asp Ser Gln Ile Ser Leu Gly Arg
                340                 345                 350

Gln Arg Ser Ile Met Ala Thr Arg Pro Arg Asn Phe Arg Ser Leu Lys
            355                 360                 365

Lys Leu Leu Gln Arg Ile Ile
            370                 375

<210> SEQ ID NO 13
<211> LENGTH: 8760
<212> TYPE: DNA
<213> ORGANISM: Arabidopsis thaliana
<220> FEATURE:
<223> OTHER INFORMATION: DMT3 (1DMT3) sequence from BAC T22K18
```

<400> SEQUENCE: 13

```
aatcaagtac taatgcagat ttaagggggg tgtattgacg gcgttaaaac ggtttctcaa        60
cggaatcgta cgtagtcaca cgtgatttta ttgtttaccc cggattggtc atgcgttcct       120
tcttttccac ttgcgcggac cactcaatga cactctcttc ttttgtagca gtggcccgac       180
accagaatgc agcatttaat ctctcaaatt accattttgc tcctacctct tttaccccct       240
ttggtatttt gtgtctttt tctttctatt tcgtgtgaaa aggatctct tccttaatcg         300
tattatttct tccgatatct acttttattc tgttttctat ttttggtagg ttacatcttt       360
tttataaaga aaatatgagc taacacgaca ttagtgttgt taaccaaaga attggaaaaa       420
agttataaga gagataataa gattctctta cagagactca cttcagtgaa aaggaagaa        480
gcaagtggtt cccttaaggg aaaaaaaagt cacgtacgtt catatacaac tttaatacgt       540
actgtgtaac tcaatagatc gtgcagtaat attcagtcgt attagtaaga aggaattat         600
ttgctaagta aactcaagcc tccttttct cttttttc ttttagtaa aaattaggct            660
agtgttttt ttgactcagc aacactctgc ttaaatttag gagtaatttg acctattcct         720
acgagtttct aagtgaattc tgttggggtc aaagaagcaa ctagttgaat tagtggaaaa       780
tcgtttcctt tctttacgca tagttcacgt tggacactca gtctcaatgc tttcacgttt       840
cacgtagcaa caacatatat tcatcagttt gtgatcgtgc catcgtggat aagttgcaat       900
tcagtgaaac tctgcaccac tttgtgcaat tatttggccg tctaatctat ttgtgagaat       960
tttacaatct aattgttcta ttatttcatt tacttgtcat caatttatta tatttgtagc      1020
caatgaacgt tgtaattaaa gaaccaaaat aaattaatat cttgaaattt gtaacagtca      1080
ctagaagctg atttcttatt aattgtatca ctaaagtatt attaaaaacg gttacaaatt      1140
atgataatta tatatttaat aaatttcgtg tgtcacattt cttttaaact acaattatga      1200
atatctaaaa ctcattcatg catatcttaa aatttgaatt caaaactttc ttatcttatc      1260
tttaggttct taattaacag tcactaaaaa tagtcaaagt tttgaagttt atgaaaaaag      1320
ataagagtat aattaatgga tacgcctcgt aacaaattct tgtaaagtat agataatata      1380
catttgttaa atatgacacg tgtttatttt tttttaaat atgatcaaaa tatattttaa       1440
ctacctagat ggtatgtatg tctccaattt tgaataacaa gtcaattgtt attagaaatg      1500
tcataatata aagaagggaa ttaaatttgc aaagaaaaag tgaaaacaa aggatttgta       1560
ttttggagaa aattaaggac tggatttgca aaaacgaaaa agtaacttca tgtatattgt      1620
cttccttata gtctctataa actattatct caaatttgt ctggactctg aaactcacaa       1680
gacttgactc tggcttactt ggcttcatct ttttctctct ggtaatctct cctgcaactt      1740
caagctttca ttttcaaata aatgtaatca aatctgttat tttcactcaa gaactaattg      1800
agttctctat cccttttcaat tgaaattgac attaaaatga aaagatttg aggaggtttc      1860
acctaccaca accgaatcac ttctttctcc aaatattgtt tctttcagtg gccaagaatc      1920
acaatcaatt tttgtatctt ccacaggtaa attaattgtg attgaacaga gaagaggaca      1980
agtgatcttg gttcaaaaga aatggaagtg gaaggtgaag tgagagagaa agaagctagg      2040
gttaaaggga gacaaccaga gacagaagtt ctacatggtc tgccacaaga acagtcaata      2100
tttaataaca tgcaacacaa ccatcagcct gactcagaca ggttttgtga ctcaaccgaa      2160
tttactctgt tcttctcccg gaatttccat attttctggt gattctgttt tgttaaattc      2220
tgcaaaagga agaaaataaa tcaaacattt ttcacttctt caaaacatga gtaaatgcaa      2280
```

```
aaactgagat atgtaaacac acagcaattt tttgatgaac tggttttggc tgtgtgatct   2340
ttgtgtctat gcaattacgt tttagttatt ttctacttta taaggagaga tgttaactga   2400
aactgttatt gatcatacag gaggaggctt agtcttgaaa acttacctgg actatacaac   2460
atgtcttgta cacaactctt ggctctggcc aatgccacag tcgccacagg ttcatcaatt   2520
ggtgcatcat catcatcgtt aagctctcag catccaacgg attcttggat taatagctgg   2580
aagatggact ctaatccgtg gactttgagt aaaatgcaaa acaacaatg tgagtaaaat    2640
ttgttcctga atttgtagga tcttttaaga gaaagtaagc gtttatgtgt agattaagtc   2700
agactgaaat cgattatctc ataataagtt ctcagtgatc tctcaaatca tgaattttat   2760
gtttacctga tatcaacttc ttgtcttggt gaaccacaga tgatgtgtca actccgcaga   2820
agtttctttg tgaccttaat cttacacctg aagagttggt gagcaccagt acgcaacgaa   2880
cagaacctga gtctcctcaa ataactttaa agacaccagg aaaaagtctg tctgaaactg   2940
atcatgagcc tcacgaccgt atcaagaagt ctgttcttgg aactggatct cctgcagcag   3000
taaagaaaag aaagatagca agaaatgatg agaaatctca gctggaaaca ccaacactaa   3060
agagaaaaaa gatcaggcca aaggttgtcc gtgaaggcaa acaaaaaaaa gcatcatcta   3120
aagcagggat taaaaaatcc tctattgctg ctactgctac taaaacttct gaagagagca   3180
attatgttcg gccaaaaaga ttaacgagaa gatctatacg attcgacttt gaccttcaag   3240
aagaagatga ggaattttgt ggaatcgatt tcacatcagc aggtcacgta gagggttctt   3300
caggtgaaga aaatctaacc gatacaacac tgggaatgtt tggtcacgtc ccaaagggaa   3360
gaagagggca agaagatcc aatggcttta aaaaaaccga caatgattgc ctcagttcta   3420
tgttgtctct tgtcaatacc ggaccaggaa gtttcatgga atcagaagaa gatcgtccga   3480
gtgattcaca aatttctctg ggaagacaga gatccattat ggcaaccaga ccgcgtaact   3540
tccgatcgtt aaagaaactt ttacaaagga ttataccaag caaacgtgat agaaaaggat   3600
gtaagcttcc tcgtggactt ccgaagctta ccgtcgcatc caagttgcaa ctaaaagtgt   3660
ttagaaagaa gcggagtcaa agaaaccgtg tagcaagcca gttcaatgca aggatattgg   3720
acttgcagtg gcgacgccaa aatccaacag gtgataaaca cacaagcaac tttcatctat   3780
aatatttttc ttagatttct atcttttgaa ttaatactag ttttacaaaa tgcaggtaca   3840
tcgctagctg atatatggga aagaagtttg actattgatg ctatcactaa gttgtttgaa   3900
gaattagaca tcaacaaaga gggtctttgc cttccacata atagagaaac tgcacttatt   3960
ctatacaaaa agtcgtatga agagcaaaag gcaatagtga agtatagcaa gaagcagaaa   4020
ccgaaagtac aattggatcc tgaaacgagt cgagtgtgga aactcttaat gtcaagtatc   4080
gactgtgacg gtgttgatgg atcagatgag gaaaaacgta aatggtggga agaggagagg   4140
aacatgttcc atggacgtgc aaactcgttc attgcgcgaa tgcgtgttgt ccaaggtatt   4200
atttattgct ttagttatga cattgttgtg tggctttata ccttagatct ttctttcttt   4260
cttttttgta tccaaagcaa catggtctta aatcaagctt atcactgcag gcaatagaac   4320
tttctcacct tggaagggt cagtagtgga ttcagtagtg ggagttttcc taacccagaa    4380
tgtcgcagac cattcatcaa ggtatatgca ttcaagagat ttctaataag tagaagatat   4440
atgcaacaga gtggtttaga aattataact tgttcacttt tgcagttctg catatatgga   4500
tttagctgct gagtttcctg tcgagtggaa cttcaacaag ggatcatgtc atgaagagtg   4560
gggaagttca gtaactcaag aaacaatact gaatttggat ccaagaactg gagtttcaac   4620
tccaagaatt cgcaatccaa ctcgcgtcat catagaggag attgatgatg atgagaacga   4680
```

-continued

```
cattgatgct gtttgtagtc aggaatcctc taaaacaagt gacagttcca taacttctgc    4740
agaccaatca aaacgatgc tgctggatcc atttaacaca gttttgatga acgagcaagt    4800
tgattcccaa atggtaaaag gcaaaggtca tataccatac acggatgatc ttaatgactt    4860
gtcccagggg atttcgatgg tctcatctgc ttctactcat tgtgagttga acctaaatga    4920
agtaccacct gaagtagagt tgtgcagcca tcaacaagac ccggagagta ccattcagac    4980
acaagaccag caagagagca caagaacgga ggatgtgaag aagaatagga aaaaccaac    5040
tacctccaaa ccaaagaaaa agtcaaagga atcagcaaag agcacgcaaa agaaaagcgt    5100
tgactgggat agtttgagaa aggaagcaga aagtggtggc cgaaagagag agagaacaga    5160
aagaacaatg gacacagttg attgggatgc acttcgatgt acagacgtac acaagatcgc    5220
taatataatc atcaaacgag ggatgaacaa catgcttgcc gaaagaatca aggtttgact    5280
aatcacagtg ctatatatac ctcatttata cattctaaca aggtgaattt ttttgactct    5340
ggaaattgga caggccttct taaacagact agttaaaaaa catggaagca ttgacttaga    5400
gtggctaaga gatgttcctc ctgataaagc caagtaagaa aattatttac aaatcttgag    5460
attatatgta gcctctggtt aaagaatata tctcagtaaa tggaatcgat agtaattgag    5520
atacatataa atgagagata cttgatagtg actactaatg gttgcaggga gtatctacta    5580
agcataaacg gattaggatt gaagagtgtg gagtgtgtta gacttttgtc actacatcag    5640
attgcattcc ctgtaagtca atgaaggata ctgaatactc agaccctaat gaatgtggaa    5700
cagatacatt aatagttacg tatttttaca aatgcaggtt gacacgaatg tcggacgcat    5760
agctgtaaga ctaggatggg ttcccttaca gccattgccc gacgagctgc aaatgcatct    5820
tttagagttg taagaaaaaa aaattaaaga tcattcttca atcatgaaag gaacatgag    5880
aaatttacag tagttccctt taattctatt caggtaccca gttctagagt cagttcaaaa    5940
gtacctctgg ccacgcctct gcaagcttga ccaaaaaacc ttgtaagtaa attacattag    6000
catcaaccat tactctagac ccttaaactt ctctaactaa ctctaactgt atcatacaat    6060
tctaggtacg agctgcatta ccacatgata acatttggaa aggtacctca aacaaatttc    6120
aagtgtttgt ggaatgaaaa catcttaaag tggcttttcc tattttgcag gtcttttgca    6180
caaaagtaaa acccaattgc aatgcatgtc caatgaaggc ggagtgtcga cattactcta    6240
gtgcacgtgc aaggttaaac cccacaaaat tctttgttat tgccattaac atgaaaaaaa    6300
aaacactagc ttaaagagaa agagatctgc tcaaaatagt cattttaatg gttgtatgtt    6360
ctaaatgctt gtgttatatc gcagcgcacg gcttgcttta ccagaaccag aggagagtga    6420
cagaacaagt gtaatgatcc atgagaggag atctaaacgc aagcctgttg tggttaattt    6480
tcgaccatcc ttatttcttt atcaagaaaa agagcaagaa gcacaaagat cccaaaactg    6540
tgaaccaatc attgaggaac cagcatcacc agaaccagag tatatagaac atgatattga    6600
agactatcct cgggacaaaa acaacgttgg aacatcagag gatccttggg aaaataagga    6660
cgtaattcct accatcatcc tcaacaagga agctggtaca tcacatgatt tggtggtcaa    6720
caaggaagct ggtacgtcac atgatttggt ggtactaagc acatatgcag cagcaatacc    6780
tagacgtaaa ctcaagatca aggaaaagct acgcacagag cacccgtgt gagttgccac    6840
tttcaatttt ttcttctatt ataccctaaa ccgtaaaatt tgagactttc ctcagcattt    6900
atctcatact aattctcttt tacagatttg agctccctga tcaccattcc attctagaag    6960
gggttagtaa ctccttgcaaa atgatttagc aagaattttt ctacttattc ccgccttaaa    7020
```

-continued

```
aactgtttga ttatcttttt ttacagtttg agaggcgaga agctgaggat atagtccctt    7080
acttgttagc catttggacg ccaggtaaga agaaataggc acacaataaa atctgattat    7140
gattttcctt ttcaagaata ccgctatatt tttacgagtt ttcatcctta gatgtatatg    7200
actaatgtct aacaagtgat tgtaatattt ttccatacca ggtgaaaccg tgaattccat    7260
tcaaccgcca aaacaaagat gtgctttatt tgaaagcaat aatacattat gcaacgaaaa    7320
caaatgtttt caatgcaaca agacacggga agaggaatca cagactgtac gaggaactat    7380
attggtaaga ttctggtgga caattttcaa gagaatatct ctaagtagaa atataaggaa    7440
ggtataaaaa tgactaattt gtttgttaac agataccttg cagaacagca atgagaggtg    7500
gattcccttt gaatggcaca tacttccaaa ctaatgaggt aattttccca aaaatgaatt    7560
taacttaaac aaatgatcaa aagcaacatt ctcgtcaaag ctcgatttgg actatacttg    7620
tgcaggtttt tgctgaccat gactctagca taaaccctat cgacgtccca acagaactga    7680
tatgggatct aaaagaaga gtcgcatact taggatcctc tgtatcctcg atttgtaaag    7740
gtaaattttc aaaacaaaac tgtcgattta tgcatgtgtt tggatatata aatccaaggt    7800
cttgtctcaa tatgttttc tcattttttt aggtttatca gtggaagcca taaaatacaa    7860
tttccaggaa ggtatgctaa tatgtcttac actgaaaaca cctttagtat caaacattga    7920
attcatgaaa agaacaaaca atagtatcaa aatcagtcac gatgtttttg ctttggcgat    7980
gtaagatgtt gataggaaag tatagaagat atagcttaag ttggttaata ctgtttttat    8040
agagctttga ggtgggtttt gactagcatt gtaatatata tgcaggatat gtctgtgtaa    8100
ggggattcga cagggagaat cgtaagccaa agagtctagt gaaaagactg cattgttctc    8160
acgtagcaat cagaactaaa gagaagacag aggaatgaaa ccttccagat tgcattaaca    8220
tgttagacat atttgattca ttggtttagg gtttacatca ccaaggtcat agaggatctt    8280
agcttttcat taacttttaa attcatgcaa ctctttttag gtgtttcttt ttgttccttg    8340
ccatagtttt gggcaatgga tggatgttct ttgcaaactc aggttttttg tagtcattaa    8400
cagaaatttg cagcactaat tcatctttcc tattatctat caaagctctc agtgtttctc    8460
cataacttga tgagatttag tcactctcaa gctaattcag tctggtccta atttcaatca    8520
gatttggtaa aggaacaact gcaattgcta agtacaaatc gatccagatt caaacaagt    8580 tccaggttta atccaaatca tcacattcaa tcaaagacca aactagaatt caaaacatat    8640
aatctctgat tcagattcaa gaaagacaaa gcatgagaca tcattctgca agttaaccaa    8700
ttccggttat tctcgaatcc tactgaatta agcatcaatc atctaaagga acttcataag    8760
```

<210> SEQ ID NO 14
<211> LENGTH: 1114
<212> TYPE: PRT
<213> ORGANISM: Arabidopsis thaliana
<220> FEATURE:
<223> OTHER INFORMATION: DMT4 (1DMT4)

<400> SEQUENCE: 14

```
Met Glu Phe Ser Ile Asp Arg Asp Lys Asn Leu Leu Met Val Val Pro
  1               5                  10                  15

Glu Thr Arg Ile Lys Thr Lys Gln Phe Glu Lys Val Tyr Val Arg Arg
             20                  25                  30

Lys Ser Ile Lys Leu Pro Gln Asn Ser Met Val His Asn Thr Leu Ile
         35                  40                  45

Lys Met Ala Arg Gln Arg Ile Gln Lys Ser Met Lys Glu Ser Val Met
     50                  55                  60
```

-continued

```
Asn Gln His Ile Phe Lys Asn Phe Asp Ser Tyr Leu Ser Val Ile Tyr
 65                  70                  75                  80

His Pro Cys Cys Phe Val Ile Asn Asn Ser Gln Thr Thr His Lys Lys
             85                  90                  95

Lys Glu Lys Lys Asn Ser Lys Glu Lys His Gly Ile Lys His Ser Glu
        100                 105                 110

Ser Glu His Leu Gln Asp Asp Ile Ser Gln Arg Val Thr Gly Lys Gly
        115                 120                 125

Arg Arg Arg Asn Ser Lys Gly Thr Pro Lys Lys Leu Arg Phe Asn Arg
130                 135                 140

Pro Arg Ile Leu Glu Asp Gly Lys Lys Pro Arg Asn Pro Ala Thr Thr
145                 150                 155                 160

Arg Leu Arg Thr Ile Ser Asn Lys Arg Lys Lys Asp Ile Asp Ser
                165                 170                 175

Glu Asp Glu Val Ile Pro Glu Leu Ala Thr Pro Thr Lys Glu Ser Phe
            180                 185                 190

Pro Lys Arg Arg Lys Asn Glu Lys Ile Lys Arg Ser Val Ala Arg Thr
        195                 200                 205

Leu Asn Phe Lys Gln Glu Ile Val Leu Ser Cys Leu Glu Phe Asp Lys
210                 215                 220

Ile Cys Gly Pro Ile Phe Pro Arg Gly Lys Lys Arg Thr Thr Thr Arg
225                 230                 235                 240

Arg Arg Tyr Asp Phe Leu Cys Phe Leu Leu Pro Met Pro Val Trp Lys
            245                 250                 255

Lys Gln Ser Arg Arg Ser Lys Arg Arg Lys Asn Met Val Arg Trp Ala
        260                 265                 270

Arg Ile Ala Ser Ser Lys Leu Leu Glu Glu Thr Leu Pro Leu Ile
        275                 280                 285

Val Ser His Pro Thr Ile Asn Gly Gln Ala Asp Ala Ser Leu His Ile
290                 295                 300

Asp Asp Thr Leu Val Arg His Val Val Ser Lys Gln Thr Lys Lys Ser
305                 310                 315                 320

Ala Asn Asn Val Ile Glu His Leu Asn Arg Gln Ile Thr Tyr Gln Lys
                325                 330                 335

Asp His Gly Leu Ser Ser Leu Ala Asp Val Pro Leu His Ile Glu Asp
            340                 345                 350

Thr Leu Ile Lys Ser Ala Ser Ser Val Leu Ser Glu Arg Pro Ile Lys
        355                 360                 365

Lys Thr Lys Asp Ile Ala Lys Leu Ile Lys Asp Met Gly Arg Leu Lys
        370                 375                 380

Ile Asn Lys Lys Val Thr Thr Met Ile Lys Ala Asp Lys Lys Leu Val
385                 390                 395                 400

Thr Ala Lys Val Asn Leu Asp Pro Glu Thr Ile Lys Glu Trp Asp Val
                405                 410                 415

Leu Met Val Asn Asp Ser Pro Ser Arg Ser Tyr Asp Asp Lys Glu Thr
            420                 425                 430

Glu Ala Lys Trp Lys Lys Glu Arg Glu Ile Phe Gln Thr Arg Ile Asp
        435                 440                 445

Leu Phe Ile Asn Arg Met His Arg Leu Gln Gly Asn Arg Lys Phe Lys
        450                 455                 460

Gln Trp Lys Gly Ser Val Val Asp Ser Val Val Gly Val Phe Leu Thr
465                 470                 475                 480
```

-continued

Gln Asn Thr Thr Asp Tyr Leu Ser Ser Asn Ala Phe Met Ser Val Ala
                485                 490                 495

Ala Lys Phe Pro Val Asp Ala Arg Glu Gly Leu Ser Tyr Tyr Ile Glu
            500                 505                 510

Glu Pro Gln Asp Ala Lys Ser Ser Glu Cys Ile Ile Leu Ser Asp Glu
            515                 520                 525

Ser Ile Ser Lys Val Glu Asp His Glu Asn Thr Ala Lys Arg Lys Asn
        530                 535                 540

Glu Lys Thr Gly Ile Ile Glu Asp Glu Ile Val Asp Trp Asn Asn Leu
545                 550                 555                 560

Arg Arg Met Tyr Thr Lys Glu Gly Ser Arg Pro Glu Met His Met Asp
                565                 570                 575

Ser Val Asn Trp Ser Asp Val Arg Leu Ser Gly Gln Asn Val Leu Glu
            580                 585                 590

Thr Thr Ile Lys Lys Arg Gly Gln Phe Arg Ile Leu Ser Glu Arg Ile
            595                 600                 605

Leu Lys Phe Leu Asn Asp Glu Val Asn Gln Asn Gly Asn Ile Asp Leu
        610                 615                 620

Glu Trp Leu Arg Asn Ala Pro Ser His Leu Val Lys Arg Tyr Leu Leu
625                 630                 635                 640

Glu Ile Glu Gly Ile Gly Leu Lys Ser Ala Glu Cys Val Arg Leu Leu
                645                 650                 655

Gly Leu Lys His His Ala Phe Pro Val Asp Thr Asn Val Gly Arg Ile
            660                 665                 670

Ala Val Arg Leu Gly Leu Val Pro Leu Glu Pro Leu Pro Asn Gly Val
        675                 680                 685

Gln Met His Gln Leu Phe Glu Tyr Pro Ser Met Asp Ser Ile Gln Lys
        690                 695                 700

Tyr Leu Trp Pro Arg Leu Cys Lys Leu Pro Gln Glu Thr Leu Tyr Glu
705                 710                 715                 720

Leu His Tyr Gln Met Ile Thr Phe Gly Lys Val Phe Cys Thr Lys Thr
                725                 730                 735

Ile Pro Asn Cys Asn Ala Cys Pro Met Lys Ser Glu Cys Lys Tyr Phe
            740                 745                 750

Ala Ser Ala Tyr Val Ser Ser Lys Val Leu Leu Glu Ser Pro Glu Glu
        755                 760                 765

Lys Met His Glu Pro Asn Thr Phe Met Asn Ala His Ser Gln Asp Val
    770                 775                 780

Ala Val Asp Met Thr Ser Asn Ile Asn Leu Val Glu Glu Cys Val Ser
785                 790                 795                 800

Ser Gly Cys Ser Asp Gln Ala Ile Cys Tyr Lys Pro Leu Val Glu Phe
                805                 810                 815

Pro Ser Ser Pro Arg Ala Glu Ile Pro Glu Ser Thr Asp Ile Glu Asp
            820                 825                 830

Val Pro Phe Met Asn Leu Tyr Gln Ser Tyr Ala Ser Val Pro Lys Ile
        835                 840                 845

Asp Phe Asp Leu Asp Ala Leu Lys Lys Ser Val Glu Asp Ala Leu Val
        850                 855                 860

Ile Ser Gly Arg Met Ser Ser Asp Glu Ile Ser Lys Ala Leu
865                 870                 875                 880

Val Ile Pro Thr Pro Glu Asn Ala Cys Ile Pro Ile Lys Pro Pro Arg
                885                 890                 895

Lys Met Lys Tyr Tyr Asn Arg Leu Arg Thr Glu His Val Val Tyr Val

-continued

```
                900             905             910
Leu Pro Asp Asn His Glu Leu Leu His Asp Phe Glu Arg Arg Lys Leu
            915                 920                 925
Asp Asp Pro Ser Pro Tyr Leu Leu Ala Ile Trp Gln Pro Gly Glu Thr
        930                 935                 940
Ser Ser Ser Phe Val Pro Pro Lys Lys Cys Ser Ser Asp Gly Ser
945                 950                 955                 960
Lys Leu Cys Lys Ile Lys Asn Cys Ser Tyr Cys Trp Thr Ile Arg Glu
                965                 970                 975
Gln Asn Ser Asn Ile Phe Arg Gly Thr Ile Leu Val Phe Ala Asp His
            980                 985                 990
Glu Thr Ser Leu Asn Pro Ile Val Phe Arg Arg Glu Leu Cys Lys Gly
        995                 1000                1005
Leu Glu Lys Arg Ala Leu Tyr Cys Gly Ser Thr Val Thr Ser Ile Phe
    1010                1015                1020
Lys Leu Leu Asp Thr Arg Arg Ile Glu Leu Cys Phe Trp Thr Gly Phe
1025                1030                1035                1040
Leu Cys Leu Arg Ala Phe Asp Arg Lys Gln Arg Asp Pro Lys Glu Leu
                1045                1050                1055
Val Arg Arg Leu His Thr Pro Pro Asp Glu Arg Gly Pro Asn Gly Phe
            1060                1065                1070
His Ile Val Val Val Asp Glu Lys Glu Glu Ser Pro Arg Val Gly Leu
        1075                1080                1085
Met Val Met Pro Gly Phe Trp Ile Gly Gly Ser Val Ile Gln Asn Arg
    1090                1095                1100
Val Tyr Val Ser Gly Val Lys Val Leu Glu
1105                1110

<210> SEQ ID NO 15
<211> LENGTH: 372
<212> TYPE: PRT
<213> ORGANISM: Arabidopsis thaliana
<220> FEATURE:
<223> OTHER INFORMATION: DMT4 (1DMT4) novel amino terminus

<400> SEQUENCE: 15

Met Glu Phe Ser Ile Asp Arg Asp Lys Asn Leu Leu Met Val Val Pro
1               5                   10                  15
Glu Thr Arg Ile Lys Thr Lys Gln Phe Glu Lys Val Tyr Val Arg Arg
            20                  25                  30
Lys Ser Ile Lys Leu Pro Gln Asn Ser Met Val His Asn Thr Leu Ile
        35                  40                  45
Lys Met Ala Arg Gln Arg Ile Gln Lys Ser Met Lys Glu Ser Val Met
    50                  55                  60
Asn Gln His Ile Phe Lys Asn Phe Asp Ser Tyr Leu Ser Val Ile Tyr
65                  70                  75                  80
His Pro Cys Cys Phe Val Ile Asn Asn Ser Gln Thr Thr His Lys Lys
                85                  90                  95
Lys Glu Lys Lys Asn Ser Lys Glu Lys His Gly Ile Lys His Ser Glu
            100                 105                 110
Ser Glu His Leu Gln Asp Asp Ile Ser Gln Arg Val Thr Gly Lys Gly
        115                 120                 125
Arg Arg Arg Asn Ser Lys Gly Thr Pro Lys Lys Leu Arg Phe Asn Arg
    130                 135                 140
Pro Arg Ile Leu Glu Asp Gly Lys Lys Pro Arg Asn Pro Ala Thr Thr
```

-continued

```
                145                 150                 155                 160
        Arg Leu Arg Thr Ile Ser Asn Lys Arg Lys Lys Asp Ile Asp Ser
                        165                 170                 175

Glu Asp Glu Val Ile Pro Glu Leu Ala Thr Pro Thr Lys Glu Ser Phe
                    180                 185                 190

Pro Lys Arg Arg Lys Asn Glu Lys Ile Lys Arg Ser Val Ala Arg Thr
                    195                 200                 205

Leu Asn Phe Lys Gln Glu Ile Val Leu Ser Cys Leu Glu Phe Asp Lys
                210                 215                 220

Ile Cys Gly Pro Ile Phe Pro Arg Gly Lys Lys Arg Thr Thr Thr Arg
        225                 230                 235                 240

Arg Arg Tyr Asp Phe Leu Cys Phe Leu Leu Pro Met Pro Val Trp Lys
                        245                 250                 255

Lys Gln Ser Arg Arg Ser Lys Arg Arg Lys Asn Met Val Arg Trp Ala
                    260                 265                 270

Arg Ile Ala Ser Ser Ser Lys Leu Leu Glu Glu Thr Leu Pro Leu Ile
                    275                 280                 285

Val Ser His Pro Thr Ile Asn Gly Gln Ala Asp Ala Ser Leu His Ile
                290                 295                 300

Asp Asp Thr Leu Val Arg His Val Val Ser Lys Gln Thr Lys Lys Ser
        305                 310                 315                 320

Ala Asn Asn Val Ile Glu His Leu Asn Arg Gln Ile Thr Tyr Gln Lys
                        325                 330                 335

Asp His Gly Leu Ser Ser Leu Ala Asp Val Pro Leu His Ile Glu Asp
                    340                 345                 350

Thr Leu Ile Lys Ser Ala Ser Ser Val Leu Ser Glu Arg Pro Ile Lys
                    355                 360                 365

Lys Thr Lys Asp
                370

<210> SEQ ID NO 16
<211> LENGTH: 8580
<212> TYPE: DNA
<213> ORGANISM: Arabidopsis thaliana

<400> SEQUENCE: 16
gctatggatg tcaacagaga gaattacgaa ttgggtttac cgatcattga gaaagccggc      60
gttgctcaca agatcgactt cagggaaggc cctgctcttc ccgttcttga tgaaatcgtt     120
gctgacgtaa gcattcttct ttctgacgta attaacaaaa aagatgatga agataatgaa     180
ataattaaaa actcatggcc taattaggtt gatttaatat cttgatgaga atttctgtat     240
acgcaaattt gtttcctttt tcatagaaga aagtgtggta actgattatt gtgtgtggtt     300
gggtgcagga gaagaaccat ggaacatatg actttatatt cgttgatgct gacaaagaca     360
actacatcaa ctaccacaag cgtttgatcg atcttgtgaa aattggagga gtgattggct     420
acgacaacac tctgtggaat ggttctgtcg tggctcctcc tgatgcacca atgaggaagt     480
acgttcgtta ctacagagac tttgttcttg agcttaacaa ggctcttgct gctgaccctc     540
ggatcgagat ctgtatgctc cctgttggtg atggaatcac tatctgccgt cggatcagtt     600
gatttgactc ctcccctactc tgagtttgtc cacagtggat tactttccat cttcttatac     660
ctttcaatcg cattttcacc aaccactaaa atggaccttt ttatgtattt gtgttaagta     720
atatctccat tgtccttgtt ttgctttctt ctgaacaaag aaataaatg taccttactt     780 ttcttcttgg tctcgttctt tgttttttct ccatgataca acatctaaag aaattatttg     840
```

-continued

```
tgtcacagca acgtaagtcg ataaaattag ttgaacatat tgagaaaaag ttatcataga      900
ccttcaattg ttgaaagtcg atgttggtat ttgtcaattg atattagatt accaaataaa      960
tattagacag taagaaacga acaaagtagg aagatgtagg tcaccggtct ttgaaaattt     1020
atcagataga attcataata cacagttagg tagtttcagt tgagagttaa aagggaaaaa     1080
tatgtaattg tgtgtgataa atacgtcaaa aattagttga tgagcaaaat cgtaaacaaa     1140
aatactttt  tgcattagtt ttgttggatt ccctataaat acgggttccc atatctaact     1200
cgtagttagc ataattataa gcaacaaata aacacaaaat actgaattta gaaattttcc     1260
agaaaattaa ttagagattt tacattattt ttacaaactt tagtgaatta tttcttaaac     1320
gtatgttagt tatttattaa ctgaagtttc acatatttga tagaataaca tttaaataaa     1380
aaaatttgaa gtaaggttag aatgttctta taatacttta taactttttt aaaaggtaca     1440
agccaaaatt atcgcaaatg taaataataa atcattgtaa aaatcttaaa ctaattaaaa     1500
gatctaacgc aatctaaaca aagatttggt atcatcgccc atttatgttt tgatataatc     1560
aaaactggtt aataattaaa ttaaattatc aatttcttaa ttagttagaa ttcttgttaa     1620
tgtaatcaac tcaccattat tttaattatt taaaatatgg gttaatatct cttaatcata     1680
tctaagatga tattttcttc catttatgaa aagaaaaata tgttaattaa gcattaaaaa     1740
gaaggaaaaa ataatttaaa taatattaaa tatatataca tcgttttttag agttcgagtt    1800
cttccgtatt tacagtttct ctttttttcca aagcagggtt tggattggta gttttttctgg   1860
attaattttg tctcaaattc tttcttcttt ttatttttt  ttgtgaaatt ctttgtttta    1920
attggtgtga catcgtttcc aaaatatttt caaatttgat tgcttttgaa gttttttttt     1980
tttttctatg ttttggaatt cattatacta gcgttgttgt ttttctttct gcaagagtaa     2040
tggagttttc aatagatcga gacaaaaatc ttctcatggt tgttccagag acacgtatca     2100
aaacaaaaca atttgaaaaa gtttatgtga gaagaaaatc tattaagctt ccacaaaatt     2160
cggtaattt  tccacatgaa atcaaagatc gtggtgaaga agagagtaag gagaaggaat     2220
ttttccatca aggtaaacaa aatctctaat accttaatta cttccgttta gtaattctcc     2280
ttttacttgt ttttttttta atgagagtat gtgacaattt cataaagaaa ttagttgttt     2340
gacatacgag atggtttttt gactaattat atttttttgtt ttgaaagatt tccaagctaa    2400
ttttaatgag catattttg  attttattga ttgaggaaat tttcagaatt tcgacattta     2460
agttttttt  ttgtttttaaa tacttttg   attcgatgat aagagattgg gaaagcagac    2520
taatgatgtt ttgttgtcac gttcattgat tagagatctc ttatattcat atttgtctac     2580
aatatatcat gcatgtgttg atttgttttcg ttaattcaat ttttttttt  tcatgttgac    2640
agatggttca caacacactt atcaaaatgg cgagacaaag aattcaaaag agcatgaaag     2700
aaagtgtgat gaatcagcac atcttcaagg taaataattt taaattcatt cttaaaaaag    2760
ttagcttatt ggtaagttca ttacaattta tatttaacca tcgtcacttt ttatttaacg     2820
agtttgataa gcatttttcaa aacctgtcct tcatctgccg atgcagatgt ggttatgttc    2880
atctttgatt ttattgattg aggattttt  cagaatttcg attcatactt gtctgtaata     2940
tatcatccat gttgtttttgt aatcagttaa ttcacttatt ttattttttaa cttttattgt   3000
aacagataat tcacaaacca cccataaaaa aaggagaag aagaattcaa aagaaaagca     3060
tggaataaag cattctgaat cagaacatct tcaaggtaaa acttttgaa ttcattcatt      3120
aaaaaaacag tttatttgta agttcattac agtttatata tatttaaatt gtttatgata    3180
```

```
atgtattttt gcacaatcga ctaatcatta cccactcatt catttatatt ttattttatg    3240
gtgaaagatg atatttcgca acgtgttacc ggaaaaggaa ggagaaggaa ttcaaaaggg    3300
acaccaaaaa aactgaggtt aataggcct cggatcttgg aagacggaaa gaaaccaaga    3360
aatcccgcca ccactcgact gagaactata tccaacaaga ggaggaaaaa ggacatagac    3420
agtgaagatg aagttatacc agagcttgca actccaacaa aggaaagctt tccaaagaga    3480
agaaagaacg agaagattaa gagatccgtg gctcggactt taaattttaa gcaagaaatt    3540
gttctgagtt gtcttgagtt cgacaagatt tgtggaccaa tttttccaag agggaaaaag    3600
aggaccacca cacgacgcag atatgatttc ctttgttttt tacttccgat gcctgtttgg    3660
aaaaaacaat caagaaggtc taagcgtagg aaaaatatgg tcagatgggc tagaattgct    3720
tcttcttcaa aactgctaga agaaactttg cctttaatag taagtcatcc gactattaat    3780
ggacaagcag atgcttcttt acacattgat ggtaatcgag ttttttttt gttaatttat    3840 ctgttacatc aaaattgttt atgcttatat ctaaagtatc attgtgtatt attttttgca    3900
gacacactcg tgagacatgt agtctcaaag caaaccaaga aagtgctaa caatgtcatt    3960 gagcatttaa atcgacaaat aacttatcag aaagatcacg tctctcatc tctggcagat    4020 gttcctttgc acattgaagg taatctagtc ttattttgt tcttttttaa tatattgatt    4080 aaaagattg tgatatattt atttaatata ttttgttat attatatcta tattttattg    4140 tttgtactt tttttttgtag atacactaat aaaatcggct agttctgtac tttcagaacg    4200
acccatcaag aaaactaagg atattgctaa gttaatcaaa gatatgggaa gattaaagat    4260
caataaaaag gtaacaacga tgatcaaagc tgacaagaaa ctcgttacgg caaaggttaa    4320
tcttgatcca gagaccatta aagagtggga tgtcttaatg gtgaatgatt caccaagccg    4380
atcatatgac gataaggaga cggaggccaa atggaaaaaa gaaagagaga ttttcaaac    4440 ccggatagat cttttcatta accggatgca tcgcttacaa ggtacattat tgttattatc    4500
attattgtta ttatgatcta tttatacttg tattctaaat tagcttacat atatatataa    4560
ggaatccaag tataagtgag tatgctaagt atatgatcat tttttgaaat tatgtttcct    4620
tccatgatgt ttaaatgatt gtcttgcagg caatagaaag tttaaacagt ggaaaggctc    4680
agttgttgac tcagtggttg gagtttttttt gacacaaaat actaccgact atctttcaag    4740
gtaaaatctt tgtttaaatt gttaagaaat ttgaaaaact aattcatata atagatgatc    4800
actttgattg tgagtttcta cagcaacgcg tttatgagcg tggctgcaaa atttcctgtt    4860
gatgcaagag aaggtctatc atactatatt gaggaacctc aagatgctaa aagttctgaa    4920
tgtatcattt tatctgatga gtcaatatca aaggtggaag atcatgagaa tactgcaaaa    4980
aggaaaaacg agaaaccgg tattatagaa gatgagatag ttgactggaa caatcttaga    5040
aggatgtaca cgaaagaagg atctcgtccc gaaatgcata tggactctgt taattggagt    5100
gacgtgagat tatctggcca aaatgttttg gaaaccacca ttaaaaacg tggacaattc    5160 aggattcttt cagaaagaat attggtaaga aaacaaaac ttctaatgaa ctttgtgaat    5220
aatttattca aatgatttaa gactaacact tttttttttt tccttgtttt ctcaagaaat    5280
ttcttaacga tgaagttaac caaaatggaa atattgatct ggaatggctt cgaaatgctc    5340
catcacattt agtgaagtat gtttatgttg gttttatgt tctcatagat ctcattatta    5400
gtaagcgatc ataaactctt tctattattt tatcaggaga tatctgttgg aaatcgaagg    5460 gataggctg aaagtgctg agtgcgtacg actgttagga cttaaacatc atgcgtttcc    5520
ggtatgaaaa tattattatg atttttcatt taacatatat tattaatttt tactgataaa    5580
```

```
acccatgtgt taatgtgtag gttgacacaa atgttggtcg tatagcagtt cgactaggtc    5640
tggttcctct tgaaccttta ccaaatggag ttcaaatgca tcaactattc gagttatgtt    5700
ttctcattaa tttgattaag aaaatacatt acaagttact aacaactatc tcctatcgat    5760
aaacatgaac tcgtttcagg taccccttcaa tggattcgat tcaaaagtac ctttggccac   5820
gattgtgtaa acttccccaa gaactttgt aagttcaaat gttttcctc aatttaagaa      5880
gccaactatt tttacgccat ttgaacacat attacctaat tttatttcta aatatttta    5940
cagatatgaa ctacattatc aaatgataac atttggaaag gtgtgcgtta ctttttttctt  6000
ttttatatta atgaataaaa taatattgtt ggtttaatca aattttgtca actttaggtt   6060
ttctgcacaa aaactattcc taattgtaat gcatgtccaa tgaagtcaga atgcaaatat   6120
tttgcaagtg catatgtcag gtacaatctt ttttctcttt cctactttga tacttagata   6180
taacttaatt tgttaattcc ataaatatta agaaaaatc ttagaataat cataaaaaat    6240
aattgctaaa cgtctcagct attttatata ataaattttc taaatattga gagtgaattt   6300
gagtttaat aattacatta tatatataaa tataataatgt tagaattgac aaattgtgtt   6360
tttttttaat agttctaaag ttcttctcga gagtccagaa gaaaagatgc atgagcctaa   6420
tacttttatg aatgcacatt ctcaagacgt tgctgtagat atgacatcaa atataaattt   6480
ggtagaagaa tgtgtttctt ctggatgtag cgatcaagct atatgttata agccactagt   6540
tgagtttcct tcgtccccaa gagcggaaat tcccgagtca acagacattg aagatgttcc   6600
attcatgaat ctttatcagt catatgctag tgttcctaaa attgattttg acttggatgc   6660
attgaagaaa agtgtagaag atgcacttgt aataagtggc aggatgagca gttctgatga   6720
agaaatatca aaagcattag tgattcccac tcctgaaaat gcatgcattc ctatcaaacc   6780
acctcggaaa atgaagtatt ataatcgact aagaactgaa catgtggtgt aagtatcttt   6840
atgtaaatac tgattatacc atataattta tatgcatttt ttgggaatat ataatctaat   6900
acttgttttt tttgcagtta tgtgcttcct gataatcatg agctgctaca cgatgtaagt   6960
atacacatac tttaagctac aaaaaaatgc aactcttttg tataattaat tagaaaatgc   7020
ttttggtttt ttacatatat tatatagttt gagagaagaa aacttgatga tccaagtcct   7080
taccttcttg cgatttggca accaggtata atacaagcat aatttatcat tgttcacata   7140
actataaact aaattttttca ttcgaataat ttttaggtga aacatcatcc tcgttcgttc   7200
caccaaagaa aaagtgtagt tctgatggat caaagctttg caagataaag aattgttcat   7260
attgttggac tatacgagaa caaaactcca acatttttcg cggaacaatt ttggtaaaca   7320
aaatttacaa tttgatattt taacattggt gacttgaaac tcacataaat tcaattgatc   7380
agattccatg tagaacagca atgcgagggg cctttccact taatggaaca tacttccaaa   7440
ccaatgaggc aagcattttt tcttataatt ttttgtctga gtttttactt aatggtttta   7500
aagagaacac aatggtttat ttttccaggt ttttgctgat catgagacaa gcttaaaccc   7560
cattgtcttt cgtagggagt tgtgtaaggg actagaaaaa cgtgcactat attgtggttc   7620
aacagtgaca tctatttta aactttgaga cacaagacgg attgaacttt gcttttggac    7680
aggtaacaaa cataaatata tattaaattt tttgttgaat tatgaagtta aaataactgt   7740
ggaatgttgt gtggtgctgt gcagggtttt tatgtttgag agcatttgat cgaaagcaac   7800
gagatccaaa agagcttgtc cgacgtctac acactccacc tgatgagaga gggccaaagt   7860
ttatgagtga tgatgatata tagtttcatt ttattctttt tggtctagtt agcaaattat   7920
```

-continued

```
ttaaacgaac gaatcttttc ttataataac aagcgattca acgattgagt aaatgcacgt    7980
acgtattgtt tcttgattta aatgcatgta cattataatt atttcacaag tggttttcat    8040
atagtagttg tggatgaaaa agaagagagc ccaagagttg gtcttatggt tatgcctggg    8100
ttttggattg gtggcagtgt cattcaaaac cgagtttatg tttctggtgt gaaggtcctt    8160
gagtgaagga tttcaggaac tgtcttaatg cttcttccca ctttgttgtg caacttttat    8220
tttctctttg ttataagcaa gcctatatgt atcaatgata cagtatcatc tattgttcaa    8280
aaaaattgga attaatatct tcttcgtctc aacatctttg ggtcgatcgt tattcgatga    8340
cagtagcaac tagcgagtct cttgtgatat atcctagcca agcgacctca aaactttttt    8400
tacttcgatt gttgtcagta tttctgtttc agacgttttt agcaaaaaag ttctcatggt    8460
gataaaatta ggcttaaaac agtatgactc tgtctttaag actcagtttc agatagtaat    8520
aataaaatta cataaacaaa gagtggtcat agacgtgtat ctgtaagtgt tgtcagagat    8580
```

<210> SEQ ID NO 17
<211> LENGTH: 1952
<212> TYPE: PRT
<213> ORGANISM: Oryza sativa
<220> FEATURE:
<223> OTHER INFORMATION: rice DMT1, DMTRICE (1DMTRICE)

<400> SEQUENCE: 17

```
Met Gln Asp Phe Gly Gln Trp Leu Pro Gln Ser Gln Thr Thr Ala Asp
  1               5                  10                  15

Leu Tyr Phe Ser Ser Ile Pro Ile Pro Ser Gln Phe Thr Ser Ile
             20                  25                  30

Glu Thr Gln Thr Arg Thr Ser Ala Val Val Ser Ser Glu Lys Glu Ser
         35                  40                  45

Ala Asn Ser Phe Val Pro His Asn Gly Thr Gly Leu Val Glu Arg Ile
     50                  55                  60

Ser Asn Asp Ala Gly Leu Thr Glu Val Val Gly Ser Ser Ala Gly Pro
 65                  70                  75                  80

Thr Glu Cys Ile Asp Leu Asn Lys Thr Pro Ala Arg Lys Pro Lys Lys
                 85                  90                  95

Lys Lys His Arg Pro Lys Val Leu Lys Asp Asp Lys Pro Ser Lys Thr
            100                 105                 110

Pro Lys Ser Ala Thr Pro Ile Pro Ser Thr Glu Lys Val Glu Lys Pro
        115                 120                 125

Ser Gly Lys Arg Lys Tyr Val Arg Lys Lys Thr Ser Pro Gly Gln Pro
    130                 135                 140

Pro Ala Glu Gln Ala Ala Ser Ser His Cys Arg Ser Glu Leu Lys Ser
145                 150                 155                 160

Val Lys Arg Ser Leu Asp Phe Gly Gly Glu Val Leu Gln Ser Thr
                165                 170                 175

Gln Ser Gly Ser Gln Val Pro Val Ala Glu Ile Cys Thr Gly Pro Lys
            180                 185                 190

Arg Gln Ser Ile Pro Ser Thr Ile Gln Arg Asp Ser Gln Ser Gln Leu
        195                 200                 205

Ala Cys His Val Val Ser Ser Thr Ser Ser Ile His Thr Ser Ala Ser
    210                 215                 220

Gln Met Val Asn Ala His Leu Phe Pro Pro Asp Asn Met Pro Asn Gly
225                 230                 235                 240

Val Leu Leu Asp Leu Asn Asn Ser Thr Ser Gln Leu Gln Asn Glu His
                245                 250                 255
```

-continued

```
Ala Lys Phe Val Asp Ser Pro Ala Arg Leu Phe Gly Ser Arg Ile Arg
            260                 265                 270

Gln Thr Ser Gly Lys Asn Ser Leu Leu Glu Ile Tyr Ala Gly Met Ser
        275                 280                 285

Asp Arg Asn Val Pro Asp Leu Asn Ser Ser Ile Ser Gln Thr His Ser
    290                 295                 300

Met Ser Thr Asp Phe Ala Gln Tyr Leu Ser Ser Ser Gln Ala Ser
305                 310                 315                 320

Val Arg Glu Thr Gln Met Ala Asn Gln Met Leu Asn Gly His Arg Met
                325                 330                 335

Pro Glu Asn Pro Ile Thr Pro Ser His Cys Ile Glu Arg Ala Ala Leu
            340                 345                 350

Lys Glu His Leu Asn His Val Pro His Ala Lys Ala Ala Val Met Asn
        355                 360                 365

Gly Gln Met Pro His Ser Tyr Arg Leu Ala Gln Asn Pro Ile Leu Pro
    370                 375                 380

Pro Asn His Ile Glu Gly Tyr Gln Val Met Glu Asn Leu Ser Glu Leu
385                 390                 395                 400

Val Thr Thr Asn Asp Tyr Leu Thr Ala Ser Pro Phe Ser Gln Thr Gly
                405                 410                 415

Ala Ala Asn Arg Gln His Asn Ile Gly Asp Ser Met His Ile His Ala
            420                 425                 430

Leu Asp Pro Arg Arg Glu Ser Asn Ala Ser Ser Gly Ser Trp Ile Ser
        435                 440                 445

Leu Gly Val Asn Phe Asn Gln Gln Asn Asn Gly Trp Ala Ser Ala Gly
    450                 455                 460

Ala Ala Asp Ala Ala Ser Ser His Ala Pro Tyr Phe Ser Glu Pro His
465                 470                 475                 480

Lys Arg Met Arg Thr Ala Tyr Leu Asn Asn Tyr Pro Asn Gly Val Val
                485                 490                 495

Gly His Phe Ser Thr Ser Ser Thr Asp Leu Ser Asn Asn Glu Asn Glu
            500                 505                 510

Asn Val Ala Ser Ala Ile Asn Ser Asn Val Phe Thr Leu Ala Asp Ala
        515                 520                 525

Gln Arg Leu Ile Ala Arg Glu Lys Ser Arg Ala Ser Gln Arg Met Ile
    530                 535                 540

Ser Phe Arg Ser Ser Lys Asn Asp Met Val Asn Arg Ser Glu Met Val
545                 550                 555                 560

His Gln His Gly Arg Pro Ala Pro His Gly Ser Ala Cys Arg Glu Ser
                565                 570                 575

Ile Glu Val Pro Asp Lys Gln Phe Gly Leu Met Thr Glu Glu Leu Thr
            580                 585                 590

Gln Leu Pro Ser Met Pro Asn Asn Pro Gln Arg Glu Lys Tyr Ile Pro
        595                 600                 605

Gln Thr Gly Ser Cys Gln Leu Gln Ser Leu Glu His Asp Met Val Lys
    610                 615                 620

Gly His Asn Leu Ala Gly Glu Leu His Lys Gln Val Thr Ser Pro Gln
625                 630                 635                 640

Val Val Ile Gln Ser Asn Phe Cys Val Thr Pro Pro Asp Val Leu Gly
                645                 650                 655

Arg Arg Thr Ser Gly Glu His Leu Arg Thr Leu Ile Ala Pro Thr His
            660                 665                 670
```

-continued

```
Ala Ser Thr Cys Lys Asp Thr Leu Lys Ala Leu Ser Cys Gln Leu Glu
        675                 680                 685

Ser Ser Arg Asp Ile Ile Arg Pro Val Asn Pro Ile Gly Pro Ser
        690                 695                 700

Ser Ala Asp Val Pro Arg Thr Asp Asn His Gln Val Lys Val Ser Glu
705                 710                 715                 720

Glu Thr Val Thr Ala Lys Leu Pro Glu Lys Arg Lys Val Gly Arg Pro
                725                 730                 735

Arg Lys Glu Leu Lys Pro Gly Glu Lys Pro Lys Pro Arg Gly Arg Pro
            740                 745                 750

Arg Lys Gly Lys Val Val Gly Glu Leu Ala Ser Lys Asp Ser His
        755                 760                 765

Thr Asn Pro Leu Gln Asn Glu Ser Thr Ser Cys Ser Tyr Gly Pro Tyr
    770                 775                 780

Ala Gly Glu Ala Ser Val Gly Arg Ala Val Lys Ala Asn Arg Val Gly
785                 790                 795                 800

Glu Asn Ile Ser Gly Ala Met Val Ser Leu Leu Asp Ser Leu Asp Ile
                805                 810                 815

Val Ile Gln Lys Ile Lys Val Leu Asp Ile Asn Lys Ser Glu Asp Pro
            820                 825                 830

Val Thr Ala Glu Pro His Gly Ala Leu Val Pro Tyr Asn Gly Glu Phe
        835                 840                 845

Gly Pro Ile Val Pro Phe Glu Gly Lys Val Arg Lys Arg Ser Arg
    850                 855                 860

Ala Lys Val Asp Leu Asp Pro Val Thr Ala Leu Met Trp Lys Leu Leu
865                 870                 875                 880

Met Gly Pro Asp Met Ser Asp Cys Ala Glu Gly Met Asp Lys Asp Lys
                885                 890                 895

Glu Lys Trp Leu Asn Glu Glu Arg Lys Ile Phe Gln Gly Arg Val Asp
            900                 905                 910

Ser Phe Ile Ala Arg Met His Leu Val Gln Gly Asp Arg Arg Phe Ser
        915                 920                 925

Pro Trp Lys Gly Ser Val Val Asp Ser Val Val Gly Val Phe Leu Thr
    930                 935                 940

Gln Asn Val Ser Asp His Leu Ser Ser Ser Ala Phe Met Ala Leu Ala
945                 950                 955                 960

Ala Lys Phe Pro Val Lys Pro Glu Ala Ser Glu Lys Pro Ala Asn Val
                965                 970                 975

Met Phe His Thr Ile Ser Glu Asn Gly Asp Cys Ser Gly Leu Phe Gly
            980                 985                 990

Asn Ser Val Lys Leu Gln Gly Glu Ile Leu Val Gln Glu Ala Ser Asn
        995                 1000                1005

Thr Ala Ala Ser Phe Ile Thr Thr Glu Asp Lys Glu Gly Ser Asn Ser
    1010                1015                1020

Val Glu Leu Leu Gly Ser Ser Phe Gly Asp Gly Val Asp Gly Ala Ala
1025                1030                1035                1040

Gly Val Tyr Ser Asn Ile Tyr Glu Asn Leu Pro Ala Arg Leu His Ala
                1045                1050                1055

Thr Arg Arg Pro Val Val Gln Thr Gly Asn Ala Val Glu Ala Glu Asp
            1060                1065                1070

Gly Ser Leu Glu Gly Val Val Ser Ser Glu Asn Ser Thr Ile Ser Ser
        1075                1080                1085

Gln Asn Ser Ser Asp Tyr Leu Phe His Met Ser Asp His Met Phe Ser
```

```
                1090              1095              1100
Ser Met Leu Leu Asn Phe Thr Ala Glu Asp Ile Gly Ser Arg Asn Met
1105              1110              1115              1120

Pro Lys Ala Thr Arg Thr Thr Tyr Thr Glu Leu Leu Arg Met Gln Glu
            1125              1130              1135

Leu Lys Asn Lys Ser Asn Glu Thr Ile Glu Ser Ser Glu Tyr His Gly
            1140              1145              1150

Val Pro Val Ser Cys Ser Asn Asn Ile Gln Val Leu Asn Gly Ile Gln
        1155              1160              1165

Asn Ile Gly Ser Lys His Gln Pro Leu His Ser Ser Ile Ser Tyr His
    1170              1175              1180

Gln Thr Gly Gln Val His Leu Pro Asp Ile Val His Ala Ser Asp Leu
1185              1190              1195              1200

Glu Gln Ser Val Tyr Thr Gly Leu Asn Arg Val Leu Asp Ser Asn Val
            1205              1210              1215

Thr Gln Thr Ser Tyr Tyr Pro Ser Pro His Pro Gly Ile Ala Cys Asn
            1220              1225              1230

Asn Glu Thr Gln Lys Ala Asp Ser Leu Ser Asn Met Leu Tyr Gly Ile
        1235              1240              1245

Asp Arg Ser Asp Lys Thr Thr Ser Leu Ser Glu Pro Thr Pro Arg Ile
1250              1255              1260

Asp Asn Cys Phe Gln Pro Leu Ser Ser Glu Lys Met Ser Phe Ala Arg
1265              1270              1275              1280

Glu Gln Ser Ser Ser Glu Asn Tyr Leu Ser Arg Asn Glu Ala Glu Ala
            1285              1290              1295

Ala Phe Val Lys Gln His Gly Thr Ser Asn Val Gln Gly Asp Asn Thr
        1300              1305              1310

Val Arg Thr Glu Gln Asn Gly Gly Glu Asn Ser Gln Ser Gly Tyr Ser
        1315              1320              1325

Gln Gln Asp Asp Asn Val Gly Phe Gln Thr Ala Thr Thr Ser Asn Leu
    1330              1335              1340

Tyr Ser Ser Asn Leu Cys Gln Asn Gln Lys Ala Asn Ser Glu Val Leu
1345              1350              1355              1360

His Gly Val Ser Ser Asn Leu Ile Glu Asn Ser Lys Asp Asp Lys Lys
            1365              1370              1375

Thr Ser Pro Lys Val Pro Val Asp Gly Ser Lys Ala Lys Arg Pro Arg
        1380              1385              1390

Val Gly Ala Gly Lys Lys Lys Thr Tyr Asp Trp Asp Met Leu Arg Lys
    1395              1400              1405

Glu Val Leu Tyr Ser His Gly Asn Lys Glu Arg Ser Gln Asn Ala Lys
    1410              1415              1420

Asp Ser Ile Asp Trp Glu Thr Ile Arg Gln Ala Glu Val Lys Glu Ile
1425              1430              1435              1440

Ser Asp Thr Ile Arg Glu Arg Gly Met Asn Asn Met Leu Ala Glu Arg
            1445              1450              1455

Ile Lys Asp Phe Leu Asn Arg Leu Val Arg Asp His Gly Ser Ile Asp
        1460              1465              1470

Leu Glu Trp Leu Arg Tyr Val Asp Ser Asp Lys Ala Lys Asp Tyr Leu
        1475              1480              1485

Leu Ser Ile Arg Gly Leu Gly Leu Lys Ser Val Glu Cys Val Arg Leu
    1490              1495              1500

Leu Thr Leu His His Met Ala Phe Pro Val Asp Thr Asn Val Gly Arg
1505              1510              1515              1520
```

```
Ile Cys Val Arg Leu Gly Trp Val Pro Leu Gln Pro Leu Pro Glu Ser
            1525                1530                1535

Leu Gln Leu His Leu Leu Glu Met Tyr Pro Met Leu Glu Asn Ile Gln
            1540                1545                1550

Lys Tyr Leu Trp Pro Arg Leu Cys Lys Leu Asp Gln Arg Thr Leu Tyr
            1555                1560                1565

Glu Leu His Tyr Gln Met Ile Thr Phe Gly Lys Val Phe Cys Thr Lys
            1570                1575                1580

Ser Lys Pro Asn Cys Asn Ala Cys Pro Met Arg Ala Glu Cys Lys His
1585                1590                1595                1600

Phe Ala Ser Ala Phe Ala Ser Ala Arg Leu Ala Leu Pro Gly Pro Glu
            1605                1610                1615

Glu Lys Ser Leu Val Thr Ser Gly Thr Pro Ile Ala Ala Glu Thr Phe
            1620                1625                1630

His Gln Thr Tyr Ile Ser Ser Arg Pro Val Val Ser Gln Leu Glu Trp
            1635                1640                1645

Asn Ser Asn Thr Cys His His Gly Met Asn Asn Arg Gln Pro Ile Ile
    1650                1655                1660

Glu Glu Pro Ala Ser Pro Glu Pro Glu His Glu Thr Glu Glu Met Lys
1665                1670                1675                1680

Glu Cys Ala Ile Glu Asp Ser Phe Val Asp Pro Glu Glu Ile Pro
            1685                1690                1695

Thr Ile Lys Leu Asn Phe Glu Glu Phe Thr Gln Asn Leu Lys Ser Tyr
            1700                1705                1710

Met Gln Ala Asn Asn Ile Glu Ile Glu Asp Ala Asp Met Ser Lys Ala
            1715                1720                1725

Leu Val Ala Ile Thr Pro Glu Val Ala Ser Ile Pro Thr Pro Lys Leu
            1730                1735                1740

Lys Asn Val Ser Arg Leu Arg Thr Glu His Gln Val Tyr Glu Leu Pro
1745                1750                1755                1760

Asp Ser His Pro Leu Leu Glu Gly Phe Asn Gln Arg Glu Pro Asp Asp
            1765                1770                1775

Pro Cys Pro Tyr Leu Leu Ser Ile Trp Thr Pro Gly Glu Thr Ala Gln
            1780                1785                1790

Ser Thr Asp Ala Pro Lys Ser Val Cys Asn Ser Gln Glu Asn Gly Glu
            1795                1800                1805

Leu Cys Ala Ser Asn Thr Cys Phe Ser Cys Asn Ser Ile Arg Glu Ala
            1810                1815                1820

Gln Ala Gln Lys Val Arg Gly Thr Leu Leu Ile Pro Cys Arg Thr Ala
1825                1830                1835                1840

Met Arg Gly Ser Phe Pro Leu Asn Gly Thr Tyr Phe Gln Val Asn Glu
            1845                1850                1855

Val Phe Ala Asp His Asp Ser Ser Arg Asn Pro Ile Asp Val Pro Arg
            1860                1865                1870

Ser Trp Ile Trp Asn Leu Pro Arg Arg Thr Val Tyr Phe Gly Thr Ser
            1875                1880                1885

Ile Pro Thr Ile Phe Lys Gly Leu Thr Thr Glu Glu Ile Gln His Cys
            1890                1895                1900

Phe Trp Arg Gly Phe Val Cys Val Arg Gly Phe Asp Arg Thr Ser Arg
1905                1910                1915                1920

Ala Pro Arg Pro Leu Tyr Ala Arg Leu His Phe Pro Ala Ser Lys Ile
            1925                1930                1935
```

```
Thr Arg Asn Lys Lys Ser Ala Gly Ser Ala Pro Gly Arg Asp Asp Glu
        1940                1945                1950

<210> SEQ ID NO 18
<211> LENGTH: 723
<212> TYPE: PRT
<213> ORGANISM: Oryza sativa
<220> FEATURE:
<223> OTHER INFORMATION: DMTRICE novel amino terminus

<400> SEQUENCE: 18

Met Gln Asp Phe Gly Gln Trp Leu Pro Gln Ser Gln Thr Thr Ala Asp
  1               5                  10                  15

Leu Tyr Phe Ser Ser Ile Pro Ile Pro Ser Gln Phe Asp Thr Ser Ile
             20                  25                  30

Glu Thr Gln Thr Arg Thr Ser Ala Val Val Ser Ser Glu Lys Glu Ser
         35                  40                  45

Ala Asn Ser Phe Val Pro His Asn Gly Thr Gly Leu Val Glu Arg Ile
     50                  55                  60

Ser Asn Asp Ala Gly Leu Thr Glu Val Val Gly Ser Ala Gly Pro
 65                  70                  75                  80

Thr Glu Cys Ile Asp Leu Asn Lys Thr Pro Ala Arg Lys Pro Lys Lys
                 85                  90                  95

Lys Lys His Arg Pro Lys Val Leu Lys Asp Asp Lys Pro Ser Lys Thr
            100                 105                 110

Pro Lys Ser Ala Thr Pro Ile Pro Ser Thr Glu Lys Val Glu Lys Pro
        115                 120                 125

Ser Gly Lys Arg Lys Tyr Val Arg Lys Thr Ser Pro Gly Gln Pro
    130                 135                 140

Pro Ala Glu Gln Ala Ala Ser Ser His Cys Arg Ser Glu Leu Lys Ser
145                 150                 155                 160

Val Lys Arg Ser Leu Asp Phe Gly Gly Glu Val Leu Gln Glu Ser Thr
                165                 170                 175

Gln Ser Gly Ser Gln Val Pro Val Ala Glu Ile Cys Thr Gly Pro Lys
            180                 185                 190

Arg Gln Ser Ile Pro Ser Thr Ile Gln Arg Asp Ser Gln Ser Gln Leu
        195                 200                 205

Ala Cys His Val Val Ser Thr Ser Ser Ile His Thr Ser Ala Ser
    210                 215                 220

Gln Met Val Asn Ala His Leu Phe Pro Pro Asp Asn Met Pro Asn Gly
225                 230                 235                 240

Val Leu Leu Asp Leu Asn Asn Ser Thr Ser Gln Leu Gln Asn Glu His
                245                 250                 255

Ala Lys Phe Val Asp Ser Pro Ala Arg Leu Phe Gly Ser Arg Ile Arg
            260                 265                 270

Gln Thr Ser Gly Lys Asn Ser Leu Leu Glu Ile Tyr Ala Gly Met Ser
        275                 280                 285

Asp Arg Asn Val Pro Asp Leu Asn Ser Ser Ile Ser Gln Thr His Ser
    290                 295                 300

Met Ser Thr Asp Phe Ala Gln Tyr Leu Leu Ser Ser Ser Gln Ala Ser
305                 310                 315                 320

Val Arg Glu Thr Gln Met Ala Asn Gln Met Leu Asn Gly His Arg Met
                325                 330                 335

Pro Glu Asn Pro Ile Thr Pro Ser His Cys Ile Glu Arg Ala Ala Leu
            340                 345                 350
```

-continued

```
Lys Glu His Leu Asn His Val Pro His Ala Lys Ala Ala Val Met Asn
        355                 360                 365
Gly Gln Met Pro His Ser Tyr Arg Leu Ala Gln Asn Pro Ile Leu Pro
    370                 375                 380
Pro Asn His Ile Glu Gly Tyr Gln Val Met Glu Asn Leu Ser Glu Leu
385                 390                 395                 400
Val Thr Thr Asn Asp Tyr Leu Thr Ala Ser Pro Phe Ser Gln Thr Gly
                405                 410                 415
Ala Ala Asn Arg Gln His Asn Ile Gly Asp Ser Met His Ile His Ala
            420                 425                 430
Leu Asp Pro Arg Arg Glu Ser Asn Ala Ser Ser Gly Ser Trp Ile Ser
        435                 440                 445
Leu Gly Val Asn Phe Asn Gln Gln Asn Gly Trp Ala Ser Ala Gly
    450                 455                 460
Ala Ala Asp Ala Ala Ser Ser His Ala Pro Tyr Phe Ser Glu Pro His
465                 470                 475                 480
Lys Arg Met Arg Thr Ala Tyr Leu Asn Asn Tyr Pro Asn Gly Val Val
                485                 490                 495
Gly His Phe Ser Thr Ser Ser Thr Asp Leu Ser Asn Asn Glu Asn Glu
            500                 505                 510
Asn Val Ala Ser Ala Ile Asn Ser Asn Val Phe Thr Leu Ala Asp Ala
        515                 520                 525
Gln Arg Leu Ile Ala Arg Glu Lys Ser Arg Ala Ser Gln Arg Met Ile
    530                 535                 540
Ser Phe Arg Ser Ser Lys Asn Asp Met Val Asn Arg Ser Glu Met Val
545                 550                 555                 560
His Gln His Gly Arg Pro Ala Pro His Gly Ser Ala Cys Arg Glu Ser
                565                 570                 575
Ile Glu Val Pro Asp Lys Gln Phe Gly Leu Met Thr Glu Glu Leu Thr
            580                 585                 590
Gln Leu Pro Ser Met Pro Asn Asn Pro Gln Arg Glu Lys Tyr Ile Pro
        595                 600                 605
Gln Thr Gly Ser Cys Gln Leu Gln Ser Leu Glu His Asp Met Val Lys
    610                 615                 620
Gly His Asn Leu Ala Gly Glu Leu His Lys Gln Val Thr Ser Pro Gln
625                 630                 635                 640
Val Val Ile Gln Ser Asn Phe Cys Val Thr Pro Pro Asp Val Leu Gly
                645                 650                 655
Arg Arg Thr Ser Gly Glu His Leu Arg Thr Leu Ile Ala Pro Thr His
            660                 665                 670
Ala Ser Thr Cys Lys Asp Thr Leu Lys Ala Leu Ser Cys Gln Leu Glu
        675                 680                 685
Ser Ser Arg Asp Ile Ile Arg Pro Pro Val Asn Pro Ile Gly Pro Ser
    690                 695                 700
Ser Ala Asp Val Pro Arg Thr Asp Asn His Gln Val Lys Val Ser Glu
705                 710                 715                 720
Glu Thr Val
```

<210> SEQ ID NO 19
<211> LENGTH: 12120
<212> TYPE: DNA
<213> ORGANISM: Oryza sativa
<220> FEATURE:
<223> OTHER INFORMATION: DMTRICE sequence from PAC P0489G09

<400> SEQUENCE: 19

```
aaatattgct taaatggata taaagttgaa aaatgtactt gagggaagtt gtaggtgcac      60
gtggggtccc acaattttc ttcactagtg cacctttagt tatatatttt ttgcgcaaga     120
ggacaaaggc gctccgtgta attttgagta agggccggcg ggatatttat ttgtgtaaag    180
gacctagcca agaaaagcat gatagtgcat atgtatcctt tcttttttctt ttcttttgtt   240
ttcataactg tcttacagaa tttcatgttg gctggtgaca cttgtctcac tcattatttg    300
gtatattttg actaaatgca acgtgttggt gctcggtagt ttatatttgt ttttacgcat    360
tcttcattga ctgtatgtat ttgatgttga taccctgggc tgtcttattt tataggtgga    420
tgctgggagg ccacatagga ggcctgtgtg atccaagtgt gctgctcctg agttgaaatt    480
gcatagccat atagcaacta ctggtgtaaa cttgagagat gaagtagtga aaggaaatat    540
gcaggatttt ggacaatggc tgcctcaatc tcagaccact gccgatctat atttctccag    600
tattccaata ccatcacagt tcgatacttc catagagacg cagactagaa cttctgcagt    660
tgtatcgtca gagaaagaat ctgctaattc gttcgtccct cataatggta ctgggcttgt    720
tgaacgcatt agcaatgatg ctgggctaac tgaagtagtt ggaagtagtg ctggaccaac    780
tgaatgtatt gacttgaaca agacaccagc acggaaaccc aagaagaaaa agcacaggcc    840
aaaggtgcta aaggacgata aaccatcgaa gacacctaaa tctgctactc caataccttc    900
aacagaaaag gtagaaaaac catctggaaa gagaaaatat gtccgcaaga agacatctcc    960
aggccaacct cctgcagaac aggcagctag ctcacactgc agatctgagc tgaagtcagt   1020
taaacgaagt ttggactttg gtggagaagt actgcaagag agtacacaat ctggatctca   1080
agttccggtg gcagaaatat gtactggtcc aagcgtcaa tcaataccttt ctaccatcca   1140
aagagattcg caaagccagt tggcttgcca cgtggtttct agcaccagct caattcacac   1200
ttcagctagt cagatggtta atgcacattt gtttcctcct gataacatgc caaatggagt   1260
attgcttgac ctcaataatt ctactagtca gttacaaaac gaacatgcta aatttgtgga   1320
cagtccggca cgtctttttg gttccagaat aagacagaca tcaggtaaaa attctttgct   1380
agaaatctat gctggcatgt cagatagaaa tgtacctgat ctcaacagtt caatcagtca   1440
gacgcatagc atgtctactg attttgctca atacttgctt tcatcctcac aagcttctgt   1500
aagggaaaca caaatggcca atcagatgct taatggtcat aggatgccag aaaatccaat   1560
tacacctagt cattgtattg aaagggctgc attgaaggaa catttgaatc atgttcctca   1620
cgcaaaagcc gcagtgatga atggccaaat gccccatagt tacaggttgg cgcaaaatcc   1680
catcctacct ccaaatcata ttgaagggta tcaagtgatg gaaaatttga gtgaacttgt   1740
cacgacaaat gactatctaa ctgctagtcc tttcagtcaa actggagctg caaataggca   1800
gcataatatt ggtgactcca tgcatataca tgcattggat cctagaagag agagtaatgc   1860
ttcaagtggt tcttggatat cattaggtgt gaactttaac caacaaaata tggatgggc   1920
atctgcaggt gctgccgatg ctgcgagctc acatgcccca tatttttcag aacctcacaa   1980
aagaatgagg acagcttatc ttaacaatta tccaaatgga gtcgtgggac attttttctac  2040
ctcatctacg gatttgtcaa ataatgagaa tgaaaatgtg gcctcagcaa tcaactcaaa   2100
cgttttttacc cttgctgatg cacaaagatt gatagcccgt gagaaatcac gagcttccca   2160
aagaatgatc agttttagat catctaaaaa tgatatggtt aacagatcag aaatggtcca   2220
tcaacatggc agacctgctc cgcatggctc tgcatgcagg gagtctattg aagtacctga   2280
caaacagttc gggctcatga cagaagaact cacacaatta cctagtatgc caaataaccc   2340
```

```
acaaagggaa aaatatattc cgcaaactgg aagttgccaa cttcagtctt tggaacatga    2400
catggttaaa gggcataact tggcaggtga attgcataag caagtaactt cacctcaagt    2460
tgttattcag agcaatttct gtgttacccc tcctgatgtg ctcggcagaa gaaccagtgg    2520
ggagcattta agaacccta tagctccaac acatgcatcg acatgtaagg acactctgaa    2580
agctttaagt tgtcaactgg agagttctag agacattatt aggcctcctg tcaatccat    2640 agggccatcc tctgccgatg ttccaagaac tgataaccat caagtcaagg tttctgaaga    2700
aaccgttaca gccaaactcc ctgagaagcg aaaagtagga cgtcccagaa aagagttaaa    2760
acctggtgag aaaccaaaac ctagaggccg tccaaggaag ggaaaagttg ttggtggaga    2820
acttgcatca aaggatagtc acactaatcc attgcaaaat gagagtactt catgttctta    2880
tggtccttat gcaggggagg cttctgttgg aagagcagtt aaagcaaata gagttggaga    2940
aaacatttct ggagctatgg tatccctact ggattcttta gatattgtta ttcaaaagat    3000
aaaggtcttg gacataaaca aatcagaaga ccctgtgaca gctgaacctc atggtgctct    3060
tgtcccttac aatggagaat ttggtcctat tgttcctttt gaggggaaag tgaaaagaaa    3120
acgctctcga gccaaagtgg atcttgaccc tgtaactgct ttaatgtgga agttactaat    3180
gggaccagat atgagtgatt gtgctgaagg tatggataag gataaagaga atggctaaa    3240 tgaagaaaga aaaatattcc aagggcgtgt tgattcattt attgctcgaa tgcatctagt    3300
tcaaggtatt tctatcattt taaaattgtt ttcctaacat gaacatgatg cttccatct    3360 tgtgattgct gccctcacat tagtgaatgg tctcaaatct tcaatattta ctgtgtaccc    3420
aaatcctatt tcttcatccc aatatattca tgtttgtact cgtactgtcc cattagactt    3480
gcattgtgct gtgaagatca acacctttac tttaggatt acctctatgt ttgcaggaga    3540
tcggcgtttt tctccttgga aaggatcagt tgtagattct gtagtgggag tatttcttac    3600
acagaatgtt tcggaccatc tttccaggtg aataatgcct agagcctatt tgaaaactgt    3660
gacttgactt gcattgtgag gttatgttgt ttttctgtct gactatttcc ttttttttca    3720
gctctgcatt tatggctctt gctgcaaaat ttcctgtaaa gccagaagcc tctgaaaaac    3780
ccgcaaatgt gatgtttcat acaatttcag aaaatggtga ttgttctggg ttgtttggta    3840
attctgtcaa gctacagggt gagatccttg ttcaggaggc cagcaacaca gcagcctctt    3900
ttatcacaac cgaggataag gaaggaagta acagtgtgga attgcttgga agttctttg    3960 gggatggagt ggatggtgca gcaggagttt attctaatat ttatgagaat ctgccagcta    4020
gactgcatgc tactaggcgt ccagtcgttc aaactggaaa cgctgtcgaa gcggaagatg    4080
ggtcactgga gggtgttgtt tcatcagaaa actccactat ttcatctcaa aattcatcag    4140
attatctatt tcacatgtct gatcatatgt tttcgagcat gttactaaat ttcactgccg    4200
aagacattgg cagcagaaat atgcccaaag caacaagaac cacatataca gaacttctac    4260
gaatgcagga gctgaagaac aagtctaatg aaaccattga atcatcagag tatcatgggg    4320
ttccagtctc atgtagtaac aacattcaag tgctcaatgg aatacaaaat atcggcagta    4380
aacatcagcc tttacattcc tctatttcat atcaccagac tggccaagtt cacctcccag    4440
acatagtaca tgcgagtgat ttggagcaat cagtatacac tggccttaat agagtgcttg    4500
attctaatgt tacacaaacc agttattatc cttcacctca tcctggaatt gcctgtaaca    4560
atgaaacaca aaaggctgac tctttaagca acatgttata tggtatagat agatcagata    4620
agactacttc cctgtctgag cctacaccaa gaatcgataa ctgttttcaa ccattaagtt    4680
```

-continued

```
cagagaaaat gtcatttgct agggaacagt cctcttctga aaattatctt tcaaggaatg    4740
aagctgaagc tgcatttgtt aaacagcatg gaacatcaaa tgtgcaaggt gataaatactg   4800 tcaggacaga gcaaaatgga ggtgaaaatt ctcaatcagg atacagccaa caggatgata    4860
atgttggatt tcaaacagcg acaaccagta atctttattc ttcaaactta tgccaaaacc    4920
agaaagcaaa ttctgaagta ctacacggag tttcttccaa cttgatagag aattctaaag    4980
atgacaaaaa gacttccccc aaagttccag tcgatggatc aaaagcaaag aggccaagag    5040
ttggggctgg taaaaagaaa acatatgatt gggatatgtt gagaaaagaa gttctttaca    5100
gtcatggtaa taaagaaaga tcccagaatg ctaaggactc aattgattgg gaaacaataa    5160
gacaagcaga ggtgaaggaa atatctgaca caattagaga gcgaggaatg aataacatgc    5220
tggcagaacg gataaaagta agtatggcat aaaacagttt acattgaaag ttgacataac    5280
tctagtcata tgtgcatgca tgctattcca tatagatttg cttatttgtt ggaattccaa    5340
gttttggatc aaccatactc atctttagca attcatgttg caggacttcc taaaccgatt    5400
ggtgagagac catgggagca tcgatcttga gtggttgcgc tatgtcgatt cagataaagc    5460
gaagtaagct aactaaattt attttgagca aacattcata atgcaattgg cccttgggca    5520
ttctataatt tgtcattttg acctctgcat tgcttagcaa tgacaattgg atgtagtgag    5580
catgggtaat aatgtaagca atgacaattg gatgtagtgg gcatggttaa taattgaaca    5640
tgtctgtgtt tgcgggataa taatgcctat cacctgtgag cctgtgacat gcaaaccttg    5700
aacgttgaac cttgaacccc ctacctcgca ctgtgtgctc tcaaccaact gagcaagtga    5760
gggaccttgt tgtatggaaa aaataatttt aaataacct tgattcaacc aaagcttcat     5820
aaaagaatat attttctatt attcatttga accagcggtt gaaccagtga accgatggtc    5880
ttgctggtcc ggatttaata ataactatgg ctagaacaga ttagagcacc gaatacttgc    5940
gcgatgctaa atatttcaat ggggacacac ctgctcgtgt gttgcatcaa ctacctaagc    6000
cacacaggca tggcaatcaa atcagcttgc ccatgtaaca tcaactatct gatcgcgaga    6060
aggccggagc tctcacttga tgtttgtcat tcaaaaaata gttattcacc aatgcaatgt    6120
caagctcccg taaagaccat gaatgtagtt tatccttctt tgatcaagtt tttatttata    6180
ttaaagtgtt taccaatgta atcctacatt atttgtacct ggttttaca tataaataca     6240 ttgtaccttt tgtgtttctt ccagggacta tctcttaagc attagaggac ttggacttaa    6300
aagtgttgag tgtgtgcgtc ttttgacact ccatcacatg gcttttcctg tatgtttcct    6360
ttcacaaata attttcaaga atcttcgttt ctttatttct ggagaagtgg agattttatc    6420
tgtatctgtt gatgatgtag gtggatacaa atgttggtag aatatgtgtg aggcttggat    6480
gggtgccact tcagcccta cccgagtctc ttcagttgca cctgttggag atgtaagtat     6540
cttaaatcca ctggttggct tcactaatgc tggagagtga taggagtttg atcatctgct    6600
attgaaggta tccaatgctg gagaacatac agaaatacct ctggccgagg ttatgcaagc    6660
ttgatcaacg acattgtgag ttttagaaaa tgcagttaaa aactatatat ataagagcat    6720
gtcattatct gagagtgtat aacaggttct tgatgatatg taggtatgag cttcactatc    6780
aaatgataac ttttggaaag gtatgagaca acaactttga taaagtgaat tcaacccaat    6840
tactgtgttt tgatggacca tctgtgttac tttccttcta ggtattttgt acaaaaagta    6900
agcccaattg caacgcatgc ccaatgagag ctgagtgcaa gcactttgca agtgcatttg    6960
ccaggtaatt ctcaagatgt acatatttta tatacattct gtgaaatcac ggtgatgatt    7020
gttaggtatg aacaattggc tgagatcccc ccctcccccc ctcccatcct tttcctggtc    7080
```

```
ctacaagttc tcctaggcta atttaactgg tgcataccac atttatgtta ttttgataca    7140
tcaaagatta tgtttgtggt tgtgaggcta tattagtgtg ttgtatgtaa ctcagttttg    7200
caattgtagt tttagttaga acacgttgtt ctctacattt taataaatac tttttgactg    7260
gacatcaatg actggtgtat ttccgatata aaaaggttga ttgttgccga gggatttcaa    7320
ttcggtccga ataggttcga caaatgcagt gggcctatta gtttaagagt gaaagttcta    7380
tcagctgttt gactccactg tgacctttac actttgtact tttgaagaaa cagactaacc    7440
tgctcatatt aaagtcttgg aatgactcca ttgcgacctt tacgctttgt attttagaag    7500
aaacagacta acctgttcat attagagtct tggaactgtg tgtgtgtgtg tttttttttt    7560
ttttgggggg gggggggcat ggagatttaa tccaacattc ctggatgacc ttatattggt    7620
aatgatatgg ttttttttatg atatagtgca aggctcgctc ttcctggacc tgaagagaag    7680
agtttagtta catctggaac cccaatagct gcagaaacct tccaccagac atatataagt    7740
tctaggcctg tagtaagtca gcttgagtgg aattcaaaca cctgtcacca tggtatgaac    7800
aatcgccagc caatcattga ggagccagca agcccagaac tgaacatga  gacagaagag    7860
atgaaagagt gtgcaataga ggatagtttt gtcgatgatc cagaagaaat ccctactatc    7920
aagcttaatt ttgaggagtt tacacagaac ctgaagagtt atatgcaagc aaataacatt    7980
gagattgaag atgctgatat gtcaaaggct ttggtcgcta taactcctga agttgcttct    8040
atcccaactc ctaagctcaa gaatgtcagt cgcctaagga cagagcacca agtgtatgat    8100
cttgtccctc ttgcaaaacc aatctcatga atatttacta ttgactatca tgtgttttgc    8160
tgcattgctt acttctctgt tttcaacata tatgtagcta tgaactgcca gattcacatc    8220
cacttcttga aggagtaagt tcataaaaca ttatagaatt ctgtactttc cttatcacca    8280
actgagaata tattgatgct tattttctta caatacacag ttcaaccaaa gagaaccaga    8340
tgatccttgc ccatacctac tctctatatg gaccccaggt aagaagtgca taaacagaac    8400
acaatatcat gggaaccaaa ctttttttcaa tggttactta taattgttga aatatgcaac    8460
aggtgaaaca gctcaatcaa ctgatgcacc taagtcggtc tgcaattcac aagagaatgg    8520
tgaactatgt gcaagcaata catgctttag ttgcaacagt ataagagaag cgcaggccca    8580
aaaagttcga gggacactgc tggtaagtag ttgtttctgt aacatatgct cagttgccct    8640
tggttcaaga tgtgctattc aagtttatca tgttcacgaa tagtgataaa gctgctatct    8700
gtcctagcta ttgtccaagc tataacagtt ctgattcact ggttgggcac cagctaggga    8760
ataggatgta aaaaacttat cccgcagttt gttgacaatc tgttttttctt tgttgaaaat    8820
taaaaataga taccatgccg aacagcaatg agaggaagct ttccacttaa tgggacatat    8880
tttcaagtca atgaggtgaa aacagaaagt tcttaaagtt gatcttagtt taattattat    8940
aataccatta aaatatatgc aagtttctac tttctagtat ctctttttatt agtgttcaaa    9000
tgttatgcgg caggtatttg ctgatcatga ctcaagccgg aacccgattg atgttccaag    9060
gagttggata tggaatctcc ctaggagaac tgtttacttt ggaacttcaa ttccgacaat    9120
atttaaaggt atttcactaa taaattttga ccaagaatag gattttttggc agcgccaaat    9180
gtgccactat ctttattgtg tgaagtccat tatgtgattg taataatttg aatcaccaag    9240
aggactaagg cctgctttgg gacatattac gagcagcttt tgcttgcaaa gaaaccagat    9300
tctggtgccg caccttctcc gctcttctgc cacccaagtc cgtccaatac ccctcattga    9360
gcgcttggat cctaaccccca tctgccatca tgcatcatcc tgctaacaac tgcttccacc    9420
```

```
attgcctgtt tctgttgttg ggaggcactc acgctgcttg ctatagttta ggttttcttt    9480
gtgtcctgat ttagatggaa tttccagctg ctgtctttta cataactagc taaatgtccg    9540
cgctttgcta tggataatag aaaatatatt ataatattgt caaataaatt aaatatgttt    9600
tatacgaaat gtgttaacaa tccttttgct atagggaata ttgaccttaa tttgattta     9660
tatgtggcta tccatttaga tttgtttgtt tttctaataa taataagttc aagggctaat    9720
gtacaaaatt gacaatggga gtaggtgggg tggcagattc actgccacca ccactacctt    9780
cttttaaagg ggtatataga tttgcagcag tggttgcttg atctgtgatt tgaaatgtca    9840
agtacacgct catgcatcag caccatatgt ctacgctcct gacccaacat gcaaccaatg    9900
caattgaggg ttggctctga tacaattact aatgtcctat atccaaaaca actataggcc    9960
tatgaccaaa cataattaat aacctcgctt gcgcttttgt cctcacttgc tccatgtaaa   10020
agggttaacc cgaggttact atgttaggaa tagctgggtt tatgaaacgg ttcaactctc   10080
aactcctcat atagcactaa ttcatgtatt gctgtcagca gtgatttgag ttccagatca   10140
tgctcataag ataggaccaa attgtcctta ctatctactc cctccgtccc aaaatataag   10200
gtatttccgg tcaaaatatc ttatatttg ggatggaggg agtactatac tacgaccca    10260
ccaccaaata gtgccgcaga agagagagag agagagagaa gaggggtgg gggtgggggt    10320
gtatgggtga aataagaata gtgccaagta tttgccaaca aatgaggcgg tcaaatgtgt   10380
cacatcaatt gggaagtatg tcagatcaac tgaaaatttg attgggaaat tattattcat   10440
gcaacaaagc tgtacaactg atcccatgtt tctatcgcag gtttgacaac tgaagaaata   10500
caacattgct tttggagagg taatcatttt tttttgtatg tacgttttgg tttccataac   10560
aaagagagat gaagtgtata ggtactatgt ttactgacaa ggataataat agtagcaagt   10620
ataggcag aggagcatgt ctctattcta ccagtattat tactcataat aactagtata    10680
tcctttttt tgccatttca gctgatagct actctccagt caaaatattt gccatctcta   10740
ttgaactttt cattgtcttc tgaatgtatc ttactcttgg atcattaata tttcattttg   10800
tcacgatata gtggtatagg acaataaaat catgggaagt atttattttc atcaccaatc   10860
tactcatata atttcaaat gacaattata aatatcttaa aaatatattg ttagttgtcc    10920
tgtataaaat aattgtcaca ccctagtcca cagcgacaag aatttgtgtc tacaggctag   10980
agtgagtact ctagaagtat cttcatagga atcggaataa aatgccaatg tgaatgaaca   11040
aggatatcaa gtatacctc aaaatctcta gagaggattg cgtaaatatg taggtgtaat    11100
taaacaattg tttcatatgg agggttttct taaaggaggg acaagactta tcaatatggg   11160
taaagtagtt tttatccata ggcattgttg gcagaaagct gcttagggta gaatgctact   11220
ccctccgtcc cacaatataa gagattttga gttttgctt gcaacgtttg accactcggc    11280
ttattcaaaa attttgaaa ttattattta ttttatttgt gacttacttt attattcaca    11340
gtactttaag tacaactttt cgtttttat atttgcaaaa aaaattgtat aagacgagtg    11400
gtcaaacgtt gtacgcaaaa actcaaaatc ccttatattg tgggacggag ggagtactta   11460
tggatgcctt ttttgtccaa gatgtcagta acatttctt tcagggatgt ggattttac    11520
ttctttttc cctaactttt tcaggatttg tgtgcgtgag aggctttgat aggacatcaa    11580
gagcacccag accactgtat gcaagactcc actttcagc aagcaaaatt accaggaata    11640
aaaaatctgc aggttctgct ccaggaagag atgatgaata ggccatctgg aaaaccagaa   11700
aggaaataaa gaggaggtac atatgatctg ccagaagatc actgacctga aatggatcgc   11760
tgaccaataa gttgccgtag gcaattcaat tatttctggc catatacatc tgctgaaagt   11820
```

-continued

```
tatgaactcc agccactgac gaattcgtgg tgctggtatt cttcggcaac atgatccatc    11880
atacagattc tatgcttggt tgttgcaagc aattcttatg cggtgacagt tgctgctgat    11940
agggagaaaa ggcatgtccg gcggctcagc ggctctaact gtactttcat atgagtggaa    12000
ccgattgttg tacatgtgaa aagtttgcca ttcaaaatgg tcattcatgt tgttaggtca    12060
ttcatgtagt cgatgtcaaa ttaatcatca attatttgat ttgattcatt cacaagttta    12120
```

<210> SEQ ID NO 20
<211> LENGTH: 177
<212> TYPE: PRT
<213> ORGANISM: Zea mays
<220> FEATURE:
<223> OTHER INFORMATION: corn DMT.1 660990 (688512 selclone ID)

<400> SEQUENCE: 20

```
Glu Pro Asp Asp Pro Cys Pro Tyr Leu Leu Ser Ile Trp Thr Pro Gly
 1               5                  10                  15

Glu Thr Ala Gln Ser Ile Asp Ala Pro Lys Thr Phe Cys Asp Ser Gly
            20                  25                  30

Glu Thr Gly Arg Leu Cys Gly Ser Ser Thr Cys Phe Ser Cys Asn Asn
        35                  40                  45

Ile Arg Glu Met Gln Ala Gln Lys Val Arg Gly Thr Leu Leu Ile Pro
    50                  55                  60

Cys Arg Thr Ala Met Arg Gly Ser Phe Pro Leu Asn Gly Thr Tyr Phe
65                  70                  75                  80

Gln Val Asn Glu Val Phe Ala Asp His Cys Ser Ser Gln Asn Pro Ile
                85                  90                  95

Asp Val Pro Arg Ser Trp Ile Trp Asp Leu Pro Arg Arg Thr Val Tyr
            100                 105                 110

Phe Gly Thr Ser Val Pro Thr Ile Phe Arg Gly Leu Thr Thr Glu Glu
        115                 120                 125

Ile Gln Arg Cys Phe Trp Arg Gly Phe Val Cys Val Arg Gly Phe Asp
    130                 135                 140

Arg Thr Val Arg Ala Pro Arg Pro Leu Tyr Ala Arg Leu His Phe Pro
145                 150                 155                 160

Val Ser Lys Val Val Arg Gly Lys Lys Pro Gly Ala Ala Arg Ala Glu
                165                 170                 175

Glu
```

<210> SEQ ID NO 21
<211> LENGTH: 798
<212> TYPE: DNA
<213> ORGANISM: Zea mays
<220> FEATURE:
<223> OTHER INFORMATION: corn DMT.1 cDNA 660990 (668512 selclone ID)

<400> SEQUENCE: 21

```
gaaccagatg atccttgtcc atatcttctt tccatatgga ccccaggtga aactgcacaa     60
tcgatcgatg cccccaagac attctgtgat cagggagga cgggtagact atgtggaagt    120
tcaacatgct ttagttgcaa caatatacga gaaatgcagg ctcagaaagt cagaggaaca    180
cttttgatac catgccgaac agcaatgaga ggaagcttcc cacttaatgg gacgtatttt    240
caagttaatg aggtatttgc tgaccattgc tcaagtcaaa atccaattga tgtcccacga    300
agttggattt gggacctccc aagacgaact gtttactttg gaacctcagt tcctacaata    360
ttcagaggtt taacgactga agagatacaa cgatgctttt ggagaggatt tgtttgcgtg    420
```

-continued

```
agggctttg ataggacagt gcgggcacca aggccccttt atgcaaggtt gcatttttcct      480 gtcagcaagg ttgttagagg caaaaagcct ggagcagcaa gagcagaaga ataatagaac      540
attgaagaaa tatagggggtg ctaaccagat gaggatggat agcccgaaat gagatgctga    600
cccaataggt cgccaaatca cctccaaatt ctaacccaat gacttccatc tgtaatgaat      660
ggcaatacct tgaaaacctg tgatggagat gtttttgtggc gacatgatct cttaaattag    720
attccgtctt tggtaacagc ctagctgttc ttgttgagtc gcatattctt tattctgaag      780
atcaatatag caaatggg                                                    798
```

```
<210> SEQ ID NO 22
<211> LENGTH: 166
<212> TYPE: PRT
<213> ORGANISM: Zea mays
<220> FEATURE:
<223> OTHER INFORMATION: corn DMT.2 371537 (441428 selclone ID)
<221> NAME/KEY: MOD_RES
<222> LOCATION: (1)..(166)
<223> OTHER INFORMATION: Xaa = any amino acid

<400> SEQUENCE: 22
```

```
Met Ile Thr Phe Gly Lys Val Phe Cys Thr Lys Arg Gln Pro Asn Cys
 1               5                  10                  15

Asn Ala Cys Pro Met Arg Ser Glu Cys Lys His Phe Ala Ser Ala Phe
            20                  25                  30

Ala Ser Ala Arg Leu Ala Leu Pro Ala Pro Gln Glu Glu Ser Leu Val
        35                  40                  45

Lys Leu Ser Asn Pro Phe Ala Phe Gln Asn Ser Ser Met His Ala Met
    50                  55                  60

Asn Ser Thr His Leu Pro Arg Leu Glu Gly Ser Ile His Ser Arg Glu
65                  70                  75                  80

Phe Leu Pro Lys Asn Ser Glu Pro Ile Ile Glu Glu Pro Ala Ser Pro
                85                  90                  95

Arg Glu Glu Arg Pro Pro Xaa Thr Met Glu Asn Asp Ile Glu Asp Phe
            100                 105                 110

Tyr Glu Asp Gly Glu Ile Pro Thr Ile Lys Leu Asn Met Glu Ala Phe
        115                 120                 125

Ala Gln Asn Leu Glu Asn Cys Ile Lys Glu Ser Asn Asn Glu Leu Gln
    130                 135                 140

Ser Asp Asp Ile Ala Lys Ala Leu Val Ala Ile Xaa Thr Glu Xaa Ala
145                 150                 155                 160

Ser Ile Pro Xaa Pro Lys
                165
```

```
<210> SEQ ID NO 23
<211> LENGTH: 506
<212> TYPE: DNA
<213> ORGANISM: Zea mays
<220> FEATURE:
<223> OTHER INFORMATION: corn DMT.2 cDNA 371537 (441428 selclone ID)

<400> SEQUENCE: 23
```

```
tatcagatga ttcatttggg aaaggtcttt tgtaccaaaa gacagccaaa ttgcaatgca      60
tgcccaatga ggagtgagtg caagcatttt gcaagtgcat ttgcaagtgc aaggcttgca    120
cttcctgctc cccaggagga aagcttagtg aagttgagca atccatttgc tttccagaat    180
agcagcatgc atgctatgaa ttcgactcac ctacctcgcc ttgaggggag tatccattca    240
```

```
agggagtttc ttcctaagaa ctcagagcca ataatcgagg agcctgcaag tccaagagag        300
gaaagacctc cakaaaccat ggaaaatgat attgaagatt tttatgaaga tggtgaaatc        360
ccaacaataa agcttaacat ggaagctttt gcacaaaact tggagaattg cattaaagaa        420
agcaataacg aactccagtc tgatgatatt gcaaaagcat tggttgctat tarcactgaa        480
rcagcttcsa ttcctgkacc gaaact                                            506
```

```
<210> SEQ ID NO 24
<211> LENGTH: 276
<212> TYPE: PRT
<213> ORGANISM: Zea mays
<220> FEATURE:
<223> OTHER INFORMATION: corn DMT.3 218853

<400> SEQUENCE: 24
```

Met Pro Arg Lys Pro Lys Arg Ala Pro Ala Ser Pro Ala Arg His
 1               5                  10                  15

Asp Pro Ser Pro Glu Pro Tyr Pro Ser His Ala Ser Pro Cys Ser Ala
            20                  25                  30

Gln Cys Leu Val Val Arg Asp Ala Leu Leu Ala Phe His Gly Phe Pro
        35                  40                  45

Glu Glu Phe Ala Ala Phe Arg Val Leu Arg Leu Gly Gly Leu Ser Pro
    50                  55                  60

Asn Arg Asp Pro Arg Pro Ser Ser Pro Thr Val Leu Asp Gly Leu Val
65                  70                  75                  80

Thr Thr Leu Leu Ser Gln Asn Thr Thr Asp Ala Ile Ser Arg Arg Ala
                85                  90                  95

Phe Ala Ser Leu Lys Ala Ala Phe Pro Ser Trp Asp Gln Val Val Asp
            100                 105                 110

Glu Glu Gly Lys Arg Leu Glu Asp Ala Ile Arg Cys Gly Gly Leu Ala
        115                 120                 125

Ala Thr Lys Ala Ala Arg Ile Arg Ser Met Leu Arg Asp Val Arg Glu
    130                 135                 140

Arg Arg Gly Lys Ile Cys Leu Glu Tyr Leu Arg Glu Leu Ser Val Asp
145                 150                 155                 160

Glu Val Lys Lys Glu Leu Ser Arg Phe Lys Gly Ile Gly Pro Lys Thr
                165                 170                 175

Val Ala Cys Val Leu Met Phe Tyr Leu Gln Lys Asp Asp Phe Pro Val
            180                 185                 190

Asp Thr His Val Leu Arg Ile Thr Lys Ala Met Gly Trp Val Pro Ala
        195                 200                 205

Thr Ala Ser Arg Glu Lys Ala Tyr Ile His Leu Asn Asn Lys Ile Pro
    210                 215                 220

Asp Asp Leu Lys Phe Asp Leu Asn Cys Leu Phe Val Thr His Gly Lys
225                 230                 235                 240

Leu Cys Gln Ser Cys Thr Lys Lys Val Gly Ser Asp Lys Arg Lys Ser
                245                 250                 255

Ser Asn Ser Ala Cys Pro Leu Ala Gly Tyr Cys Cys Ile Gly Glu Lys
            260                 265                 270

Leu Gln Gln Leu
        275

```
<210> SEQ ID NO 25
<211> LENGTH: 183
<212> TYPE: PRT
<213> ORGANISM: Triticum sp.
```

```
<220> FEATURE:
<223> OTHER INFORMATION: wheat DMT.1 614028 (887053 selclone ID)

<400> SEQUENCE: 25

Met Arg Ala Glu Cys Lys His Phe Ala Ser Ala Phe Ala Ser Ala Arg
 1               5                  10                  15

Leu Ala Leu Pro Gly Pro Glu Lys Ser Leu Val Thr Ser Gly Asn
                20                  25                  30

Pro Ile Ala Ser Gly Ser Cys Gln Gln Pro Tyr Ile Ser Ser Met Arg
            35                  40                  45

Leu Asn Gln Leu Asp Trp Asn Ala Asn Ala His Asp His Ile Leu Asp
 50                  55                  60

Asn Arg Gln Pro Ile Ile Glu Glu Pro Ala Ser Pro Glu Pro Glu Pro
 65                  70                  75                  80

Glu Thr Ala Glu Met Arg Glu Ser Ala Ile Glu Asp Ile Phe Leu Asp
                85                  90                  95

Asp Pro Glu Glu Ile Pro Thr Ile Lys Leu Asn Phe Glu Glu Phe Ala
            100                 105                 110

Gln Asn Leu Lys Asn Tyr Met Gln Val Asn Asn Ile Glu Met Glu Asp
        115                 120                 125

Ala Asp Met Ser Ser Ala Leu Val Ala Ile Thr Pro Glu Ala Ala Ser
130                 135                 140

Ile Pro Thr Pro Arg Leu Lys Asn Val Ser Arg Leu Arg Thr Glu His
145                 150                 155                 160

Gln Val Tyr Glu Leu Pro Asp Ser His Pro Leu Leu Glu Gly Tyr Asp
                165                 170                 175

Gln Arg Glu Pro Asp Asp Pro
            180

<210> SEQ ID NO 26
<211> LENGTH: 557
<212> TYPE: DNA
<213> ORGANISM: Triticum sp.
<220> FEATURE:
<223> OTHER INFORMATION: wheat DMT.1 614028 (887053 selclone ID)

<400> SEQUENCE: 26
tgcccaatga gagctgaatg caagcacttt gcaagtgcat ttgcaagtgc tagacttgct      60
cttcctggac ctgaagagaa gagtttggtt acgtcaggaa acccaattgc ttcagggagc     120
tgccagcagc catacataag ttctatgcgt ttaaatcaac ttgactggaa tgcaaatgcc     180
catgaccata ttctggacaa tcgccagcca atcattgagg agccagcaag tccggaacca     240
gaaccagaga ctgcagagat gagagagagt gccatagagg atattttct tgatgatcct      300 gaagaaattc ctacaatcaa gcttaatttc gaggagtttg cacagaatct caagaattat     360
atgcaagtca ataacattga atggaagat gctgatatgt caagtgcctt ggttgccata     420
actccggaag ctgcatctat cccgactcct aggctcaaga atgttagtcg cctaagaaca     480
gagcatcaag tctatgaact gccggactca catccacttc tggaaggata cgaccaaaga     540
gagcctgatg atccttg                                                    557

<210> SEQ ID NO 27
<211> LENGTH: 145
<212> TYPE: PRT
<213> ORGANISM: Triticum sp.
<220> FEATURE:
<223> OTHER INFORMATION: wheat DMT.2 568842 (908118 selclone ID)
```

```
<400> SEQUENCE: 27

Asn Arg Val Asp Glu Ser Thr Val Gly Gly Ala Asp Lys Ala Ala Ser
 1               5                  10                  15

Pro Lys Lys Thr Arg Thr Thr Arg Lys Lys Asn Thr Glu Asn Phe Asp
            20                  25                  30

Trp Asp Lys Phe Arg Arg Gln Ala Cys Ala Asp Gly His Met Lys Glu
        35                  40                  45

Arg Lys Ser Glu Arg Arg Asp Ser Val Asp Trp Glu Ala Val Arg Cys
    50                  55                  60

Ala Asp Val Gln Arg Ile Ser Gln Ala Ile Arg Glu Arg Gly Met Asn
 65                  70                  75                  80

Asn Val Leu Ser Glu Arg Ile Gln Glu Phe Leu Asn Arg Leu Val Arg
                85                  90                  95

Asp His Gly Ser Ile Asp Leu Glu Trp Leu Arg Asp Ile Pro Pro Asp
            100                 105                 110

Ser Ala Lys Asp Tyr Leu Leu Ser Ile Arg Gly Leu Gly Leu Lys Ser
        115                 120                 125

Val Glu Cys Val Arg Leu Leu Thr Leu His His Leu Ala Phe Pro Val
    130                 135                 140

Asp
145

<210> SEQ ID NO 28
<211> LENGTH: 439
<212> TYPE: DNA
<213> ORGANISM: Triticum sp.
<220> FEATURE:
<223> OTHER INFORMATION: wheat DMT.2 568842 (908118 selclone ID)

<400> SEQUENCE: 28
caaacagggt ggatgaatct actgtcggag gagcagataa agcagcaagt ccaaagaaaa        60
caagaaccac aagaaaaaaa aatactgaaa acttcgactg ggacaaattt cgaagacagg       120
cctgtgctga tggccacatg aaagaaagga agtctgaaag aagagactct gttgattggg       180
aagcagtacg atgtgcagat gtacaaagaa tttctcaggc catccgggaa cgaggaatga       240
ataatgtttt atcagaacga atccaggaat tcctgaatcg cttggttaga gatcatggaa       300
gcattgatct tgaatggtta agagatatcc cccctgactc agcaaggac tacttgctta       360 gcatacgtgg actggggctc aaaagtgttg aatgtgttcg tctactgaca ttacatcatc       420
tcgctttccc tgtwgacac                                                    439

<210> SEQ ID NO 29
<211> LENGTH: 108
<212> TYPE: PRT
<213> ORGANISM: Triticum sp.
<220> FEATURE:
<223> OTHER INFORMATION: wheat DMT.3 611792 (838515 selclone ID)

<400> SEQUENCE: 29

Asn Arg Lys Gln Val Asn Glu Val Phe Ala Asp His Lys Ser Ser Tyr
 1               5                  10                  15

Asp Pro Ile Tyr Val Ala Arg Glu Gln Leu Trp Lys Leu Glu Arg Arg
            20                  25                  30

Met Val Tyr Phe Gly Thr Ser Val Pro Ser Ile Phe Lys Gly Leu Thr
        35                  40                  45

Thr Glu Glu Ile Gln Gln Cys Phe Trp Lys Gly Phe Val Cys Val Arg
    50                  55                  60
```

```
Gly Phe Glu Arg Glu Thr Gly Ala Pro Arg Pro Leu Cys Gln His Leu
 65                  70                  75                  80

His Val Ala Ala Ser Lys Val Pro Arg Ser Arg Asn Ala Ala Ala Ala
                 85                  90                  95

Gly Leu Asn Ser Asp Ser Ala Lys Ala Ser Ala Pro
            100                 105

<210> SEQ ID NO 30
<211> LENGTH: 624
<212> TYPE: DNA
<213> ORGANISM: Triticum sp.
<220> FEATURE:
<223> OTHER INFORMATION: wheat DMT.3 611792 (838515 selclone ID)

<400> SEQUENCE: 30
aatcgaaaac aagttaatga ggtatttgca gaccacaaat ctagctacga tcccatatac     60
gttgcaaggg agcagttatg gaagttggaa agacgaatgg tctactttgg aacttcagtg    120
ccctccatat tcaaaggtct aacaactgaa gaaatacagc agtgcttctg gaaaggattt    180
gtctgtgtgc ggggattcga gagggaaacc ggggcaccaa ggcctctatg ccaacatctg    240
cacgtcgcgg ctagcaaagt gccgagatca cgcaacgcgg cagcagctgg gctgaactcg    300
gattcagcaa aggcatcggc tccatgagta tcatcacacc ggctatcgac ctgtgcatgg    360
gtacgctagt gttggttcct gccgggcwac agccgttytt gtaggaaata aaccsctgcg    420
caaragaatt atcatccagt tggtytgagt gtatacttyt gctgtagkac ctttttttaa    480
aatccctgtg agctytattg taccttgaat ttactttccg accagtttat ccgcttgcaa    540
araggccttt gttatgkacc ggcatcttgt tgtatataca tcatggttcc tctraaaaac    600
ttgtcttgcc akacgacctt acgt                                           624

<210> SEQ ID NO 31
<211> LENGTH: 145
<212> TYPE: PRT
<213> ORGANISM: Triticum sp.
<220> FEATURE:
<223> OTHER INFORMATION: wheat DMT.4 615131 (861906 selclone ID)

<400> SEQUENCE: 31

Met Arg Ser Glu Cys Arg His Phe Ala Ser Ala Phe Ala Ser Ala Arg
  1               5                  10                  15

Leu Ala Leu Pro Ala Pro Gln Glu Lys Ser Leu Val Met Ser Ser Asn
                 20                  25                  30

Gln Phe Ser Phe Gln Ser Gly Gly Met Pro Thr Pro Tyr Ser Thr Val
             35                  40                  45

Leu Pro Gln Leu Glu Gly Ser Ala Gln Gly Gln Asp Phe Cys Thr Asn
         50                  55                  60

Asn Ser Glu Pro Ile Ile Glu Glu Pro Ala Ser Pro Ala Arg Glu Glu
 65                  70                  75                  80

Cys Pro Glu Thr Leu Glu Asn Asp Ile Glu Asp Tyr Asp Pro Asp Thr
                 85                  90                  95

Gly Glu Ile Pro Leu Ile Lys Leu Asn Leu Gln Ala Phe Ala Gln Asn
            100                 105                 110

Leu Glu Asn Cys Ile Lys Glu Ser Asn Met Asp Leu Gly Ser Asp Asp
        115                 120                 125

Ile Ala Lys Ala Leu Val Ala Val Ser Thr Gly Ser Ala Ser Ile Pro
    130                 135                 140
```

```
Val
145

<210> SEQ ID NO 32
<211> LENGTH: 492
<212> TYPE: DNA
<213> ORGANISM: Triticum sp.
<220> FEATURE:
<223> OTHER INFORMATION: wheat DMT.4 615131 (861906 selclone ID)

<400> SEQUENCE: 32 tactttgga aggtgttct gtacaaaaaa caagccaaat tgcaatgctt gtccaatgag      60
aagcgaatgc aggcatttcg caagtgcctt cgcaagtgca cggcttgcac ttcctgcacc     120
tcaggagaaa agtttggtga tgtcgagcaa tcaattcagt ttccagagtg gtggcatgcc    180
aactccatac tcaactgtgc ttcctcagct tgagggaagt gcccagggac aggattttg     240 cactaacaat tcagagccaa ttattgagga gccagcaagt ccagcacggg aagaatgtcc    300
agaaactctt gaaatgata ttgaagatta cgatccagat actggtgaaa tcccactaat     360
taagcttaac ttgcaagctt ttgctcagaa cttggaaaac tgcattaaag aaagcaatat    420
ggatcttggg tctgatgata tcgcgaaagc acttgttgct gttagcactg gatcagcttc    480
aattcctgtc cc                                                       492

<210> SEQ ID NO 33
<211> LENGTH: 298
<212> TYPE: PRT
<213> ORGANISM: Glycine max
<220> FEATURE:
<223> OTHER INFORMATION: soybean DMT.1 449122 (557119 selclone ID)
<221> NAME/KEY: MOD_RES
<222> LOCATION: (1)..(298)
<223> OTHER INFORMATION: Xaa = any amino acid

<400> SEQUENCE: 33

Met Asp Ser Leu Asp Trp Asp Ala Val Arg Cys Ala Asp Val Ser Glu
  1               5                  10                  15

Ile Ala Glu Thr Ile Lys Glu Arg Gly Met Asn Asn Arg Leu Ala Asp
             20                  25                  30

Arg Ile Lys Asn Phe Leu Asn Arg Leu Val Glu Glu His Gly Ser Ile
         35                  40                  45

Asp Leu Glu Trp Leu Arg Asp Val Pro Pro Asp Lys Ala Lys Glu Tyr
     50                  55                  60

Leu Leu Ser Ile Arg Gly Leu Gly Leu Lys Ser Val Glu Cys Val Arg
 65                  70                  75                  80

Leu Leu Thr Leu His His Leu Ala Phe Pro Val Asp Thr Asn Val Gly
                 85                  90                  95

Arg Ile Ala Val Arg Leu Gly Trp Val Pro Leu Gln Pro Leu Pro Glu
            100                 105                 110

Ser Leu Gln Leu His Leu Leu Glu Leu Tyr Pro Val Leu Glu Ser Ile
        115                 120                 125

Gln Lys Tyr Leu Trp Pro Arg Leu Cys Lys Leu Asp Gln Glu Thr Leu
    130                 135                 140

Tyr Glu Leu His Tyr Gln Met Ile Thr Phe Gly Lys Xaa Phe Cys Thr
145                 150                 155                 160

Lys Ser Lys Pro Asn Cys Asn Ala Cys Pro Met Arg Xaa Glu Cys Arg
                165                 170                 175

His Phe Ala Ser Ala Phe Ala Ser Ala Arg Phe Ala Leu Pro Gly Pro
            180                 185                 190
```

-continued

Glu Gln Lys Ser Ile Val Ser Thr Thr Gly Asn Ser Val Ile Asn Gln
            195                 200                 205

Asn Pro Ser Glu Ile Ile Ser Gln Leu His Leu Pro Pro Pro Glu Asn
        210                 215                 220

Thr Ala Gln Glu Asp Glu Ile Gln Leu Thr Glu Val Ser Arg Gln Leu
225                 230                 235                 240

Glu Ser Lys Phe Glu Ile Asn Ile Cys Gln Pro Ile Ile Glu Glu Pro
                245                 250                 255

Arg Thr Pro Glu Pro Glu Cys Leu Gln Glu Ser Gln Thr Asp Ile Glu
            260                 265                 270

Asp Ala Phe Tyr Glu Asp Ser Ser Glu Ile Pro Thr Ile Asn Leu Asn
        275                 280                 285

Ile Glu Glu Phe Thr Leu Asn Leu Gln Asn
        290                 295

<210> SEQ ID NO 34
<211> LENGTH: 638
<212> TYPE: DNA
<213> ORGANISM: Glycine max
<220> FEATURE:
<223> OTHER INFORMATION: soybean DMT.1 449122 (557119 selclone ID)

<400> SEQUENCE: 34
aataaaattt aakagcaagg aacaagaaaa agagaaaaag gatgayttg actgggatag      60
tttaagaatt gaagcacagg ctaaggctgg gaaaagagaa aagacagata acaccatgga    120
ttctttggac tgggatgctg tgagatgtgc agatgtcagt gaaatcgctg agaccatcaa    180
agaaagggc atgaacaaca ggcttgcaga tcgtattaag aatttcttaa atcgattggt    240
tgaagaacat ggaagcattg accttgaatg gcttagagac gttccacctg acaaagcaaa    300
agaatacttg ctcagcataa gaggattggg actaaaaagt gtggaatgtg tgcggctttt    360
aacactgcac catcttgcct tcccggtaga cacaaatgtc ggacgtatag cagtacgact    420
gggatgggtc cctctacagc cactgcctga gtcactgcag ttgcatctcc tagaattgta    480
cccagtgttg gagtcaatac aaaaatatct ctggcctcga ctatgcaagc tagatcagga    540
aacactatat gagctacatt accagatgat tacatttgga aaggkcttct gtacaaaaag    600
caaaccaaat tgtaatgcat gcccaatgag aggagaat                            638

<210> SEQ ID NO 35
<211> LENGTH: 251
<212> TYPE: PRT
<213> ORGANISM: Glycine max
<220> FEATURE:
<223> OTHER INFORMATION: soybean DMT.2 387990 (473695 selclone ID)

<400> SEQUENCE: 35

Met Arg Met Thr Ile Asp Leu Val Ser Gln Gln Ser Leu Thr Ala Arg
1               5                  10                  15

Leu Gln Leu Ser Ile Leu Lys Asp Lys Leu Lys Ile Gln Cys Arg Lys
            20                  25                  30

Ala Arg Gly Leu Asp Phe Gly Arg Asn Glu Ser Ser Lys Ile Asp Ser
        35                  40                  45

Ser Pro Val Lys Leu Arg Ser Arg Glu His Gly Lys Glu Lys Lys Asn
    50                  55                  60

Asn Phe Asp Trp Asp Ser Leu Arg Ile Gln Ala Glu Ala Lys Ala Gly
65                  70                  75                  80

-continued

```
Lys Arg Glu Lys Thr Glu Asn Thr Met Asp Ser Leu Asp Trp Asp Ala
                 85                  90                  95

Val Arg Arg Ala Asp Val Ser Glu Ile Ala Asn Ala Ile Lys Glu Arg
            100                 105                 110

Gly Met Asn Asn Met Leu Ala Glu Arg Ile Gln Ser Phe Leu Asn Leu
        115                 120                 125

Leu Val Asp Lys His Gly Gly Ile Asp Leu Glu Trp Leu Arg Asp Val
    130                 135                 140

Pro Pro Asp Gln Ala Lys Glu Phe Leu Leu Ser Ile Arg Gly Leu Gly
145                 150                 155                 160

Leu Lys Ser Val Glu Cys Val Arg Leu Leu Thr Leu His His Leu Ala
                165                 170                 175

Phe Pro Val Asp Thr Asn Val Gly Arg Ile Ala Val Arg Leu Gly Trp
            180                 185                 190

Val Pro Leu Gln Pro Leu Pro Glu Ser Leu Gln Leu His Leu Leu Glu
        195                 200                 205

Leu Tyr Pro Val Leu Glu Ser Ile Gln Lys Tyr Leu Trp Pro Arg Leu
    210                 215                 220

Cys Lys Leu Asp Gln Arg Thr Leu Tyr Glu Leu His Tyr Gln Leu Ile
225                 230                 235                 240

Thr Phe Gly Lys Val Phe Cys Thr Lys Ser Lys
                245                 250

<210> SEQ ID NO 36
<211> LENGTH: 1134
<212> TYPE: DNA
<213> ORGANISM: Glycine max
<220> FEATURE:
<223> OTHER INFORMATION: soybean DMT.2 387990 (473695 selclone ID)

<400> SEQUENCE: 36
gaaaagatag gatcattctc agatagcaac tcagaaatag aagacctgtc tagcgctgcc          60
aagtacaata gttattataa tagaatttct ttcagtgagc ttttagaaat ggcaagttca         120
accatgttgc atgaagttaa cagtcaaaga agcaaatcaa ctgagaactt aggagataca         180
tgtgatcagt ctatagacat gaagcatgac aacctggcag aaaacttgga aaaatcggat         240
gttactcaag gctccgcaga agcacccatc accaatggat atacttttaa ataaccccca         300
aactcaggag tacttgaggt taactgttat gatcctctca aaatagaagt cccatcaagt         360
ggctcctcaa agggtaaaga tgagaatgac aatagatcta gtttcccaac agagtctgac         420
tgccaggctg caattgtcca ttctcaagga caaactgaag atccaatgca ggaaagcaag         480
gggactagat tttggtagga atgaaagcag taagatagat tcttcccctg taaaattaag         540
gagcagggag catggaaaag agaaaaagaa taactttgat tgggatagtt taagaataca         600
agcagaagct aaggcaggga aaagagaaaa gacagagaac accatggact ccttggactg         660
ggatgctgtt agacgcgcag atgtcagtga aattgccaat gcaatcaaag aaagggcat         720 gaacaacatg cttgctgaac gtattcgaga tttcctgaat ctattggttg acaagcatgg         780
gggcatcgat cttgagtggc tgagagatgt tccacctgat caagcaaaag aattcttgct         840
cagcataagg ggattgggat tgaaaagtgt ggagtgtgta cgactcttaa cactacacca         900
tcttgccttt ccggtggaca caaatgttgg acgtatagca gtaagattgg gatgggtgcc         960
tctccagcca ctgccagagt cactacagtt gcatcttcta gaattgtacc cagtgttgga        1020
gtccatacaa aaatatctct ggccccggct ctgcaagcta gaccaaagaa cattgtatga        1080
```
gctgcattac cagctgatta catttggaaa ggtcttctgt actaaaagca agcc    1134

<210> SEQ ID NO 37
<211> LENGTH: 209
<212> TYPE: PRT
<213> ORGANISM: Glycine max
<220> FEATURE:
<223> OTHER INFORMATION: soybean DMT.3 657152 (546665 selclone ID)
<221> NAME/KEY: MOD_RES
<222> LOCATION: (1)..(209)
<223> OTHER INFORMATION: Xaa = any amino acid

<400> SEQUENCE: 37

Ile Asn Gln Ala Glu Leu Gln Gln Thr Glu Val Ile Arg Gln Leu Glu
 1               5                  10                  15

Ala Lys Ser Glu Ile Asn Ile Ser Gln Pro Ile Glu Glu Pro Ala
            20                  25                  30

Thr Pro Glu Pro Glu Cys Ser Gln Val Ser Glu Asn Asp Ile Glu Asp
        35                  40                  45

Thr Phe Asn Glu Glu Ser Cys Glu Ile Pro Thr Ile Lys Leu Asp Ile
    50                  55                  60

Glu Glu Phe Thr Leu Asn Leu Gln Asn Tyr Met Gln Glu Asn Met Glu
65                  70                  75                  80

Leu Gln Glu Gly Glu Met Ser Lys Ala Leu Val Ala Leu His Pro Gly
                85                  90                  95

Ala Ala Cys Ile Pro Thr Pro Lys Leu Lys Asn Val Ser Arg Leu Arg
            100                 105                 110

Thr Glu His Tyr Val Tyr Glu Leu Pro Asp Ser His Pro Leu Leu Asn
        115                 120                 125

Gly Trp Asn Lys Arg Glu Pro Asp Pro Gly Lys Tyr Leu Leu Ala
    130                 135                 140

Ile Trp Thr Pro Gly Glu Thr Ala Asx Ser Ile Gln Pro Pro Glu Ser
145                 150                 155                 160

Lys Cys Ser Ser Gln Glu Glu Cys Gly Xaa Leu Cys Asn Glu Asn Glu
                165                 170                 175

Cys Phe Ser Cys Asn Ser Phe Arg Glu Ala Xaa Phe Xaa Asp Ser Xaa
            180                 185                 190

Arg Asp Thr Pro Asp Thr Met Ser Asn Ser Xaa Xaa Xaa Gly Ala Phe
        195                 200                 205

His

<210> SEQ ID NO 38
<211> LENGTH: 616
<212> TYPE: DNA
<213> ORGANISM: Glycine max
<220> FEATURE:
<223> OTHER INFORMATION: soybean DMT.3 657152 (546665 selclone ID)

<400> SEQUENCE: 38
tataaaccaa gcagaacttc aacaaacaga agtgatcagg caactagaag caaatctga     60 aatcaacatc agccaaccta ttattgaaga gccagcaact ccagagccag aatgctccca    120
agtatccgaa atgatatag aggatacctt caatgaggaa tcatgtgaaa ttcccaccat    180
caaactagac atagaagagt tcactttgaa cttacaaaac tatatgcaag aaaacatgga    240
acttcaagaa ggtgaaatgt caaaggcctt ggttgctcta catccaggtg ctgcatgcat    300
tcctacaccc aagctgaaga atgtgagccg gttgcgaaca gagcattatg tttatgaact    360
ccctgattca catccccttc tgaatgggtg gaacaagcga gaacctgatg atccaggcaa    420

```
ataccttcta gctatatgga ctccagggga gacagcagat tctatacagc caccagaaag    480
caaatgcagc tctcaggaat gtggccggct ctgtaatgag aatgaatgtt tttcatgcaa    540
cagtttccgt gaagcaaggt tcacagatag ttcgagggac actcctgata ccatgtcgaa    600
cagctwtgar agggag                                                    616
```

```
<210> SEQ ID NO 39
<211> LENGTH: 102
<212> TYPE: PRT
<213> ORGANISM: Glycine max
<220> FEATURE:
<223> OTHER INFORMATION: soybean DMT.4 432980 (663678 selclone ID)

<400> SEQUENCE: 39
```

Glu Ala Ala Ser Ile Pro Met Pro Lys Leu Lys Asn Val Ser Arg Leu
 1               5                  10                  15

Arg Thr Glu His Cys Val Tyr Glu Leu Pro Asp Thr His Pro Leu Leu
                20                  25                  30

Gln Gly Trp Asp Thr Arg Glu Pro Asp Asp Pro Gly Lys Tyr Leu Leu
            35                  40                  45

Ala Ile Trp Thr Pro Gly Glu Thr Ala Asn Ser Ile Gln Pro Pro Glu
        50                  55                  60

Ser Lys Cys Ser Ser Gln Glu Glu Cys Gly Gln Leu Cys Asn Glu Asn
 65                  70                  75                  80

Glu Cys Phe Ser Cys Asn Ser Phe Arg Glu Ala Asn Ser Gln Ile Val
                85                  90                  95

Arg Gly Thr Leu Leu Val
            100

```
<210> SEQ ID NO 40
<211> LENGTH: 457
<212> TYPE: DNA
<213> ORGANISM: Glycine max
<220> FEATURE:
<223> OTHER INFORMATION: soybean DMT.4 432980 (663678 selclone ID)

<400> SEQUENCE: 40
agaagctgct tccattccta tgcccaagct aaagaatgtg agccgattac gaacagagca    60
ttgtgtttat gaactcccag atacgcatcc tcttctccaa gggtgggaca cacgagagcc    120
tgatgatcca ggcaaatatc ttcttgctat atggactcca ggtgagacag caaattctat    180
acagccacca gaaagcaaat gcagctctca agaagaatgt ggccaactct gtaatgagaa    240
tgaatgtttc tcgtgcaaca gtttccgtga agcaaattct cagatagtta gagggacact    300
cctggtctga atgcttatca aaatcattgt tttaaccata tgtagcttac taattcttat    360
acattatggg aacaggggag ggaatacatc tccatagaaa ttcaagcatt ataatagact    420
gacttgaatt tatgataaat atgagcagat accatgt                             457
```

```
<210> SEQ ID NO 41
<211> LENGTH: 217
<212> TYPE: PRT
<213> ORGANISM: Medicago truncatula
<220> FEATURE:
<223> OTHER INFORMATION: Medicago 6654943

<400> SEQUENCE: 41
```

Met Glu Leu Gln Glu Gly Glu Met Ser Lys Ala Leu Val Ala Leu Asn
 1               5                  10                  15

```
Gln Glu Ala Ser Tyr Ile Pro Thr Thr Lys Leu Lys Asn Val Ser Arg
             20                  25                  30

Leu Arg Thr Glu His Ser Val Tyr Glu Leu Pro Asp Ser His Pro Leu
         35                  40                  45

Leu Glu Gly Trp Glu Lys Arg Glu Pro Asp Asp Pro Gly Lys Tyr Leu
     50                  55                  60

Leu Ala Ile Trp Thr Pro Gly Glu Thr Ala Asn Ser Ile Gln Pro Pro
 65                  70                  75                  80

Asp Arg Arg Cys Ser Ala Gln Asp Cys Gly Gln Leu Cys Asn Glu Glu
                 85                  90                  95

Glu Cys Phe Ser Cys Asn Ser Phe Arg Glu Ala Asn Ser Gln Ile Val
            100                 105                 110

Arg Gly Thr Ile Leu Ile Pro Cys Arg Thr Ala Met Arg Gly Ser Phe
        115                 120                 125

Pro Leu Asn Gly Thr Tyr Phe Gln Val Asn Glu Val Phe Ala Asp His
    130                 135                 140

Glu Ser Ser Leu Asn Pro Ile Ser Val Pro Arg Ser Leu Ile Trp Asn
145                 150                 155                 160

Leu Asp Arg Arg Thr Val His Phe Gly Thr Ser Val Thr Ser Ile Phe
                165                 170                 175

Lys Gly Leu Ala Thr Pro Glu Ile Gln Gln Cys Phe Trp Arg Gly Phe
            180                 185                 190

Val Cys Val Arg Ser Phe Glu Arg Ser Thr Arg Ala Pro Arg Pro Leu
        195                 200                 205

Met Ala Arg Leu His Phe Pro Ala Ser
    210                 215

<210> SEQ ID NO 42
<211> LENGTH: 657
<212> TYPE: DNA
<213> ORGANISM: Medicago truncatula
<220> FEATURE:
<223> OTHER INFORMATION: Medicago 6654943 EST306265

<400> SEQUENCE: 42
gagaacatgg aacttcaaga aggtgaaatg tcaaaggcct tggttgctct aaatcaagaa      60
gcttcttaca ttcctacaac gaagctgaag aacgtgagtc ggttgcgcac agagcattct     120
gtttatgaac tcccagattc tcatcctctt ctggaagggt gggaaaagcg agaacctgat     180
gatccaggaa ataccttcta gctatatgg acgccaggtg agactgcaaa ttctatacag      240
ccaccagaca gaagatgcag cgctcaagat tgtggccaac tctgtaatga ggaggaatgt     300
ttttcgtgca acagcttccg tgaagcaaat tcacagatag ttcgagggac aatcctgata     360
ccatgtcgaa cagctatgag agggagcttt ccgctaaacg gaacctattt tcaagtcaat     420
gaggtttttg cagaccatga atcaagtctt aatccgatta gcgttcccag aagtttgata     480
tggaaccttg ataggaggac agtgcatttt ggaacctccg taacaagcat attcaaaggt     540
ttagcaacac cagaaattca acagtgcttc tggagagggt ttgtctgtgt gcggagcttt     600
gaaaggtcaa cgagagcacc ccgtccttta atggccagac tgcatttccc agcaagc        657

<210> SEQ ID NO 43
<211> LENGTH: 210
<212> TYPE: PRT
<213> ORGANISM: Lycopersicon esculentum
<220> FEATURE:
<223> OTHER INFORMATION: tomato 12624037
```

```
<400> SEQUENCE: 43

Met Glu Leu Gln Glu Gly Glu Met Ser Lys Ala Leu Val Ala Leu Asn
  1               5                  10                  15

Gln Glu Ala Ser Tyr Ile Pro Thr Thr Lys Leu Lys Asn Val Ser Arg
             20                  25                  30

Leu Arg Thr Glu His Ser Val Tyr Glu Leu Pro Asp Ser His Pro Leu
         35                  40                  45

Leu Glu Gly Trp Glu Lys Arg Glu Pro Asp Pro Gly Lys Tyr Leu
     50                  55                  60

Leu Ala Ile Trp Thr Pro Gly Thr Ala Asn Ser Ile Gln Pro Pro
 65              70                  75                  80

Asp Arg Arg Cys Ser Ala Gln Asp Cys Gly Gln Leu Cys Asn Glu Glu
                 85                  90                  95

Glu Cys Phe Ser Cys Asn Ser Phe Arg Glu Ala Asn Ser Gln Ile Val
            100                 105                 110

Arg Gly Thr Ile Leu Ile Pro Cys Arg Thr Ala Met Arg Gly Ser Phe
        115                 120                 125

Pro Leu Asn Gly Thr Tyr Phe Gln Val Asn Glu Val Phe Ala Asp His
    130                 135                 140

Glu Ser Ser Leu Asn Pro Ile Ser Val Pro Arg Ser Leu Ile Trp Asn
145                 150                 155                 160

Leu Asp Arg Arg Thr Val His Phe Gly Thr Ser Val Thr Ser Ile Phe
                165                 170                 175

Lys Gly Leu Ala Thr Pro Glu Ile Gln Gln Cys Phe Trp Arg Gly Phe
            180                 185                 190

Val Cys Val Arg Ser Phe Glu Arg Ser Thr Arg Ala Pro Arg Pro Leu
        195                 200                 205

Met Ala
    210

<210> SEQ ID NO 44
<211> LENGTH: 758
<212> TYPE: DNA
<213> ORGANISM: Lycopersicon esculentum
<220> FEATURE:
<223> OTHER INFORMATION: tomato 12624037 EST469495

<400> SEQUENCE: 44
gcttgagaaa ggaagtccaa tcaaagagtg ggaaaaaaga aagaagcaag gatgcaatgg      60
actcattgaa ctacgaagca gtcagaagtg cagcagttaa agaaatttct gatgctatta     120
aggaacgagg gatgaacaac atgctggcag agcgaattaa ggacttcctc gatagactgg     180
tgagggatca tggaagtatt gacctagaat ggttgagaga tgtggcccca gacaaagcga     240
aagagtatct tttgagtatt cgtggactgg gtctgaaaag tgtagaatgt gtgcggctat     300
taacacttca taaccttgct tttccagttg acacaaatgt tggacgaata gctgtgagat     360
taggatgggt tcctctccaa ccacttcctg agtccctgca gttgcatctt cttgaactgt     420
atccaattct ggagtcaatt cagaagtatc tctggccacg actctgcaag ctcgatcaga     480
gaacactgta tgagttgcac taccacatga ttacctttgg aaaggttttc tgcaccaaaa     540
gtaagcctaa ctgtaatgca tgcccactga gagctgaatg cagacacttt gctagtgctt     600
acgcaagtgc aagacttgcc cttcctggcc cagaggagaa gagtatagtg agttcagcag     660
ttccgatccc tagtgaggga aatgcagctg ccgcattcaa gcccatgcta ttaccccag      720
agctgaagta gggatggcgt acccatatgc tccaattg                             758
```

-continued

<210> SEQ ID NO 45
<211> LENGTH: 203
<212> TYPE: PRT
<213> ORGANISM: Hordeum vulgare
<220> FEATURE:
<223> OTHER INFORMATION: barley 13256964
<221> NAME/KEY: MOD_RES
<222> LOCATION: (1)..(203)
<223> OTHER INFORMATION: Xaa = any amino acid

<400> SEQUENCE: 45

```
Met Ala Ser Glu Thr Glu Thr Phe Ala Phe Gln Ala Glu Ile Asn Gln
  1               5                  10                  15

Leu Leu Ser Leu Ile Ile Asn Thr Phe Tyr Ser Asn Lys Glu Ile Phe
             20                  25                  30

Leu Arg Glu Leu Ile Ser Asn Ala Ser Asp Ala Leu Asp Lys Ile Arg
         35                  40                  45

Phe Glu Ser Leu Thr Asp Lys Ser Lys Leu Asp Ala Gln Pro Glu Leu
     50                  55                  60

Phe Ile His Ile Ile Pro Asp Lys Ala Thr Asn Thr Leu Thr Leu Ile
 65                  70                  75                  80

Asp Ser Gly Ile Gly Met Thr Lys Ser Asp Leu Val Asn Asn Leu Gly
                 85                  90                  95

Thr Ile Ala Arg Ser Gly Thr Lys Asp Phe Met Glu Ala Leu Ala Ala
            100                 105                 110

Gly Ala Asp Val Ser Met Ile Gly Gln Phe Gly Val Gly Phe Tyr Ser
        115                 120                 125

Ala Tyr Pro Cys Ala Glu Arg Val Xaa Val Thr Ser Lys His Asn Asp
    130                 135                 140

Asp Glu Gln Tyr Gly Gly Glu Xaa Gln Ala Gly Trp Leu Leu Tyr Cys
145                 150                 155                 160

Gly His Val Ile Leu Leu Glu Ser Pro Phe Gly Val Leu Arg Ser
                165                 170                 175

Pro Ser Thr Ser Arg Thr Asn Ser Trp Ser Thr Leu Glu Arg Arg Ala
            180                 185                 190

Phe Lys Asp Leu Gly Lys Asn Thr Pro Ser Ser
        195                 200
```

<210> SEQ ID NO 46
<211> LENGTH: 883
<212> TYPE: DNA
<213> ORGANISM: Hordeum vulgare
<220> FEATURE:
<223> OTHER INFORMATION: barley 13256964 HVSMEi0014B12f
<221> NAME/KEY: modified_base
<222> LOCATION: (1)..(883)
<223> OTHER INFORMATION: n = g, a, c or t

<400> SEQUENCE: 46

```
cgagaacccc gctccaaagc cctaacccta ggccatcccc tctccctccc ctcaaccctc      60
gtcgactccg cgcgcgcctg cgttccagga gcttccgctg ccggcggcgc catggcctca     120
gagaccgaga ccttcgcctt ccaggcggag atcaaccagc tgctctcgct catcatcaac     180
accttctact ccaacaagga gatcttcctc cgcgagctca tctccaacgc ctccgatgcg     240
ttggataaga tcaggtttga gagcctcact gacaagagca agctggatgc tcagccagag     300
ctgttcatcc acattatccc tgacaaggcc accaacacac tcaccctat cgacagtggc      360 attggtatga ccaagtcaga cctcgtgaac aaccttggta ccattgcaag gtctggcacc     420
```

-continued

```
aaggatttca tggaggcatt ggctgctggt gccgatgtgt ccatgattgg tcagtttggt      480
gttggtttct actctgctta cccttgtgct gagagagtcg ntgtgaccag caagcacaac      540
gatgacgagc agtatggggg ggagtnccag gctgggtggc ttctttactg tggacacgtg      600
atactcttgg agagccccctt tggaggggta ctaagatccc cctctacctc aaggacgaac     660
agttggagta ccttggagag gcgcgccttt aaggatttgg ggaaaaacac tccgagttca      720 taacttttc atctcctctg gacggggaaa accctgaaa aggaattttt gcgctggaaa        780
gtgggtggaa aaatgggttc ctgggggggc ccggttgagg gattgttggt cacataaaca      840
actatcgtct tctatcttag cacctaatag tccttcacat gag                        883
```

<210> SEQ ID NO 47
<211> LENGTH: 164
<212> TYPE: PRT
<213> ORGANISM: Zea mays
<220> FEATURE:
<223> OTHER INFORMATION: corn BE511860

<400> SEQUENCE: 47

```
Leu Leu Glu Gly Phe Glu Gln Arg Glu Pro Asp Asp Pro Cys Pro Tyr
 1               5                  10                  15

Leu Leu Ser Ile Trp Thr Pro Gly Glu Thr Ala Gln Ser Ile Asp Ala
            20                  25                  30

Pro Lys Thr Phe Cys Asp Ser Gly Glu Thr Gly Arg Leu Cys Gly Ser
        35                  40                  45

Ser Thr Cys Phe Ser Cys Asn Asn Ile Arg Glu Met Gln Ala Gln Lys
    50                  55                  60

Val Arg Gly Thr Leu Leu Ile Pro Cys Arg Thr Ala Met Arg Gly Ser
65                  70                  75                  80

Phe Pro Leu Asn Gly Thr Tyr Phe Gln Val Asn Glu Val Phe Ala Asp
                85                  90                  95

His Cys Ser Ser Gln Asn Pro Ile Asp Val Pro Arg Ser Trp Ile Trp
            100                 105                 110

Asp Leu Pro Arg Arg Thr Val Tyr Phe Gly Thr Ser Val Pro Thr Ile
        115                 120                 125

Phe Arg Gly Leu Thr Thr Glu Glu Ile Gln Arg Cys Phe Trp Arg Gly
    130                 135                 140

Phe Val Cys Val Arg Gly Phe Asp Arg Thr Val Arg Ala Pro Arg Ala
145                 150                 155                 160

Leu Tyr Ala Arg
```

<210> SEQ ID NO 48
<211> LENGTH: 517
<212> TYPE: DNA
<213> ORGANISM: Zea mays
<220> FEATURE:
<223> OTHER INFORMATION: corn BE511860 EST946063H01.Y1 946

<400> SEQUENCE: 48

```
tatgaactgc cagattcaca cgcctcttct ggaaggattc gaacagagag aaccagatga      60
tccctgtcca tatcttcttt ccatatggac cccaggtgaa actgcacaat cgatcgatgc     120
ccccaagaca ttctgtgatt caggggagac gggtagacta tgtggaagtt caacatgctt     180
tagttgcaac aatatacgag aaatgcaggc tcagaaagtc agaggaacac ttttgatacc     240
atgccgaaca gcaatgagag gaagcttccc acttaatggg acgtattttc aagttaatga     300
```

-continued

| | |
|---|---|
| ggtatttgct gaccattgct caagtcaaaa tccaattgat gtcccacgaa gttggatttg | 360 |
| ggacctccca agacgaactg tttactttgg aacctcagtt cctacaatat tcagaggttt | 420 |
| aacgactgaa gagatacaac gatgcttttg gagaggattt gtttgcgtga ggggctttga | 480 |
| taggacagtg cgggcaccaa gggcccttta tgcaagg | 517 |

<210> SEQ ID NO 49
<211> LENGTH: 137
<212> TYPE: PRT
<213> ORGANISM: Gossypium arboreum
<220> FEATURE:
<223> OTHER INFORMATION: cotton 11206330

<400> SEQUENCE: 49

Met Gln Gly Asn Met Glu Leu Gln Glu Gly Asp Leu Ser Lys Ala Leu
1               5                   10                  15

Val Ala Leu Asn Pro Asp Ala Ala Ser Ile Pro Thr Pro Lys Leu Lys
            20                  25                  30

Asn Val Ser Arg Leu Arg Thr Glu His Tyr Val Tyr Glu Leu Pro Asp
        35                  40                  45

Lys His Pro Leu Leu Lys Gln Met Glu Lys Arg Glu Pro Asp Asp Pro
    50                  55                  60

Ser Pro Tyr Leu Leu Ala Ile Trp Thr Pro Gly Glu Thr Ala Asn Ser
65                  70                  75                  80

Ile Gln Pro Pro Glu Gln Ser Cys Gly Ser Gln Glu Pro Gly Arg Leu
                85                  90                  95

Cys Asn Glu Lys Thr Cys Phe Ala Cys Asn Ser Val Arg Glu Ala Asn
            100                 105                 110

Thr Glu Thr Val Arg Gly Thr Ile Leu Ile Pro Cys Arg Asn Ala Met
        115                 120                 125

Arg Gly Ser Phe Ser Leu Asn Gly Thr
    130                 135

<210> SEQ ID NO 50
<211> LENGTH: 766
<212> TYPE: DNA
<213> ORGANISM: Gossypium arboreum
<220> FEATURE:
<223> OTHER INFORMATION: cotton 11206330 GA_Eb0023J04f

<400> SEQUENCE: 50

| | |
|---|---|
| ctccgccagt gcataacttg cttaaagtag ggcctaatgt tggcaacaat gaacctatca | 60 |
| ttgaggagcc tgcaacacct gaaccagagc atgcagaagg atcagagagt gatattgaag | 120 |
| atgcaagcta tgatgatcca gatgaaattc ccacaataaa actcaacatt gaagagttca | 180 |
| cagcaaacct acagcattac atgcagggca atatggaact ccaagaaggg gacttgtcaa | 240 |
| aggctttagt agctttgaat cctgatgctg cttctatccc tactccaaaa ttgaagaatg | 300 |
| taagcaggct acgaacagag cactatgtat atgagcttcc agataaacat cctctcttga | 360 |
| aacagatgga aaagcgggaa cctgatgatc ctagccccta tcttcttgca atatggacac | 420 |
| caggtgaaac tgcaaactca attcaaccac agaacaaag ttgtgggtcc caagaaccag | 480 |
| gaagactgtg caatgagaag acctgctttg cttgcaacag tgtaagagaa gctaacactg | 540 |
| agacagtccg aggaaccatc ttgataccttt gtagaaatgc aatgagagga agcttttccc | 600 |
| ttaatgggac ttaattttca agttaatgag gtcttttgca gatcatgaat caagcctcaa | 660 |
| cccaatcgac gttccaaggg gaatggattg ggaatttaac aagaacgaac tgtatacttg | 720 |

```
gaacatcctg gttcatcaat atttaaagga cttttcgacg agggaa          766
```

<210> SEQ ID NO 51
<211> LENGTH: 179
<212> TYPE: PRT
<213> ORGANISM: Glycine max
<220> FEATURE:
<223> OTHER INFORMATION: soybean 5606759
<221> NAME/KEY: MOD_RES
<222> LOCATION: (167)
<223> OTHER INFORMATION: Xaa = His or Gln

<400> SEQUENCE: 51

```
Met Gly Trp Val Pro Leu Gln Pro Leu Pro Glu Ser Leu Gln Leu His
 1               5                  10                  15

Leu Leu Glu Leu Tyr Pro Val Leu Glu Ser Ile Gln Lys Tyr Leu Trp
            20                  25                  30

Pro Arg Leu Cys Lys Leu Asp Gln Glu Thr Leu Tyr Glu Leu His Tyr
        35                  40                  45

Gln Met Ile Thr Phe Gly Lys Val Phe Cys Thr Lys Ser Lys Pro Asn
    50                  55                  60

Cys Asn Ala Cys Pro Met Arg Ala Glu Cys Arg His Phe Ala Ser Ala
65                  70                  75                  80

Phe Ala Ser Ala Arg Phe Ala Leu Pro Gly Pro Glu Gln Lys Ser Ile
                85                  90                  95

Val Ser Thr Thr Gly Asn Ser Val Ile Asn Gln Asn Pro Ser Glu Ile
            100                 105                 110

Ile Ser Gln Leu His Leu Pro Pro Glu Asn Thr Ala Gln Glu Asp
        115                 120                 125

Glu Ile Gln Leu Thr Glu Val Ser Arg Gln Leu Glu Ser Lys Phe Glu
    130                 135                 140

Ile Tyr Ile Cys Gln Pro Ile Ile Glu Glu Pro Arg Thr Pro Glu Pro
145                 150                 155                 160

Glu Cys Leu Gln Glu Ser Xaa Thr Asp Ile Glu Asp Ala Val Tyr Glu
                165                 170                 175

Asp Ser Ser
```

<210> SEQ ID NO 52
<211> LENGTH: 583
<212> TYPE: DNA
<213> ORGANISM: Glycine max
<220> FEATURE:
<223> OTHER INFORMATION: soybean 5606759 sb95c12.y1
<221> NAME/KEY: modified_base
<222> LOCATION: (546)
<223> OTHER INFORMATION: n = g, a, c or t

<400> SEQUENCE: 52

```
acgagcttcc cggtagacac aaatgtcgga cgtattgccg tacgactggg atgggtgcct    60
ctgcagccac tgcctgagtc actgcagttg catctcctag aattgtaccc ggtgttggag   120
tcaatacaaa aatatctctg gcctcgactg tgcaagctag atcaggaaac actatatgag   180
ctacattacc agatgattac atttggaaag gtcttctgta caaaaagcaa accaaattgt   240
aatgcatgcc caatgagagc agaatgtaga cactttgcta gtgcatttgc aagtgcaagg   300
tttgcactgc ctggaccaga gcagaagagt atagttagca caactggaaa tagtgtgatt   360
aaccagaacc catctgaaat catcagtcag ttgcacttgc ctccacctga gaacacagcc   420
caagaagatg aaattcaact aacagaagtg agcagacaat tggaatcaaa atttgaaata   480
```

```
tatatttgcc aacctatcat tgaagagccc agaactccag agccagaatg cttgcaagaa    540
tcacanactg atatagagga tgctgtctat gaggattcaa gtg                     583
```

<210> SEQ ID NO 53
<211> LENGTH: 155
<212> TYPE: PRT
<213> ORGANISM: Triticum aestivum
<220> FEATURE:
<223> OTHER INFORMATION: wheat 12019155

<400> SEQUENCE: 53

```
Met Phe His Cys His Gly Thr Arg Gly Ser Asp Leu Gly Phe Asp Leu
  1               5                  10                  15

Asn Lys Thr Pro Glu Gln Lys Ala Pro Gln Arg Arg Lys His Arg Pro
                 20                  25                  30

Lys Val Ile Lys Glu Ala Lys Pro Lys Ser Thr Arg Lys Pro Ala Thr
             35                  40                  45

Gln Lys Thr Gln Met Lys Glu Asn Pro His Lys Lys Arg Lys Tyr Val
         50                  55                  60

Arg Lys Thr Ala Ala Thr Pro Gln Thr Asn Val Thr Glu Glu Ser Val
 65                  70                  75                  80

Asp Ser Ile Val Ala Thr Lys Lys Ser Cys Arg Arg Ala Leu Asn Phe
                 85                  90                  95

Asp Leu Glu His Asn Lys Tyr Ala Ser Gln Ser Thr Ile Ser Cys Gln
                100                 105                 110

Gln Glu Ile Asp His Arg Asn Glu Lys Ala Phe Asn Thr Thr Ser Asp
            115                 120                 125

His Lys Ala Lys Glu Pro Lys Asn Thr Asp Asp Asn Thr Leu Leu Leu
        130                 135                 140

His Glu Lys Gln Ala Asn Asn Phe Gln Ser Glu
145                 150                 155
```

<210> SEQ ID NO 54
<211> LENGTH: 902
<212> TYPE: DNA
<213> ORGANISM: Triticum aestivum
<220> FEATURE:
<223> OTHER INFORMATION: wheat 12019155 ESTBRY_901
<221> NAME/KEY: modified_base
<222> LOCATION: (1)..(902)
<223> OTHER INFORMATION: n = g, a, c or t

<400> SEQUENCE: 54

```
aacagtcagg acaaaggcaa caagatcagc agtcaggaca agggcagcaa ccgggacaaa    60
ggcagccagg gtactactca acttctccgc aacaattagg acaaggccaa ccaaggtact   120
acccaacttc tccgcagcag ccaggacaag agcagcagcc aagacaattg caacaaccag   180
aacaagggca acaaggtcag cagccagaac aagggcagca aggtcagcag caaagacaag   240
gggagcaagg tcagcagcca ggacaagggc aacaagggca gcaaccggga caagggcagc   300
cagggtacta cccaacttct ccgcagcagt caggacaagg caaccagggg tactacccaa   360
cttctccaca gcagtcagga caattgcaac aaccagcaca gggcagcaa ccaggacaag    420 agcaacaagg tcaacagcca ggacaagggc agcaaccggg acaagggcaa gccagggtac   480
tacccaactt ctccgcagca gtcaggacaa gagcaacagc tagaacaatg gcaacagtca   540 ggacagggc aaccagggca ctacccaact tctccgttgc aagccaggac aagggcaacc    600
agggtactac ccaacttctc acaacagata ggacaagggc agcagccaag aacaatttgc   660
```

```
acaaccaaca caagggcaac aangggcagc aaccaaggac aagggcaac aaggtcaaca    720 gcccangaaa aaaggcaaca aaggtcaagc aaccaagnac aagggcagc aanccaggac    780 aagggcagcc anggtcctac ccaacttntt ttgagcaagt canggaaaag gggcaccanc   840
cnagganaaa tgggnaccac ccagnacaag acaaccccg ggtcttcccc aaanttttn    900 cn                                                                 902
```

```
<210> SEQ ID NO 55
<211> LENGTH: 255
<212> TYPE: PRT
<213> ORGANISM: Lycopersicon esculentum
<220> FEATURE:
<223> OTHER INFORMATION: tomato 8106032
<221> NAME/KEY: MOD_RES
<222> LOCATION: (1)..(255)
<223> OTHER INFORMATION: Xaa = any amino acid

<400> SEQUENCE: 55
```

| | | | | | | | | | | | | | | |
|---|---|---|---|---|---|---|---|---|---|---|---|---|---|---|
| Met | Ser | Leu | Ala | Ala | His | Phe | Pro | Leu | Lys | Thr | Asp | Ser | Thr | Gln | Lys |
| 1 | | | | 5 | | | | | 10 | | | | | 15 | |
| His | Glu | Gly | Asn | Thr | Gly | Ile | Ile | Glu | Glu | Pro | Glu | Glu | Cys | Ala |
| | | | 20 | | | | | 25 | | | | | 30 | |
| Thr | Asp | Pro | Asn | Val | Ser | Ile | Arg | Trp | Tyr | Glu | Asp | Gln | Pro | Asn | Gln |
| | | 35 | | | | | 40 | | | | | 45 | | | |
| Ser | Thr | His | Cys | Gln | Asp | Ser | Ser | Gly | Val | Tyr | Asn | Thr | Asp | Ser | Asn |
| | 50 | | | | | 55 | | | | | 60 | | | | |
| Glu | Glu | Lys | Pro | Ala | Val | Asn | Asp | Ser | Glu | Ser | Ser | Glu | Asn | Ser | Thr |
| 65 | | | | | 70 | | | | | 75 | | | | | 80 |
| Glu | Cys | Ile | Lys | Ser | Ala | Glu | Cys | Ser | Val | Ile | Leu | Gln | Ser | Asp | Ser |
| | | | | 85 | | | | | 90 | | | | | 95 | |
| Ser | Arg | Glu | Gly | Ser | Asp | Leu | Tyr | His | Gly | Ser | Thr | Val | Thr | Ser | Ser |
| | | | 100 | | | | | 105 | | | | | 110 | | |
| Gln | Asp | Arg | Lys | Glu | Leu | Asn | Asp | Leu | Pro | Ser | Ser | Pro | Ser | Ser | Val |
| | | | 115 | | | | | 120 | | | | | 125 | | |
| Val | Ser | Ser | Glu | Ile | Ser | Ala | Val | Ile | Gln | Ala | Ser | Glu | Gly | Thr | Asp |
| | 130 | | | | | 135 | | | | | 140 | | | | |
| Ser | Ser | Asn | Phe | Cys | Ser | Ser | Thr | Ser | Phe | Leu | Lys | Leu | Leu | Gln | Met |
| 145 | | | | | 150 | | | | | 155 | | | | | 160 |
| Ala | Gly | Thr | Ser | Gly | Ala | Gln | Gly | Thr | Arg | Cys | Thr | Glu | His | Leu | His |
| | | | | 165 | | | | | 170 | | | | | 175 | |
| Asn | Gln | His | Lys | Gly | Asn | Xaa | Gly | Gln | Gln | Pro | Arg | Thr | Xaa | Gly | Asn |
| | | | 180 | | | | | 185 | | | | | 190 | | |
| Lys | Val | Asn | Ser | Pro | Xaa | Lys | Lys | Ala | Thr | Lys | Val | Lys | Gln | Pro | Xaa |
| | | | 195 | | | | | 200 | | | | | 205 | | |
| Thr | Arg | Gly | Ser | Xaa | Pro | Gly | Gln | Gly | Gln | Pro | Xaa | Ser | Tyr | Pro | Thr |
| | | 210 | | | | | 215 | | | | | 220 | | | |
| Xaa | Phe | Glu | Gln | Val | Xaa | Glu | Lys | Gly | His | Xaa | Pro | Arg | Xaa | Asn | Gly |
| 225 | | | | | 230 | | | | | 235 | | | | | 240 |
| Xaa | His | Pro | Xaa | Gln | Gly | Gln | Pro | Arg | Val | Phe | Pro | Lys | Xaa | Phe |
| | | | | 245 | | | | | 250 | | | | | 255 | |

```
<210> SEQ ID NO 56
<211> LENGTH: 589
<212> TYPE: DNA
<213> ORGANISM: Lycopersicon esculentum
<220> FEATURE:
<223> OTHER INFORMATION: tomato 8106032 EST356474
```

<400> SEQUENCE: 56

```
ctcgtgccgg ttgggggtata tcttacacag aatgtttcag atcacctttc tagttctgca       60
ttcatgtcac tcgctgccca ctttcctctg aaaacagaca gtactcagaa gcatgaagga      120
aatacaggta ttataattga agaacctgaa gagtgtgcaa cagaccccaa tgtttccatc      180
agatggtatg aagatcaacc aaatcagtca acccattgtc aggattcttc aggagtctat      240
aatacagatt caaatgaaga aaaaccagct gtcaatgact ctgaatcaag tgaaaatagc      300
acagaatgca taaaatcagc agaatgttct gtaattctgc aatcagattc ttctagagaa      360
ggctcagatc tgtatcatgg atcaacagtt acaagttccc aagatcgaaa agagttgaat      420
gatttgcctt cttctccgag ttctgttgtt tcttctgaga tctctgctgt tattcaagct      480
tcagaaggaa ctgactcaag caacttttgc agctccactt cttttttgaa gctattacag      540
atggcaggaa cttcaggagc acaaggaacc aggtgcactg aacatctac                  589
```

<210> SEQ ID NO 57
<211> LENGTH: 179
<212> TYPE: PRT
<213> ORGANISM: Zea mays
<220> FEATURE:
<223> OTHER INFORMATION: corn AW042334

<400> SEQUENCE: 57

```
Asp Ala His Pro Leu Leu Gln Gln Leu Gly Leu Asp Gln Arg Glu His
 1               5                  10                  15

Asp Asp Pro Thr Pro Tyr Leu Leu Ala Ile Trp Thr Pro Asp Gly Ile
            20                  25                  30

Lys Glu Ile Thr Lys Thr Pro Lys Pro Cys Cys Asp Pro Gln Met Gly
        35                  40                  45

Gly Asp Leu Cys Asn Asn Glu Met Cys His Asn Cys Thr Ala Glu Lys
    50                  55                  60

Glu Asn Gln Ser Arg Tyr Val Arg Gly Thr Ile Leu Val Pro Cys Arg
65                  70                  75                  80

Thr Ala Met Arg Gly Ser Phe Pro Leu Asn Gly Thr Tyr Phe Gln Val
                85                  90                  95

Asn Glu Val Phe Ala Asp His Arg Ser Ser His Asn Pro Ile His Val
            100                 105                 110

Glu Arg Glu Met Leu Trp Asn Leu Gln Arg Arg Met Val Phe Phe Gly
        115                 120                 125

Thr Ser Val Pro Thr Ile Phe Lys Gly Leu Arg Thr Glu Glu Ile Gln
    130                 135                 140

Gln Cys Phe Trp Arg Gly Phe Val Cys Val Arg Gly Phe Asp Met Glu
145                 150                 155                 160

Thr Arg Ala Pro Arg Pro Leu Cys Pro His Leu His Val Ile Ala Arg
                165                 170                 175

Pro Lys Ala
```

<210> SEQ ID NO 58
<211> LENGTH: 595
<212> TYPE: DNA
<213> ORGANISM: Zea mays
<220> FEATURE:
<223> OTHER INFORMATION: corn AW042334 EST614027C01.y1 614

<400> SEQUENCE: 58

```
gaattcggca ccagcagatg cacatccact tttacaacag ctaggacttg accaacggga       60
```

| | |
|---|---|
| acatgatgat cctaccccat acttattggc catatggaca ccagatggaa taaaggaaat | 120 |
| aactaagaca ccaaaaccat gctgtgaccc tcaaatggga ggcgatttat gcaataatga | 180 |
| aatgtgccac aattgtactg cagagaaaga aaaccaatct agatatgtca gaggcacaat | 240 |
| tctggttcct tgtcgaacag ctatgagggg tagtttccca cttaatggca cttactttca | 300 |
| agtcaatgag gtatttgctg accacagatc tagccacaac ccaatccatg tggaaaggga | 360 |
| gatgctatgg aacttgcaaa ggcgcatggt cttttcggg acttcagtac ccaccatatt | 420 |
| caaaggtcta agaacagaag aaatacaaca atgcttctgg aggggatttg tctgtgtgcg | 480 |
| aggattcgac atggagacta gagcaccaag gcctctgtgc ccccatttgc acgttatagc | 540 |
| aaggccgaaa gcccgcaaga cagcagcaac tgagcaagta ctctaatcag caaag | 595 |

<210> SEQ ID NO 59
<211> LENGTH: 150
<212> TYPE: PRT
<213> ORGANISM: Zea mays
<220> FEATURE:
<223> OTHER INFORMATION: corn AW076298

<400> SEQUENCE: 59

Pro Cys Arg Thr Ala Met Arg Gly Ser Phe Pro Leu Asn Gly Thr Tyr
 1               5                  10                  15

Phe Gln Val Asn Glu Val Phe Ala Asp His Cys Ser Ser Gln Asn Pro
            20                  25                  30

Ile Asp Val Pro Arg Ser Trp Ile Trp Asp Leu Pro Arg Arg Thr Val
        35                  40                  45

Tyr Phe Gly Thr Ser Val Pro Thr Ile Phe Arg Gly Leu Ser Thr Glu
    50                  55                  60

Gln Ile Gln Phe Cys Phe Trp Lys Gly Phe Val Cys Val Arg Gly Phe
65                  70                  75                  80

Glu Gln Lys Thr Arg Ala Pro Arg Pro Leu Met Ala Arg Leu His Phe
                85                  90                  95

Pro Ala Ser Lys Leu Lys Asn Asn Lys Leu Thr Thr Glu Glu Ile Gln
            100                 105                 110

Gln Cys Phe Trp Arg Gly Phe Val Cys Val Arg Gly Phe Asp Arg Thr
        115                 120                 125

Val Arg Ala Pro Arg Pro Leu Tyr Ala Arg Leu His Phe Pro Ala Ser
    130                 135                 140

Lys Val Val Arg Gly Lys
145                 150

<210> SEQ ID NO 60
<211> LENGTH: 640
<212> TYPE: DNA
<213> ORGANISM: Zea mays
<220> FEATURE:
<223> OTHER INFORMATION: corn AW076298 EST614065C03.y1 614

<400> SEQUENCE: 60

| | |
|---|---|
| cggccccaga ccatgccgga cagcaatgag aggaagcttc ccacttaatg ggacatattt | 60 |
| tcaagttaat gaggtatttg ctgaccattg ttcaagccaa atccaattg atgtcccacg | 120 |
| aagttggata tgggacctcc caagacgaac tgtttacttt ggaacctcag ttcctacaat | 180 |
| atttagaggt ttaacgactg aagagataca acaatgcttt tggagaggat cgtttgtgt | 240 |
| gaggggcttt gataggacag taaggggcacc aaggcccctt tatgcaaggt tgcattttcc | 300 |
| tgccagcaag gttgttagag gcaaaaagcc tggagcggca agcgtcgaag aataataggt | 360 |

```
acatcgaaga aatatagagg agctaacaaa acggatggat agccctaaat gagatgctga    420
cccaataagt cgccgaatca cctccaagtt ctaacccaat ttttgaggcg acatgacctg    480
ttaaattatg ttccatctat ggtaacagct tagatgttct tgtgagtcgc atattcttta    540
ctctgaaatt caatatagca aatgaaaaaa aacacagtgc atagtctagt tctaattgta    600
cctgtgagtg gaatcagttg ttgtacaaca tgaagatggg                         640
```

<210> SEQ ID NO 61
<211> LENGTH: 140
<212> TYPE: PRT
<213> ORGANISM: Zea mays
<220> FEATURE:
<223> OTHER INFORMATION: corn BE639158

<400> SEQUENCE: 61

```
Lys Asn Ser Glu Pro Ile Ile Glu Glu Pro Ala Ser Pro Arg Glu Glu
 1               5                  10                  15

Arg Pro Pro Glu Thr Met Glu Asn Asp Ile Glu Asp Phe Tyr Glu Asp
            20                  25                  30

Gly Glu Ile Pro Thr Ile Lys Leu Asn Met Glu Ala Phe Ala Gln Asn
        35                  40                  45

Leu Glu Asn Cys Ile Lys Glu Ser Asn Asn Glu Leu Gln Ser Asp Asp
    50                  55                  60

Ile Ala Lys Ala Leu Val Ala Ile Ser Thr Glu Ala Ala Ser Ile Pro
65                  70                  75                  80

Val Pro Lys Leu Lys Asn Val Leu Arg Leu Arg Thr Glu His Tyr Val
                85                  90                  95

Tyr Glu Leu Pro Asp Ala His Pro Leu Leu Gln Gln Leu Gly Leu Asp
            100                 105                 110

Gln Arg Glu His Asp Asp Pro Thr Pro Tyr Leu Leu Ala Ile Trp Thr
        115                 120                 125

Pro Asp Gly Ile Lys Glu Ile Thr Lys Thr Pro Lys
    130                 135                 140
```

<210> SEQ ID NO 62
<211> LENGTH: 561
<212> TYPE: DNA
<213> ORGANISM: Zea mays
<220> FEATURE:
<223> OTHER INFORMATION: corn BE639158 EST946021E09.y1 946

<400> SEQUENCE: 62

```
tgagctgcat tatcagatga ttacatttgg aaaggtcttt tgtaccaaaa gacagccaaa     60
ttgcaatgca tgctatgaat tcgactcacc tacctcgcct tgaggggagt atccattcaa    120
gggagtttct tcctaagaat tcagagccaa taatcgagga gcctgcaagt ccaagagagg    180
aaagacctcc agaaaccatg gaaatgata ttgaagattt ttatgaagat ggtgaaatcc    240
caacaataaa gcttaacatg gaagcttttg cacaaaactt ggagaattgc attaaagaaa    300
gcaataacga actccagtct gatgatattg caaaagcatt ggttgctatt agcactgaag    360
cagcttcgat tcctgtaccg aaactaaaga atgtgcttag gcttcgaaca gaacactatg    420
tgtatgagct tccagatgca catccacttt tacaacagct aggacttgac caacgggaac    480
atgatgatcc tacccatac ttattggcca tatggacacc agatggaata aaggaaataa    540
ctaagacacc aaaaccatgc t                                              561
```

<210> SEQ ID NO 63
<211> LENGTH: 138
<212> TYPE: PRT
<213> ORGANISM: Zea mays
<220> FEATURE:
<223> OTHER INFORMATION: corn T25243
<221> NAME/KEY: MOD_RES
<222> LOCATION: (63)
<223> OTHER INFORMATION: Xaa = Asp or Glu
<221> NAME/KEY: MOD_RES
<222> LOCATION: (114)
<223> OTHER INFORMATION: Xaa = Cys, Trp, Arg, Ser or Gly

<400> SEQUENCE: 63

Asn His Gln Pro Ile Ile Glu Glu Pro Leu Ser Pro Glu Cys Glu Thr
 1               5                  10                  15

Glu Asn Ile Glu Ala His Glu Gly Ala Ile Glu Asp Phe Phe Cys Glu
            20                  25                  30

Glu Ser Asp Glu Ile Pro Thr Ile Asn Leu Asn Ile Glu Glu Phe Thr
        35                  40                  45

Gln Asn Leu Lys Asp Tyr Met Gln Ala Asn Asn Val Glu Ile Xaa Tyr
    50                  55                  60

Ala Asp Met Ser Lys Ala Leu Val Ala Ile Thr Pro Asp Ala Ala Ser
65                  70                  75                  80

Ile Pro Thr Pro Lys Leu Lys Asn Val Asn Arg Leu Arg Thr Glu His
                85                  90                  95

Gln Val Tyr Glu Leu Pro Asp Ser His Pro Leu Leu Glu Gly Phe Glu
            100                 105                 110

Gln Xaa Glu Pro Asp Asp Pro Cys Pro Tyr Leu Leu Ser Ile Trp Thr
        115                 120                 125

Pro Gly Glu Leu His Asn Arg Ser Met Pro
    130                 135

<210> SEQ ID NO 64
<211> LENGTH: 422
<212> TYPE: DNA
<213> ORGANISM: Zea mays
<220> FEATURE:
<223> OTHER INFORMATION: corn T25243 EST5c10h02
<221> NAME/KEY: modified_base
<222> LOCATION: (1)..(422)
<223> OTHER INFORMATION: n = g, a, c or t

<400> SEQUENCE: 64
ctggtaatca tcagccaatc atcgaggaac cactgagccc agaatgtgaa actgaaaata      60
tagaggcaca tgagggtgca attgaggatt tcttttgtga agaatctgat gaaattccta     120
ccattaatct taatatcgag gagttcacac aaaacttgaa ggactatatg caagcaaaca     180
atgttgagat tgantatgct gacatgtcaa aggcattggt tgccatcacg cctgatgctg     240
cttccattcc aactccaaag ctcaagaatg tcaatcgtct gaggacagaa caccaagttt     300
atgaactgcc agattcacac cctcttctgg aaggattcga acagngngaa ccagatgatc     360
cctgtccata tcttctttcc atatggaccc caggtgaact gcacaatcga tcgatgcccc     420
aa                                                                    422

<210> SEQ ID NO 65
<211> LENGTH: 89
<212> TYPE: PRT
<213> ORGANISM: Zea mays
<220> FEATURE:
<223> OTHER INFORMATION: corn AW453174

```
<400> SEQUENCE: 65

Phe Gln Gly Asn Glu Val Phe Ala Asp His Cys Ser Arg Gln Asn Pro
 1               5                  10                  15

Ile Asp Gly Pro Arg Ser Trp Ile Trp Asp Leu Pro Arg Arg Thr Gly
                20                  25                  30

Tyr Phe Gly Thr Ser Gly Pro Thr Ile Phe Arg Gly Leu Thr Thr Glu
            35                  40                  45

Glu Ile Gln Arg Cys Phe Trp Arg Gly Phe Val Cys Val Arg Gly Phe
 50                  55                  60

Asp Arg Thr Val Arg Ala Pro Arg Pro Leu Tyr Ala Arg Leu His Phe
 65                  70                  75                  80

Pro Val Ser Lys Val Val Arg Gly Lys
                85

<210> SEQ ID NO 66
<211> LENGTH: 488
<212> TYPE: DNA
<213> ORGANISM: Zea mays
<220> FEATURE:
<223> OTHER INFORMATION: corn AW453174 EST 660032D01.y1 660

<400> SEQUENCE: 66
catgccgaac agcaatgaga ggaagcttcc cacttaatgg gacgattttc aaggtaatga        60
ggtatttgct gaccattgct caaggcaaaa tccaattgat ggcccacgaa gttggatttg       120
ggaccttcca agacgaactg gttactttgg aacctcaggt cctacaatat tcagagggtt       180
aacgactgaa gagatacaac gatgcttttg gagaggattt gtttgcgtga ggggctttga       240
taggacagtg cgggcaccaa ggcccctttta tgcaaggttg cattttcctg tcagcaaggt       300
tgttagaggc aaaaagcctg gagcagcaag agcagaagaa taatagaaca ttgaagaaat       360
ataggggtgc taaccagatg aggatggata gcccgaaatg agatgctgac ccaataggtc       420
gccaaatcac ctccaaattc taacccaatg acttccatct gtaatgaatg gcaataccttt      480
gaaaacct                                                                488

<210> SEQ ID NO 67
<211> LENGTH: 93
<212> TYPE: PRT
<213> ORGANISM: Zea mays
<220> FEATURE:
<223> OTHER INFORMATION: corn BE509759

<400> SEQUENCE: 67

Asn Gly Thr Tyr Phe Gln Val Asn Glu Val Phe Ala Asp His Arg Ser
 1               5                  10                  15

Ser His Asn Pro Ile His Val Glu Arg Glu Met Leu Trp Asn Leu Gln
                20                  25                  30

Arg Arg Met Val Phe Phe Gly Thr Ser Val Pro Thr Ile Phe Lys Gly
            35                  40                  45

Leu Arg Thr Glu Glu Ile Gln Gln Cys Phe Trp Arg Gly Phe Val Cys
 50                  55                  60

Val Arg Gly Phe Asp Met Glu Thr Arg Ala Pro Arg Pro Leu Cys Pro
 65                  70                  75                  80

His Leu His Ile Ile Ala Arg Pro Lys Ala Arg Lys Thr
                85                  90

<210> SEQ ID NO 68
<211> LENGTH: 570
```

```
<212> TYPE: DNA
<213> ORGANISM: Zea mays
<220> FEATURE:
<223> OTHER INFORMATION: corn BE509759 EST946021E09.x1 946

<400> SEQUENCE: 68
tggcatctta catggactaa cagctagatg ctaatttaca tacagtagat ctgaaacaaa      60
aaagtgaaaa ttattggtgc ttcctgatgc ttcattagtc ctctcgtctc agaaactaac     120
agtctcggac cccatccatg gcttaaattt cctaaacaat ggctcttttt taggcaggaa     180
gtaatatgat tccatgcata ggtcgagagc tattgatgtc atatcacaat aaacatgatg     240
ttcataaaac tgatatcttt gctgattaga gtacttgctc agttgctgct gtcttgcggg     300
ccttcggcct tgctataatg tgcaaatggg ggcacagagg ccttggtgct ctagtctcca     360
tgtcgaatcc tcgcacacag acaaatcccc tccagaagca ttgttgtatt tcttctgttc     420
ttagaccttt gaatatggtg ggtactgaag tcccgaaaaa gaccatgcgc ctttgcaagt     480
tccatagcat ctccctttcc acatggattg ggttgtggct agatctgtgg tcagcaaata     540
cctcattgac ttgaaagtaa gtgccattaa                                      570

<210> SEQ ID NO 69
<211> LENGTH: 71
<212> TYPE: PRT
<213> ORGANISM: Zea mays
<220> FEATURE:
<223> OTHER INFORMATION: corn AW017984

<400> SEQUENCE: 69

Val Pro Arg Ser Trp Ile Trp Asp Leu Pro Arg Arg Thr Val Tyr Phe
 1               5                  10                  15

Gly Thr Ser Val Pro Thr Ile Phe Arg Gly Leu Thr Thr Glu Glu Ile
                20                  25                  30

Gln Gln Cys Phe Trp Arg Gly Phe Val Cys Val Arg Gly Phe Asp Arg
            35                  40                  45

Thr Val Arg Ala Pro Arg Pro Leu Tyr Ala Arg Leu His Phe Pro Ala
        50                  55                  60

Ser Lys Val Val Arg Gly Lys
 65                  70

<210> SEQ ID NO 70
<211> LENGTH: 613
<212> TYPE: DNA
<213> ORGANISM: Zea mays
<220> FEATURE:
<223> OTHER INFORMATION: corn AW017984 EST614065C03.x1 614

<400> SEQUENCE: 70
cctgaaacaa tcaaataacg gccgatgagg ttacattgtt tatagtatat gatcaaagaa      60
catgtatgac cattgtacaa ataggcccat cttcatgttg tacaacaact gattccactc     120
acaggtacaa ttagaactag actatgcact gtgttttttt tcatttgcta tattgaattt     180
cagagtaaag aatatgcgac tcacaagaac atctaagctg ttaccataga tggaacataa     240
tttaacaggt catgtcgcct caaaaattgg gttagaactt ggaggtgatt cggcgactta     300
ttgggtcagc atctcattta gggctatcca tccgttttgt tagctcctct atatttcttc     360
gatgtaccta ttattcttcg acgcttgccg ctccaggctt tttgcctcta caaccttgc     420
tggcaggaaa atgcaacctt gcataaaggg gccttggtgc ccttactgtc ctatcaaagc     480
ccctcacaca aacgaatcct ctccaaaagc attgttgtat ctcttcagtc gttaaacctc     540
```

```
taaatattgt aggaactgag gttccaaagt aaacagttcg tcttgggagg tcccatatcc    600
aacttcgtgg gac                                                      613
```

<210> SEQ ID NO 71
<211> LENGTH: 90
<212> TYPE: PRT
<213> ORGANISM: Artificial Sequence
<220> FEATURE:
<223> OTHER INFORMATION: Description of Artificial Sequence:DMT Domain A
      consensus sequence
<221> NAME/KEY: MOD_RES
<222> LOCATION: (3)
<223> OTHER INFORMATION: Xaa = any amino acid
<221> NAME/KEY: MOD_RES
<222> LOCATION: (4)
<223> OTHER INFORMATION: Xaa = Ile or Leu
<221> NAME/KEY: MOD_RES
<222> LOCATION: (6)
<223> OTHER INFORMATION: Xaa = Asp or Pro
<221> NAME/KEY: MOD_RES
<222> LOCATION: (7)
<223> OTHER INFORMATION: Xaa = Glu or Val
<221> NAME/KEY: MOD_RES
<222> LOCATION: (9)..(11)
<223> OTHER INFORMATION: Xaa = any amino acid
<221> NAME/KEY: MOD_RES
<222> LOCATION: (13)
<223> OTHER INFORMATION: Xaa = any amino acid
<221> NAME/KEY: MOD_RES
<222> LOCATION: (14)
<223> OTHER INFORMATION: Xaa = Leu or Val
<221> NAME/KEY: MOD_RES
<222> LOCATION: (16)
<223> OTHER INFORMATION: Xaa = Met or Leu
<221> NAME/KEY: MOD_RES
<222> LOCATION: (17)
<223> OTHER INFORMATION: Xaa = Glu or Asp
<221> NAME/KEY: MOD_RES
<222> LOCATION: (18)..(19)
<223> OTHER INFORMATION: Xaa = any amino acid, Xaa at positions 18 and
      19 may be present or absent
<221> NAME/KEY: MOD_RES
<222> LOCATION: (21)
<223> OTHER INFORMATION: Xaa = Lys or Glu
<221> NAME/KEY: MOD_RES
<222> LOCATION: (22)
<223> OTHER INFORMATION: Xaa = any amino acid
<221> NAME/KEY: MOD_RES
<222> LOCATION: (23)
<223> OTHER INFORMATION: Xaa = Lys or Thr
<221> NAME/KEY: MOD_RES
<222> LOCATION: (24)
<223> OTHER INFORMATION: Xaa = any amino acid
<221> NAME/KEY: MOD_RES
<222> LOCATION: (25)
<223> OTHER INFORMATION: Xaa = Lys or Ala
<221> NAME/KEY: MOD_RES
<222> LOCATION: (26)
<223> OTHER INFORMATION: Xaa = Trp or Lys
<221> NAME/KEY: MOD_RES
<222> LOCATION: (27)
<223> OTHER INFORMATION: Xaa = Trp or Leu
<221> NAME/KEY: MOD_RES
<222> LOCATION: (28)
<223> OTHER INFORMATION: Xaa = any amino acid
<221> NAME/KEY: MOD_RES
<222> LOCATION: (32)..(33)
<223> OTHER INFORMATION: Xaa = any amino acid
<221> NAME/KEY: MOD_RES
<222> LOCATION: (35)
<223> OTHER INFORMATION: Xaa = any amino acid
<221> NAME/KEY: MOD_RES
<222> LOCATION: (36)
<223> OTHER INFORMATION: Xaa = Gly or Thr
<221> NAME/KEY: MOD_RES
<222> LOCATION: (38)

```
<223> OTHER INFORMATION: Xaa = any amino acid
<221> NAME/KEY: MOD_RES
<222> LOCATION: (39)
<223> OTHER INFORMATION: Xaa = Asp or Asn
<221> NAME/KEY: MOD_RES
<222> LOCATION: (40)
<223> OTHER INFORMATION: Xaa = Ser or Leu
<221> NAME/KEY: MOD_RES
<222> LOCATION: (43)
<223> OTHER INFORMATION: Xaa = Ala or Asn
<221> NAME/KEY: MOD_RES
<222> LOCATION: (46)
<223> OTHER INFORMATION: Xaa = His or Arg
<221> NAME/KEY: MOD_RES
<222> LOCATION: (47)
<223> OTHER INFORMATION: Xaa = any amino acid
<221> NAME/KEY: MOD_RES
<222> LOCATION: (48)
<223> OTHER INFORMATION: Xaa = Val or Leu
<221> NAME/KEY: MOD_RES
<222> LOCATION: (51)
<223> OTHER INFORMATION: Xaa = Asp or Asn
<221> NAME/KEY: MOD_RES
<222> LOCATION: (53)
<223> OTHER INFORMATION: Xaa = any amino acid
<221> NAME/KEY: MOD_RES
<222> LOCATION: (55)
<223> OTHER INFORMATION: Xaa = any amino acid
<221> NAME/KEY: MOD_RES
<222> LOCATION: (56)
<223> OTHER INFORMATION: Xaa = Pro or Gln
<221> NAME/KEY: MOD_RES
<222> LOCATION: (66)
<223> OTHER INFORMATION: Xaa = Ile or Val
<221> NAME/KEY: MOD_RES
<222> LOCATION: (74)
<223> OTHER INFORMATION: Xaa = Val or Thr
<221> NAME/KEY: MOD_RES
<222> LOCATION: (76)
<223> OTHER INFORMATION: Xaa = Val or Thr
<221> NAME/KEY: MOD_RES
<222> LOCATION: (77)
<223> OTHER INFORMATION: Xaa = Leu or Ser
<221> NAME/KEY: MOD_RES
<222> LOCATION: (80)
<223> OTHER INFORMATION: Xaa = Ser or Asn
<221> NAME/KEY: MOD_RES
<222> LOCATION: (82)
<223> OTHER INFORMATION: Xaa = Phe or Tyr
<221> NAME/KEY: MOD_RES
<222> LOCATION: (84)
<223> OTHER INFORMATION: Xaa = any amino acid
<221> NAME/KEY: MOD_RES
<222> LOCATION: (85)
<223> OTHER INFORMATION: Xaa = Leu or Val
<221> NAME/KEY: MOD_RES
<222> LOCATION: (87)
<223> OTHER INFORMATION: Xaa = Ala or Ser
<221> NAME/KEY: MOD_RES
<222> LOCATION: (88)
<223> OTHER INFORMATION: Xaa = any amino acid

<400> SEQUENCE: 71

Lys Val Xaa Xaa Asp Xaa Xaa Thr Xaa Xaa Xaa Trp Xaa Xaa Leu Xaa
 1               5                  10                  15

Xaa Xaa Xaa Asp Xaa Xaa Xaa Xaa Xaa Xaa Xaa Xaa Glu Arg Xaa
            20                  25                  30

Xaa Phe Xaa Xaa Arg Xaa Xaa Xaa Phe Ile Xaa Arg Met Xaa Xaa Xaa
        35                  40                  45

Gln Gly Xaa Arg Xaa Phe Xaa Xaa Trp Lys Gly Ser Val Val Asp Ser
    50                  55                  60

Val Xaa Gly Val Phe Leu Thr Gln Asn Xaa Asp Xaa Xaa Ser Ser Xaa
65                  70                  75                  80
```

```
Ala Xaa Met Xaa Xaa Ala Xaa Xaa Phe Pro
            85                  90

<210> SEQ ID NO 72
<211> LENGTH: 230
<212> TYPE: PRT
<213> ORGANISM: Artificial Sequence
<220> FEATURE:
<223> OTHER INFORMATION: Description of Artificial Sequence:DMT Domain B
      consensus sequence
<221> NAME/KEY: MOD_RES
<222> LOCATION: (2)
<223> OTHER INFORMATION: Xaa = Asp or Asn
<221> NAME/KEY: MOD_RES
<222> LOCATION: (3)
<223> OTHER INFORMATION: Xaa = any amino acid
<221> NAME/KEY: MOD_RES
<222> LOCATION: (4)
<223> OTHER INFORMATION: Xaa = Leu or Phe
<221> NAME/KEY: MOD_RES
<222> LOCATION: (6)..(10)
<223> OTHER INFORMATION: Xaa = any amino acid
<221> NAME/KEY: MOD_RES
<222> LOCATION: (12)..(17)
<223> OTHER INFORMATION: Xaa = any amino acid, Xaa at positions 15-17
      may be present or absent
<221> NAME/KEY: MOD_RES
<222> LOCATION: (19)
<223> OTHER INFORMATION: Xaa = Ser or Thr
<221> NAME/KEY: MOD_RES
<222> LOCATION: (20)
<223> OTHER INFORMATION: Xaa = any amino acid
<221> NAME/KEY: MOD_RES
<222> LOCATION: (21)
<223> OTHER INFORMATION: Xaa = Asp or Asn
<221> NAME/KEY: MOD_RES
<222> LOCATION: (22)
<223> OTHER INFORMATION: Xaa = Tyr or Trp
<221> NAME/KEY: MOD_RES
<222> LOCATION: (23)..(25)
<223> OTHER INFORMATION: Xaa = any amino acid
<221> NAME/KEY: MOD_RES
<222> LOCATION: (27)..(36)
<223> OTHER INFORMATION: Xaa = any amino acid
<221> NAME/KEY: MOD_RES
<222> LOCATION: (38)..(39)
<223> OTHER INFORMATION: Xaa = any amino acid
<221> NAME/KEY: MOD_RES
<222> LOCATION: (42)
<223> OTHER INFORMATION: Xaa = Met or Gln
<221> NAME/KEY: MOD_RES
<222> LOCATION: (43)
<223> OTHER INFORMATION: Xaa = Asn or Phe
<221> NAME/KEY: MOD_RES
<222> LOCATION: (44)..(45)
<223> OTHER INFORMATION: Xaa = any amino acid
<221> NAME/KEY: MOD_RES
<222> LOCATION: (47)
<223> OTHER INFORMATION: Xaa = Ala or Ser
<221> NAME/KEY: MOD_RES
<222> LOCATION: (48)
<223> OTHER INFORMATION: Xaa = any amino acid
<221> NAME/KEY: MOD_RES
<222> LOCATION: (51)..(62)
<223> OTHER INFORMATION: Xaa = any amino acid, Xaa at positions 53-62
      may be present or absent
<221> NAME/KEY: MOD_RES
<222> LOCATION: (65)..(67)
<223> OTHER INFORMATION: Xaa = any amino acid
<221> NAME/KEY: MOD_RES
<222> LOCATION: (69)..(70)
<223> OTHER INFORMATION: Xaa = any amino acid
<221> NAME/KEY: MOD_RES
<222> LOCATION: (71)
<223> OTHER INFORMATION: Xaa = His or Asn
<221> NAME/KEY: MOD_RES
<222> LOCATION: (73)
<223> OTHER INFORMATION: Xaa = any amino acid
```

```
<221> NAME/KEY: MOD_RES
<222> LOCATION: (81)..(82)
<223> OTHER INFORMATION: Xaa = any amino acid
<221> NAME/KEY: MOD_RES
<222> LOCATION: (83)
<223> OTHER INFORMATION: Xaa = Pro or Asp
<221> NAME/KEY: MOD_RES
<222> LOCATION: (84)
<223> OTHER INFORMATION: Xaa = Pro or Ser
<221> NAME/KEY: MOD_RES
<222> LOCATION: (85)
<223> OTHER INFORMATION: Xaa = Asp or His
<221> NAME/KEY: MOD_RES
<222> LOCATION: (86)
<223> OTHER INFORMATION: Xaa = any amino acid
<221> NAME/KEY: MOD_RES
<222> LOCATION: (87)
<223> OTHER INFORMATION: Xaa = Ala or Val
<221> NAME/KEY: MOD_RES
<222> LOCATION: (89)
<223> OTHER INFORMATION: Xaa = any amino acid
<221> NAME/KEY: MOD_RES
<222> LOCATION: (90)
<223> OTHER INFORMATION: Xaa = Tyr or Phe
<221> NAME/KEY: MOD_RES
<222> LOCATION: (93)
<223> OTHER INFORMATION: Xaa = Ser or Glu
<221> NAME/KEY: MOD_RES
<222> LOCATION: (94)
<223> OTHER INFORMATION: Xaa = Ile or Phe
<221> NAME/KEY: MOD_RES
<222> LOCATION: (95)
<223> OTHER INFORMATION: Xaa = any amino acid
<221> NAME/KEY: MOD_RES
<222> LOCATION: (97)
<223> OTHER INFORMATION: Xaa = Leu or Ile
<221> NAME/KEY: MOD_RES
<222> LOCATION: (102)
<223> OTHER INFORMATION: Xaa = Val or Ala
<221> NAME/KEY: MOD_RES
<222> LOCATION: (109)
<223> OTHER INFORMATION: Xaa = any amino acid
<221> NAME/KEY: MOD_RES
<222> LOCATION: (111)
<223> OTHER INFORMATION: Xaa = His or Lys
<221> NAME/KEY: MOD_RES
<222> LOCATION: (112)..(113)
<223> OTHER INFORMATION: Xaa = any amino acid
<221> NAME/KEY: MOD_RES
<222> LOCATION: (125)
<223> OTHER INFORMATION: Xaa = Ala or Cys
<221> NAME/KEY: MOD_RES
<222> LOCATION: (128)
<223> OTHER INFORMATION: Xaa = Met or Leu
<221> NAME/KEY: MOD_RES
<222> LOCATION: (130)
<223> OTHER INFORMATION: Xaa = Trp or Leu
<221> NAME/KEY: MOD_RES
<222> LOCATION: (134)
<223> OTHER INFORMATION: Xaa = Gln or Glu
<221> NAME/KEY: MOD_RES
<222> LOCATION: (138)..(139)
<223> OTHER INFORMATION: Xaa = any amino acid
<221> NAME/KEY: MOD_RES
<222> LOCATION: (140)
<223> OTHER INFORMATION: Xaa = Leu or Val
<221> NAME/KEY: MOD_RES
<222> LOCATION: (142)
<223> OTHER INFORMATION: Xaa = Leu or Met
<221> NAME/KEY: MOD_RES
<222> LOCATION: (144)
<223> OTHER INFORMATION: Xaa = Leu or Gln
<221> NAME/KEY: MOD_RES
<222> LOCATION: (146)
<223> OTHER INFORMATION: Xaa = Glu or Phe
<221> NAME/KEY: MOD_RES
<222> LOCATION: (147)
<223> OTHER INFORMATION: Xaa = any amino acid
<221> NAME/KEY: MOD_RES
```

-continued

```
<222> LOCATION: (150)
<223> OTHER INFORMATION: Xaa = any amino acid
<221> NAME/KEY: MOD_RES
<222> LOCATION: (151)
<223> OTHER INFORMATION: Xaa = Leu or Met
<221> NAME/KEY: MOD_RES
<222> LOCATION: (152)
<223> OTHER INFORMATION: Xaa = Glu or Asp
<221> NAME/KEY: MOD_RES
<222> LOCATION: (153)
<223> OTHER INFORMATION: Xaa = Ser or Asn
<221> NAME/KEY: MOD_RES
<222> LOCATION: (154)
<223> OTHER INFORMATION: Xaa = Ile or Val
<221> NAME/KEY: MOD_RES
<222> LOCATION: (166)
<223> OTHER INFORMATION: Xaa = Asp or Pro
<221> NAME/KEY: MOD_RES
<222> LOCATION: (168)
<223> OTHER INFORMATION: Xaa = any amino acid
<221> NAME/KEY: MOD_RES
<222> LOCATION: (176)
<223> OTHER INFORMATION: Xaa = Gln or His
<221> NAME/KEY: MOD_RES
<222> LOCATION: (177)
<223> OTHER INFORMATION: Xaa = Leu or Met
<221> NAME/KEY: MOD_RES
<222> LOCATION: (183)..(184)
<223> OTHER INFORMATION: Xaa = any amino acid, Xaa at positions 183 and
      184 may be present of absent
<221> NAME/KEY: MOD_RES
<222> LOCATION: (189)..(190)
<223> OTHER INFORMATION: Xaa = any amino acid
<221> NAME/KEY: MOD_RES
<222> LOCATION: (199)
<223> OTHER INFORMATION: Xaa = Arg or Lys
<221> NAME/KEY: MOD_RES
<222> LOCATION: (200)..(201)
<223> OTHER INFORMATION: Xaa = any amino acid, Xaa at positions 200 and
      201 may be present or absent
<221> NAME/KEY: MOD_RES
<222> LOCATION: (204)
<223> OTHER INFORMATION: Xaa = Arg or Lys
<221> NAME/KEY: MOD_RES
<222> LOCATION: (205)
<223> OTHER INFORMATION: Xaa = His or Tyr
<221> NAME/KEY: MOD_RES
<222> LOCATION: (206)
<223> OTHER INFORMATION: Xaa = Phe or Tyr
<221> NAME/KEY: MOD_RES
<222> LOCATION: (207)
<223> OTHER INFORMATION: Xaa = Ala or Ser
<221> NAME/KEY: MOD_RES
<222> LOCATION: (210)
<223> OTHER INFORMATION: Xaa = any amino acid
<221> NAME/KEY: MOD_RES
<222> LOCATION: (211)
<223> OTHER INFORMATION: Xaa = Ala or Val
<221> NAME/KEY: MOD_RES
<222> LOCATION: (212)..(221)
<223> OTHER INFORMATION: Xaa = any amino acid, Xaa at positions 212-221
      may be present or absent
<221> NAME/KEY: MOD_RES
<222> LOCATION: (223)
<223> OTHER INFORMATION: Xaa = Ala or Ser
<221> NAME/KEY: MOD_RES
<222> LOCATION: (224)
<223> OTHER INFORMATION: Xaa = Arg or Lys
<221> NAME/KEY: MOD_RES
<222> LOCATION: (225)
<223> OTHER INFORMATION: Xaa = any amino acid
<221> NAME/KEY: MOD_RES
<222> LOCATION: (226)
<223> OTHER INFORMATION: Xaa = Ala or Leu
<221> NAME/KEY: MOD_RES
<222> LOCATION: (228)
<223> OTHER INFORMATION: Xaa = Pro or Glu
<221> NAME/KEY: MOD_RES
<222> LOCATION: (229)
```

<223> OTHER INFORMATION: Xaa = any amino acid
<221> NAME/KEY: MOD_RES
<222> LOCATION: (230)
<223> OTHER INFORMATION: Xaa = Pro or Thr

<400> SEQUENCE: 72

Trp Xaa Xaa Xaa Arg Xaa Xaa Xaa Xaa Glu Xaa Xaa Xaa Xaa Xaa
1               5                   10                  15

Xaa Asp Xaa Xaa Xaa Xaa Xaa Xaa Arg Xaa Xaa Xaa Xaa Xaa Xaa
            20                  25                  30

Xaa Xaa Xaa Xaa Ile Xaa Xaa Arg Gly Xaa Xaa Xaa Xaa Leu Xaa Xaa
        35                  40                  45

Arg Ile Xaa Xaa Xaa Xaa Xaa Xaa Xaa Xaa Xaa Xaa Xaa Phe Leu
    50                  55                  60

Xaa Xaa Xaa Val Xaa Xaa Xaa Gly Xaa Ile Asp Leu Glu Trp Leu Arg
65              70                  75                  80

Xaa Xaa Xaa Xaa Xaa Xaa Xaa Lys Xaa Xaa Leu Leu Xaa Xaa Xaa Gly
                85                  90                  95

Xaa Gly Leu Lys Ser Xaa Glu Cys Val Arg Leu Leu Xaa Leu Xaa Xaa
        100                 105                 110

Xaa Ala Phe Pro Val Asp Thr Asn Val Gly Arg Ile Xaa Val Arg Xaa
        115                 120                 125

Gly Xaa Val Pro Leu Xaa Pro Leu Pro Xaa Xaa Xaa Gln Xaa His Xaa
    130                 135                 140

Leu Xaa Xaa Tyr Pro Xaa Xaa Xaa Xaa Xaa Gln Lys Xaa Leu Trp Pro
145                 150                 155                 160

Arg Leu Cys Lys Leu Xaa Gln Xaa Thr Leu Tyr Glu Leu His Tyr Xaa
                165                 170                 175

Xaa Ile Thr Phe Gly Lys Xaa Xaa Phe Cys Thr Lys Xaa Xaa Pro Asn
        180                 185                 190

Cys Asn Ala Cys Pro Met Xaa Xaa Xaa Glu Cys Xaa Xaa Xaa Xaa Ser
        195                 200                 205

Ala Xaa Xaa Xaa Xaa Xaa Xaa Xaa Xaa Xaa Xaa Xaa Ser Xaa Xaa
    210                 215                 220

Xaa Xaa Leu Xaa Xaa Xaa
225             230

<210> SEQ ID NO 73
<211> LENGTH: 292
<212> TYPE: PRT
<213> ORGANISM: Artificial Sequence
<220> FEATURE:
<223> OTHER INFORMATION: Description of Artificial Sequence:DMT Domain C
      consensus sequence
<221> NAME/KEY: MOD_RES
<222> LOCATION: (2)
<223> OTHER INFORMATION: Xaa = Ile or Leu
<221> NAME/KEY: MOD_RES
<222> LOCATION: (3)
<223> OTHER INFORMATION: Xaa = Ile or Val
<221> NAME/KEY: MOD_RES
<222> LOCATION: (5)
<223> OTHER INFORMATION: Xaa = Glu or Phe
<221> NAME/KEY: MOD_RES
<222> LOCATION: (7)
<223> OTHER INFORMATION: Xaa = any amino acid
<221> NAME/KEY: MOD_RES
<222> LOCATION: (8)
<223> OTHER INFORMATION: Xaa = Ser or Thr
<221> NAME/KEY: MOD_RES
<222> LOCATION: (10)..(14)
<223> OTHER INFORMATION: Xaa = any amino acid, Xaa at positions 12-14
      may be present or absent -continued

```
<221> NAME/KEY: MOD_RES
<222> LOCATION: (16)..(30)
<223> OTHER INFORMATION: Xaa = any amino acid, Xaa at positions 16-30
      may be present or absent
<221> NAME/KEY: MOD_RES
<222> LOCATION: (31)
<223> OTHER INFORMATION: Xaa = Asp or Ala
<221> NAME/KEY: MOD_RES
<222> LOCATION: (34)
<223> OTHER INFORMATION: Xaa = Asp or Glu
<221> NAME/KEY: MOD_RES
<222> LOCATION: (35)..(57)
<223> OTHER INFORMATION: Xaa = any amino acid, Xaa at positions 39-57
      may be present or absent
<221> NAME/KEY: MOD_RES
<222> LOCATION: (58)
<223> OTHER INFORMATION: Xaa = Ile or Val
<221> NAME/KEY: MOD_RES
<222> LOCATION: (60)
<223> OTHER INFORMATION: Xaa = any amino acid
<221> NAME/KEY: MOD_RES
<222> LOCATION: (62)
<223> OTHER INFORMATION: Xaa = any amino acid
<221> NAME/KEY: MOD_RES
<222> LOCATION: (63)
<223> OTHER INFORMATION: Xaa = Leu or Phe
<221> NAME/KEY: MOD_RES
<222> LOCATION: (64)
<223> OTHER INFORMATION: Xaa = Asn or Asp
<221> NAME/KEY: MOD_RES
<222> LOCATION: (65)..(81)
<223> OTHER INFORMATION: Xaa = any amino acid, Xaa at positions 73-81
      may be present or absent
<221> NAME/KEY: MOD_RES
<222> LOCATION: (82)
<223> OTHER INFORMATION: Xaa = Ser or Ala
<221> NAME/KEY: MOD_RES
<222> LOCATION: (83)
<223> OTHER INFORMATION: Xaa = any amino acid
<221> NAME/KEY: MOD_RES
<222> LOCATION: (84)
<223> OTHER INFORMATION: Xaa = Ala or Asp
<221> NAME/KEY: MOD_RES
<222> LOCATION: (87)..(94)
<223> OTHER INFORMATION: Xaa = any amino acid
<221> NAME/KEY: MOD_RES
<222> LOCATION: (95)
<223> OTHER INFORMATION: Xaa = Ile or Leu
<221> NAME/KEY: MOD_RES
<222> LOCATION: (97)..(101)
<223> OTHER INFORMATION: Xaa = any amino acid, Xaa at positions 99-101
      may be present or absent
<221> NAME/KEY: MOD_RES
<222> LOCATION: (102)
<223> OTHER INFORMATION: Xaa = Lys or Arg
<221> NAME/KEY: MOD_RES
<222> LOCATION: (103)
<223> OTHER INFORMATION: Xaa = Leu or Met
<221> NAME/KEY: MOD_RES
<222> LOCATION: (105)..(108)
<223> OTHER INFORMATION: Xaa = any amino acid
<221> NAME/KEY: MOD_RES
<222> LOCATION: (114)
<223> OTHER INFORMATION: Xaa = any amino acid
<221> NAME/KEY: MOD_RES
<222> LOCATION: (116)
<223> OTHER INFORMATION: Xaa = Tyr or Phe
<221> NAME/KEY: MOD_RES
<222> LOCATION: (117)
<223> OTHER INFORMATION: Xaa = Glu or Val
<221> NAME/KEY: MOD_RES
<222> LOCATION: (121)
<223> OTHER INFORMATION: Xaa = any amino acid
<221> NAME/KEY: MOD_RES
<222> LOCATION: (123)
<223> OTHER INFORMATION: Xaa = any amino acid
<221> NAME/KEY: MOD_RES
<222> LOCATION: (124)
<223> OTHER INFORMATION: Xaa = Leu or Ile
```

-continued

```
<221> NAME/KEY: MOD_RES
<222> LOCATION: (126)
<223> OTHER INFORMATION: Xaa = Glu or Lys
<221> NAME/KEY: MOD_RES
<222> LOCATION: (127)
<223> OTHER INFORMATION: Xaa = any amino acid
<221> NAME/KEY: MOD_RES
<222> LOCATION: (128)
<223> OTHER INFORMATION: Xaa = Asp or Glu
<221> NAME/KEY: MOD_RES
<222> LOCATION: (130)
<223> OTHER INFORMATION: Xaa = Pro or Ile
<221> NAME/KEY: MOD_RES
<222> LOCATION: (131)..(132)
<223> OTHER INFORMATION: Xaa = any amino acid
<221> NAME/KEY: MOD_RES
<222> LOCATION: (136)
<223> OTHER INFORMATION: Xaa = Ala or Ser
<221> NAME/KEY: MOD_RES
<222> LOCATION: (139)
<223> OTHER INFORMATION: Xaa = Thr or Gln
<221> NAME/KEY: MOD_RES
<222> LOCATION: (141)
<223> OTHER INFORMATION: Xaa = Gly or Asp
<221> NAME/KEY: MOD_RES
<222> LOCATION: (142)
<223> OTHER INFORMATION: Xaa = Glu or Gly
<221> NAME/KEY: MOD_RES
<222> LOCATION: (143)..(150)
<223> OTHER INFORMATION: Xaa = any amino acid, Xaa at positions 149 and
      150 may be present or absent
<221> NAME/KEY: MOD_RES
<222> LOCATION: (151)
<223> OTHER INFORMATION: Xaa = Pro or Ser
<221> NAME/KEY: MOD_RES
<222> LOCATION: (152)..(154)
<223> OTHER INFORMATION: Xaa = any amino acid
<221> NAME/KEY: MOD_RES
<222> LOCATION: (156)..(165)
<223> OTHER INFORMATION: Xaa = any amino acid, Xaa at positions 162-165
      may be present or absent
<221> NAME/KEY: MOD_RES
<222> LOCATION: (166)
<223> OTHER INFORMATION: Xaa = Met or Leu
<221> NAME/KEY: MOD_RES
<222> LOCATION: (168)..(171)
<223> OTHER INFORMATION: Xaa = any amino acid
<221> NAME/KEY: MOD_RES
<222> LOCATION: (173)..(174)
<223> OTHER INFORMATION: Xaa = any amino acid
<221> NAME/KEY: MOD_RES
<222> LOCATION: (176)..(178)
<223> OTHER INFORMATION: Xaa = any amino acid
<221> NAME/KEY: MOD_RES
<222> LOCATION: (179)
<223> OTHER INFORMATION: Xaa = Arg or Lys
<221> NAME/KEY: MOD_RES
<222> LOCATION: (181)..(185)
<223> OTHER INFORMATION: Xaa = any amino acid
<221> NAME/KEY: MOD_RES
<222> LOCATION: (186)
<223> OTHER INFORMATION: Xaa = Val or Phe
<221> NAME/KEY: MOD_RES
<222> LOCATION: (190)
<223> OTHER INFORMATION: Xaa = Leu or Ile
<221> NAME/KEY: MOD_RES
<222> LOCATION: (192)..(213)
<223> OTHER INFORMATION: Xaa = any amino acid, Xaa at positions 192-213
      may be present or absent
<221> NAME/KEY: MOD_RES
<222> LOCATION: (214)
<223> OTHER INFORMATION: Xaa = Leu or Val
<221> NAME/KEY: MOD_RES
<222> LOCATION: (219)
<223> OTHER INFORMATION: Xaa = any amino acid
<221> NAME/KEY: MOD_RES
<222> LOCATION: (220)
<223> OTHER INFORMATION: Xaa = Ser or Thr
<221> NAME/KEY: MOD_RES
```

-continued

```
<222> LOCATION: (221)
<223> OTHER INFORMATION: Xaa = Ser or Arg
<221> NAME/KEY: MOD_RES
<222> LOCATION: (222)..(223)
<223> OTHER INFORMATION: Xaa = any amino acid
<221> NAME/KEY: MOD_RES
<222> LOCATION: (226)..(228)
<223> OTHER INFORMATION: Xaa = any amino acid
<221> NAME/KEY: MOD_RES
<222> LOCATION: (229)
<223> OTHER INFORMATION: Xaa = Arg or Thr
<221> NAME/KEY: MOD_RES
<222> LOCATION: (230)..(232)
<223> OTHER INFORMATION: Xaa = any amino acid
<221> NAME/KEY: MOD_RES
<222> LOCATION: (233)
<223> OTHER INFORMATION: Xaa = Trp or Lys
<221> NAME/KEY: MOD_RES
<222> LOCATION: (234)
<223> OTHER INFORMATION: Xaa = any amino acid
<221> NAME/KEY: MOD_RES
<222> LOCATION: (236)
<223> OTHER INFORMATION: Xaa = any amino acid
<221> NAME/KEY: MOD_RES
<222> LOCATION: (237)
<223> OTHER INFORMATION: Xaa = Arg or Lys
<221> NAME/KEY: MOD_RES
<222> LOCATION: (239)..(242)
<223> OTHER INFORMATION: Xaa = any amino acid
<221> NAME/KEY: MOD_RES
<222> LOCATION: (244)
<223> OTHER INFORMATION: Xaa = Thr or Ser
<221> NAME/KEY: MOD_RES
<222> LOCATION: (245)
<223> OTHER INFORMATION: Xaa = Ser or Thr
<221> NAME/KEY: MOD_RES
<222> LOCATION: (246)..(247)
<223> OTHER INFORMATION: Xaa = any amino acid
<221> NAME/KEY: MOD_RES
<222> LOCATION: (248)
<223> OTHER INFORMATION: Xaa = Ser or Thr
<221> NAME/KEY: MOD_RES
<222> LOCATION: (250)
<223> OTHER INFORMATION: Xaa = Phe or Cys
<221> NAME/KEY: MOD_RES
<222> LOCATION: (251)
<223> OTHER INFORMATION: Xaa = Arg or Lys
<221> NAME/KEY: MOD_RES
<222> LOCATION: (252)
<223> OTHER INFORMATION: Xaa = Gly or Leu
<221> NAME/KEY: MOD_RES
<222> LOCATION: (254)
<223> OTHER INFORMATION: Xaa = any amino acid
<221> NAME/KEY: MOD_RES
<222> LOCATION: (255)
<223> OTHER INFORMATION: Xaa = Thr or Val
<221> NAME/KEY: MOD_RES
<222> LOCATION: (256)..(257)
<223> OTHER INFORMATION: Xaa = any amino acid
<221> NAME/KEY: MOD_RES
<222> LOCATION: (259)..(260)
<223> OTHER INFORMATION: Xaa = any amino acid
<221> NAME/KEY: MOD_RES
<222> LOCATION: (261)
<223> OTHER INFORMATION: Xaa = Cys or Asn
<221> NAME/KEY: MOD_RES
<222> LOCATION: (263)
<223> OTHER INFORMATION: Xaa = Trp or Gln
<221> NAME/KEY: MOD_RES
<222> LOCATION: (264)
<223> OTHER INFORMATION: Xaa = any amino acid
<221> NAME/KEY: MOD_RES
<222> LOCATION: (266)
<223> OTHER INFORMATION: Xaa = Phe or Tyr
<221> NAME/KEY: MOD_RES
<222> LOCATION: (267)
<223> OTHER INFORMATION: Xaa = Val or Leu
<221> NAME/KEY: MOD_RES
<222> LOCATION: (269)
```

```
-continued

<223> OTHER INFORMATION: Xaa = Val or Leu
<221> NAME/KEY: MOD_RES
<222> LOCATION: (271)
<223> OTHER INFORMATION: Xaa = any amino acid
<221> NAME/KEY: MOD_RES
<222> LOCATION: (273)
<223> OTHER INFORMATION: Xaa = Glu or Asp
<221> NAME/KEY: MOD_RES
<222> LOCATION: (274)..(276)
<223> OTHER INFORMATION: Xaa = any amino acid
<221> NAME/KEY: MOD_RES
<222> LOCATION: (277)
<223> OTHER INFORMATION: Xaa = Arg or Gly
<221> NAME/KEY: MOD_RES
<222> LOCATION: (278)
<223> OTHER INFORMATION: Xaa = any amino acid
<221> NAME/KEY: MOD_RES
<222> LOCATION: (280)
<223> OTHER INFORMATION: Xaa = Arg or Lys
<221> NAME/KEY: MOD_RES
<222> LOCATION: (281)
<223> OTHER INFORMATION: Xaa = any amino acid
<221> NAME/KEY: MOD_RES
<222> LOCATION: (283)..(284)
<223> OTHER INFORMATION: Xaa = any amino acid
<221> NAME/KEY: MOD_RES
<222> LOCATION: (285)
<223> OTHER INFORMATION: Xaa = Arg or His
<221> NAME/KEY: MOD_RES
<222> LOCATION: (288)..(289)
<223> OTHER INFORMATION: Xaa = any amino acid
<221> NAME/KEY: MOD_RES
<222> LOCATION: (290)
<223> OTHER INFORMATION: Xaa = Ala or Val

<400> SEQUENCE: 73

Pro Xaa Xaa Glu Xaa Pro Xaa Xaa Pro Xaa Xaa Xaa Xaa Xaa Glu Xaa
 1               5                  10                  15

Xaa Xaa Xaa Xaa Xaa Xaa Xaa Xaa Xaa Xaa Xaa Xaa Xaa Xaa Xaa Ile
                20                  25                  30

Glu Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Pro Xaa Ile Xaa Xaa Xaa
        50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Leu Val Xaa Xaa Xaa Xaa Xaa Xaa Xaa Xaa Xaa Pro
                85                  90                  95

Xaa Xaa Xaa Xaa Xaa Xaa Xaa Lys Xaa Xaa Xaa Xaa Leu Arg Thr Glu
            100                 105                 110

His Xaa Val Xaa Xaa Leu Pro Asp Xaa His Xaa Xaa Leu Xaa Xaa Xaa
            115                 120                 125

Asp Xaa Xaa Xaa Tyr Leu Leu Xaa Ile Trp Xaa Pro Xaa Xaa Xaa Xaa
        130                 135                 140

Xaa Xaa Xaa Xaa Xaa Xaa Xaa Xaa Xaa Cys Xaa Xaa Xaa Xaa Xaa Xaa
145                 150                 155                 160

Xaa Xaa Xaa Xaa Xaa Cys Xaa Xaa Xaa Xaa Cys Xaa Xaa Cys Xaa
            165                 170                 175

Xaa Xaa Xaa Glu Xaa Xaa Xaa Xaa Xaa Xaa Arg Gly Thr Xaa Leu Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Phe Ala Asp His Xaa Xaa Xaa Xaa Xaa Pro
210                 215                 220
```

```
Ile Xaa Xaa Xaa Xaa Xaa Xaa Xaa Xaa Leu Xaa Xaa Arg Xaa Xaa
225                 230                 235                 240

Xaa Xaa Gly Xaa Xaa Xaa Xaa Ile Xaa Xaa Xaa Leu Xaa Xaa Xaa
            245                 250                 255

Xaa Ile Xaa Xaa Xaa Phe Xaa Xaa Gly Xaa Xaa Cys Xaa Arg Xaa Phe
        260                 265                 270

Xaa Xaa Xaa Xaa Xaa Xaa Pro Xaa Xaa Leu Xaa Xaa Xaa Leu His Xaa
        275                 280                 285

Xaa Xaa Ser Lys
    290

<210> SEQ ID NO 74
<211> LENGTH: 1269
<212> TYPE: PRT
<213> ORGANISM: Artificial Sequence
<220> FEATURE:
<223> OTHER INFORMATION: Description of Artificial Sequence:DMT
      consensus sequence spanning Domains A, B and C
<221> NAME/KEY: MOD_RES
<222> LOCATION: (1)..(14)
<223> OTHER INFORMATION: Xaa = any amino acid, Xaa at positions 10-14
      may be present or absent
<221> NAME/KEY: MOD_RES
<222> LOCATION: (15)
<223> OTHER INFORMATION: Xaa = Thr or Gln
<221> NAME/KEY: MOD_RES
<222> LOCATION: (16)
<223> OTHER INFORMATION: Xaa = Ala or Ile
<221> NAME/KEY: MOD_RES
<222> LOCATION: (17)
<223> OTHER INFORMATION: Xaa = Ser or Lys
<221> NAME/KEY: MOD_RES
<222> LOCATION: (18)
<223> OTHER INFORMATION: Xaa = Ile or Leu
<221> NAME/KEY: MOD_RES
<222> LOCATION: (19)..(21)
<223> OTHER INFORMATION: Xaa = any amino acid
<221> NAME/KEY: MOD_RES
<222> LOCATION: (22)
<223> OTHER INFORMATION: Xaa = Ala or Arg
<221> NAME/KEY: MOD_RES
<222> LOCATION: (23)
<223> OTHER INFORMATION: Xaa = Ser or Lys
<221> NAME/KEY: MOD_RES
<222> LOCATION: (24)
<223> OTHER INFORMATION: Xaa = any amino acid
<221> NAME/KEY: MOD_RES
<222> LOCATION: (25)
<223> OTHER INFORMATION: Xaa = Gly or Met
<221> NAME/KEY: MOD_RES
<222> LOCATION: (26)..(27)
<223> OTHER INFORMATION: Xaa = any amino acid
<221> NAME/KEY: MOD_RES
<222> LOCATION: (28)
<223> OTHER INFORMATION: Xaa = Ser or Arg
<221> NAME/KEY: MOD_RES
<222> LOCATION: (29)
<223> OTHER INFORMATION: Xaa = Pro or Lys
<221> NAME/KEY: MOD_RES
<222> LOCATION: (30)..(31)
<223> OTHER INFORMATION: Xaa = any amino acid
<221> NAME/KEY: MOD_RES
<222> LOCATION: (32)
<223> OTHER INFORMATION: Xaa = Lys or Phe
<221> NAME/KEY: MOD_RES
<222> LOCATION: (33)..(34)
<223> OTHER INFORMATION: Xaa = any amino acid
<221> NAME/KEY: MOD_RES
<222> LOCATION: (35)
<223> OTHER INFORMATION: Xaa = Glu or Leu
<221> NAME/KEY: MOD_RES
<222> LOCATION: (37)
<223> OTHER INFORMATION: Xaa = any amino acid, Xaa at position 37 may be
      present or absent
```

```
<221> NAME/KEY: MOD_RES
<222> LOCATION: (39)..(41)
<223> OTHER INFORMATION: Xaa = any amino acid, Xaa at positions 39-41
      may be present or absent
<221> NAME/KEY: MOD_RES
<222> LOCATION: (42)
<223> OTHER INFORMATION: Xaa = Pro or Arg
<221> NAME/KEY: MOD_RES
<222> LOCATION: (43)..(44)
<223> OTHER INFORMATION: Xaa = any amino acid
<221> NAME/KEY: MOD_RES
<222> LOCATION: (45)
<223> OTHER INFORMATION: Xaa = Pro or Arg
<221> NAME/KEY: MOD_RES
<222> LOCATION: (46)
<223> OTHER INFORMATION: Xaa = any amino acid
<221> NAME/KEY: MOD_RES
<222> LOCATION: (47)
<223> OTHER INFORMATION: Xaa = Lys or Arg
<221> NAME/KEY: MOD_RES
<222> LOCATION: (48)
<223> OTHER INFORMATION: Xaa = Lys or Arg
<221> NAME/KEY: MOD_RES
<222> LOCATION: (49)
<223> OTHER INFORMATION: Xaa = Gly or Asp
<221> NAME/KEY: MOD_RES
<222> LOCATION: (50)
<223> OTHER INFORMATION: Xaa = Arg or Lys
<221> NAME/KEY: MOD_RES
<222> LOCATION: (51)
<223> OTHER INFORMATION: Xaa = any amino acid
<221> NAME/KEY: MOD_RES
<222> LOCATION: (52)
<223> OTHER INFORMATION: Xaa = Gly or Val
<221> NAME/KEY: MOD_RES
<222> LOCATION: (53)
<223> OTHER INFORMATION: Xaa = any amino acid
<221> NAME/KEY: MOD_RES
<222> LOCATION: (54)
<223> OTHER INFORMATION: Xaa = Lys or Gly
<221> NAME/KEY: MOD_RES
<222> LOCATION: (55)..(59)
<223> OTHER INFORMATION: Xaa = any amino acid, Xaa at positions 58 and
      59 may be present or absent
<221> NAME/KEY: MOD_RES
<222> LOCATION: (60)
<223> OTHER INFORMATION: Xaa = Pro or Ser
<221> NAME/KEY: MOD_RES
<222> LOCATION: (61)
<223> OTHER INFORMATION: Xaa = Pro or Lys
<221> NAME/KEY: MOD_RES
<222> LOCATION: (62)..(64)
<223> OTHER INFORMATION: Xaa = any amino acid
<221> NAME/KEY: MOD_RES
<222> LOCATION: (65)
<223> OTHER INFORMATION: Xaa = Ser or Asn
<221> NAME/KEY: MOD_RES
<222> LOCATION: (66)
<223> OTHER INFORMATION: Xaa = any amino acid
<221> NAME/KEY: MOD_RES
<222> LOCATION: (67)
<223> OTHER INFORMATION: Xaa = Ile or Leu
<221> NAME/KEY: MOD_RES
<222> LOCATION: (68)..(69)
<223> OTHER INFORMATION: Xaa = any amino acid, Xaa at positions 68 and
      69 may be present or absent
<221> NAME/KEY: MOD_RES
<222> LOCATION: (70)
<223> OTHER INFORMATION: Xaa = Gln or Asp
<221> NAME/KEY: MOD_RES
<222> LOCATION: (71)..(79)
<223> OTHER INFORMATION: Xaa = any amino acid
<221> NAME/KEY: MOD_RES
<222> LOCATION: (80)
<223> OTHER INFORMATION: Xaa = Pro or Gln
<221> NAME/KEY: MOD_RES
<222> LOCATION: (81)..(84)
<223> OTHER INFORMATION: Xaa = any amino acid
<221> NAME/KEY: MOD_RES
```

-continued

```
<222> LOCATION: (85)
<223> OTHER INFORMATION: Xaa = Lys or Ala
<221> NAME/KEY: MOD_RES
<222> LOCATION: (86)
<223> OTHER INFORMATION: Xaa = Pro or Ser
<221> NAME/KEY: MOD_RES
<222> LOCATION: (87)..(102)
<223> OTHER INFORMATION: Xaa = any amino acid, Xaa at positions 100-102
      may be present or absent
<221> NAME/KEY: MOD_RES
<222> LOCATION: (103)
<223> OTHER INFORMATION: Xaa = Pro or Ala
<221> NAME/KEY: MOD_RES
<222> LOCATION: (104)..(107)
<223> OTHER INFORMATION: Xaa = any amino acid
<221> NAME/KEY: MOD_RES
<222> LOCATION: (109)..(118)
<223> OTHER INFORMATION: Xaa = any amino acid, Xaa at positions 109-118
      may be present or absent
<221> NAME/KEY: MOD_RES
<222> LOCATION: (120)
<223> OTHER INFORMATION: Xaa = any amino acid
<221> NAME/KEY: MOD_RES
<222> LOCATION: (121)
<223> OTHER INFORMATION: Xaa = Ile or Leu
<221> NAME/KEY: MOD_RES
<222> LOCATION: (122)..(125)
<223> OTHER INFORMATION: Xaa = any amino acid, Xaa at positions 122-125
      may be present or absent
<221> NAME/KEY: MOD_RES
<222> LOCATION: (126)
<223> OTHER INFORMATION: Xaa = Leu or Asn
<221> NAME/KEY: MOD_RES
<222> LOCATION: (127)..(172)
<223> OTHER INFORMATION: Xaa = any amino acid, Xaa at positions 138-172
      may be present or absent
<221> NAME/KEY: MOD_RES
<222> LOCATION: (173)
<223> OTHER INFORMATION: Xaa = Lys or Asp
<221> NAME/KEY: MOD_RES
<222> LOCATION: (174)..(180)
<223> OTHER INFORMATION: Xaa = any amino acid, Xaa at positions 176-180
      may be present or absent
<221> NAME/KEY: MOD_RES
<222> LOCATION: (181)
<223> OTHER INFORMATION: Xaa = Pro or Ala
<221> NAME/KEY: MOD_RES
<222> LOCATION: (184)
<223> OTHER INFORMATION: Xaa = any amino acid
<221> NAME/KEY: MOD_RES
<222> LOCATION: (185)
<223> OTHER INFORMATION: Xaa = Ile or Leu
<221> NAME/KEY: MOD_RES
<222> LOCATION: (187)
<223> OTHER INFORMATION: Xaa = Asp or Pro
<221> NAME/KEY: MOD_RES
<222> LOCATION: (188)
<223> OTHER INFORMATION: Xaa = Glu or Val
<221> NAME/KEY: MOD_RES
<222> LOCATION: (190)..(192)
<223> OTHER INFORMATION: Xaa = any amino acid
<221> NAME/KEY: MOD_RES
<222> LOCATION: (194)
<223> OTHER INFORMATION: Xaa = any amino acid
<221> NAME/KEY: MOD_RES
<222> LOCATION: (195)
<223> OTHER INFORMATION: Xaa = Leu or Val
<221> NAME/KEY: MOD_RES
<222> LOCATION: (197)
<223> OTHER INFORMATION: Xaa = Met or Leu
<221> NAME/KEY: MOD_RES
<222> LOCATION: (198)
<223> OTHER INFORMATION: Xaa = Glu or Asp
<221> NAME/KEY: MOD_RES
<222> LOCATION: (199)..(200)
<223> OTHER INFORMATION: Xaa = any amino acid, Xaa at positions 199 and
      200 may be present or absent
<221> NAME/KEY: MOD_RES
<222> LOCATION: (202)
```

-continued

```
<223> OTHER INFORMATION: Xaa = Lys or Glu
<221> NAME/KEY: MOD_RES
<222> LOCATION: (203)
<223> OTHER INFORMATION: Xaa = any amino acid
<221> NAME/KEY: MOD_RES
<222> LOCATION: (204)
<223> OTHER INFORMATION: Xaa = Lys or Thr
<221> NAME/KEY: MOD_RES
<222> LOCATION: (205)
<223> OTHER INFORMATION: Xaa = any amino acid
<221> NAME/KEY: MOD_RES
<222> LOCATION: (206)
<223> OTHER INFORMATION: Xaa = Lys or Ala
<221> NAME/KEY: MOD_RES
<222> LOCATION: (207)
<223> OTHER INFORMATION: Xaa = Trp or Lys
<221> NAME/KEY: MOD_RES
<222> LOCATION: (208)
<223> OTHER INFORMATION: Xaa = Trp or Leu
<221> NAME/KEY: MOD_RES
<222> LOCATION: (209)
<223> OTHER INFORMATION: Xaa = any amino acid
<221> NAME/KEY: MOD_RES
<222> LOCATION: (210)
<223> OTHER INFORMATION: Xaa = Glu or Lys
<221> NAME/KEY: MOD_RES
<222> LOCATION: (213)..(214)
<223> OTHER INFORMATION: Xaa = any amino acid
<221> NAME/KEY: MOD_RES
<222> LOCATION: (216)
<223> OTHER INFORMATION: Xaa = any amino acid
<221> NAME/KEY: MOD_RES
<222> LOCATION: (217)
<223> OTHER INFORMATION: Xaa = Gly or Thr
<221> NAME/KEY: MOD_RES
<222> LOCATION: (219)
<223> OTHER INFORMATION: Xaa = any amino acid
<221> NAME/KEY: MOD_RES
<222> LOCATION: (220)
<223> OTHER INFORMATION: Xaa = Asp or Asn
<221> NAME/KEY: MOD_RES
<222> LOCATION: (221)
<223> OTHER INFORMATION: Xaa = Ser or Leu
<221> NAME/KEY: MOD_RES
<222> LOCATION: (224)
<223> OTHER INFORMATION: Xaa = Ala or Asn
<221> NAME/KEY: MOD_RES
<222> LOCATION: (227)
<223> OTHER INFORMATION: Xaa = His or Arg
<221> NAME/KEY: MOD_RES
<222> LOCATION: (228)
<223> OTHER INFORMATION: Xaa = any amino acid
<221> NAME/KEY: MOD_RES
<222> LOCATION: (229)
<223> OTHER INFORMATION: Xaa = Val or Leu
<221> NAME/KEY: MOD_RES
<222> LOCATION: (232)
<223> OTHER INFORMATION: Xaa = Asp or Asn
<221> NAME/KEY: MOD_RES
<222> LOCATION: (234)
<223> OTHER INFORMATION: Xaa = any amino acid
<221> NAME/KEY: MOD_RES
<222> LOCATION: (236)
<223> OTHER INFORMATION: Xaa = any amino acid
<221> NAME/KEY: MOD_RES
<222> LOCATION: (237)
<223> OTHER INFORMATION: Xaa = Pro or Gln
<221> NAME/KEY: MOD_RES
<222> LOCATION: (247)
<223> OTHER INFORMATION: Xaa = Ile or Val
<221> NAME/KEY: MOD_RES
<222> LOCATION: (255)
<223> OTHER INFORMATION: Xaa = Val or Thr
<221> NAME/KEY: MOD_RES
<222> LOCATION: (257)
<223> OTHER INFORMATION: Xaa = His or Tyr
<221> NAME/KEY: MOD_RES
<222> LOCATION: (258)
<223> OTHER INFORMATION: Xaa = Leu or Ser
```

```
<221> NAME/KEY: MOD_RES
<222> LOCATION: (261)
<223> OTHER INFORMATION: Xaa = Ser or Asn
<221> NAME/KEY: MOD_RES
<222> LOCATION: (263)
<223> OTHER INFORMATION: Xaa = Phe or Tyr
<221> NAME/KEY: MOD_RES
<222> LOCATION: (265)
<223> OTHER INFORMATION: Xaa = any amino acid
<221> NAME/KEY: MOD_RES
<222> LOCATION: (266)
<223> OTHER INFORMATION: Xaa = Leu or Val
<221> NAME/KEY: MOD_RES
<222> LOCATION: (268)
<223> OTHER INFORMATION: Xaa = Ala or Ser
<221> NAME/KEY: MOD_RES
<222> LOCATION: (269)
<223> OTHER INFORMATION: Xaa = any amino acid
<221> NAME/KEY: MOD_RES
<222> LOCATION: (272)..(287)
<223> OTHER INFORMATION: Xaa = any amino acid, Xaa from positions
      272-287 may be present or absent
<221> NAME/KEY: MOD_RES
<222> LOCATION: (288)
<223> OTHER INFORMATION: Xaa = Pro or Val
<221> NAME/KEY: MOD_RES
<222> LOCATION: (289)..(303)
<223> OTHER INFORMATION: Xaa = any amino acid, Xaa at positions 295-303
      may be present or absent
<221> NAME/KEY: MOD_RES
<222> LOCATION: (304)
<223> OTHER INFORMATION: Xaa = Ser or His
<221> NAME/KEY: MOD_RES
<222> LOCATION: (305)..(307)
<223> OTHER INFORMATION: Xaa = any amino acid
<221> NAME/KEY: MOD_RES
<222> LOCATION: (308)
<223> OTHER INFORMATION: Xaa = Glu or Asp
<221> NAME/KEY: MOD_RES
<222> LOCATION: (309)..(332)
<223> OTHER INFORMATION: Xaa = any amino acid, Xaa at positions 319-332
      may be present or absent
<221> NAME/KEY: MOD_RES
<222> LOCATION: (333)
<223> OTHER INFORMATION: Xaa = Ser or Thr
<221> NAME/KEY: MOD_RES
<222> LOCATION: (334)
<223> OTHER INFORMATION: Xaa = any amino acid
<221> NAME/KEY: MOD_RES
<222> LOCATION: (335)
<223> OTHER INFORMATION: Xaa = Ser or Glu
<221> NAME/KEY: MOD_RES
<222> LOCATION: (336)..(341)
<223> OTHER INFORMATION: Xaa = any amino acid
<221> NAME/KEY: MOD_RES
<222> LOCATION: (342)
<223> OTHER INFORMATION: Xaa = Lys or Asn
<221> NAME/KEY: MOD_RES
<222> LOCATION: (343)..(397)
<223> OTHER INFORMATION: Xaa = any amino acid, Xaa at positions 351-397
      may be present or absent
<221> NAME/KEY: MOD_RES
<222> LOCATION: (398)
<223> OTHER INFORMATION: Xaa = Glu or Ile
<221> NAME/KEY: MOD_RES
<222> LOCATION: (399)..(407)
<223> OTHER INFORMATION: Xaa = any amino acid, Xaa at position 407 may
      be present or absent
<221> NAME/KEY: MOD_RES
<222> LOCATION: (408)
<223> OTHER INFORMATION: Xaa = Ile or Val
<221> NAME/KEY: MOD_RES
<222> LOCATION: (409)
<223> OTHER INFORMATION: Xaa = any amino acid
<221> NAME/KEY: MOD_RES
<222> LOCATION: (410)
<223> OTHER INFORMATION: Xaa = Asn or Ser
<221> NAME/KEY: MOD_RES
<222> LOCATION: (411)..(414)
```

-continued

```
<223> OTHER INFORMATION: Xaa = any amino acid, Xaa at positions 412-414
      may be present or absent
<221> NAME/KEY: MOD_RES
<222> LOCATION: (415)
<223> OTHER INFORMATION: Xaa = Glu or Asp
<221> NAME/KEY: MOD_RES
<222> LOCATION: (416)
<223> OTHER INFORMATION: Xaa = any amino acid
<221> NAME/KEY: MOD_RES
<222> LOCATION: (417)
<223> OTHER INFORMATION: Xaa = Glu or Ser
<221> NAME/KEY: MOD_RES
<222> LOCATION: (418)..(421)
<223> OTHER INFORMATION: Xaa = any amino acid
<221> NAME/KEY: MOD_RES
<222> LOCATION: (422)
<223> OTHER INFORMATION: Xaa = Gln or Leu
<221> NAME/KEY: MOD_RES
<222> LOCATION: (423)..(433)
<223> OTHER INFORMATION: Xaa = any amino acid, Xaa at positions 423-433
      may be present or absent
<221> NAME/KEY: MOD_RES
<222> LOCATION: (434)
<223> OTHER INFORMATION: Xaa = Asp or His
<221> NAME/KEY: MOD_RES
<222> LOCATION: (435)
<223> OTHER INFORMATION: Xaa = any amino acid
<221> NAME/KEY: MOD_RES
<222> LOCATION: (436)
<223> OTHER INFORMATION: Xaa = Phe or Met
<221> NAME/KEY: MOD_RES
<222> LOCATION: (437)..(441)
<223> OTHER INFORMATION: Xaa = any amino acid
<221> NAME/KEY: MOD_RES
<222> LOCATION: (442)
<223> OTHER INFORMATION: Xaa = Gln or Asn
<221> NAME/KEY: MOD_RES
<222> LOCATION: (443)..(445)
<223> OTHER INFORMATION: Xaa = any amino acid, Xaa at positions 443-445
      may be present or absent
<221> NAME/KEY: MOD_RES
<222> LOCATION: (446)
<223> OTHER INFORMATION: Xaa = Gly or Glu
<221> NAME/KEY: MOD_RES
<222> LOCATION: (447)..(448)
<223> OTHER INFORMATION: Xaa = any amino acid
<221> NAME/KEY: MOD_RES
<222> LOCATION: (449)
<223> OTHER INFORMATION: Xaa = Gly or Asp
<221> NAME/KEY: MOD_RES
<222> LOCATION: (451)
<223> OTHER INFORMATION: Xaa = any amino acid
<221> NAME/KEY: MOD_RES
<222> LOCATION: (452)
<223> OTHER INFORMATION: Xaa = Lys or Asp
<221> NAME/KEY: MOD_RES
<222> LOCATION: (453)..(463)
<223> OTHER INFORMATION: Xaa = any amino acid, Xaa at positions 460-463
      may be present or absent
<221> NAME/KEY: MOD_RES
<222> LOCATION: (464)
<223> OTHER INFORMATION: Xaa = Thr or Met
<221> NAME/KEY: MOD_RES
<222> LOCATION: (465)..(466)
<223> OTHER INFORMATION: Xaa = any amino acid
<221> NAME/KEY: MOD_RES
<222> LOCATION: (467)
<223> OTHER INFORMATION: Xaa = Val or Leu
<221> NAME/KEY: MOD_RES
<222> LOCATION: (468)..(470)
<223> OTHER INFORMATION: Xaa = any amino acid
<221> NAME/KEY: MOD_RES
<222> LOCATION: (471)
<223> OTHER INFORMATION: Xaa = Ser or Gln
<221> NAME/KEY: MOD_RES
<222> LOCATION: (472)..(481)
<223> OTHER INFORMATION: Xaa = any amino acid, Xaa at positions 478-481
      may be present or absent
<221> NAME/KEY: MOD_RES
```

```
<222> LOCATION: (482)
<223> OTHER INFORMATION: Xaa = Ser or Glu
<221> NAME/KEY: MOD_RES
<222> LOCATION: (483)..(485)
<223> OTHER INFORMATION: Xaa = any amino acid, Xaa at position 485 may
      be present or absent
<221> NAME/KEY: MOD_RES
<222> LOCATION: (486)
<223> OTHER INFORMATION: Xaa = Ser or Val
<221> NAME/KEY: MOD_RES
<222> LOCATION: (487)..(511)
<223> OTHER INFORMATION: Xaa = any amino acid, Xaa at positions 506-511
      may be present or absent
<221> NAME/KEY: MOD_RES
<222> LOCATION: (512)
<223> OTHER INFORMATION: Xaa = Thr or Ser
<221> NAME/KEY: MOD_RES
<222> LOCATION: (513)..(540)
<223> OTHER INFORMATION: Xaa = any amino acid, Xaa at positions 529-540
      may be present or absent
<221> NAME/KEY: MOD_RES
<222> LOCATION: (541)
<223> OTHER INFORMATION: Xaa = Arg or Ser
<221> NAME/KEY: MOD_RES
<222> LOCATION: (542)..(547)
<223> OTHER INFORMATION: Xaa = any amino acid, Xaa at positions 544-547
      may be present or absent
<221> NAME/KEY: MOD_RES
<222> LOCATION: (548)
<223> OTHER INFORMATION: Xaa = Thr or Pro
<221> NAME/KEY: MOD_RES
<222> LOCATION: (549)..(553)
<223> OTHER INFORMATION: Xaa = any amino acid
<221> NAME/KEY: MOD_RES
<222> LOCATION: (554)
<223> OTHER INFORMATION: Xaa = Pro or Lys
<221> NAME/KEY: MOD_RES
<222> LOCATION: (555)..(564)
<223> OTHER INFORMATION: Xaa = any amino acid
<221> NAME/KEY: MOD_RES
<222> LOCATION: (565)
<223> OTHER INFORMATION: Xaa = Gln or Glu
<221> NAME/KEY: MOD_RES
<222> LOCATION: (566)..(569)
<223> OTHER INFORMATION: Xaa = any amino acid
<221> NAME/KEY: MOD_RES
<222> LOCATION: (570)
<223> OTHER INFORMATION: Xaa = Asp or Ser
<221> NAME/KEY: MOD_RES
<222> LOCATION: (571)..(574)
<223> OTHER INFORMATION: Xaa = any amino acid, Xaa at positions 572-574
      may be present or absent
<221> NAME/KEY: MOD_RES
<222> LOCATION: (575)
<223> OTHER INFORMATION: Xaa = Ser or Arg
<221> NAME/KEY: MOD_RES
<222> LOCATION: (576)..(580)
<223> OTHER INFORMATION: Xaa = any amino acid
<221> NAME/KEY: MOD_RES
<222> LOCATION: (581)
<223> OTHER INFORMATION: Xaa = Asp or Pro
<221> NAME/KEY: MOD_RES
<222> LOCATION: (582)..(584)
<223> OTHER INFORMATION: Xaa = any amino acid
<221> NAME/KEY: MOD_RES
<222> LOCATION: (585)
<223> OTHER INFORMATION: Xaa = Asn or Asp
<221> NAME/KEY: MOD_RES
<222> LOCATION: (586)..(588)
<223> OTHER INFORMATION: Xaa = any amino acid
<221> NAME/KEY: MOD_RES
<222> LOCATION: (589)
<223> OTHER INFORMATION: Xaa = Pro or Tyr
<221> NAME/KEY: MOD_RES
<222> LOCATION: (590)..(591)
<223> OTHER INFORMATION: Xaa = any amino acid
<221> NAME/KEY: MOD_RES
<222> LOCATION: (592)
<223> OTHER INFORMATION: Xaa = Phe or Ser
```

-continued

```
<221> NAME/KEY: MOD_RES
<222> LOCATION: (593)
<223> OTHER INFORMATION: Xaa = any amino acid
<221> NAME/KEY: MOD_RES
<222> LOCATION: (594)
<223> OTHER INFORMATION: Xaa = Arg or Lys
<221> NAME/KEY: MOD_RES
<222> LOCATION: (595)
<223> OTHER INFORMATION: Xaa = any amino acid
<221> NAME/KEY: MOD_RES
<222> LOCATION: (596)
<223> OTHER INFORMATION: Xaa = Gly or Ser
<221> NAME/KEY: MOD_RES
<222> LOCATION: (597)
<223> OTHER INFORMATION: Xaa = any amino acid
<221> NAME/KEY: MOD_RES
<222> LOCATION: (598)
<223> OTHER INFORMATION: Xaa = Ser or Ala
<221> NAME/KEY: MOD_RES
<222> LOCATION: (599)
<223> OTHER INFORMATION: Xaa = Val or Arg
<221> NAME/KEY: MOD_RES
<222> LOCATION: (600)
<223> OTHER INFORMATION: Xaa = Pro or Glu
<221> NAME/KEY: MOD_RES
<222> LOCATION: (601)..(603)
<223> OTHER INFORMATION: Xaa = any amino acid
<221> NAME/KEY: MOD_RES
<222> LOCATION: (604)
<223> OTHER INFORMATION: Xaa = Thr or Ser
<221> NAME/KEY: MOD_RES
<222> LOCATION: (605)..(610)
<223> OTHER INFORMATION: Xaa = any amino acid, Xaa at positions 608-610
      may be present or absent
<221> NAME/KEY: MOD_RES
<222> LOCATION: (611)
<223> OTHER INFORMATION: Xaa = Ile or Leu
<221> NAME/KEY: MOD_RES
<222> LOCATION: (612)..(614)
<223> OTHER INFORMATION: Xaa = any amino acid
<221> NAME/KEY: MOD_RES
<222> LOCATION: (615)
<223> OTHER INFORMATION: Xaa = Pro or Glu
<221> NAME/KEY: MOD_RES
<222> LOCATION: (616)
<223> OTHER INFORMATION: Xaa = any amino acid
<221> NAME/KEY: MOD_RES
<222> LOCATION: (618)..(622)
<223> OTHER INFORMATION: Xaa = any amino acid,Xaa at positions 621 and
      622 may be present or absent
<221> NAME/KEY: MOD_RES
<222> LOCATION: (623)
<223> OTHER INFORMATION: Xaa = Leu or Gln
<221> NAME/KEY: MOD_RES
<222> LOCATION: (624)
<223> OTHER INFORMATION: Xaa = any amino acid
<221> NAME/KEY: MOD_RES
<222> LOCATION: (625)
<223> OTHER INFORMATION: Xaa = Gly or Cys
<221> NAME/KEY: MOD_RES
<222> LOCATION: (626)
<223> OTHER INFORMATION: Xaa = any amino acid
<221> NAME/KEY: MOD_RES
<222> LOCATION: (627)
<223> OTHER INFORMATION: Xaa = Ser or His
<221> NAME/KEY: MOD_RES
<222> LOCATION: (628)
<223> OTHER INFORMATION: Xaa = Ser or Asn
<221> NAME/KEY: MOD_RES
<222> LOCATION: (629)
<223> OTHER INFORMATION: Xaa = any amino acid
<221> NAME/KEY: MOD_RES
<222> LOCATION: (630)
<223> OTHER INFORMATION: Xaa = Val or Gln
<221> NAME/KEY: MOD_RES
<222> LOCATION: (631)
<223> OTHER INFORMATION: Xaa = any amino acid
<221> NAME/KEY: MOD_RES
<222> LOCATION: (632)
```

```
<223> OTHER INFORMATION: Xaa = Glu or Asp
<221> NAME/KEY: MOD_RES
<222> LOCATION: (633)..(635)
<223> OTHER INFORMATION: Xaa = any amino acid
<221> NAME/KEY: MOD_RES
<222> LOCATION: (637)
<223> OTHER INFORMATION: Xaa = Gln or Glu
<221> NAME/KEY: MOD_RES
<222> LOCATION: (638)..(639)
<223> OTHER INFORMATION: Xaa = any amino acid, Xaa at position 639 may
      be present or absent
<221> NAME/KEY: MOD_RES
<222> LOCATION: (640)
<223> OTHER INFORMATION: Xaa = Asn or Gly
<221> NAME/KEY: MOD_RES
<222> LOCATION: (641)..(643)
<223> OTHER INFORMATION: Xaa = any amino acid
<221> NAME/KEY: MOD_RES
<222> LOCATION: (644)
<223> OTHER INFORMATION: Xaa = Glu or Asn
<221> NAME/KEY: MOD_RES
<222> LOCATION: (645)..(674)
<223> OTHER INFORMATION: Xaa = any amino acid, Xaa at positions 665-674
      may be present or absent
<221> NAME/KEY: MOD_RES
<222> LOCATION: (675)
<223> OTHER INFORMATION: Xaa = Asn or Ala
<221> NAME/KEY: MOD_RES
<222> LOCATION: (676)
<223> OTHER INFORMATION: Xaa = Pro or Gly
<221> NAME/KEY: MOD_RES
<222> LOCATION: (677)..(682)
<223> OTHER INFORMATION: Xaa = any amino acid, Xaa at positions 678-682
      may be present or absent
<221> NAME/KEY: MOD_RES
<222> LOCATION: (683)
<223> OTHER INFORMATION: Xaa = Ser or Leu
<221> NAME/KEY: MOD_RES
<222> LOCATION: (684)..(729)
<223> OTHER INFORMATION: Xaa = any amino acid, Xaa at positions 709-729
      may be present or absent
<221> NAME/KEY: MOD_RES
<222> LOCATION: (730)
<223> OTHER INFORMATION: Xaa = Gln or Asp
<221> NAME/KEY: MOD_RES
<222> LOCATION: (732)
<223> OTHER INFORMATION: Xaa = Asp or Asn
<221> NAME/KEY: MOD_RES
<222> LOCATION: (733)
<223> OTHER INFORMATION: Xaa = any amino acid
<221> NAME/KEY: MOD_RES
<222> LOCATION: (734)
<223> OTHER INFORMATION: Xaa = Leu or Phe
<221> NAME/KEY: MOD_RES
<222> LOCATION: (736)..(740)
<223> OTHER INFORMATION: Xaa = any amino acid
<221> NAME/KEY: MOD_RES
<222> LOCATION: (742)..(747)
<223> OTHER INFORMATION: Xaa = any amino acid, Xaa at positions 745-747
      may be present or absent
<221> NAME/KEY: MOD_RES
<222> LOCATION: (749)
<223> OTHER INFORMATION: Xaa = Ser or Thr
<221> NAME/KEY: MOD_RES
<222> LOCATION: (750)
<223> OTHER INFORMATION: Xaa = any amino acid
<221> NAME/KEY: MOD_RES
<222> LOCATION: (751)
<223> OTHER INFORMATION: Xaa = Asp or Asn
<221> NAME/KEY: MOD_RES
<222> LOCATION: (752)
<223> OTHER INFORMATION: Xaa = Tyr or Trp
<221> NAME/KEY: MOD_RES
<222> LOCATION: (753)..(755)
<223> OTHER INFORMATION: Xaa = any amino acid
<221> NAME/KEY: MOD_RES
<222> LOCATION: (757)..(766)
<223> OTHER INFORMATION: Xaa = any amino acid
<221> NAME/KEY: MOD_RES
```

```
<222> LOCATION: (768)..(769)
<223> OTHER INFORMATION: Xaa = any amino acid
<221> NAME/KEY: MOD_RES
<222> LOCATION: (772)
<223> OTHER INFORMATION: Xaa = Met or Gln
<221> NAME/KEY: MOD_RES
<222> LOCATION: (773)
<223> OTHER INFORMATION: Xaa = Asn or Phe
<221> NAME/KEY: MOD_RES
<222> LOCATION: (774)..(775)
<223> OTHER INFORMATION: Xaa = any amino acid
<221> NAME/KEY: MOD_RES
<222> LOCATION: (777)
<223> OTHER INFORMATION: Xaa = Ala or Ser
<221> NAME/KEY: MOD_RES
<222> LOCATION: (778)
<223> OTHER INFORMATION: Xaa = any amino acid
<221> NAME/KEY: MOD_RES
<222> LOCATION: (781)..(792)
<223> OTHER INFORMATION: Xaa = any amino acid, Xaa at positions 783-792
      may be present or absent
<221> NAME/KEY: MOD_RES
<222> LOCATION: (795)..(797)
<223> OTHER INFORMATION: Xaa = any amino acid
<221> NAME/KEY: MOD_RES
<222> LOCATION: (799)..(800)
<223> OTHER INFORMATION: Xaa = any amino acid
<221> NAME/KEY: MOD_RES
<222> LOCATION: (801)
<223> OTHER INFORMATION: Xaa = His or Asn
<221> NAME/KEY: MOD_RES
<222> LOCATION: (803)
<223> OTHER INFORMATION: Xaa = any amino acid
<221> NAME/KEY: MOD_RES
<222> LOCATION: (811)..(812)
<223> OTHER INFORMATION: Xaa = any amino acid
<221> NAME/KEY: MOD_RES
<222> LOCATION: (813)
<223> OTHER INFORMATION: Xaa = Pro or Asp
<221> NAME/KEY: MOD_RES
<222> LOCATION: (814)
<223> OTHER INFORMATION: Xaa = Pro or Ser
<221> NAME/KEY: MOD_RES
<222> LOCATION: (815)
<223> OTHER INFORMATION: Xaa = Asp or His
<221> NAME/KEY: MOD_RES
<222> LOCATION: (816)
<223> OTHER INFORMATION: Xaa = any amino acid
<221> NAME/KEY: MOD_RES
<222> LOCATION: (817)
<223> OTHER INFORMATION: Xaa = Ala or Val
<221> NAME/KEY: MOD_RES
<222> LOCATION: (819)
<223> OTHER INFORMATION: Xaa = any amino acid
<221> NAME/KEY: MOD_RES
<222> LOCATION: (820)
<223> OTHER INFORMATION: Xaa = Tyr or Phe
<221> NAME/KEY: MOD_RES
<222> LOCATION: (823)
<223> OTHER INFORMATION: Xaa = Ser or Glu
<221> NAME/KEY: MOD_RES
<222> LOCATION: (824)
<223> OTHER INFORMATION: Xaa = Ile or Phe
<221> NAME/KEY: MOD_RES
<222> LOCATION: (825)
<223> OTHER INFORMATION: Xaa = any amino acid
<221> NAME/KEY: MOD_RES
<222> LOCATION: (827)
<223> OTHER INFORMATION: Xaa = Leu or Ile
<221> NAME/KEY: MOD_RES
<222> LOCATION: (832)
<223> OTHER INFORMATION: Xaa = Val or Ala
<221> NAME/KEY: MOD_RES
<222> LOCATION: (839)
<223> OTHER INFORMATION: Xaa = any amino acid
<221> NAME/KEY: MOD_RES
<222> LOCATION: (841)
<223> OTHER INFORMATION: Xaa = His or Lys
<221> NAME/KEY: MOD_RES
```

```
<222> LOCATION: (842)..(843)
<223> OTHER INFORMATION: Xaa = any amino acid
<221> NAME/KEY: MOD_RES
<222> LOCATION: (855)
<223> OTHER INFORMATION: Xaa = Ala or Cys
<221> NAME/KEY: MOD_RES
<222> LOCATION: (858)
<223> OTHER INFORMATION: Xaa = Met or Leu
<221> NAME/KEY: MOD_RES
<222> LOCATION: (860)
<223> OTHER INFORMATION: Xaa = Trp or Leu
<221> NAME/KEY: MOD_RES
<222> LOCATION: (864)
<223> OTHER INFORMATION: Xaa = Gln or Glu
<221> NAME/KEY: MOD_RES
<222> LOCATION: (868)..(869)
<223> OTHER INFORMATION: Xaa = any amino acid
<221> NAME/KEY: MOD_RES
<222> LOCATION: (870)
<223> OTHER INFORMATION: Xaa = Leu or Val
<221> NAME/KEY: MOD_RES
<222> LOCATION: (872)
<223> OTHER INFORMATION: Xaa = Leu or Met
<221> NAME/KEY: MOD_RES
<222> LOCATION: (874)
<223> OTHER INFORMATION: Xaa = Leu or Gln
<221> NAME/KEY: MOD_RES
<222> LOCATION: (876)
<223> OTHER INFORMATION: Xaa = Glu or Phe
<221> NAME/KEY: MOD_RES
<222> LOCATION: (877)
<223> OTHER INFORMATION: Xaa = any amino acid
<221> NAME/KEY: MOD_RES
<222> LOCATION: (880)
<223> OTHER INFORMATION: Xaa = any amino acid
<221> NAME/KEY: MOD_RES
<222> LOCATION: (881)
<223> OTHER INFORMATION: Xaa = Leu or Met
<221> NAME/KEY: MOD_RES
<222> LOCATION: (882)
<223> OTHER INFORMATION: Xaa = Glu or Asp
<221> NAME/KEY: MOD_RES
<222> LOCATION: (883)
<223> OTHER INFORMATION: Xaa = Ser or Asn
<221> NAME/KEY: MOD_RES
<222> LOCATION: (884)
<223> OTHER INFORMATION: Xaa = Ile or Val
<221> NAME/KEY: MOD_RES
<222> LOCATION: (887)
<223> OTHER INFORMATION: Xaa = Phe or Tyr
<221> NAME/KEY: MOD_RES
<222> LOCATION: (896)
<223> OTHER INFORMATION: Xaa = Asp or Pro
<221> NAME/KEY: MOD_RES
<222> LOCATION: (898)
<223> OTHER INFORMATION: Xaa = any amino acid
<221> NAME/KEY: MOD_RES
<222> LOCATION: (906)
<223> OTHER INFORMATION: Xaa = Gln or His
<221> NAME/KEY: MOD_RES
<222> LOCATION: (907)
<223> OTHER INFORMATION: Xaa = Leu or Met
<221> NAME/KEY: MOD_RES
<222> LOCATION: (913)..(914)
<223> OTHER INFORMATION: Xaa = any amino acid, Xaa at positions 913 and
      914 may be present or absent
<221> NAME/KEY: MOD_RES
<222> LOCATION: (919)..(920)
<223> OTHER INFORMATION: Xaa = any amino acid
<221> NAME/KEY: MOD_RES
<222> LOCATION: (929)
<223> OTHER INFORMATION: Xaa = Arg or Lys
<221> NAME/KEY: MOD_RES
<222> LOCATION: (930)..(931)
<223> OTHER INFORMATION: Xaa = any amino acid, Xaa at positions 930 and
      931 may be present or absent
<221> NAME/KEY: MOD_RES
<222> LOCATION: (934)
<223> OTHER INFORMATION: Xaa = Arg or Lys
```

```
<221> NAME/KEY: MOD_RES
<222> LOCATION: (935)
<223> OTHER INFORMATION: Xaa = His or Tyr
<221> NAME/KEY: MOD_RES
<222> LOCATION: (936)
<223> OTHER INFORMATION: Xaa = Phe or Tyr
<221> NAME/KEY: MOD_RES
<222> LOCATION: (937)
<223> OTHER INFORMATION: Xaa = Ala or Ser
<221> NAME/KEY: MOD_RES
<222> LOCATION: (940)
<223> OTHER INFORMATION: Xaa = any amino acid
<221> NAME/KEY: MOD_RES
<222> LOCATION: (941)
<223> OTHER INFORMATION: Xaa = Ala or Val
<221> NAME/KEY: MOD_RES
<222> LOCATION: (942)..(951)
<223> OTHER INFORMATION: Xaa = any amino acid, Xaa at positions 942-951
      may be present or absent
<221> NAME/KEY: MOD_RES
<222> LOCATION: (953)
<223> OTHER INFORMATION: Xaa = Ala or Ser
<221> NAME/KEY: MOD_RES
<222> LOCATION: (954)
<223> OTHER INFORMATION: Xaa = Arg or Lys
<221> NAME/KEY: MOD_RES
<222> LOCATION: (955)
<223> OTHER INFORMATION: Xaa = any amino acid
<221> NAME/KEY: MOD_RES
<222> LOCATION: (956)
<223> OTHER INFORMATION: Xaa = Ala or Leu
<221> NAME/KEY: MOD_RES
<222> LOCATION: (958)
<223> OTHER INFORMATION: Xaa = Pro or Glu
<221> NAME/KEY: MOD_RES
<222> LOCATION: (959)
<223> OTHER INFORMATION: Xaa = any amino acid
<221> NAME/KEY: MOD_RES
<222> LOCATION: (960)
<223> OTHER INFORMATION: Xaa = Pro or Thr
<221> NAME/KEY: MOD_RES
<222> LOCATION: (961)
<223> OTHER INFORMATION: Xaa = Glu or Gln
<221> NAME/KEY: MOD_RES
<222> LOCATION: (962)..(977)
<223> OTHER INFORMATION: Xaa = any amino acid, Xaa at positions 969-977
      may be present or absent
<221> NAME/KEY: MOD_RES
<222> LOCATION: (979)
<223> OTHER INFORMATION: Xaa = Ile or Leu
<221> NAME/KEY: MOD_RES
<222> LOCATION: (980)
<223> OTHER INFORMATION: Xaa = Ile or Val
<221> NAME/KEY: MOD_RES
<222> LOCATION: (982)
<223> OTHER INFORMATION: Xaa = Glu or Phe
<221> NAME/KEY: MOD_RES
<222> LOCATION: (984)
<223> OTHER INFORMATION: Xaa = any amino acid
<221> NAME/KEY: MOD_RES
<222> LOCATION: (985)
<223> OTHER INFORMATION: Xaa = Ser or Thr
<221> NAME/KEY: MOD_RES
<222> LOCATION: (987)..(991)
<223> OTHER INFORMATION: Xaa = any amino acid, Xaa at positions 989-991
      may be present or absent
<221> NAME/KEY: MOD_RES
<222> LOCATION: (993)..(1007)
<223> OTHER INFORMATION: Xaa = any amino acid, Xaa at positions 993-1007
      may be present or absent
<221> NAME/KEY: MOD_RES
<222> LOCATION: (1008)
<223> OTHER INFORMATION: Xaa = Asp or Ala
<221> NAME/KEY: MOD_RES
<222> LOCATION: (1011)
<223> OTHER INFORMATION: Xaa = Asp or Glu
<221> NAME/KEY: MOD_RES
<222> LOCATION: (1012)..(1034)
<223> OTHER INFORMATION: Xaa = any amino acid, Xaa at positions
```

-continued

```
        1016-1034 may be present or absent
<221> NAME/KEY: MOD_RES
<222> LOCATION: (1035)
<223> OTHER INFORMATION: Xaa = Ile or Val
<221> NAME/KEY: MOD_RES
<222> LOCATION: (1037)
<223> OTHER INFORMATION: Xaa = any amino acid
<221> NAME/KEY: MOD_RES
<222> LOCATION: (1039)
<223> OTHER INFORMATION: Xaa = any amino acid
<221> NAME/KEY: MOD_RES
<222> LOCATION: (1040)
<223> OTHER INFORMATION: Xaa = Leu or Phe
<221> NAME/KEY: MOD_RES
<222> LOCATION: (1041)
<223> OTHER INFORMATION: Xaa = Asn or Asp
<221> NAME/KEY: MOD_RES
<222> LOCATION: (1042)..(1058)
<223> OTHER INFORMATION: Xaa = any amino acid, Xaa at positions
        1050-1058 may be present or absent
<221> NAME/KEY: MOD_RES
<222> LOCATION: (1059)
<223> OTHER INFORMATION: Xaa = Ser or Ala
<221> NAME/KEY: MOD_RES
<222> LOCATION: (1060)
<223> OTHER INFORMATION: Xaa = any amino acid
<221> NAME/KEY: MOD_RES
<222> LOCATION: (1061)
<223> OTHER INFORMATION: Xaa = Ala or Asp
<221> NAME/KEY: MOD_RES
<222> LOCATION: (1064)..(1071)
<223> OTHER INFORMATION: Xaa = any amino acid
<221> NAME/KEY: MOD_RES
<222> LOCATION: (1072)
<223> OTHER INFORMATION: Xaa = Ile or Leu
<221> NAME/KEY: MOD_RES
<222> LOCATION: (1074)..(1078)
<223> OTHER INFORMATION: Xaa = any amino acid, Xaa at positions
        1076-1078 may be present or absent
<221> NAME/KEY: MOD_RES
<222> LOCATION: (1079)
<223> OTHER INFORMATION: Xaa = Lys or Arg
<221> NAME/KEY: MOD_RES
<222> LOCATION: (1080)
<223> OTHER INFORMATION: Xaa = Leu or Met
<221> NAME/KEY: MOD_RES
<222> LOCATION: (1082)..(1085)
<223> OTHER INFORMATION: Xaa = any amino acid
<221> NAME/KEY: MOD_RES
<222> LOCATION: (1091)
<223> OTHER INFORMATION: Xaa = any amino acid
<221> NAME/KEY: MOD_RES
<222> LOCATION: (1093)
<223> OTHER INFORMATION: Xaa = Tyr or Phe
<221> NAME/KEY: MOD_RES
<222> LOCATION: (1094)
<223> OTHER INFORMATION: Xaa = Glu or Val
<221> NAME/KEY: MOD_RES
<222> LOCATION: (1098)
<223> OTHER INFORMATION: Xaa = any amino acid
<221> NAME/KEY: MOD_RES
<222> LOCATION: (1100)
<223> OTHER INFORMATION: Xaa = any amino acid
<221> NAME/KEY: MOD_RES
<222> LOCATION: (1101)
<223> OTHER INFORMATION: Xaa = Leu or Ile
<221> NAME/KEY: MOD_RES
<222> LOCATION: (1103)
<223> OTHER INFORMATION: Xaa = Glu or Lys
<221> NAME/KEY: MOD_RES
<222> LOCATION: (1104)
<223> OTHER INFORMATION: Xaa = any amino acid
<221> NAME/KEY: MOD_RES
<222> LOCATION: (1105)
<223> OTHER INFORMATION: Xaa = Asp or Glu
<221> NAME/KEY: MOD_RES
<222> LOCATION: (1107)
<223> OTHER INFORMATION: Xaa = Pro or Ile
<221> NAME/KEY: MOD_RES
```

```
<222> LOCATION: (1108)..(1109)
<223> OTHER INFORMATION: Xaa = any amino acid
<221> NAME/KEY: MOD_RES
<222> LOCATION: (1113)
<223> OTHER INFORMATION: Xaa = Ala or Ser
<221> NAME/KEY: MOD_RES
<222> LOCATION: (1116)
<223> OTHER INFORMATION: Xaa = Thr or Gln
<221> NAME/KEY: MOD_RES
<222> LOCATION: (1118)
<223> OTHER INFORMATION: Xaa = Gly or Asp
<221> NAME/KEY: MOD_RES
<222> LOCATION: (1119)
<223> OTHER INFORMATION: Xaa = Glu or Gly
<221> NAME/KEY: MOD_RES
<222> LOCATION: (1120)..(1127)
<223> OTHER INFORMATION: Xaa = any amino acid, Xaa at positions 1126 and
      1127 may be present or absent
<221> NAME/KEY: MOD_RES
<222> LOCATION: (1128)
<223> OTHER INFORMATION: Xaa = Pro or Ser
<221> NAME/KEY: MOD_RES
<222> LOCATION: (1129)..(1131)
<223> OTHER INFORMATION: Xaa = any amino acid
<221> NAME/KEY: MOD_RES
<222> LOCATION: (1133)..(1142)
<223> OTHER INFORMATION: Xaa = any amino acid, Xaa at positions
      1139-1142 may be present or absent
<221> NAME/KEY: MOD_RES
<222> LOCATION: (1143)
<223> OTHER INFORMATION: Xaa = Met or Leu
<221> NAME/KEY: MOD_RES
<222> LOCATION: (1145)..(1148)
<223> OTHER INFORMATION: Xaa = any amino acid
<221> NAME/KEY: MOD_RES
<222> LOCATION: (1150)..(1151)
<223> OTHER INFORMATION: Xaa = any amino acid
<221> NAME/KEY: MOD_RES
<222> LOCATION: (1153)..(1155)
<223> OTHER INFORMATION: Xaa = any amino acid
<221> NAME/KEY: MOD_RES
<222> LOCATION: (1156)
<223> OTHER INFORMATION: Xaa = Arg or Lys
<221> NAME/KEY: MOD_RES
<222> LOCATION: (1158)..(1162)
<223> OTHER INFORMATION: Xaa = any amino acid
<221> NAME/KEY: MOD_RES
<222> LOCATION: (1163)
<223> OTHER INFORMATION: Xaa = Val or Phe
<221> NAME/KEY: MOD_RES
<222> LOCATION: (1167)
<223> OTHER INFORMATION: Xaa = Leu or Ile
<221> NAME/KEY: MOD_RES
<222> LOCATION: (1169)..(1190)
<223> OTHER INFORMATION: Xaa = any amino acid, Xaa at positions
      1169-1190 may be present or absent
<221> NAME/KEY: MOD_RES
<222> LOCATION: (1191)
<223> OTHER INFORMATION: Xaa = Leu or Val
<221> NAME/KEY: MOD_RES
<222> LOCATION: (1196)
<223> OTHER INFORMATION: Xaa = any amino acid
<221> NAME/KEY: MOD_RES
<222> LOCATION: (1197)
<223> OTHER INFORMATION: Xaa = Ser or Thr
<221> NAME/KEY: MOD_RES
<222> LOCATION: (1198)
<223> OTHER INFORMATION: Xaa = Ser or Arg
<221> NAME/KEY: MOD_RES
<222> LOCATION: (1199)..(1200)
<223> OTHER INFORMATION: Xaa = any amino acid
<221> NAME/KEY: MOD_RES
<222> LOCATION: (1203)..(1205)
<223> OTHER INFORMATION: Xaa = any amino acid
<221> NAME/KEY: MOD_RES
<222> LOCATION: (1206)
<223> OTHER INFORMATION: Xaa = Arg or Thr
<221> NAME/KEY: MOD_RES
<222> LOCATION: (1207)..(1209)
```

```
<223> OTHER INFORMATION: Xaa = any amino acid
<221> NAME/KEY: MOD_RES
<222> LOCATION: (1210)
<223> OTHER INFORMATION: Xaa = Trp or Lys
<221> NAME/KEY: MOD_RES
<222> LOCATION: (1211)
<223> OTHER INFORMATION: Xaa = any amino acid
<221> NAME/KEY: MOD_RES
<222> LOCATION: (1213)
<223> OTHER INFORMATION: Xaa = any amino acid
<221> NAME/KEY: MOD_RES
<222> LOCATION: (1214)
<223> OTHER INFORMATION: Xaa = Arg or Lys
<221> NAME/KEY: MOD_RES
<222> LOCATION: (1216)..(1219)
<223> OTHER INFORMATION: Xaa = any amino acid
<221> NAME/KEY: MOD_RES
<222> LOCATION: (1221)
<223> OTHER INFORMATION: Xaa = Thr or Ser
<221> NAME/KEY: MOD_RES
<222> LOCATION: (1222)
<223> OTHER INFORMATION: Xaa = Ser or Thr
<221> NAME/KEY: MOD_RES
<222> LOCATION: (1223)..(1224)
<223> OTHER INFORMATION: Xaa = any amino acid
<221> NAME/KEY: MOD_RES
<222> LOCATION: (1225)
<223> OTHER INFORMATION: Xaa = Ser or Thr
<221> NAME/KEY: MOD_RES
<222> LOCATION: (1227)
<223> OTHER INFORMATION: Xaa = Phe or Cys
<221> NAME/KEY: MOD_RES
<222> LOCATION: (1228)
<223> OTHER INFORMATION: Xaa = Arg or Lys
<221> NAME/KEY: MOD_RES
<222> LOCATION: (1229)
<223> OTHER INFORMATION: Xaa = Gly or Leu
<221> NAME/KEY: MOD_RES
<222> LOCATION: (1231)
<223> OTHER INFORMATION: Xaa = any amino acid
<221> NAME/KEY: MOD_RES
<222> LOCATION: (1232)
<223> OTHER INFORMATION: Xaa = Thr or Val
<221> NAME/KEY: MOD_RES
<222> LOCATION: (1233)..(1234)
<223> OTHER INFORMATION: Xaa = any amino acid
<221> NAME/KEY: MOD_RES
<222> LOCATION: (1236)..(1237)
<223> OTHER INFORMATION: Xaa = any amino acid
<221> NAME/KEY: MOD_RES
<222> LOCATION: (1238)
<223> OTHER INFORMATION: Xaa = Cys or Asn
<221> NAME/KEY: MOD_RES
<222> LOCATION: (1240)
<223> OTHER INFORMATION: Xaa = Trp or Gln
<221> NAME/KEY: MOD_RES
<222> LOCATION: (1241)
<223> OTHER INFORMATION: Xaa = any amino acid
<221> NAME/KEY: MOD_RES
<222> LOCATION: (1243)
<223> OTHER INFORMATION: Xaa = Phe or Tyr
<221> NAME/KEY: MOD_RES
<222> LOCATION: (1244)
<223> OTHER INFORMATION: Xaa = Val or Leu
<221> NAME/KEY: MOD_RES
<222> LOCATION: (1246)
<223> OTHER INFORMATION: Xaa = Val or Leu
<221> NAME/KEY: MOD_RES
<222> LOCATION: (1248)
<223> OTHER INFORMATION: Xaa = any amino acid
<221> NAME/KEY: MOD_RES
<222> LOCATION: (1250)
<223> OTHER INFORMATION: Xaa = Glu or Asp
<221> NAME/KEY: MOD_RES
<222> LOCATION: (1251)..(1253)
<223> OTHER INFORMATION: Xaa = any amino acid
<221> NAME/KEY: MOD_RES
<222> LOCATION: (1254)
<223> OTHER INFORMATION: Xaa = Arg or Gly
```

```
<221> NAME/KEY: MOD_RES
<222> LOCATION: (1255)
<223> OTHER INFORMATION: Xaa = any amino acid
<221> NAME/KEY: MOD_RES
<222> LOCATION: (1257)
<223> OTHER INFORMATION: Xaa = Arg or Lys
<221> NAME/KEY: MOD_RES
<222> LOCATION: (1258)
<223> OTHER INFORMATION: Xaa = any amino acid
<221> NAME/KEY: MOD_RES
<222> LOCATION: (1260)..(1261)
<223> OTHER INFORMATION: Xaa = any amino acid
<221> NAME/KEY: MOD_RES
<222> LOCATION: (1262)
<223> OTHER INFORMATION: Xaa = Arg or His
<221> NAME/KEY: MOD_RES
<222> LOCATION: (1265)..(1266)
<223> OTHER INFORMATION: Xaa = any amino acid
<221> NAME/KEY: MOD_RES
<222> LOCATION: (1267)
<223> OTHER INFORMATION: Xaa = Ala or Val

<400> SEQUENCE: 74

Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Lys Xaa Lys Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Leu Xaa Xaa Xaa Xaa
            100                 105                 110

Xaa Xaa Xaa Xaa Xaa Asp Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Lys Val Xaa Xaa Asp Xaa Xaa Thr Xaa Xaa Xaa
            180                 185                 190

Trp Xaa Xaa Leu Xaa Xaa Xaa Xaa Asp Xaa Xaa Xaa Xaa Xaa Xaa
        195                 200                 205

Xaa Xaa Glu Arg Xaa Xaa Phe Xaa Xaa Arg Xaa Xaa Xaa Phe Ile Xaa
    210                 215                 220

Arg Met Xaa Xaa Xaa Gln Gly Xaa Arg Xaa Phe Xaa Xaa Trp Lys Gly
225                 230                 235                 240

Ser Val Val Asp Ser Val Xaa Gly Val Phe Leu Thr Gln Asn Xaa Asp
                245                 250                 255

Xaa Xaa Ser Ser Xaa Ala Xaa Met Xaa Xaa Ala Xaa Xaa Phe Pro Xaa
            260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
```

-continued

```
            290                 295                 300
Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
            435                 440                 445

Xaa Ser Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa Xaa
            515                 520                 525

Xaa Xaa Xaa Xaa Xaa Xaa Xaa Xaa Xaa Xaa Xaa Xaa Xaa Xaa Xaa Xaa
            530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa Xaa
            595                 600                 605

Xaa Xaa Xaa Xaa Xaa Xaa Xaa Xaa Glu Xaa Xaa Xaa Xaa Xaa Xaa Xaa
            610                 615                 620

Xaa Xaa Xaa Xaa Xaa Xaa Xaa Xaa Xaa Xaa Thr Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa Xaa
            675                 680                 685

Xaa Xaa Xaa Xaa Xaa Xaa Xaa Xaa Xaa Xaa Xaa Xaa Xaa Xaa Xaa Xaa
            690                 695                 700

Xaa Xaa Xaa Xaa Xaa Xaa Xaa Xaa Xaa Xaa Xaa Xaa Xaa Xaa Xaa Xaa
705                 710                 715                 720
```

```
Xaa Xaa Xaa Xaa Xaa Xaa Xaa Xaa Xaa Xaa Trp Xaa Xaa Arg Xaa
                725                 730                 735

Xaa Xaa Xaa Xaa Glu Xaa Xaa Xaa Xaa Xaa Asp Xaa Xaa Xaa Xaa
                740                 745                 750

Xaa Xaa Xaa Arg Xaa Xaa Xaa Xaa Xaa Xaa Xaa Xaa Xaa Ile Xaa
                755                 760                 765

Xaa Arg Gly Xaa Xaa Xaa Xaa Leu Xaa Xaa Arg Ile Xaa Xaa Xaa Xaa
        770                 775                 780

Xaa Xaa Xaa Xaa Xaa Xaa Xaa Xaa Phe Leu Xaa Xaa Xaa Val Xaa Xaa
785                 790                 795                 800

Xaa Gly Xaa Ile Asp Leu Glu Trp Leu Arg Xaa Xaa Xaa Xaa Xaa
            805                 810                 815

Xaa Lys Xaa Xaa Leu Leu Xaa Xaa Xaa Gly Xaa Gly Leu Lys Ser Xaa
            820                 825                 830

Glu Cys Val Arg Leu Leu Xaa Leu Xaa Xaa Xaa

-continued

```
Xaa Xaa Xaa Xaa Xaa Xaa Xaa Cys Xaa Xaa Xaa Xaa Cys Xaa Xaa Cys
        1140                1145                1150

Xaa Xaa Xaa Xaa Glu Xaa Xaa Xaa Xaa Xaa Xaa Arg Gly Thr Xaa Leu
    1155                1160                1165

Xaa Xaa Xaa Xaa Xaa Xaa Xaa Xaa Xaa Xaa Xaa Xaa Xaa Xaa Xaa Xaa
    1170                1175                1180

Xaa Xaa Xaa Xaa Xaa Xaa Xaa Phe Ala Asp His Xaa Xaa Xaa Xaa Xaa
1185                1190                1195                1200

Pro Ile Xaa Xaa Xaa Xaa Xaa Xaa Xaa Xaa Leu Xaa Xaa Arg Xaa
            1205                1210                1215

Xaa Xaa Xaa Gly Xaa Xaa Xaa Xaa Ile Xaa Xaa Xaa Leu Xaa Xaa
        1220                1225                1230

Xaa Xaa Ile Xaa Xaa Xaa Phe Xaa Xaa Gly Xaa Xaa Cys Xaa Arg Xaa
        1235                1240                1245

Phe Xaa Xaa Xaa Xaa Xaa Xaa Pro Xaa Xaa Leu Xaa Xaa Xaa Leu His
    1250                1255                1260

Xaa Xaa Xaa Ser Lys
1265

<210> SEQ ID NO 75
<211> LENGTH: 34
<212> TYPE: PRT
<213> ORGANISM: Artificial Sequence
<220> FEATURE:
<223> OTHER INFORMATION: Description of Artificial Sequence:DMT
      conserved HhH-GPD motif

<400> SEQUENCE: 75

Asp Lys Ala Lys Asp Tyr Leu Leu Ser Ile Arg Gly Leu Gly Leu Lys
 1               5                  10                  15

Ser Val Glu Cys Val Arg Leu Leu Thr Leu His Asn Leu Ala Phe Pro
            20                  25                  30

Val Asp

<210> SEQ ID NO 76
<211> LENGTH: 29
<212> TYPE: DNA
<213> ORGANISM: Artificial Sequence
<220> FEATURE:
<223> OTHER INFORMATION: Description of Artificial Sequence:primer
      Xba-SKEN-7

<400> SEQUENCE: 76
cctctagagg aattgtcggc aaaatcgag                                    29

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence:primer SKB-8

<400> SEQUENCE: 77
ggagagacgg ttattgtcaa cc                                           22

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence:primer SKB-7
```

```
<400> SEQUENCE: 78
aaaagtctac aagggagaga gagt                                              24

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence:primer SKB-5

<400> SEQUENCE: 79
gtagatgtac atacgtacc                                                    19

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence:primer
      SKEN-8

<400> SEQUENCE: 80
gcatcctcca acaagtaaca atccactc                                          28

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence:primer SKB-6

<400> SEQUENCE: 81
cactgagatt aattcttcag actcg                                             25

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence:primer
      SKEN-3.5

<400> SEQUENCE: 82
ctcaggcgag tcaatgccgg agaacac                                           27

<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence:primer
      SKEN-3

<400> SEQUENCE: 83
cgagggctga tccgggggat agatatttt                                         29

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence:primer
      SKEN-2

<400> SEQUENCE: 84
cccccggatc agccctcgaa ttc                                               23
```

<210> SEQ ID NO 85
<211> LENGTH: 26
<212> TYPE: DNA
<213> ORGANISM: Artificial Sequence
<220> FEATURE:
<223> OTHER INFORMATION: Description of Artificial Sequence:primer
      SKEN-1

<400> SEQUENCE: 85
cccctgtcta caaattcacc acctgg                                    26

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence:primer
      SKEL-4

<400> SEQUENCE: 86
ctgacccaac tgcttctctt c                                         21

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence:primer
      skes1.5

<400> SEQUENCE: 87
tcacctgttc tgaacagact gg                                        22

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence:primer
      SKES-1.4

<400> SEQUENCE: 88
cagcagacga gtccataatg ctctgc                                    26

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence:primer
      SKES-2.4

<400> SEQUENCE: 89
ggtttgcctt ccacgaccac c                                         21

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence:primer
      SKES-1

<400> SEQUENCE: 90
ggaagccacg caaagctgca actcagg                                   27

```
<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence:primer
      SKES-2.45

<400> SEQUENCE: 91
gagttgcagc tttgcgtggc ttcc                                             24

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence:primer
      SKES2.5

<400> SEQUENCE: 92
ttcagactca gagtcacctt gc                                               22

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence:primer
      SKES-2

<400> SEQUENCE: 93
accagcagcc ttgcttggcc                                                  20

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence:primer
      SKES-3

<400> SEQUENCE: 94
catgccagag aagcagggct cc                                               22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence:primer
      SKES3.5

<400> SEQUENCE: 95
cgatgatact gtctcttcga gc                                               22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence:primer
      SKES-6

<400> SEQUENCE: 96
cctccgcctg ctcatgcctc ag                                               22
```

<210> SEQ ID NO 97
<211> LENGTH: 29
<212> TYPE: DNA
<213> ORGANISM: Artificial Sequence
<220> FEATURE:
<223> OTHER INFORMATION: Description of Artificial Sequence:primer SKEN-4

<400> SEQUENCE: 97
gtccatcagg agaacttctg tgtcaggat                29

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence:primer SKES-4

<400> SEQUENCE: 98
gggaacaagt gcaccatctc c                21

<210> SEQ ID NO 99
<211> LENGTH: 29
<212> TYPE: DNA
<213> ORGANISM: Artificial Sequence
<220> FEATURE:
<223> OTHER INFORMATION: Description of Artificial Sequence:primer SKEN-6

<400> SEQUENCE: 99
gctctcatag ggaacaagtg caccatctc                29

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence:primer SKES-5

<400> SEQUENCE: 100
cgctcgcatg cacctggtac                20

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence:primer SKB-1

<400> SEQUENCE: 101
ggagggaatc gagcagctag ag                22

<210> SEQ ID NO 102
<211> LENGTH: 26
<212> TYPE: DNA
<213> ORGANISM: Artificial Sequence
<220> FEATURE:
<223> OTHER INFORMATION: Description of Artificial Sequence:primer SKB-2

<400> SEQUENCE: 102
gagcagctaa gggactgttc aaactc                26

<210> SEQ ID NO 103
<211> LENGTH: 20
<212> TYPE: DNA

```
<213> ORGANISM: Artificial Sequence
<220> FEATURE:
<223> OTHER INFORMATION: Description of Artificial Sequence:primer SKB-3

<400> SEQUENCE: 103
ccaggaatgg gattgtccgg                                              20

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence:primer
      3'RACE-2

<400> SEQUENCE: 104
cttggacggc gcttgaggaa cc                                           22

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence:primer
      3'RACE-1

<400> SEQUENCE: 105
gcctacaagc cagtgggata g                                            21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence:primer
      cDNA-1

<400> SEQUENCE: 106
gccaaggact atctcttgag c                                            21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence:primer SKB-4

<400> SEQUENCE: 107
ggatggactc gagcactggg                                              20

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence:primer
      SKE2.2-4

<400> SEQUENCE: 108
agaggagagt gcagacactt tg                                           22

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence:primer
``` cDNA-3

<400> SEQUENCE: 109
gaggaccctg acgagatccc aac 23

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence:primer
      cDNA-9

<400> SEQUENCE: 110
ccatgtgttc ccgtagagtc attcc 25

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence:primer
      2.2+SKE-1

<400> SEQUENCE: 111
atggagctcc aagaaggtga catg 24

<210> SEQ ID NO 112
<211> LENGTH: 27
<212> TYPE: DNA
<213> ORGANISM: Artificial Sequence
<220> FEATURE:
<223> OTHER INFORMATION: Description of Artificial Sequence:primer
      cDNA-5

<400> SEQUENCE: 112
cagaagtgtg gagggaaagc gtctggc 27

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence:primer
      cDNA-4

<400> SEQUENCE: 113
ccctcagact gttacactca gaac 24

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence:primer
      cDNA-2

<400> SEQUENCE: 114
cccgttgagc ggaaaacttc ctctcatggc 30

<210> SEQ ID NO 115
<211> LENGTH: 25
<212> TYPE: DNA
<213> ORGANISM: Artificial Sequence
<220> FEATURE:
<223> OTHER INFORMATION: Description of Artificial Sequence:primer
      cDNA-7

```
<400> SEQUENCE: 115
ggaaaggatt cgtatgtgtc cgtgg                                         25

<210> SEQ ID NO 116
<211> LENGTH: 29
<212> TYPE: DNA
<213> ORGANISM: Artificial Sequence
<220> FEATURE:
<223> OTHER INFORMATION: Description of Artificial Sequence:primer
      SKEN-5

<400> SEQUENCE: 116
gcaatgcgtt tgctttcttc cagtcatct                                     29

<210> SEQ ID NO 117
<211> LENGTH: 28
<212> TYPE: DNA
<213> ORGANISM: Artificial Sequence
<220> FEATURE:
<223> OTHER INFORMATION: Description of Artificial Sequence:primer
      cDNA-6

<400> SEQUENCE: 117
gaggagagca gagaagcaat gcgtttgc                                      28

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence:primer
      cDNA-8

<400> SEQUENCE: 118
gttagagaga aaataaataa ccc                                           23

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence:primer
      2.2+SKE-3

<400> SEQUENCE: 119
ccgtaaacaa caccggatac ac                                            22
```

METHODS FOR MODULATING FLORAL ORGAN IDENTITY, MODULATING FLORAL ORGAN NUMBER, INCREASING OF MERISTEM SIZE, AND DELAYING FLOWERING TIME

CROSS-REFERENCES TO RELATED APPLICATIONS

This application is a continuation-in-part of U.S. patent application Ser. No. 09/553,690, filed Apr. 21, 2000 now U.S. Pat. No. 6,476,296, the contents of which are incorporated by reference.

STATEMENT AS TO RIGHTS TO INVENTIONS MADE UNDER FEDERALLY SPONSORED RESEARCH AND DEVELOPMENT

This invention was made with Government support under Grant No. 97-35304-4941, awarded by the United States Department of Agriculture. The government has certain rights in this invention.

FIELD OF THE INVENTION

This invention is directed to plant genetic engineering. It relates to, for example, modulating seed (and in particular endosperm, embryo and seed coat) development, flowering time, chromosomal DNA methylation and modulating transcription in plants.

BACKGROUND OF THE INVENTION

A fundamental problem in biology is to understand how seed development. In flowering plants, the ovule generates the female gametophyte, which is composed of egg, central, synergid and antipodal cells (Reiser, et al., *Plant Cell*, 1291–1301 (1993)). All are haploid except the central cell which contains two daughter nuclei that fuse prior to fertilization. One sperm nucleus fertilizes the egg to form the zygote, whereas another sperm nucleus fuses with the diploid central cell nucleus to form the triploid endosperm nucleus (van Went, et al., *Embryology of Angiosperms*, pp. 273–318 (1984)). The two fertilization products undergo distinct patterns of development. In *Arabidopsis*, the embryo passes through a series of stages that have been defined morphologically as preglobular, globular, heart, cotyledon and maturation (Goldberg, R. B., et al., *Science* (1994) 266: 605–614; Mansfield, S. G., et al., *Arabidopsis: An Atlas of Morphology and Development*, pp. 367–383 (1994)). The primary endosperm nucleus undergoes a series of mitotic divisions to produce nuclei that migrate into the expanding central cell (Mansfield, S. G., et al., *Arab Inf Serv* 27: 53–64 (1990); Webb, M. C., et al, *Planta* 184:187–195 (1991)). Cytokinesis sequesters endosperm cytoplasm and nuclei into discrete cells (Mansfield, S. G., et al., *Arab Inf Serv* 27:65–72 (1990)) that produce storage proteins, starch, and lipids which support embryo growth (Lopes, M. A. et al., *Plant Cell* 5:1383–1399 (1993)). Fertilization also activates development of the integument cell layers of the ovule that become the seed coat, and induces the ovary to grow and form the fruit, or silique, in *Arabidopsis*.

Of particular interest are recent discoveries of genes that control seed, and in particular endosperm, development. For instance, MEDEA (MEA) (also known as *FIE*1 (see, e.g., copending U.S. patent application Ser. No. 09/071,838) and F644 (see, e.g., Kiyosue T, et al. (1999) *Proc Natl Acad Sci U.S.A* 96(7):4186–91) encodes an *Arabidopsis* SET domain polycomb protein that appears to play a role in endosperm development. Inheritance of a maternal loss-of-function mea allele results in embryo abortion and prolonged endosperm production, irrespective of the genotype of the paternal allele. Thus, only the maternal wild-type MEA allele is required for proper embryo, endosperm, and seed coat development (Kinoshita T, et al. (1999) *Plant Cell* 10:1945–52). These results reveal functions for plant polycomb proteins in the suppression of central cell proliferation and endosperm development (Kiyosue T, et al. supra).

Another gene product that controls seed development is FIE, also known as FIE3 (see, e.g., copending U.S. patent application Ser. No. 09/071,838). The FIE protein is a homolog of the WD motif-containing Polycomb proteins from Drosophila and mammals (Ohad, N. et al. *Plant Cell* 11(3):407–16 (1999)). In Drosophila, these proteins function as repressors of homeotic genes. Loss of function mutations in the FIE gene result in endosperm phenotypes that are identical to medea loss of function mutations. A female gametophyte with a loss-of-function allele of fie undergoes replication of the central cell nucleus and initiates endosperm development without fertilization. These results suggest that the FIE Polycomb protein functions to suppress a critical aspect of early plant reproduction, namely, endosperm development, until fertilization occurs. Moreover, hypomethylation of fie mutants leads to the development of differentiated endosperm. Vinkenoog et al., *Plant Cell* 12:2271–2282 (2000).

Control of the expression of genes that control egg and central cell differentiation, or those that control reproductive development, i.e. embryo, endosperm and seed coat, is useful in the production of plants with a range of desired traits. These and other advantages are provided by the present application.

SUMMARY OF THE INVENTION

This invention provides isolated nucleic acids comprising a polynucleotide sequence, or its complement, encoding a DMT polypeptide comprising an amino acid sequence with at least 70% sequence identity to at least one of the following consensus sequences:

DMT Domain A
KV<1>(I,l)D(D,p)(E,v)T<3>W<1>(L,v)L(M,l)(E,d)
<0–2>D(K,e)<1>(K,t)<1>(K,a)(W,k)(W,l)<1>(E,k)
ER<2>F<1>(G,t)R<1>(D,n)(S,l)FI(A,n)RM(H,r)<1>(V,l)
QG(D,n)R<1>F<1>(P,q)WKGSVVDSV(I,v)GVFLTQN(V,
t)D(H,y)(L,s)SS(S,n)A(F,y)M<1>(L,v)A(A,s)<1>FP (SEQ ID NO:71)

DMT Domain B
W(D,n)<1>(L,f)R<5>E<3–6>D(S,t)<1>(D,n)(Y,w)
<3>R<10I<2>RG(M,q)(N,f)<2>L(A,s)<1>RI<2–
12>FL<3>V<2>(H,n)G<1>IDLEWLR<2>(P,d)(P,s)(D,h)
<1>(A,v)K<1>(Y,f)LL(S,e)(I,f)<1>G(L,i)GLKS(V,a)
ECVRLL<1>L(H,k)<2>AFPVDTNVGRI(A,c)VR (M,l)G
(W,l)VPL(Q,e)PLP<2>(L,v)Q (L,m)H(L,q)L(E,f)
<1>YP<1>(L,m)(E,d)(S,n)(I,v)QK(F,y)LWPRLCKL(D,p)
Q<1>TLYELHY(Q,h) (L,m)
ITFGK<0–2>FCTK<2>PNCNACPM(R,k)<0–2>EC(R,k)
(H,y)(F,y)(A,s)SA<1>(A,v)<0–10>S(A,s)(R,k)<1>(A,l)L(P,
e)<1>(P,t) (SEQ ID No: 72)

DMT Domain C
P(I,l)(I,v)E(E,f)P<1>(S,t)P<2–5>E<0–15>(D,a)IE(D,e)
<4–23>(I,v)P<1>I<1>(L,f)(N,d)<8–17>(S,a)<1>(A,d)
LV<8>(I,l)P<2–5>(K,r)(L,m)K<4>LRTEH<1>V(Y,f)(E,v)
LPD<1>H<1(L,i)L(E,k)<1>(D,e)D(P,i)<2>YLL(A,s) IW(T, q)P(G,d)(E,g)<6–8>(P,s)<3>C<6–10>(M,l) C<4>C<2>C<3>(R,k)E<5>(V,f)RGT(L,i)L<0–22>(L,v) FADH<1>(S,t)(S,r)<2>PI<3>(R,t)<3>(W,k)<1 >L<1>(R,k) R<4>G(T,s)(s,t)<2>(S,t) I(F,c)(R,k)(G,l)L<1>(T,v)<2>I<2> (C,n)F(W,q)<1>G(F,y)(V,l)C(V,l)R<1>F(E,d)<3>(R,g) <1>P(R,k)<1>L<2>(R,h)LH<2>(A,v)SK (SEQ ID: 73)

In some embodiments, the nucleic acids of the invention do not encode a polypeptide at least 40% identical to SEQ ID NO:2, or alternatively at least 45%, 50%, 55%, 60%, 65%, 70%, 75%, 80%, 85%, 90%, 95%, 99% or 100% to SEQ ID NO:2. In some embodiments, the DMT polypeptide comprises an amino acid sequence 100% identical to the above-listed consensus sequences.

In some embodiments, the DMT polypeptides ar at least 45%, 50%, 55%, 60%, 65%, 70%, 75%, 80%, 85%, 90%, 95%, 97%, 98%, 99% or 100% identical to DMT domains A, B and/or C.

In one aspect, the invention provides DMt polypeptides capable of exhibiting at least one of the following biological activities:

(a) glycosylase activity;

(b) demethylation of polynucleotides;

(c) DNA repair;

(d) wherein expression of the polypeptide in a plant modulates organ identity;

(e) wherein expression of the polypeptide in a plant modulates organ number;

(f) wherein expression of the polypeptide in a plant modulate meristem stem and/or activity;

(g) wherein enhanced expression of the polypeptide in a plant results in a delay in flowering time;

(h) wherein introduction of the polypeptide into a cell results in modulation of methylation of chromosomal DNA in the cell;

(i) wherein reduction of expression of the polypeptide in a plant results in modulation of endosperm development;

(j) wherein expression of the polypeptide in an *Arabidopsis* leaf results in modulation of expression of the MEDEA gene.

In some aspects, the polypeptide comprises either a (i) basic region;

(ii) nuclear localization signal;

(iii) leucine zipper;

(iv) helix-hairpin-helix structure;

(v) glycine-proline rich loop with a terminal aspartic acid or (vi) helix that is capable of binding DNA.

In one aspect, the invention provides methods of modulating in a plant one or more of the following:

(a) DNA repair;

(b) wherein expression of the polypeptide in a plant modulates organ identity;

(c) wherein expression of the polypeptide in a plant modulates organ number;

(d) wherein expression of the polypeptide in a plant modulate meristem stem and/or activity;

(e) wherein enhanced expression of the polypeptide in a plant results in a delay in flowering time;

(f) wherein introduction of the polypeptide into a cell results in modulation of methylation of chromosomal DNA in the cell;

(g) wherein reduction of expression of the polypeptide in a plant results in modulation of endosperm development;

(h) wherein expression of the polypeptide in an *Arabidopsis* leaf results in expression of the MEDEA gene, wherein the method comprises:, (a) introducing into a plant cell a nucleic acid of claim 1; and (b) generating conditions where the plant cell can transcribe the nucleic acid described above.

In some embodiments, the polypeptides comprise between 1500 and 2000 amino acids. In some aspects, the polypeptide has glycosylase activity. In some embodiments, introduction of the nucleic acid into a cell results in modulation of methylation of chromosomal DNA in the cell. In some embodiments, enhanced expression of the nucleic acids of the invention into a plant results in a delay in flowering time. In some embodiments, reduction of expression of a DMT polypeptide in a plant results in enhanced endosperm development. In addition, in some embodiments, expression of the nucleic acid of the invention in an *Arabidopsis* leaf results in expression of the MEDEA gene.

This invention provides isolated nucleic acids comprising a polynucleotide sequence, or its complement, encoding a DMT polypeptide exhibiting at least 60% sequence identity to SEQ ID NO:2 or exhibiting at least 70% sequence identity to at least one of DMT domain A, B, or C. For instance, the nucleic acid can encode the DMT polypeptide displayed in SEQ ID NO:2. In one aspect, the polynucleotide sequence comprises SEQ ID NO:5 or SEQ ID NO:1. In some aspects of the invention, the nucleic acid further comprises a promoter operably linked to the polynucleotide. In some embodiments, the promoter is constitutive. In other embodiments, the promoter is from a DMT gene. For example, the promoter can comprise a polynucleotide at least 70% identical to SEQ ID NO:3. In some aspects, the promoter comprises SEQ ID NO:3. In some aspects of this invention, the promoter further comprises a polynucleotide at least 70% identical to SEQ ID NO:4. For example, in some aspects the promoter comprises SEQ ID NO:4. In some aspects, the polynucleotide sequence is linked to the promoter in an antisense orientation.

The invention also provides an isolated nucleic acid molecule comprising a polynucleotide sequence exhibiting at least 60% sequence identity to SEQ ID NO:1.

The invention also provides an expression cassette comprising a promoter operably linked to a heterologous polynucleotide sequence, or complement thereof, encoding a DMT polypeptide exhibiting at least 60% sequence identity to SEQ ID NO:2. For instance, the nucleic acid can encode the DMT polypeptide displayed in SEQ ID NO:2. In some aspects, the polynucleotide sequence comprises SEQ ID NO:5 or SEQ ID NO:1. In some aspects of the invention, the nucleic acid further comprises a promoter operably linked to the polynucleotide. In some embodiments, the promoter is constitutive. In other embodiments, the promoter is from a DMT gene. For example, the promoter can comprise a polynucleotide at least 70% identical to SEQ ID NO:3. In some aspects, the promoter comprises SEQ ID NO:3. In some aspects of this invention, the promoter further comprises a polynucleotide at least 70% identical to SEQ ID NO:4. For example, in some aspects the promoter comprises SEQ ID NO:4. In some aspects, the polynucleotide sequence is linked to the promoter in an antisense orientation.

The invention also provides an expression cassette for the expression of a heterologous polynucleotide in a plant cell. In some aspects, the expression cassette comprises a promoter polynucleotide at least 70% identical to SEQ ID NO:3 that is operably linked to a heterologous polynucleotide. In some aspects, the promoter comprises SEQ ID NO:3. In some aspects, the promoter further comprises a polynucleotide at least 70% identical to SEQ ID NO:4. For instance, in some embodiments, the promoter comprises SEQ ID NO:4. In some aspects, the promoter further comprises a polynucleotide at least 70% identical to SEQ ID NO:6. In some aspects, the promoter comprises SEQ ID NO:6.

The present invention also provides a host cell comprising an exogenous polynucleotide sequence comprising a polynucleotide sequence, or complement thereof, encoding a DMT polypeptide exhibiting at least 60% sequence identity to SEQ ID NO:2 or exhibiting at least 70% sequence identity to at least one of DMT domain A, B, or C. In some aspects of the invention, the nucleic acid further comprises a promoter operably linked to the polynucleotide sequence. In some aspects, the promoter is constitutive. In some aspects, the promoter comprises a polynucleotide at least 70% identical to SEQ ID NO:3. The promoter, for instance, can comprise SEQ ID NO:3. In some aspects, the promoter further comprises a polynucleotide at least 70% identical to SEQ ID NO:4. For instance, in some embodiments, the promoter comprises SEQ ID NO:4. In some aspects, the promoter is operably linked to the exogenous polynucleotide sequence in an antisense orientation.

The present invention also provides an isolated polypeptide comprising an amino acid sequence at least 60% identical to SEQ ID NO:2 or an amino acid sequence at least 70% sequence identical to at least one of DMT domain A, B, or C and capable of exhibiting at least one biological activity of the polypeptide displayed in SEQ ID NO:2, or fragment thereof. The present invention also provides for an antibody capable of binding such polypeptides.

The present invention also provides a method of introducing an isolated nucleic acid into a host cell comprising, (a) providing an isolated nucleic acid or its complement, encoding a DMT polypeptide exhibiting at least 60% sequence identity to SEQ ID NO:2 or exhibiting at least 70% sequence identity to at least one of DMT domain A, B, or C and (b) contacting the nucleic acid with the host cell under conditions that permit insertion of the nucleic acid into the host cell.

The present invention also provides a method of modulating transcription, comprising introducing into a host cell an expression cassette comprising a promoter operably linked to a heterologous DMT polynucleotide, the heterologous DMT polynucleotide encoding a DMT polypeptide at least 60% identical to SEQ ID NO:2 or at least 70% sequence identical to at least one of DMT domain A, B, or C, and detecting a host cell with modulated transcription. In some aspects of the invention, the heterologous DMT polynucleotide encodes SEQ ID NO:2. In some aspect, the polynucleotide sequence comprises SEQ ID NO:5 or SEQ ID NO:1. In some aspects, the expression cassette is introduced into a host cell by *Agrobacterium*. In some aspects, the expression cassette is introduced by a sexual cross. In some aspects of the method of the invention, modulating transcription results in the modulation of endosperm development in a plant. In some aspects, endosperm development is enhanced. In other aspects, endosperm development is decreased. In some aspects of the methods of the invention, the promoter is operably linked to the DMT polynucleotide in an antisense orientation.

The present invention also provides a method of detecting a nucleic acid in a sample, comprising (a) providing an isolated nucleic acid molecule comprising a polynucleotide sequence, or its complement, encoding a DMT polypeptide exhibiting at least 60% sequence identity to SEQ ID NO:2 or exhibiting at least 70% sequence identity to at least one of DMT domain A, B, or C, (b) contacting the isolated nucleic acid molecule with a sample under conditions that permit a comparison of the sequence of the isolated nucleic acid molecule with the sequence of DNA in the sample, and (c) analyzing the result of the comparison. In some aspects of the method, the isolated nucleic acid molecule and the sample are contacted under conditions that permit the formation of a duplex between complementary nucleic acid sequences.

The present invention also provides a transgenic plant cell or transgenic plant comprising a polynucleotide sequence, or its complement, encoding a DMT polypeptide exhibiting at least 60% sequence identity to SEQ ID NO:2 or exhibiting at least 70% sequence identity to at least one of DMT domain A, B, or C. For instance, the nucleic acid can encode the DMT polypeptide displayed in SEQ ID NO:2. In one aspect, the polynucleotide sequence comprises SEQ ID NO:5 or SEQ ID NO:1. In some aspects of the invention, the nucleic acid further comprises a promoter operably linked to the polynucleotide. In some embodiments, the promoter is constitutive. In other embodiments, the promoter comprises a polynucleotide at least 70% identical to SEQ ID NO:3. In some aspects, the promoter comprises SEQ ID NO:3. In some aspects of this invention, the promoter further comprises a polynucleotide at least 70% identical to SEQ ID NO:4. For example, in some aspects the promoter comprises SEQ ID NO:4. In some aspects, the polynucleotide sequence is linked to the promoter in an antisense orientation. The present invention also provides a plant that is regenerated from a plant cell as described above.

The present invention also provides an expression cassette for the expression of a heterologous polynucleotide in a plant cell, wherein the expression cassette comprises a promoter at least 70% identical to SEQ ID NO:3 and the promoter is operably linked to a heterologous polynucleotide. In some embodiments, the promoter comprises a polynucleotide at least 70% identical to SEQ ID NO:4 and/or SEQ ID NO:6. In some embodiments, the promoter specifically directs expression of the heterologous polynucleotide in a female gametophyte when the expression cassette is introduced into a plant.

DEFINITIONS

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants which can be used in the method of the invention is generally as broad as the class of flowering plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include Agrobacterium-mediated transformation, biolistic methods, electroporation, in planta techniques, and the like. "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below, and include Agrobacterium-mediated transformation (of dicots—e.g. Salomon et al. EMBO J. 3:141 (1984); Herrera-Estrella et al. EMBO J. 2:987 (1983); of monocots, representative papers are those by Escudero et al., Plant J. 10:355 (1996), Ishida et al., Nature Biotechnology 14:745 (1996), May et al., Bio/Technology 13:486 (1995)), biolistic methods (Armaleo et al., Current Genetics 17:97 1990)), electroporation, in planta techniques, and the like. Such a plant containing the exogenous nucleic acid is referred to here as a T0 for the primary transgenic plant and T1 for the first generation. The term "exogenous" as used herein is also intended to encompass inserting a naturally found element into a non-naturally found location.

The phrase "host cell" refers to a cell from any organism. Preferred host cells are derived from plants, bacteria, yeast, fungi, insects or other animals, including humans. Methods for introducing polynucleotide sequences into various types of host cells are well known in the art.

The "biological activity of a polypeptide" refers to any molecular activity or phenotype that is caused by the polypeptide. For example, the ability to transfer a phosphate to a substrate or the ability to bind a specific DNA sequence is a biological activity. One biological activity of DMT is glycosylase activity, i.e., cleavage of the nucleotide base from the nucleotide sugar). Another biological activity of DMT is to demethylate nucleotides (e.g., DMT has 5'-methylcytosine glycosylase activity). In addition, DMT has the ability to modulate endosperm production, as described herein, and to modulate flowering time in plants. For example, when DMT expression or DMT activity is increased in a plant, the flowering time of the plant is delayed. Moreover, expression of a DMT polypeptide in a plant tissue (e.g., a leaf) that does not typically express the MEDEA gene (Grossniklaus U, et al., Science 280(5362): 446–50 (1998)) results in the expression of MEDEA.

Additional biological activities of DMT polypeptides include: nuclear localization (e.g., as localized by amino acids 43–78 of SEQ ID NO:2); the ability to modulate plant organ size and/or number; the ability to modulate meristem size and/or activity; and to perform DNA repair, including nucleotide methylation or demethylation and/or repair and/or removal of mis-matched nucleotides from DNA.

An "expression cassette" refers to a nucleic acid construct, which when introduced into a host cell, results in transcription and/or translation of an RNA or polypeptide, respectively. Antisense or sense constructs that are not or cannot be translated are expressly included by this definition.

A "DMT nucleic acid" or "DMT polynucleotide sequence" of the invention is a subsequence or full length polynucleotide sequence of a gene which encodes a polypeptide involved in control of reproductive development and which, when the maternal allele is mutated or when DMT activity is reduced or eliminated in a maternal tissue or plant, allows for increased production of the endosperm and/or abortion of the embryo. In addition, overexpression of DMT in plants results in delayed time to flowering. Moreover, DMT is necessary and sufficient for expression of MEDEA in a plant cell. An exemplary nucleic acid of the invention is the *Arabidopsis* DMT sequence (SEQ ID NO:1). Additional DMT nucleic acid sequences from a variety of plant species are also provided (e.g., SEQ ID NOs: 7–70). DMT polynucleotides are defined by their ability to hybridize under defined conditions to the exemplified nucleic acids or PCR products derived from them. A DMT polynucleotide is typically at least about 30–40 nucleotides to about 7000, usually less than about 10,000 nucleotides in length. More preferably, DMT polynucleotides contain a coding sequence of from about 100 to about 5500 nucleotides, often from about 500 to about 3600 nucleotides in length. A DMT polypeptide is typically at least 500 amino acids, typically at least 1000 amino acids, more typically at least 1500 amino acids. In some embodiments, a DMT polypeptide comprises fewer than 2000 amino acids, more typically fewer than 3000 amino acid and still more typically fewer than 5000 or 7500 amino acid in length.

As described below, DMT nucleic acid sequences encode polypeptides with substantial identity to at least one of following the consensus sequences:

DMT Domain A
KV<1>(I,l)D(D,p)(E,v)T<3>W<1>(L,v)L(M,l)(E,d)
<0–2>D(K,e)<1>(K,t)<1>(K,a)(W,k)(W,l)<1>(E,k)
ER<2>F<1>(G,t)R<1>(D,n)(S,l)FI(A,n)RM(H,r)<1>(V,l)
QG(D,n)R<1>F<1>(P,q)WKGSVVDSV(I,v)GVFLTQN(V,
t)D(H,y)(L,s)SS(S,n)A(F,y)M<1>(L,v)A(A,s)<1>FP (SEQ
ID NO: 71)

DMT Domain B
W(D,n)<1>(L,f)R<5>E<3–6>D(S,t)<1>(D,n)(Y,w)
<3>R<10>I<2>RG(M,q)(N,f)<2>L(A,s)<1>RI<2–
12>FL<3>V<2>(H,n)G<1>IDLEWLR<2>(P,d)(P,s)(D,h)
<1>(A,v)K<1>(Y,f)LL(S,e)(I,f)<1>G(L,i)GLKS(V,a)
ECVRLL<1>L(H,k)<2>AFPVDTNVGRI(A,c)VR(M,l)G
(W,l)VPL(Q,e)PLP<2>(L,v)Q(L,m)H(L,q)L(E,f)
<1>YP<1>(L,m)(E,d)(S,n)(I,v)QK(F,y)LWPRLCKL(D,p)
Q<1>TLYELHY(Q,h)                                    (L,m)
ITFGK<0–2>FCTK<2>PNCNACPM(R,k)<0–2>EC(R,k)
(H,y)(F,y)(A,s)SA<1>(A,v)<0–10>S(A,s)(R,k)<1>(A,l)L(P,
e)<1>(P,t) (SEQ ID NO:72)

DMT Domain C
P(I,l)(I,v)E(E,f)P<1>(S,t)P<2–5>E<0–15>(D,a)IE(D,e)
<4–23>(I,v)P<1>I<1>(L,f)(N,d)<8–17>(S,a)<1>(A,d)
LV<8>(I,l)P<2–5>(K,r)(L,m)K<4>LRTEH<1>V(Y,f)(E,v)

LPD<1>H<1>(L,i)L(E,k)<1>(D,e)D(P,i)<2>YLL(A,s)IW(T,q)P(G,d)(E,g)<6–8>(P,s)<3>C<6–10>(M,l)C<4>C<2>C<3>(R,k)E<5>(V,f)RGT(L,i)L<0–22>(L,v)FADH<1>(S,t)(S,r)<2>PI<3>(R,t)<3>(W,k)<1>L<1>(R,k)R<4>G(T,s)(s,t)<2>(s,t) I(F,c)(R,k)(G,l)L<1>(T,v)<2>I<2>(C,n)F(W,q)<1>G(F,y)(V,l)C(V,l)R<1>F(E,d)<3>(R,g)<1>P(R,k)<1>L<2>(R,h)LH<2>(A,v)SK (SEQ ID NO:73)

In addition, the following cansensus sequence spanning all three domains were identified:

<9–14>(T,q)(A,i)(S,k)(I,1)<3>(A,r)(S,k)<1>(G,m)<2>(S,r)(P,k)<2>(K,f)<2>(E,l)K<0–1>K<0–3>(P,r)<2>(P,r)<1>(K,r)(K,r)(G,d)(R,k)<1>(G,v)<1>(K,g)<3–5>(P,s)(P,k)<3>(S,n)<1>(I,1)<0–2>(Q,d)<9>(P,q)<4>(K,a)(P,s)<14–16>(P,a)<4>L<0–10>D<1>(I,l)<0–4>(L,n)<12–46>(K,d)<2–7>(P,a)KV<1>(I,l)D(D,p)(E,v)T<3>W<1>(L,v)L(M,l)(E,d)<0–2>D(K,e)<1>(K,t)<1>(K,a)(W,k)(W,l)<1>(E,k)ER<2>F<1>(G,t)R<1>(D,n)(S,l)FI(A,n)RM(H,r)<1>(V,l)QG(D,n)R<1>F<1>(P,q)WKGSVVDSV(I,v)GVFLTQN(V,t)D(H,y)(L,s)SS(S,n)A(F,y)M<1>(L,v)A(A,s)<1>FP<0–16>(P,v)<6–15>(S,h)<3>(E,d)<10–24>(S,t)<1>(S,e)<6>(K,n)<8–55>(E,i)<8–9>(I,v)<1>(N,s)<1–4>(E,d)<1>(E,s)<4>(Q,l)<0–11>(D,h)<1>(F,m)<5>(Q,n)<0–3>(G,e)<2>(G,d)S<1>(K,d)<7–11>(T,m)<2>(V,l)<3>(S,q)<6–10>(S,e)<2–3>(S,v)<19–25>(T,s)<16–28>(R,s)<2–6>(T,p)<5>(P,k)<10>(Q,e)<4>(D,s)<1–4>(S,r)<5>(D,p)<3>(N,d)<3>(P,y)<2>(F,s)<1>(R,k)<1>(G,s)<1>(S,a)(V,r)(P,e)<3>(T,s)<3–6>(I,l)<3>(P,e)<1>E<3–5>(L,q)<1>(G,c)<1>(S,h)(S,n)<1>(V,q)<1>(E,d)<3>T(Q,e)<1–2>(N,g)<3>(E,n)<20–30>(N,a)(P,g)<1–6>(S,1)<25–46>(Q,d)W(D,n)<1>(L,f)R<5>E<3–6>D(S,t)<1>(D,n)(Y,w)<3>R<10>I<2>RG(M,q)(N,f)<2>L(A,s)<1>RI<2–12>FL<3>V<2>(H,n)G<1>IDLEWLR<2>(P,d)(P,s)(D,h)<1>(A,v)K<1>(Y,f)LL(S,e)(I,f)<1>G(L,i)GLKS(V,a)ECVRLL<1>L(H,k)<2>AFPVDTNVGRI(A,c)VR(M,l)G(W,l)VPL(Q,e)PLP<2>(L,v)Q (L,m)H(L,q)L(E,f)<1>YP<1>(L,m)(E,d)(S,n)(I,v)QK(F,y)LWPRLCKL(D,p)Q<1>TLYELHY(Q,h)(L,m)ITFGK<0–2>FCTK<2>PNCNACPM(R,k)<0–2>EC(R,k)(H,y)(F,y)(A,s)SA<1>(A,v)<0–10>S(A,s)(R,k)<1>(A,l)L(P,e)<1>(P,t)(E,q)<7–16>P(I,l)(I,v)E(E,f)P<1>(S,t)P<2–5>E<0–15>(D,a)IE(D,e)<4–23>(I,v)P<1>I<1>(L,f)(N,d)<8–17>(S,a)<1>(A,d)LV<8>(I,l)P<2–5>(K,r)(L,m)K<4>LRTEH<1>V(Y,f)(E,v)LPD<1>H<1>(L,i)L(E,k)<1>(D,e)D(P,i)<2>YLL(A,s) IW(T,q)P(G,d)(E,g)<6–8>(P,s)<3>C<6–10>(M,l)C<4>C<2>C<3>(R,k)E<5>(V,f)RGT(L,i)L<0–22>(L,v)FADH<1>(S,t)(S,r)<2>PI<3>(R,t)<3>(W,k)<1>L<1>(R,k)R<4>G(T,s)(S,t)<2>(S,t) I(F,c)(R,k)(G,l)L<1>(T,v)<2>I<2>(C,n)F(W,q)<1>G(F,y)(V,l)C(V,l)R<1>F(E,d)<3>(R,g)<1>P(R,k)<1>L<2>(R,h)LH<2>(A,v)SK (SEQ ID NO:74)

DMT domain A corresponds to amino acid positions 697 through 796 of SEQ ID NO:2. DMT domain B corresponds to amino acid positions 1192 through 1404 of SEQ ID NO:2. DMT domain C corresponds to amino acid positions 1452 through 1722 of SEQ ID NO:2. The consensus sequence provides amino acid sequences by position using single letter amino acid abbreviations. Numbers in carrots ("<" or ">") refer to amino acid positions where there is no consensus and which therefore, can be any amino acid. Amino acid abbreviations in parentheses indicate alternative amino acids at the same position. Capitalized letters refer to predominant consensus amino acids and lower case letters refer to amino acids that are commonly found in DMT sequences, but are not predominant. Thus, it is a simple matter to identify whether any particular nucleic acid sequence is a DMT nucleic acid and/or encodes a DMT polypeptide.

The structure of full-length DMT polypeptides comprises the following domains and regions. These regions are generally described with reference to SEQ ID NO:2. First, as described above, domain B DMT polypeptides can comprise a bipartite nuclear localization signal (e.g., amino acid positions 43–60 and 61–78 in SEQ ID NO:2) comprised of basic amino acids. Amino acids 36–91 are homologous to human G/T mismatch-specific thymine DNA glycosylase (Genbank accession number AAC50540. 1), which has 5-methylcytosine glycosylase activity (Zhu et al., *Nuc. Acids Res.* 28:4157–4165 (2000)). DMT polypeptides also contain a leucine zipper sequence (e.g., positions 1330–1351 of SEQ ID NO:2), that can be involved in protein-protein interactions as well as DNA binding. In addition, the amino portion of the DMT polypeptide (amino acids 43–78) is generally basic, similar to histone H1. Thus, without intending to limit the scope of the invention, it is believed this basic portion of DMT facilitates interactions with DNA and/or chromatic proteins.

In addition, amino acids 1–800 is related to the beta subunit of bacterial DNA-dependent RNA polymerases. Without intending to limit the scope of the invention, it is believed the RNA polymerase-like domain facilitates interaction of DMT with DNA.

Amino acids 1167–1368 is related to proteins in the HhH-GPD superfamily. Amino acids 1,271 to 1,304 correspond to the conserved HhH-GPD motif. The corresponding DMT sequence is DKAKDYLLSIRGLGLKSVECVRLLTLHNLAFPVD (SEQ ID NO:75). Secondary structure prediction (Jpred program) indicates that DMT has two alpha-helices (1,271–1,279 and 1,286 to 1,295) that correspond to the conserved alphaK and alphaL helices in the HhH-GPD motif of the crystallized hOGG1 DNA repair protein (Bruner et al *Nature* 403:859–866 (2000)). In between the two helices (1280 to 1285), is a hairpin with conserved glycines (G1282 and G1284). Amino acids 1286 to 1295 are related to the alphaL helix of hOGG1, which contacts the DNA backbone (Bruner et al *Nature* 403:859–866 (2000). Thus, without intending to limit the scope of the invention, it is believed this region of DMT contacts the DNA. The catalytic lysine (K1286) and aspartic acid (D1304) residues are conserved in the HhH-GPD motif of DMT. Without intending to limit the scope of the invention, by analogy to hOGG1, K1286 is predicted to displace the modified base and to promote conjugate elimination of the 3'-phosphodiester bond. Without intending to limit the scope of the invention, by analogy to hOGG1, D1304 is believed to assist the reaction by transferring protons to and from K1286.

DMT nucleic acids are a new class of plant regulatory genes that encode polypeptides with sequence identity to members of the endonuclease III genes found in a diverse collection of organisms. Endonuclease III is implicated in various DNA repair reactions. Thus proteins related to endonuclease III are likely to have a chromosomal function. DMT (SEQ ID NO:1) is most related to endonuclease III from *Deinococcus radiodurans* Genbank Accession No. AE002073 (see, e.g., White, O. et al. *Science* 286:1571–1577 (1999)). DMT polypeptides have glycosylase activity (i.e., the capability to cleave the base portion of a nucleotide from the sugar portion). More particularly, DMT polypeptides have demethylase activity, and in more preferred embodiments, have 5-methylcytosine glycosylase activity. Demethylation activity can be assayed in vivo by expressing a candidate polypeptide in the nucleus of a cell and then assaying for a change in methylation of the cell's DNA. See, e.g., Vong, et al., *Science* 260:1926–1928 (1993).

Changes in chromosomal methylation can be measured by comparing the ability of methylation sensitive and insensitive endonucleases to cleave DNA from a cell expressing a polypeptide suspected of having demethylase or methylase activity. Alternatively, bisulfate sequencing can be used to identify which base pairs are methylated in a DNA sequence. For a discussion of both methods, see Soppe et al., *Molec. Cell.* 6:791–802 (2000). In vitro assays to measure demethylase activity using labeled substrates are also known to those of skill in the art. See, e.g., Vhu et al., *Proc. Natl. Acad. Sci. USA* 97:5135–5139 (2000).

In the case of both expression of transgenes and inhibition of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by the term DMT nucleic acid.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "DMT nucleic acid". In addition, the term specifically includes those sequences substantially identical (determined as described below) with a DMT polynucleotide sequence disclosed here and that encode polypeptides that are either mutants of wild type DMT polypeptides or retain the function of the DMT polypeptide (e.g., resulting from conservative substitutions of amino acids in the DMT polypeptide). In addition, variants can be those that encode dominant negative mutants as described below.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif. USA).

The phrase "substantially identical," in the context of two nucleic acids or polypeptides, refers to a sequence or subsequence that has at least 40% sequence identity with a reference sequence. Alternatively, percent identity can be any integer from 40% to 100%. More preferred embodiments include at least: 40%, 45%, 50%, 55%, 60%, 65%, 70%, 75%, 80%, 85%, 90%, 95%, or 99% compared to a reference sequence using the programs described herein; preferably BLAST using standard parameters, as described below. This definition also refers to the complement of a test sequence, when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci.* USA 89:10915 (1989)) alignments (B) of 50, expectation (E) of 10, M=5, N=−4 comparison of both strands.

The BLAST algorithm also performs a statistical analysis of the similarity between two sequences (see, e.g., Karlin & Altschul, *Proc. Nat'l. Acad. Sci.* USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 55° C., sometimes 60° C., and sometimes 65° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising DMT nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2× SSC at a temperature of at least about 50° C., usually about 55° C. to about 60° C. and sometimes 65° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

DETAILED DESCRIPTION

This invention provides molecular strategies for controlling plant development, including methylation of chromosomal DNA, endosperm development and flowering time.

Reproduction in flowering plants involves two fertilization events in the haploid female gametophyte. One sperm nucleus fertilizes the egg to form the embryo. A second sperm nucleus fertilizes the central cell to form the endosperm, a unique tissue that supports the growth of the embryo. Fertilization also activates maternal tissue differentiation, the ovule integuments form the seed coat and the ovary forms the fruit.

The present invention is based, at least in part, on the discovery of a set of female-gametophytic mutations and the subsequent cloning of the gene involved, termed DEMETER (DMT), formally known as ATROPOS (ATR). Two mutant alleles of DMT disclosed here were created using a T-DNA tag, thereby disrupting an exon of the gene. The dmt mutations affect endosperm production, allowing for increased endosperm development. Generally, the mutant dmt alleles are not transmitted by the female gametophyte. Inheritance of a mutant dmt allele by the female gametophyte usually results in embryo abortion and endosperm overproduction, even when the pollen bears the wild-type DMT allele.

In contrast, transmission of dmt mutant alleles through the male gametophyte (i.e., pollen) is ecotype-dependent in *Arabidopsis*. For instance, in some ecotypes (e.g., Columbia), transmission of dmt mutant alleles is less than 50%. However, in Landsberg erecta, transmission is almost normal.

DMT is a repressor of endosperm both before and after fertilization. DMT is both necessary and sufficient for MEDEA transcription. DMT is related to 5-methylcytosine glycosylases. DMT regulates transcription of specific target genes (i.e., MEA) by a demethylation mechanism. DMT is also required for maintaining the proper global pattern of methylation of chromosomal DNA in cells.

The isolated sequences prepared as described herein, can be used in a number of techniques, for example, to suppress or enhance endogenous DMT gene expression. Modulation of DMT gene expression or DMT activity in plants is particularly useful, for example, in producing embryo-less or embryo-reduced seed, seed with increased endosperm, as part of a system to generate seed, to modulate time to flowering, organ identity, size and/or number, meristem size or activity in plants, or to modulate methylation, and thus gene expression in plants. Another use is the expression of DMT polynucleotides in animal cells, for instance as a DNA repair enzyme useful in preventing the unnatural proliferation of cells (including cancer) due to chromosomal lesions. See, e.g., Bruner, et al, *Nature* 403:859 (2000).

As described in more detail below, reduction of expression of DMT in plants results in a number of diverse phenotypes. Without intending to limit the invention to particular embodiments, it is belived that some of the phenotypes that are generated in plants are epigenetic mutations, i.e., effects due to differences in the methylation state of the chromosome that result in altered gene expression. Thus, DMT provides a powerful tool to develop any number of plant lines with a variety of desired phenotypes.

Isolation of DMT Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y. (1989).

The isolation of DMT nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as ovules, and a cDNA library which contains the DMT gene transcript is prepared from the mRNA. Alternatively, cDNA may be prepared from mRNA extracted from other tissues in which DMT genes or homologs are expressed.

The cDNA or genomic library can then be screened using a probe based upon the sequence of a cloned DMT gene disclosed here. Probes may be used to hybridize with genomic DNA or cDNA sequences to isolate homologous genes in the same or different plant species. Alternatively, antibodies raised against a DMT polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the DMT genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: *A Guide to Methods and Applications*. (Innis, M, Gelfand, D., Sninsky, J. and White, T., eds.), Academic Press, San Diego (1990).

Appropriate primers and probes for identifying DMT sequences from plant tissues are generated from comparisons of the sequences provided here with other related genes. For instance, DMT can be compared to the other endonuclease III genes, such as Genbank Accession No. AE002073. Using these techniques, one of skill can identify conserved regions in the nucleic acids disclosed here to prepare the appropriate primer and probe sequences. Primers that specifically hybridize to conserved regions in DMT genes can be used to amplify sequences from widely divergent plant species. Appropriate primers for amplification of the genomic region or cDNA of DMT include the following primers (SEQ ID NOS:76–119):

Xba-SKEN-7; CCTCTAGAGGAATTGTCGGCAAAATCGAG
SKB-8; GGAGAGACGGTTATTGTCAACC
SKB-7; AAAAGTCTACAAGGGAGAGAGT
SKB-5; GTAGATGTACATACGTACC
SKEN-8; GCATCCTCCAACAAGTAACAATCCACTC
SKB-6; CACTGAGATTAATTCTTCAGACTCG
SKEN-3.5; CTCAGGCGAGTCAATGCCGGAGAACAC
SKEN-3; CGAGGGCTGATCCGGGGGATAGATATTTT
SKEN-2; CCCCCGGATCAGCCCTCGAATTC
SKEN-1; CCGGTGTCTACAAATTCACCACCTGG
SKEL-4; CTGACCCAACTGCTTTCTCTTC
skes5; TCACCTGTTCTGAACAGACTGG
SKES-1.4; CAGCAGACGAGTCCATAATGCTCTGC
SKES-2.4; GGTPTGCCTTCCACGACCACC
SKES-1; GGAAGCCACGCAAAGCTGCAACTCAGG
SKES-2.45; GAGTTGCAGCTTTGCGTGGCTTCC
SKES2.5; TTCAGACTCAGAGTCACCTTGC
SKES-2; ACCAGCAGCTTGCTTGGCC
SKES-3; CATGCCAGAGAAGCAGGGCTCC
SKES3.5; CGATGATACTGTCTCTTCGAGC
SKES-6; CCTCCGCCTGCTCATGCCTCAG
SKEN-4; GTCCATCAGGAGAACYECTGTGTCAGGAT
SKES-4; GGGAACAAGTGCACCATCTCC
SKEN-6; GCTCTCATAGGGAACAAGTGCACCATCTC
SKES-5; CGCTCGCATGCACCTGGTAC
SKB-1; GGAGGGAATCGAGCAGCTAGAG
SKB-2; GAGCAGCTAAGGGACTUFfCAAACTC
SKB-3; CCAGGAATGGGATLTGTCCGG
3'RACE-2; CTTGGACGGCGCTTGAGGAACC
3'RACE-1; GCCTACAAGCCAGTGGGATAG
cDNA-1; GCCAAGGACTATCTCTTGAGC
SKB-4; GGATGGACTCGAGCACTGGG
SKE2.2-4; AGAGGAGAGTGCAGACACTTTG
cDNA-3; GAGGACCCTGACGAGATCCCAAC
cDNA-9; CCATGTGTTCCCGTAGAGTCATTCC
2.2+SKE-1; ATGGAGCTCCAAGAAGGTGACATG
cDNA.-5; CAGAAGTGTGGAGGGAAAGCGTCTGGC
cDNA-4; CCCTCAGACTGTFJTACACTCAGAAC
cDNA-2; CCCGTTGAGCGGAAAACTTCCTCTCATGGC
cDNA-7; GGAAAGGATTCGTATGTGTCCGTGG
SKEN-5; GCAATGCGTTTJGCTTTCTTCCAGTCATCT
cDNA-6; GAGGAGAGCAGAGAAGCAATGCGTTTTGC
cDNA-8; GTTAGAGAGAAAATAAATAACCC
2.2+SKE-3; CCGTAAACAACACCGGATACAC.

| | |
|---|---|
| Xba-SKEN-7; | CCTCTAGAGGAATTGTCGGCAAAATCGAG |
| SKB-8; | GGAGAGACGGTTATTGTCAACC |
| SKB-7; | AAAAGTCTACAAGGGAGAGAGT |
| SKB-5; | GTAGATGTACATACGTACC |
| SKEN-8; | GCATCCTCCAACAAGTAACAATCCACTC |
| SKB-6; | CACTGAGATTAATTCTTCAGACTCG |
| SKEN-3.5; | CTCAGGCGAGTCAATGCCGGAGAACAC |
| SKEN-3; | CGAGGGCTGATCCGGGGGATAGATATTTT |
| SKEN-2; | CCCCCGGATCAGCCCTCGAATTC |
| SKEN-1; | CCCCTGTCTACAAATTCACCACCTGG |
| SKEL-4; | CTGACCCAACTGCTTCTCTTC |
| skes1.5; | TCACCTGTTCTGAACAGACTGG |
| SKES-1.4; | CAGCAGACGAGTCCATAATGCTCTGC |
| SKES-2.4; | GGTTTGCCTTCCACGACCACC |
| SKES-1; | GGAAGCCACGCAAAGCTGCAACTCAGG |
| SKES-2.45; | GAGTTGCAGCTTTGCGTGGCTTCC |
| SKES-2.5; | TTCAGACTCAGAGTCACCTTGC |
| SKES-2; | ACCAGCAGCCTTGCTTGGCC |
| SKES-3; | CATGCCAGAGAAGCAGGGCTCC |
| SKES-3.5; | CGATGATACTGTCTCTTCGAGC |
| SKES-6; | CCTCCGCCTGCTCATGCCTCAG |
| SKEN-4; | GTCCATCAGGAGAACTTCTGTGTCAGGAT |
| SKES-4; | GGGAACAAGTGCACCATCTCC |
| SKEN-6; | GCTCTCATAGGGAACAAGTGCACCATCTC |
| SKES-5; | CGCTCGCATGCACCTGGTAC |
| SKB-1; | GGAGGGAATCGAGCAGCTAGAG |
| SKB-2; | GAGCAGCTAAGGGACTGTTCAAACTC |
| SKB-3; | CCAGGAATGGGATTGTCCGG |
| 3' RACE-2; | CTTGGACGGCGCTTGAGGAACC |
| 3' RACE-1; | GCCTACAAGCCAGTGGGATAG |
| cDNA-1; | GCCAAGGACTATCTCTTGAGC |
| SKB-4; | GGATGGACTCGAGCACTGGG |
| SKE2.2-4; | AGAGGAGAGTGCAGACACTTTG |
| cDNA-3; | GAGGACCCTGACGAGATCCCAAC |

| | -continued |
|---|---|
| cDNA-9; | CCATGTGTTCCCGTAGAGTCATTCC |
| 2.2 + SKE-1; | ATGGAGCTCCAAGAAGGTGACATG |
| cDNA-5; | CAGAAGTGTGGAGGGAAAGCGTCTGGC |
| cDNA-4; | CCCTCAGACTGTTACACTCAGAAC |
| cDNA-2; | CCCGTTGAGCGGAAAACTTCCTCTCATGGC |
| cDNA-7; | GGAAAGGATTCGTATGTGTCCGTGG |
| SKEN-5; | GCAATGCGTTTGCTTTCTTCCAGTCATCT |
| cDNA-6; | GAGGAGAGCAGAGAAGCAATGCGTTTGC |
| cDNA-8; | GTTAGAGAGAAAATAAATAACCC |
| 2.2 + SKE-3; | CCGTAAACAACACCGGATACAC |

The amplification conditions are typically as follows. Reaction components: 10 mM Tris-HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per ml Taq polymerase. Program: 96 C for 3 min., 30 cycles of 96 C for 45 sec., 50 C for 60 sec., 72 for 60 sec, followed by 72 C for 5 min.

Standard nucleic acid hybridization techniques using the conditions disclosed above can then be used to identify full-length cDNA or genomic clones.

Alternatively, a number of methods for designing modifications of polynucleotide sequences are known to those of skill in the art. For example, oligonucleotide directed mutagenesis can be used to introduce site-specific mutations in a nucleic acid sequence of interest. Examples of such techniques are found in the references above and, e.g., in Reidhaar-Olson et al. *Science,* 241:53–57 (1988) and Ausubel et al. Similarly, gene shuffling (Stemmer *Proc. Natl. Acad. Sci. USA* 91:10747–10751(1994); Ostermeier et al. *Proc. Natl. Acad. Sci. USA,* 96: 3562–67(1999))) can be used to introduce variation into one or more DMT sequences or subsequences. For example, orthologous (between species) or homologous (within a species) DMT nucleic acids can be interchanged, combined or shuffled to produce novel variations within the scope of the invention.

Additionally, error prone PCR can also be used to introduce variation into a nucleic acid sequence. See, Leung et al. (1989) *Technique* 1:11–15 and Caldwell et al. (1992) *PCR Methods Applic.* 2:28–33.

Control of DMT Activity or Gene Expression

Since DMT genes are involved in controlling seed, in particular endosperm, development, inhibition of endogenous DMT activity or gene expression is useful in a number of contexts. For instance, reduction of DMT activity can be used for production of seed with enhanced endosperm. By reducing and/or eliminating DMT activity, plants with seed containing increased endosperm can be produced.

Alternatively, substantial inhibition of DMT activity can be used for production of fruit with small and/or degraded seed (referred to here as "seedless fruit") after fertilization. In many plants, particularly dicots, the endosperm is not persistent and eventually is degraded. Thus, in plants of the invention in which DMT activity is inhibited, embryo-less seed do not persist and seedless fruit are produced. For production of dicots with enhanced endosperm, the most beneficial effect may be to reduce, but not eliminate DMT activity. On the other hand, in monocots, which have persistent endosperm, it is advantageous to eliminate DMT activity.

Alternatively, plants of the invention can be used to prevent pre-harvest sprouting in seeds, especially those derived from cereals. In these plants, the endosperm persists and is the major component of the mature seed. Premature growth of embryos in stored grain causes release of degradative enzymes which digest starch and other components of the endosperm. Plants of the present invention are useful in addressing this problem because the seeds lack an embryo and thus will not germinate.

Moreover, as discussed herein, time to flowering and DNA methylation can also be modulate by modulating DMT activity in a cell. For example, DMT can be used to modulate the amnount of methylated DNA in a cell. Indeed, since expression of many genes is dependent on thier methylation state, modulation of DMT activity modulates gene expression in a cell. Examples of genes whose expression is modulated by DMT include MEDEA.

One of skill will recognize that a number of methods can be used to modulate DMT activity or gene expression. DMT activity can be modulated in the plant cell at the gene, transcriptional, posttranscriptional, translational, or post-translational, levels. Techniques for modulating DMT activity at each of these levels are generally well known to one of skill and are discussed briefly below.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used.

Alternatively, homologous recombination can be used to induce targeted gene disruptions by specifically deleting or altering the DMT gene in vivo (see, generally, Grewal and Klar, *Genetics* 146:1221–1238 (1997) and Xu et al., *Genes Dev.* 10:2411–2422 (1996). Homologous recombination has been demonstrated in plants (Puchta et al., *Experimentia* 50:227–284 (1994), Swoboda et al., *EMBO J.* 13:484–489 (1994); Offringa et al., *Proc. Natl. Acad. Sci. USA* 90:7346–7350 (1993); and Kempin et al. *Nature* 389:802–803 (1997)).

In applying homologous recombination technology to the genes of the invention, mutations in selected portions of a DMT gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al. *Proc. Natl. Acad. Sci. USA* 91;4303–4307 (1994); and Vaulont et al. *Transgenic Res.* 4:247–255 (1995) are conveneiently used to increase the efficiency of selecting for altered DMT gene expression in transgenic plants. The mutated gene will interact with the target wild-type gene in such a way that homologous recombination and targeted replacement of the wild-type gene will occur in transgenic plant cells, resulting in suppression of DMT activity.

Alternatively, oligonucleotides composed of a contiguous stretch of RNA and DNA residues in a duplex conformation with double hairpin caps on the ends can be used. The RNA/DNA sequence is designed to align with the sequence of the target DMT gene and to contain the desired nucleotide change. Introduction of the chimeric oligonucleotide on an extrachromosomal T-DNA plasmid results in efficient and specific DMT gene conversion directed by chimeric molecules in a small number of transformed plant cells. This method is described in Cole-Strasuu et al. *Science* 273: 1386–1389(1996) and Yoon et al. *Proc. Natl. Acad. Sci. USA* 93:2071–2076 (1996).

Gene expression can be inactivated using recombinant DNA techniques by transforming plant cells with constructs comprising trasposons or T-DNA sequences. DMT mutants prepared by these methods are identified according to standard techniques. For instance, mutants can be detected by PCR or by detecting the presence or absence of DMT in mRNA, e.g., by Northern blots. Mutants can also be selected by assaying for development of endosperm in the absence of fertilization.

The isolated nucleic acid sequences prepared as described herein, can also be used in a number of techniques to control endogenous DMT gene expression at various levels. Subsequences from the sequences disclosed here can be used to control, transcription, RNA accumulation, translation, and the like.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (Limerick) 105:125–149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al. *Plant Sci.* (Shannon) 127:61–69 (1997)) and by preventing the accumulation of mRNA which encodes the protein of interest, (see, Baulcombe *Plant Mol. Bio.* 32:79–88 (1996); Prins and Goldbach *Arch. Virol.* 141:2259–2276 (1996); Metzlaff et al. *Cell* 88:845–854 (1997), Sheehy et al., *Proc. Nat. Acad. Sci. USA*, 85:8805–8809 (1988), and Hiatt et al., U.S. Pat. No. 4,801,340).

The nucleic acid segment to be introduced generally will be substantially identical to at least a portion of the endogenous DMT gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be in full length relative to either the primary transcription product or fully processed mRNA. Generally, higher homology can be used to compensate for the use of a shorter sequence. Furthermore, the introduced sequence need not have the same intron or exton pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 7000 nucleotides is especially preferred.

A number of gene regions can be targeted to suppress DMT gene expression. The targets can include, for instance, the coding regions, introns, sequences from exon/intron junctions, 5' or 3' untranslated regions, and the like. In some embodiments, the constructs can be designed to eliminate the ability of regulatory proteins to bind to DMT gene sequences that are required for its cell- and/or tissue-specific expression. Such transcriptional regulatory sequences can be located either 5'-, 3'-, or within the coding region of the gene and can be either promote (positive regulatory element) or repress (negative regulatory element) gene transcription. These sequences can be identified using standard deletion analysis, well known to those of skill in the art. Once the sequences are identified, an antisense construct targeting these sequences is introduced into plants to control gene transcription in particular tissue, for instance, in developing ovules and/or seed. In one embodiment, transgenic plants are selected for DMT activity that is reduced but not eliminated.

Oligonucleotide-based triple-helix formation can be used to disrupt DMT gene expression. Triple DNA can inhibit DNA transcription and replication, generate site-specific mutations, cleave DNA, and induce homologous recombination (see, e.g., Havre and Glazer *J. Virology* 67:7324–7331 (1993); Scanlon et al *FASEB J.* 9:1288–1296 (1995); Giovannangeli et al. *Biochemistry* 35:10539–10548 (1996); Chan and Glazer *J. Mol. Medicine* (Berlin) 75:267–282 (1997)). Triple heliz DNAs can be used to target the same sequences identified for antisense regulation.

Catalytic RNA molecules or ribozymes can also be used to inhibit expression of DMT genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Zhao and Pick *Nature* 365:448–451 (1993); Eastham and Ahlering *J. Urology* 156:1186–1188 (1996); Sokol and Murray *Transgenic Res.* 5:363–371 (1996); Sun et al. *Mol. Biotechnology* 7:241–251 (1997); and Haseloff et al. *Nature,* 334:585–591 (1988).

Another method of suppression is sense cosuppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.* 22:1067–1085 (1993); Flavell *Proc. Natl. Acad. Sci. USA* 91:3490–3496 (1994); Stam et al. *Annals Bot.* 79:3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substanitally identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using cosuppression technologies.

In a preferred embodiment, expression of a nucleic acid of interest can be suppressed by the simultaneous expression of both sense and antisense constructs (Waterhouse et al., *Proc. Natl. Acad. Sci. USA* 95:13959–13964 (1998). See also Tabara et al. *Science* 282:430–431 (1998).

Alternatively, DMT activity may be modulated by eliminating the proteins that are required for DMT cell-specific gene expression. Thus, expression of regulatory proteins and/or the sequences that control DMT gene expression can be modulated using the methods described here.

Another method is use of engineered tRNA suppression of DMT mRNA translation. This method involves the use of suppressor tRNAs to transactivate target genes containing premature stop codons (see, Betzner et al. *Plant J.* 11:587–595 (1997); and Choisne et al. *Plant J.* 11:597–604 (1997). A plant line containing constitutively expressed DMT gene that contains an amber stop codon is first created. Multiple lines of plants, each containing tRNA suppressor gene constructs under the direction of cell-type specific promoters are also generated. The tRNA gene construct is then crossed into the DMT line to activate DMT activity in a targeted manner. These tRNA suppressor lines could also be used to target the expression of any type of gene to the same cell or tissue types.

DMT proteins may form homogeneous to heterologous complexes in vivo. Thus, production of dominant-negative forms of DMT polypeptides that are defective in their abilities to bind to other proteins in the complex is a convenient means to inhibit endogenous DMT activity. This approach involves transformation of plants with constructs encoding mutant DMT polypeptides that form defective complexes and thereby prevent the complex from forming properly. The mutant polypeptide may vary from the naturally occurring sequence at the primary structure level by amino acid substitutions, additions, deletions, and the like. These modifications can be used in a number of combinations to produce the final modified protein chain. Use of dominant negative mutants to inactivate target genes is described in Mizukami et al. *Plant Cell* 8:831–845 (1996).

Another strategy to affect the ability of a DMT protein to interact with itself or with other proteins involves the use of antibodies specific to DMT. In this method cell-specific expression of DMT-specific Abs is used inactivate functional domains through antibody:antigen recognition (see, Hupp et al. *Cell* 83:237–245 (1995)).

After plants with reduced DMT activity are identified, a recombinant construct capable of expressing low levels of DMT in embryos can be introduced using the methods discussed below. In this fashion, the level of DMT activity can be regulated to produce preferred plant phenotypes. For example, a relatively weak promoter such as the ubiquitin promoter (see, e.g., Garbarino et al. *Plant Physiol.* 109(4): 1371–8 (1995); Christensen et al *Transgenic Res.* 5(3): 213–8 (1996); and Holtorf et al. *Plant Mol. Biol.* 29(4): 637–46 (1995)) is useful to produce plants with reduced levels of DMT activity or expression. Such plants are useful for producing, for instance, plants that produce seed with enhanced endosperm.

Use of Nucleic Acids of the Invention to Enhance DMT Gene Expression

Isolated sequences prepared as described herein can also be introduced into a plant cell, thereby modulating expression of a particular DMT nucleic acid to enhance or increase endogenous gene expression. For instance, without being bound to any theory, in light of DMT's relation to Exonuclease III and DNA glycosylases, applicants believe that DMT binds DNA or chromatin and acts to modulated transcription by modulating the methylation state of DNA. Enhanced expression can therefore be used to control plant morphology by controlling expression of genes under DMT's control, such as MEDEA, in desired tissues or cells. Enhanced expression can also be used, for instance, to increase vegetative growth by preventing the plant from setting seed. Where overexpression of a gene is desired, the desired gene from a different species may be used to decrease potential sense suppression effects.

Moreover, as discussed herein, time to flowering and DNA methylation can also be modulated by modulating DMT activity in a cell. For example, increased expression of DMT in a plant results in delayed time to flowering. Similarly, DMT can be used to modulate the amount of methylated DNA in a cell. Indeed, since expression of many genes is dependent on their methylation state, modulation of DMT activity modulates gene expression in a cell. Examples of genes whose expression is modulated by DMT include MEDEA.

One of skill will recognize that the polypeptides encoded by the genes of the invention, like other proteins, have different domains that perform functions. Thus, the gene sequences need not be full length, so long as the desired functional domain of the protein is expressed.

Modified protein chains can also be readily designed utilizing various recombinant DNA techniques well known to those skilled in the art and described in detail, below. For example, the chains can vary from the naturally occurring sequences at the primary structure level by amino acid substitutions, additions, deletions, and the like. These modifications can be used in a number of combinations to produce the final modified protein chain.

Preparation of Recombinant Vectors

To use isolated sequences in the above techniques, recombinant DNA vectors suitable for transformation of plant cells are prepared. Techniques for transforming a wide variety of flowering plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transciption initiation regions from various plant genes known to those of skill. Such genes include for example, ACT11 from *Arabidopsis* (Huand et al. *Plant Mol. Biol.* 33:125–139 (1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinex et al. *J. Mol. Biol* 208: 551–565 (1989)), and Gpc2 from maize (GenBank No. U45855, Manjunath et al., *Plant Mol. Biol.* 33:97–112 (1997)).

Alternatively, the plant promoter may direct expression of the DMT nucleic acid in a specific tissue or may be otherwise under more precise environmental or developmental control. Examples of environment conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under development control include promoters that initiate transcription only (or primarily only) in certain tissues, such as fruit, seeds, or flowers. Promoters that direct expression of nucleic acids in ovules, flowers or seeds are particularly useful in the present invention. As used herein a seed-specific promoter is one which directs expression in seed tissues, such promoters may be, for example, ovule-specific (which includes promoters which direct expression in maternal tissues or the female gametophyte, such as egg cells or the central cell), embryo-specific, endosperm-specific, integument-specific, seed coat-specific, or some combination thereof. Examples include a promoter from the ovule-specific BEL1 gene described in Reiser et al. *Cell* 83:735–742 (1995) (GenBank No. U39944). Other suitable seed specific promoters are derived from the following genes: MAC1 from maize (Sheridan et al. *Genetics* 142:1009–1020 (1996), Cat3 from maize (GenBank No. L05934, Abler et al. *Plant Mol. Biol.* 22:10131–1038 (1993), the gene encoding oleosin 18 kD from maize (GenBank No. J05212, Lee et al. *Plant Mol. Biol.* 26:1981–1987 (1994)), vivparous-1 from *Arabidopsis* (Genbank No. U93215), the gene encoding oleosin from *Arabidopsis* (Genbank No. Z17657). Atmyc1 from *Arabidopsis* (Urao et al. *Plant Mol. Biol.* 32:571–576 (1996), the 2s seed storage protein gene family from *Arabidopsis* (Conceicao et al. *Plant* 5:493–505 (1994)) the gene encoding oleosin 20 kD from *Brassica napus* (GenBank No. M63985), napA from *Brassica napus* (GenBank No. J02798, Josefsson et al. *JBL* 26:196–1301 (1987), the napin gene family from *Brassica napus* (Sjodahl et al. *Planta* 197:264–271 (1995), the gene encoding the 2S storage protein from *Brassica napus* (Dasgupta et al. *Gene* 133: 301–302 (1993)), the genes encoding oleosin A (Genbank No. U09118) and oleosin B (Genbank No. U09119) from soybean and the gene encoding low molecular weight sulphur rich protein from soybean (Choi et al. *Mol Gen, Genet.* 246:266–268 (1995)).

In addition, the promoter sequences from the DMT genes disclosed here can be used to drive expression of the DMT polynucleotides of the invention or heterologous sequences. The sequences of the promoters are identified below.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Promoter and Enhancer Nucleic Acids of the Invention

The present invention provides polynucleotides useful as promoters and enhancers. The invention also provides methods of targeting heterologous polypeptides to a female gametrophye of a plant, including, e.g., the polar nuclei, the eggs and synergids and central cells. Promoter polynucleotides of the invention include, for example, sequences and subsequences of the DMT 5' flanking DNA (SEQ ID NO:3), the 5' UTR region (SEQ ID NO:6) and the 3' flanking region (SEQ ID NO:4). In some embodiments, the promoter sequences are operably linked to the 5' end of the DMT coding region, which is in turn fused to a polynucleotide of interest, typically encoding a polypeptide. An exemplary promoter sequence includes the last 3424 nucleotides of SEQ ID NO:3 linked to the first 1478 nucleotides of SEQ ID NO:5. In some embodiments, a further 444 nucletoides (e.g., the first 444 nucleotides of the DMT coding region) are incorporated into the promoter. In some embodiments, the promoter sequences of the invention specifically direct expression of polynucleotides to the female gametophye and does not direct expression in tissues following fertilization.

Production of Transgenic Plants

DNA constructs of the invention may be introduced into the genome of the desired plant host by a variety of conventional techniques. For example, the DNA construct may be introduced directly into the genomic DNA of the plant cell using techniques such as electoporation and microinjection of plant cell protoplasts, or the DNA constructs can be introduced directly to plant tissue using methods, such as DNA particle bombardment.

Microinjection techniques are known in the art and well described in the scientific and patent literature. The introduction of DNA constructs using polyethylene glycol precipitation is described in Paskowski et al. *Embo. J.* 3:2717–2722 (1984). Electroporation techniques are described in Fromm et al. *Proc. Natl. Acad. Sci. USA* 82:5824 (1985). Ballistic information techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraly et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publsihing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanas, Ricinus, Secale, Senecio, Sinapis, Solanum, Sorghum, Theobromus, Trigonella, Triticum, Vicia, Vigna*, and *Zea*.

One of skill will recognize that after the expression cassette is stably incorporated in transgenic plants and confirmed to be operable, it can be introduced into other plants by sexual crossing. Any of a number of standard breeding technioques can be used, depending upon the species to be crossed.

Seed obtained from plants of the present invention can be analyzed according to well known procedures to identify plants with the desired trait. If antisense or other techniques are used to control DMT gene expression. Northern blot analysis can be used to screen for desired plants. In addition, the presence of fertilization independent reproductive development can be detected. Plants can be screened, for instance, for the ability to form embryo-less seed, form seed that abort after fertilization, or set fruit in the absence of fertilization. These procedures will depend, part on the particular plant species being used, but will be carried out according to methods well known to those of skill.

DMT Mutations, Fragments and Fusions

As discussed above, DMT polynucleotides and polypeptides are not limited to the sequences disclosed herein. Those of skill in the art that conservative amino acid substitutions, as well as amino acid additions or deletions may not result in any change in biological activity. Moreover, sequence variants with at least one modulated biological activity of DMT are also contemplated. For example, at least one DMT activity can be increased or decreased by introduction of single or multiple amino acid changes from the sequences disclosed herein. Those of skill in the art will recognize that conservative amino acid substitutions in important domains are typically useful in generating more active DMT polypeptides. Conversely, non-conservative substitutions of amino acid residues in functional domains, such as the HhH region of DMT (e.g., amino acids 1272–1304 of SEQ ID NO:2) are likely to disrupt at least one biological activity such as DNA binding. In some embodiments, the fragments of the invention consist of about 100, 200, 300 400, 500, 600, 700, 800, 900, or 1000 amino acids.

Alternatively, fragments of the sequences disclosed herein are contemplated. In some preferred embodiments, the polypeptide fragments have at least one biological activity of DMT. For example, amino acid sequences comprising DMT domain B represent polypeptide fragments with glycosylase or demthylase activity. In some embodiments, a fragment comprising amino acids 1167–1404, 1192–1404, 1192–1368 or 1167–1368 of SEQ ID NO:2 have glycosylase activity.

Mutations, fragments and fusions are also useful as dominant negative mutations. For instance, different regions of the DMT protein are responsible for different biological activities. Thus, mutation or deletion of one functional domain can eliminate one but not all activities. For example, mutation or deletion of the DNA binding domain may result in proteins that interact with proteins necessary for DMT function, effectively titrating out those proteins and preventing an active DMT protein from acting. Similarly, DMT fragments comprising the DNA binding portion of the protein with an inactive enzymatic domain or lacking an enzymatic domain are also useful as dominant negative mutants by competing with active DMT polypeptides for DNA binding sites. As described herein, domains of DMT that can be modulated include: the leucine zipper, nuclear localization sequence, HhH domain, the aspartic acid of the GPD domain, as well a DMT domains A, B or C. Without intending to limit the scope of the invention, based on the data provided herein, DMT has glycosylase and demethylase activity and is a DNA repair enzyme.

Targeting the Polypeptides of the Invention to Chromosomal Regions

Without intending to limit the scope of the invention, based on the data provided herein, it is believed that DMT has glycosylase and/or demthylase activity and is a DNA repair enzyme. DNA methylation plays an important role in the repression of gene transcription during animal development including embyrogenesis, myogeneis and blood cell development. Methylated DNA is recognized by MeCP2 which in turn represses gene transcription by recruiting the Sin3 repressor complex that contains catalytically active histone deacetylase (Jones et al. *Nature Genetics* 19(2): 187–191 (1998)). Histone H3 and H4 deactylation contributes to the formation of transcriptionally inactive chromatin. Thus, DMT can be used for the purpose of modulating the activity of target genes through chromatin architecture in animal cells as well as plant cells. For example, in some embodiments, DMT is used to catalytically remove 5-MeC from target gene DNA in several ways: e.g., (1) by fusing DMT to a sequence specific DNA binding protein, or (2) by fusing DMT to a subunit of the target repressor complex such as MeCP2 or Sin3. When combined with cell, tissue, or developmentally specific promoters DMT can be used to modulate specific sets of target genes.

In addition, reactive oxygen species, partially species that are produced as intermediates of aerobic respiration, are powerful oxidizing agents that escape the mitochondria and attach vial cellular components. Ionizing radiation and other agents that generate free radicals also produce reactive oxygen species that can attack the genome and cause lesions that are thought to have a key role in in causing cancer and ageing. For example, 7,8-dihydro-8-oxoguanine (oxoG) is a very deleterious adduct generated by oxidation of the guanine base in DNA. The oxoG protein can pair with either cytosine or adenine during DNA replication. Thus, oxoG residues in DNA give rise to G/C to T/A transversion mutations. These transversions are common somatic mutations found in human cancers. HhH-GPD enzymes, such as those described herein, represent a defense against oxoG bycatalysing the expulsion of the oxoG. Thus, in some embodiments, enhanced DMT activity is a method to reduce the incidence of mutations in animal cells. Also, DMT can be used to catalytically remove oxoG from a target gene by fusing DMT to a sequence specific DNA binding protein. When combined with a cell, tissue, or developmentally specific promoters DMT can be used to modulate repair of target genes.

As described above, the polypeptides of the invention can be targeted to chromosomal regions of interest by linking the polypeptides of the invention, including fragments with demethylase activity, to a DNA-binding domain that binds a target sequence. For example, it is known that an enzyme that methylates DNA (Dam methylase) can be targeted to specific sites in the genome (B. V. Steensel and S. Henikoff, *Nature Biotechnology* 18:424–428 (2000)). Specifically, the methylase was tethered to the DNA-binding domain of GAL4. When recombinant GAL4-methylase protein was expressed in transgenic Drosophila, targeted methylation occurred in a region of a few kilobases surrounding the GAL4 DNA binding sequence. In a analogous fashion, DMT, or a portion of DMT that has biological activity (e.g., a potion containing the HhH-GpD motif amino acids such as 1167 to 1368 of SEQ ID NO:2), can be tethered (e.g., as a translational fusion or chemically linked) to proteins that interact as specific sites in the genome. As a result, specific targeted regions of the genome are hypomethylated by DMT. As discussed above, typically hypomethylation promotes transcription of genes (S. E. Jacobesen, *Current Biology* 9, 617 (1999). The invention provides compositions and methods for methylation of a desired are of the chromosome by targeting DMT to those regions. Thus, these embodiments provide additional ways to activate transcription of a desired gene in a targeted chromosomal region.

The following Examples are offered by way of illustration, not limitation.

EXAMPLE

Example 1

This example shows the characterization of dmt mutant plants and the isolation of DMT.

Arabisopsis plants were transformed by infiltrating them with *Agrobacterium* containing the SKI15 T-DNA vector (generaously provided by D. Weigel (Salk Institute, La Jolla, Calif.). T1 seeds were harvested. The SKI15 vector has the bialaphos resistance (BAR) gene that allowed us to directly select transgenic plants in soil after spraying with the commercially available herbicide, Basta. Siliques from approximately 5,000 Basta resistant plants were opened, and those displaying approximately 50% seed abortion were identified.

Two lines, B13 and B33, were identified for further characterization. Genetic analysis of the mutants revealed that the dmt mutants were female sterile. Male fertility, however, depended on the genetic background of the mutant alleles. For instance, in the Columbia background, transmission of the dmt mutation is less than 50%. However, in the Landsberg erecta background, transmission through the male was almost normal.

Molecular analysis confirmed that the two mutations were allelic. For example, both the B13 and B33 alleles carry the SKI15 T-DNA within a DMT exon, confirming that disruption of the DMT gene resulted in the observed B13 and B33 phenotypes.

5'- and 3'-RACE were used to delineate the 5'- and 3'-ends of the cDNA, respectively. 5'-RACE was carried out using reagents and protocols provided by 5' RACE System for Rapid Amplification of cDNA Ends, Version 2.0, GIBCO BRL, LIFE TECHNOLOGIES, Grand Island, N.Y. and Marathon cDNA Amplification Kit, Clontech, Palo Alta, Calif. Final gene specific 5'-RACE primers were SKES-4 (GGGAACAAGTGCACCARCTCC; SEQ ID NO:97) and SKES3.5 (CGATGATAXTGTCTCTTCGAGC; SEQ ID NO:95)3'-RACE was carried out using reagents and protocols provided by Marathon cDNA Amplification Kit, Clontech, Palo Alto. Final gene-specific 3' end was obtained from cDNA library screening.

The nucleotide sequence of the genomic copy of DMT was also determined (SEQ ID NO:1). The 5'-end of the DMT RNA is located at position 3,425 of SEQ ID NO:1. The position of the 3'-end of the DMT RNA is at position 12,504 of SEQ ID NO:1. The position of the ATG translation initiation codon is at position 4,903 of SEQ ID NO:1. The position of the TAA translation termination codon is at position 12,321 of SEQ ID NO:1.

A portion of the DMT polynucleotide sequence, including the first exon, is encompassed by the bacterial artificial chromosome (BAC) clone T9J15TRB. For example, sequences 3820–4299, 4319–4558, 4546–5025 and 9320–9777 of SEQ ID NO:1 were previously determined using the BAC clone as a template. Moreover, a separate independently sequenced region (Bork, C. et al *Gene* 28:147–153 (1998)) also overlaps the DMT sequence at positions 11,087 to 12,785 of SEQ ID NO:1.

The predicted DMT protein has 1,729 amino acids. This sequence was compared to known protein sequences using BLAST and revealed homology to several Endonuclease III proteins. The highest homology was to the Endonuclease III protein from *Deinococcus radiodurans*, Genbank Accession No. AE002073 (see, e.g., White, O. et al. *Science* 286: 1571–1577 (1999)). Other DMT motifs include two consecutive nuclear localization signals at positions 43–60 and 61–78 and a leucine zipper at positions 1330–1351.

Example 2

This example provides further evidence that mutant phenotypes are caused by loss-of-function mutations.

A new allele, dmt-3, was obtained. The dmt-3 allele was caused by insertion of the simple pD991 T-DNA vector (M. R. Sussman, et al., *Plant Physiol*. 124:1465 (2000) into the 2nd exon of the DMT gene. In contrast, the previous two alleles, dmt-1 and dmt-2, caused by insertion of the activation T-DNA vector, SKI015 vector. The mutant phenotypes generated by all three dmt alleles are the same. Because pD991 does not have activation sequences, it suggests that all three mutant alleles are loss-of-function alleles. Consistent with the conclusion, seed abortion can be rescued with a transgene with 3,373 base pairs of 5'-DMT flanking sequences plus 1,478 base pairs of 5'-UTR ligated to a cDNA encoding the full-length DMT polypeptide (i.e., DMTp::DMT). Thus, dmt/DMT heterozygous plants that are hemizygous for the DMTp::DMT transgene displayed 25% seed abortion. Control dmt/DMT plants displayed 50% seed abortion.

Example 3

This example shows that DMT is necessary and sufficient for MEA gene expression.

As discussed above, when fertilization of dmt/dmt homozygous mutant flowers was prevented, fertilization-independent endosperm development was observed. This is very similar to when fertilization of mutant mea flowers is prevented. Thus, before fertilization, both DMT and mEA, a polycomb protein (T. Kiyosue et al., Proc. Natl. Acad. USA 96:4186 (1999)), prevent the central cell of the female gametophyte from forming an endosperm. This is consistent with DMT being a positive regulator of MEDEA (MEA).

As further evidence of this relationship, MEA RNA accumulates in immature floral (IF) buds and open flowers (OF). However, in dmt/dmt mutant plants there was no detectable MEA RNA. Thus, DMT is necessary for MEA gene expression.

In addition, we have generated plants with a transgene, CaMV::DMT, designed to overexpress DMT. The full-length DMT cDNA was ligated to the constitutive cauliflower mosaic virus promoter, CaMV (S. G. Rogers, H. J. Klee, R. B. Horsch, R. T. Fraley, Meth Enzymol 153:253 (1987)). In control wild type plants, the DMT and MEA genes were not significantly expressed in the leaf. However, in 35S::DMT plants, both DMT and MEA RNA level increased significantly. This shows that DMT is sufficient to induce MEA gene expression in the leaf.

Example 4

This example shows that DMT is a member of the HhH-GPD superfamily of DNA repair enzymes.

A BLAST search, followed by a conserved domain search, revealed that DMT is highly related to the HhH-GPD superfamily of base excision DNA repair proteins (i.e., score of 70.1, E-value of $8e^{-13}$). This family contains a diverse range of structurally related DNA repair proteins. The superfamily is called the HhH-GPD family after its hallmark helix-hairpin-helix and Gly/Pro rich loop followed by a conserved apsartate (S. D. Bruner, et al., Nature 403:859 (2000)). Thi includes endonuclease III (EC:4.9.99.18), 8-oxoguanine DNA glycosylases (i.e., yeast OGG1), the thymine DNA glycosylase of methyl-CPG binding protein MBD4 (B. Hendrich, et al. Nature 401:301 (1999)), and DNA-3-methyladenine glycosylase II (EC:3.2.2.21). The predicted amino acid sequence of DMT contains many of the conserved amino acids of this superfamily.

The hallmark of the superfamily of base-excision DNA repair proteins is a helix-hairpin-helix structural element followed by a Gly/Pro-rich loop and a conserved aspartic acid (i.e., HhH-GPD motif). The DMT polypeptide is 1,729 amino acids in length. Amino acids 1,271 to 1,304 correspond to the conserved HhH-GPD motif. The DMT sequence is DKAKDYLLSIRGLGLKSVECVR-LLTLHNLAFPVD (SEQ ID NO:75). The catalytic lysin (K1286) and aspartic acid (D1304) residues are conserved in the HhH-GPD motif of DMT. Secondary structure prediction (Jpred program) indicates that DMT has two alpha-helices (amino acids 1,271–1,279 and 1,286 to 1,295) that correspond to the conserved alphaK and alphaL helices in the HhH-GPD motif of the crystallized hOGG1 DNA repair protein (Bruner et al Nature 403:859–866 (2000)).

The Arabidopsis DMT coding sequence were also used to identify homologous sequences in both public and proprietary databases using both the BLAST and PSI-BLAST computer algorithms. This analysis revealed amino acid sequences from several plant species, including wheat, maize, rice, soybean and Arabidopsis (SEQ ID NOS:8,9,11, 12,14,15,17,18,20,22,24,25,27, and 29) (SEQ ID NOs: 7–29). Based on these sequences, the following consensus sequences for DMT were determined:

DMT Domain A

KV<1>(I,l)D(D,p) (E,v)T<3>W<1>(L,v)L(M,l) (E,d)<0–2>D(K,e)<1>(K,t)<1>(K,a) (W,k) (W,l)<1>(E,k) ER<2>F<1>(G,t)R<1>(D,n) (S,l)FI(A,n)RM(H,r)<1>(V,l) QG(D,n)R<1>F<1>(P,q)WKGSVVDSV(I,v)GVFLTQN(V, t)D(H,y) (L,s)SS(S,n)A(F,y)M<1>(L,v)A(A,s)<1>FP (SEQ ID NO:71)

DMT Domain B

W(D,n)<1>(L,f)R<5>E<3–6>D(S,t)<1>(D,n) (Y,w) <3>R<10>I<2>RG(M,q) (N,f)<2>L(A,s)<1>RI<2–12>FL<3>V<2>(H,n)G<1>IDLEWLR<2>(P,d) (P,s) (D,h) <1>(Y,f)LL(S,e) (I,f)<1>G(L,i)(GLK(V,a)ECVRLL<1>L (H,k)<2>AFPVDTNVGRI(A,c)VR(M,l)G(W,l)VPL(Q,e) PLP<2>(L,v)Q (L,m)H(L,q)L(E,f)<1>YP<1>(L,m)(E,d)(S, n)(I,v)QK(F,y)LWPRLCKL(D,p)Q<1>TLYRLHY(Q,h) (L,m)ITFGK<0–2>FCTK<2>PNCNACPM (R,k)<0–2>(R, k)(H,y)(F,y)(A,s)SA<1>(A,v)<0–10>S(A,s) (R,k)<1>(A,l) L(P,e)<1>(P,t) (SEQ ID NO:72)

DMT Domain C

P(I,l)(I,v)E(E,f)P<1>(S,t)P<2–5>E<0–15>(D,a)IE(D,e) <4–23>(I,v)P<1>I<1>(L,f)(N,d)<8–17>(S,a)<1>(A,d) LV<8>(I,l)P<2–5>(K,r)(L,m)K<4>LRTEH<1>V(Y,f)(E,v) LPD<1>H<1>(L,i)L(E,k)<1>(D,e)D(P,i)<2>YLL(A,s) IW(T,q)P(G,d)(E,g)<6–8>(P,s)<3>C<6–10>(M,l) C<4>C<2>C<3>(R,k)E<5>(V,f)RGT(L,i)L<0–22>(L,v) FADH<1>(S,t)(S,r)<2>PI<3>(W,k)<1>L<1>(R,k)R<4>G (T,s)(S,t)<2>(S,t) I(F,c)(R,k)(G,l)L<1>(T,v)<2>I<2>(C,n)F (W,q)<1>G(F,y)(V,l)C(V,l)R<1>F(E,d)<3>(R,g)<1>P(R,k) <1>L<2(R,h)LH<2>(A,v)SK (SEQ ID NO:73)

The first consensus sequence listed above corresponds to amino acid positions 586 throuh 937 of SEQ ID NO:2. The second consensus sequence listed above corresponds to amino acide position 1117 through 1722 of SEQ ID NO:2. The consensus sequence provides amino acid sequences by position using single letter amino acid abbreviations. Number in carrots ("<" or ">") refer to amino acid position where there is no consensus and which therefore, can be any amino acid. Amino acid abbreviation in parentheses indicate alternative amino acids at the same position. Capitalized letter refer to predominant consensus amino acids and lower case letters refer to amino acids that are commonly found in DMT sequence, but are not predominant.

The consensus sequence provides amino acid sequences by position using single letter amino acid abbreviations. Numbers in carrots ("<" or ">") refer to amino acid position were there is no consensus and which therefore, can be any amino acid. Amino acid abbreviations in parentheses indicate alternative amino acids at the same position. Capitalized letters refer to predominant consensus amino acids and lower case letters refer to amino acids that are commonly found in DMT sequences, but are no predominant.

Example 5

This example demonstrates the relationship between DNA repair and demethylation.

For many years, attention was focused on the ability of DNA glycosylases to repair DNA. For example, glycosylases are involved in the repair of G/T mismatched bases by depurinating the thymidine base moiety. Recently it was shown that avian (B. Zhu et al., *Proc. Natl. Acad. Sci. USA* 97:5135 (2000)) and mammalian (B. Zhu et al., *Nucl. Acid Res.* 28:4157 (2000)). G/T mismatch DNA glycosylases also have 5-methylcytosine-DNA glycosulase activity. That is, these enzymes are demthylases that remove 5-methylcytosine that is later replaced by cytosine. Without intending to limit the scope of the invention, it is believed that as a member of this superfamily, DMT is a demthylase (i.e., 5-methylcytosine glycosylase).

The methylation (i.e., amount of 5-methylcytosine) state of a gene can have a profound effect on its expression. In general, hypomethylation is associated with elevated gene expression, whereas hypermethylation is associated with decreased gene expression (S. E. Jacobsen, *Current Biology* 9:617 (1999)). Thus, it is likely that DMT activates MEA gene expression by reducing its level of methylation.

Mutations in the DDM1 gene in *Arabidopsis* reduce by 70% the overall genome cytosine methylation (E. J. Finnegan, et al., *Proc. Natl. Acad. Sci. USA* 93:8449 (1996); M. J. Ronemus, et al., *Science* 273:654 (1996)). Such plants develop a number of phenotypuc abnormalities including floral phenotypes (T. Kakutani, et al., *Proc. Natl. Acad. Sci. USA* 93:12406 (1996)). Similarly, phenotypic abnormalities have been observed developing in dmt/dmt homozygous plants that affect petal number, floral organ fusion, and floral organ identity. Moreover, independent CaMV::DMT transgenic lines that overexpress DMT frequently are late-flowering. This is particularly interesting because late flowering of ddm1 plants was shown to be due to hypomethylation of the FWA gene (W. J. J. Soppe et al., *Mol Cell* 6:791 (2000)). Thus, without intending to limit the scope of the invention, it is believed that both ddm1 loss-of-function mutations and overexpression of DMT (i.e., CaMV::DMT) may result in genome hypomethylation.

Example 6

This example demonstrates targeting gene expression to the female gametophyte using a DMT promoter sequence.

DMT RNA accumulates in many plant organs such as immature flowers, mature flowers, open flowers, stems and to a lesser extent, leaves. To understand the spatial and temporal regulation of DMT RNA accumulation, the expression of the DMT promoter fused to reporter genes was analyzed. We fused 2,282 base pairs of 5'-DMT sequences, the full-length 5'-UTR (1,478 base pairs), 444 base pairs of DMT coding sequences that contain a nuclear localization signal to two reported genes, the green fluorescent protein (GFP; (Y. Niwa, et al., *Plant J.* 18:455 (199))) and β-glucuronidase (GUS;; (R. A. Jefferson, T. A. Kavanaugh, M. V. Bevan, *EMBO J.* 6:3901 (1987))). Reported gene expression was observed in the developing female gametophyte, in the polar nuclei before they fuse, in the egg and synergids, and in the central cell. Expression was not detected after fertilization. Thus, this promoter is useful for targeting gene expression to the female gametophyte.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

```
SEQ ID NO:1 DMT genomic sequence
DMT genomic sequence (12,785 bp)

AAGCTTAAAGCTACCAACATCGAATTTAGTAAAAGACCCATGATTTGAAATTGGAATTGTCGG
CAAAATCGAGAAGATAT

AGAGCCGACACGGGAACAGTGAAAACCACAAAGCGCGTAAGAATGAAACAGTGGGAGAAGG
AAGAGAGAATCTTACCGAT

CATTCGAGGGAAAAGATGGGAATCAGAGAAAAATCTGGAAAAAAAGAAATTAAGAGAAAGA
GAGAGAAGAAAGTGAGGAG

GAAGATGCAGTGAAGACTGCTATAGCCACATCCCACATGGTGTGATGAGAGAGAGAGAGA
GAGGTTAAAGCAGCAAAT

TGTGGAGAGATAAAGAGAGAGAGAGACTGAGCGAGTCAAGTTCGTCGTCGTGTTTAAAAGAA
AGAATCCTATATTTGCCT

TTTTCTTTACTACTTTATTTTCAGACTATTTGCTTATTTTGCCTCAAACTTTTTTGATTGTCACTT
TTCGATCCTAAAGT

GTTTGACAATTTACCTGCCTTTTTCTCCAAGAAAAATCAGAACAGACCACAGCAAATTTATGTA
TTTTCTATTAAAAAAG

AAAGAAAGAATTCATATTACTTATAGAATTAAAAGCTAAGCAGTTGAAAACGTGAAAGCAGA
ATTTCTAAAAAAAATAGT

AAACTGCTACAAACTTATTTATGTGTATATAACATATCTATAAAGAAACTCAAATATATGATA
AATCATTTTAACAAAAT

TTCTATGAAATTATAATAAAAAAAGTCACTTTTGACACTTAAAAGGTTGACAATAACCGTCTCT
CCAAAAAAAAATCAAA
```

-continued

```
ACATTTATAATTTCTAAAACTATGGTGTAATTTTGCTGAAATCAAAAAGAAAAGAAGGATTTC
TATATCATAAGTTTCAT

TATTGTATCAAACTTTCAAATTTCATGTAATTTGAAAGGAAAAAAATTAAGATATAATGTTGTT
TTTGTTTCTTATGTTA

CATTTTCATGGAATATATATTCATAACAAAAAATGTATTTTAATATGATGAGAGATTACCATCC
AAAAGGTCGAACTTAT

ATAAAACAAGTTAATAACTAAACAATACATGTGATCACAATCAATGACAGTTTTGATCTTAAA
ATAGAAATGATTGAGCA

AACCTCAAAAATGTCTTCTTAGGATCACAAAATCTTTCCTTTAGCTTATTAAAGCCGGGAGTTC
AACTCTCTCTCCCTTG

TAGACTTTTTGTTTTCAAATCTTTTTCTTTCAAAAAATCAATAATTAGTTAATGGGCATAATATT
TGGTTTTAATTAAGT

CCATAGATTTTTTAGGACCATCTCTAATCACGACAAATATCCTAAATTGTAACACATTTAAAAC
TTAAAAGTATTGCATT

CACAATCCTTAAAATATATATATATATATATATATATATATATATATATATATATATGAAAGTTAT
ATAGAAACGATAACTC

CTTACTCAACAATTAGCCCAAAAAAACATCCATAATGCATTTAAACTAGGAATTTTAACAAAC
TCAAATAGGTTGGTAGT

TAAAAAAAAACAAATAGTAGATGTACATACGTACCTTTAAAAATATATACTCATATCGAAAGT
TTTTAAATTTTGCGAAAT

TAAATACATTTATCTATCAATTAAAATACATTTAATAATGCATAATTCTGTAATATCTATCTTT
AATTTCCATATAGAAC

CAAAACAAAATAAACATATCAAATAGTTTTAACTTAACAAAAACGTTAGGGAAAAGTTGACCT
AACTAGCTTGATTGACG

TTGAACTTGTCAATGCGAAAGCGATATTTCCAATATATACTACATGTAGTATTATTTATATGGA
AGTTTCTAAAAAGGTG

TTGAGTGGATTGTTACTTGTTGGAGGATGCTATTTTTTCCTTCTTGCCATAATATTTTACGAGTA
TGGGATAACTACATA

CTCATGATTATGAAACGCTCACTTTATTTGAAAAACCTCCTAATACACCAAATATGTCACTAGA
TTCCAAAACGTAGACC

AATTGTATCTAATCTCAAATTCTCAATCAAAGTATTAATTTACCGATGGTAAGAAAAGTTAACC
GATATAATTATCAAAA

GAAAGAATAAGTCAACAGATTCTTAATCTCTTTATTTTGGTATATGAACATTTGTACAAAAATC
TCAAAAGATATGTAAC

TGTTTAAAATATAAATTCACTGAGATTAATTCTTCAGACTCGTGTTAGCTATAATAATGTCAAG
AGTTCTTCTTGTTTCA

AGGAAAAACCTTAAAGATATGTATATTTTCTGTAATTATGATGATATAATTTGCTATTCATTGT
CACAAACATTACTTTA

AAAAATCGTATTTTCATTACTACAATGTTGACTAAGAACAAAAATACATTGATTATTGATATAT
CGTCAACTGAATTTTC

TTCCGAGGGATATAATTCTCAAACATAGCAAGAATCTCATAATAATGTTTCGTGACTACCTTTA
GACGAAATTTTTTTAA

GATTCGTAACGTGACTTATGGTCTCTTGCTGTGGGGGTCAATGCGAATAAATCTAAATGTATG
GGAGTCAAATAAAATAC

CAAGAAAAATAAAGGAGCAGCACCCAATAAACTATATGGGACCAGAAATCCTTTCATTGGTTT
AAAATAGGATTATCCCG

AAAGATGAAGGACTAAATTGAAACTGATTGGGGGTAGGAAGAGATCCGTCACAATCATTAAT
GGCTTCCACGCGGAAACT

TGTCGTTTATACAATTTCATTAACTTTCGGGTCGGGTTTATATTCCAAATGGGTCAAATAATAT
TAGTTTAATACACTAA

CGGAGTAATTAATTGGTGACTACAATTTTATCAGTTTGGTGCAATTAGAAACGAACATAGTCG
TAAAATACGAGTTCGGT
```

-continued

GTTATACCTTTATTTACGTTAAAAAAATACGAGAATTTTGTGTCAAATTTCAAATTAATTTCAT
GAATATATGGAAATTA

TTAGATACTCTAGCGAAAATAGTGATTATGAGCGTTTTACAAAAATACGATTTTAGCATTGAA
CTTCCTTTATGTAATTC

GGTCAAATGTTGGCATGAAGAAGCAAGTTTGCAACATTAAATTTCATTTAAAAATCGTGTTTGA
CATACTTTAAAATCTAA

ATATAGGAAGAAGACCAAAACATTAAATTTAGTAAGATTCTAATGAACATTTATAAGTTATAA
CTTATAACCAACAAAAG

TTGGGTTTAGCGTTGTTGCTTTATCTGAAAACTTGCAAACTAAACCATTTTAATAGGACTAATG
ACAATTAACAACAAAA

TACACTTAAGCAACAACGTCCTCGTGAATATAATTTGGGCCTCAGGCCCATATTGCTAACGCC
AACTGATATTTCACTTT

ATTCCTTCTTCATCTCACCACACTCTCTCTCTATCTCTATCTCTAACGGCATAGCTGACTCAGTG
TTCTCCGGCATTGAC

TCGCCTGAGAATCAGAAAGCTTAGATCGGTGAGCTTTTAGCTCCATTTTCTGTTTATTTACATA
TTATTTCCTTTTTTTC

TCTCTCCCTTTTTTATCTGGAATTTGTTCTGCTAAATTTTCCAGCTGTTACATTTTCCGATCACG
AGAAGAATCACTGGG

TTTTTATGTTAATCAATACATGTTCCTGTTTTCTGATCATAAATCTCAGCTATTAACACCTGATT
TTGATTCTGCGTAAT

AAAAACCTCTGATTTGCTTTTATCTTCACTTTCCCCATAAACATTGCTTACTTTATTCGCTCTTC
TTTTACCGTTTCCAG

CTAAAAAATTCTTCGCTATTCAATGTGTTTCTCGTTTTGTTGATGAGAAAAATATCTGACAAAA
AATCATTTATTGCATT

TTATGGTGCAGATTCTTAGTTAATGTCGCCTTCTCTAACCAAGTCAGATTAAAAAGGAGTGTTC
GTCCATGTTGCTTTGT

TTTGGTGTTTGGAGAGAGTTTTCGGAGAGTTAGGTGAGTGTTATTTGGGGTGAGGTAGTGATA
AGGTTTGAAGGGGGAGT

GATTCATCAAGTGTGTTATGAATTCGAGGGCTGATCCGGGGGATAGATATTTTCGAGTTCCTTT
GGAGAATCAAACTCAA

CAAGAGTTCATGGGTTCTTGGATTCCATTTACACCCAAAAAACCTAGATCAAGTCTGATGGTA
GATGAGAGAGTGATAAA

CCAGGATCTAAATGGGTTTCCAGGTGGTGAATTTGTAGACAGGGGATTCTGCAACACTGGTGT
GGATCATAATGGGGTTT

TTGATCATGGTGCTCATCAGGGCGTTACCAACTTAAGTATGATGATCAATAGCTTAGCGGGAT
CACATGCACAAGCTTGG

AGTAATAGTGAGAGAGATCTTTTGGGCAGGAGTGAGGTGACTTCTCCTTTAGCACCAGTTATC
AGAAACACCACCGGTAA

TGTAGAGCCGGTCAATGGAAATTTTACTTCAGATGTGGGTATGGTAAATGGTCCTTTCACCCA
GAGTGGCACTTCTCAAG

CTGGCTATAATGAGTTTGAATTGGATGACTTGTTGAATCCTGATCAGATGCCCTTCTCCTTCAC
AAGCTTGCTGAGTGGT

GGGGATAGCTTATTCAAGGTTCGTCAATGTGAGTGATCAAATCTATTTTCAGTTTTTTTTTTCC
CTTTCTTCCGTTCTT

GCAGTACTTAGAGTAGAACATGAATTTAGAATATCTTAAGAAAGTCATGGTTTTGAACAGATGG
ACCTCCAGCGTGTAACA

AGCCTCTTTACAATTTGAATTCACCAATTAGAAGAGAAGCAGTTGGGTCAGTCTGTGAAAGTT
CGTTTCAATATGTACCG

TCAACGCCCAGTCTGTTCAGAACAGGTGAAAAGACTGGATTCCTTGAACAGATAGTTACAACT
ACTGGACATGAAATCCC

AGAGCCGAAATCTGACAAAAGTATGCAGAGCATTATGGACTCGTCTGCTGTTAATGCGACGGA
AGCTACTGAACAAAATG

-continued

```
ATGGCAGCAGACAAGATGTTCTGGAGTTCGACCTTAACAAAACTCCTCAGCAGAAACCCTCCA
AAAGGAAAAGGAAGTTC

ATGCCCAAGGTGGTCGTGGAAGGCAAACCTAAAAGAAAGCCACGCAAACCTGCAGAACTTCC
CAAAGTGGTCGTGGAAGG

CAAACCTAAAAGGAAGCCACGCAAAGCTGCAACTCAGGAAAAAGTGAAATCTAAAGAAACCG
GGAGTGCCAAAAAGAAAA

ATTTGAAAGAATCAGCAACTAAAAAGCCAGCCAATGTTGGAGATATGAGCAACAAAAGCCCT
GAAGTCACACTCAAAAGT

TGCAGAAAAGCTTTGAATTTTGACTTGGAGAATCCTGGAGATGCGAGGCAAGGTGACTCTGAG
TCTGAAATTGTCCAGAA

CAGTAGTGGCGCAAACTCGTTTTGAGATCAGAGATGCCATTGGTGGAACTAATGGTAGTTT
CCTGGATTCAGTGTCAC

AAATAGACAAGACCAATGGATTGGGGGCTATGAACCAGCCACTTGAAGTGTCAATGGGAAAC
CAGCCAGATAAACTATCT

ACAGGAGCGAAACTGGCCAGAGACCAACAACCTGATTTATTGACTAGAAACCAGCAATGCCA
GTTCCCAGTGGCAACCCA

GAACACCCAGTTCCCAATGGAAAACCAACAAGCTTGGCTTCAGATGAAAAACCAACTTATTGG
CTTTCCATTTGGTAACC

AGCAACCTCGCATGACCATAAGAAACCAGCAGCCTTGCTTGGCCATGGGTAATCAACAACCTA
TGTATCTGATAGGAACT

CCACGGCCTGCATTAGTAAGTGGAAACCAGCAACTAGGAGGTCCCCAAGGAAACAAGCGGCC
TATATTTTTGAATCACCA

GACTTGTTTACCTGCTGGAAATCAGCTATATGGATCACCTACAGACATGCATCAACTTGTTATG
TCAACCGGAGGGCAAC

AACATGGACTACTGATAAAAAACCAGCAACCTGGATCATTAATAAGAGGCCAGCAGCCTTGC
GTACCTTTGATTGACCAG

CAACCTGCAACTCCAAAAGGTTTTACTCACTTGAATCAGATGGTAGCTACCAGCATGTCATCG
CCTGGGCTTCGACCTCA

TTCTCAGTCACAAGTTCCTACAACATATCTACATGTGGAATCTGTTTCCAGGATTTTGAATGGG
ACTACAGGTACATGCC

AGAGAAGCAGGGCTCCTGCATACGATTCTTTACAGCAAGATATCCATCAAGGAAATAAGTACA
TACTTTCTCATGAGATA

TCCAATGGTAATGGGTGCAAGAAAGCGTTACCTCAAAACTCTTCTCTGCCAACTCCAATTATG
GCTAAACTTGAGGAAGC

CAGGGGCTCGAAGAGACAGTATCATCGTGCAATGGGACAGACGGAAAAGCATGATCTAAACT
TAGCTCAACAGATTGCTC

AATCACAAGATGTGGAGAGACATAACAGCAGCACGTGTGTGGAATATTTAGATGCTGCAAAG
AAAACGAAAATCCAGAAA

GTAGTCCAAGAAAATTTGCATGGCATGCCACCTGAGGTTATAGAAATCGAGGATGATCCAACT
GATGGGGCAAGAAAAGG

TAAAAATACTGCCAGCATCAGTAAAGGTGCATCTAAAGGAAACTCGTCTCCAGTTAAAAAGAC
AGCAGAAAAGGAGAAAT

GTATTGTCCCAAAAACGCCTGCAAAAAAGGGTCGAGCAGGTAGAAAAAAATCAGTACCTCCG
CCTGCTCATGCCTCAGAG

ATCCAGCTTTGGCAACCTACTCCTCCAAAGACACCTTTATCAAGAAGCAAGCCTAAAGGAAAA
GGGAGAAAGTCCATACA

AGATTCAGGAAAAGCAAGAGGTAACTAATGTATTCTACAATCTCTGTGATATAATTTTGAGAT
TTTAGTAACTGATGTGT

CCAAACCAGCTCCTTATCACTGTTGGTGCGTTGTATAGGTCCATCAGGAGAACTTCTGTGTCAG
GATTCTATTGCGGAAA

TAATTTACAGGATGCAAAATCTGTATCTAGGAGACAAAGAAAGAGAACAAGAGCAAAATGCA
ATGGTCTTGTACAAAGGA
```

-continued

```
GATGGTGCACTTGTTCCCTATGAGAGCAAGAAGCGAAAACCAAGACCCAAAGTTGACATTGA
CGATGAAACAACTCGCAT

ATGGAACTTACTGATGGGAAAGGAGATGAAAAGAAGGGGATGAAGAGAAGGATAAAAAG
AAAGAGAAGTGGTGGGAAG

AAGAAAGAAGAGTCTTCCGAGGAAGGGCTGATTCCTTCATCGCTCGCATGCACCTGGTACAAG
GTGAAGATCCACTTCTC

TTCTCAACTCCATTTTTATTCACACAAATTAGTAGAATACTCAAAAATGATGTTTTGTTTGCAA
AATTTTAAAATTCACT

AGTTAACCATGTCAAATAATATTCATAATGCATCTTGTGAAGAACAGGTGTGCATTTATGGTG
ACAGCTGAATGGTTTAT

GTGCCTATTATTTCTTTTACTGCTATAGATGACCAATTGAACTTAAACGTTTACAGGAGATAGA
CGTTTTTCGCCATGGA

AGGGATCGGTGGTTGATTCGGTCATTGGAGTTTTCCTTACACAGAATGTCTCGGATCACCTTTC
AAGGTATATGAGTTGC

CTTAATAAATTGAGTTCCAAAACATAGAAATTAACCCATGGTGGTTTTACAATGCAGCTCTGC
GTTCATGTCTCTAGCTG

CTCGATTCCCTCCAAAATTAAGCAGCAGCCGAGAAGATGAAAGGAATGTTAGAAGCGTAGTT
GTTGAAGATCCAGAAGGA

TGCATTCTGAACTTAAATGAAATTCCTTCGTGGCAGGAAAAGGTTCAACATCCATCTGACATG
GAAGTTTCTGGGGTTGA

TAGTGGATCAAAAGAGCAGCTAAGGGACTGTTCAAACTCTGGAATTGAAAGATTTAATTTCTT
AGAGAAGAGTATTCAAA

ATTTAGAAGAGGAAGTATTATCATCACAAGATTCTTTTGATCCGGCGATATTTCAGTCGTGTGG
GAGAGTTGGATCCTGT

TCATGTTCCAAATCAGACGCAGAGTTTCCTACAACCAGGTGTGAAACAAAAACTGTCAGTGGA
ACATCACAATCAGTGCA

AACTGGGAGCCCAAACTTGTCTGATGAAATTTGTCTTCAAGGGAATGAGAGACCGCATCTATA
TGAAGGATCTGGTGATG

TTCAGAAACAAGAAACTACAAATGTCGCTCAGAAGAAACCTGATCTTGAAAAAACAATGAAT
TGGAAAGACTCTGTCTGT

TTTGGTCAGCCAAGAAATGATACTAATTGGCAAACAACTCCTTCCAGCAGCTATGAGCAGTGT
GCGACTCGACAGCCACA

TGTACTAGACATAGAGGATTTTGGAATGCAGGGTGAAGGCCTTGGTTATTCTTGGATGTCCAT
CTCACCAAGAGTTGACA

GAGTAAAGAACAAAAATGTACCACGCAGGTTTTTCAGACAAGGTGGAAGTGTTCCAAGAGAA
TTCACAGGTCAGATCATA

CCATCAACGCCTCATGAATTACCAGGAATGGGATTGTCCGGTTCCTCAAGCGCCGTCCAAGAA
CACCAGGACGATACCCA

ACATAATCAACAAGATGAGATGAATAAAGCATCCCATTTACAAAAAACATTTTTGGATCTGCT
CAACTCCTCTGAAGAAT

GCCTTACAAGACAGTCCAGTACCAAACAGAACATCACGGATGGCTGTCTACCGAGAGATAGA
ACTGCTGAAGACGTGGTT

GATCCGCTCAGTAACAATTCAAGCTTACAGAACATATTGGTCGAATCAAATTCCAGCAATAAA
GAGCAGACGGCAGTTGA

ATACAAGGAGACAAATGCCACTATTTTACGAGAGATGAAAGGGACGCTTGCTGATGGGAAAA
AGCCTACAAGCCAGTGGG

ATAGTCTCAGAAAAGATGTGGAGGGGAATGAAGGGAGACAGGAACGAAACAAAAACAATAT
GGATTCCATAGACTATGAA

GCAATAAGACGTGCTAGTATCAGCGAGATTTCTGAGGCTATCAAGGAAAGAGGGATGAATAA
CATGTTGGCCGTACGAAT

TAAGGTAAATCTACTAATTTCAGTTGAGACCCTCATCAAATCTGTCAGAAGGCTTGAACATCA
GTAAATTATGTAACCAT
```

-continued

ATTTACAACATTGCAGGATTTCCTAGAACGGATAGTTAAAGATCATGGTGGTATCGACCTTGA
ATGGTTGAGAGAATCTC

CTCCTGATAAAGCCAAGTGGGTAAATCACATTTTTAGTGACTGCAACACTAGCACGATCGATT
TACTCAACAATTACGTC

AAACTGAGTATTAACAAGTTGCTCATGAACATTTCACAGGGACTATCTCTTGAGCATAAGAGG
TCTGGGTTTGAAAAGTG

TTGAATGCGTGCGACTCTTAACACTCCACAATCTTGCTTTCCCTGTGAGTCAGACTATTCCATT
ATCTACTAAAAACTTA

GAATAACTCCGGCTAACTAAGCTGGAACTTGTATTTGATGATATGAAGGTTGACACGAATGTTG
GAAGGATAGCAGTTAGG

ATGGGATGGGTGCCTCTACAACCCCTACCTGAATCACTTCAGTTACACCTCCTGGAGCTGTAA
GTTTCTTTTTGTTTGTC

ATCTAAACAACGAAATTTTTATGCAAGTCATAACCATGCTGTGTTTTCACAGATACCCAGTGCT
CGAGTCCATCCAAAAA

TTTCTTTGGCCAAGACTTTGCAAACTCGATCAACGAACACTGTATGCTCATAAACTCTAACAAA
TCATCTGTCTGAAAAA

CCAATATTTCTTTGGTAGAATTCTATTGTCATTACTCATTACTAACAGCGAAATTAATTAACGT
TCTTTTTCTTACTCAG

GTATGAATTACACTACCAACTGATTACGTTTGGAAAGGTATTATTGCTCTAAGCTTTGAATTTA
TCATATGGTAATTTCA

AGCATTGTAGGCACCTGATCAATTATGTGTCTAAATCATGTGAATTCATGTCAGGTATTTGCA
CAAAGAGTAGACCAAA

TTGTAATGCATGTCCAATGAGAGGAGAGTGCAGACACTTTTGCCAGTGCTTATGCTAGGTAAGC
AAGCTTTCATGTACTTA

TATGCAATAATTAAAGATAAAATTTAGGATTATGGGTAAGTTACAAAAAATTAGGCTCAGTTT
CATGGTAGCTAGCTGGA

AATAGTATTACAAGAACAACATAAAGATCAAAGACAGAATCATGGATCCATATGCACTATCAT
TTTAGCTCTTGTAATCC

ATACATGAACACTATATGCCAAAGTAGGGATTTCAAATATGAGATTCGATGACTGATGCCATT
GTAACAGTGCAAGACTT

GCTTTACCGGCACCAGAGGAGAGGAGCTTAACAAGTGCAACTATTCCGGTCCCTCCCGAGTCC
TATCCTCCTGTAGCCAT

CCCGATGATAGAACTACCTCTTCCGTTGGAGAAATCCCTAGCAAGTGGAGCACCATGGAATAG
AGAAAACTGTGAACCAA

TAATTGAAGAGCCGGCCTCGCCCGGGCAAGAGTGCACTGAAATAACCGAGAGTGATATTGAA
GATGCTTACTACAATGAG

GACCCTGACGAGATCCCAACAATAAAACTCAACATTGAACAGTTTGGAATGACTCTACGGGAA
CACATGGAAAGAAACAT

GGAGCTCCAAGAAGGTGACATGTCCAAGGCTTTGGTTGCTTTGCATCCAACAACTACTTCTATT
CCAACTCCCAAACTAA

AGAACATTAGCCGTCTCAGGACAGAGCACCAAGTGTAAGCTAATATCTCCTCCTATATTTTATC
TTCCATATAAATTTTG

GGGAAAAAATCGCTCTCCATCTGGTTTTAGAACATGCGGGTCAGCCAGGGTTATGGCATTTTT
ATATATTTCACCGATCG

GCCCGAGCTGGCTCTGGTTGACTCGTATGCCACCCTGCATTGAACAAACCAGTAGGAGACAAG
CAAGCAAAACGTTTTAA

GATAAGGTCTATGGTAAAATGACAAGGTAACTGATAAATGTGTCGTCTATTTGCAGGTACGAG
CTCCCAGATTCACATCG

TCTCCTTGATGGTGTAAGTCAATTTTTAACTCTCTCTATACTCGAGTTGTTTCACTTGAGCAACA
CTGTTTAAAAGTCCT

CATTTGATAAAATAACAGATGGATAAAAGAGAACCAGATGATCCAAGTCCTTATCTCTTAGCT
ATATGGACACCAGGTGA

-continued

```
GAATAAAACTGCAATGTTTCATTCATGTGTCTACAGTATCAAAGAAAGTACAGCTAGAGCTAA
AAAGCATTTGAAATAGA

GTCGGTTAAATATGAAAGTTTGAATCTGTAAATGAAAGCCGGAACGTAGCATTGGTGGATGTT
ATATGTAAATTAGTTTT

TGAGATTGGTCTAATGTAGTTGTTTGACTGCCAGGTGAAACAGCGAATTCGGCACAACCGCCT
GAACAGAAGTGTGGAGG

GAAAGCGTCTGGCAAAATGTGCTTTGACGAGACTTGTTCTGAGTGTAACAGTCTGAGGGAAGC
AAACTCACAGACAGTTC

GAGGAACTCTTCTGGTGAGATTATCTTGATCTTTTGTGTTGCTCATGAAAAGGAGAAGTGAGA
ATACAAGTTTGCTAATA

TCATTTTTTCGTCATTCACAGATACCTTGTCGGACTGCCATGAGAGGAAGTTTTCCGCTCAACG
GGACATATTTCCAAGT

CAACGAGGTTAGATGAAATAAAACTCAAACAGACAGACGAAACATTATTTCTGTTTAGTGTTG
GTTCTTTATCCTCCTTG

CCATTTTTTATCTTGCAGTTATTTGCAGACCACGAGTCCAGTCTCAAACCCATCGATGTTCCTA
GAGATTGGATATGGGA

TCTCCCAAGAAGGACTGTTTACTTCGGAACATCAGTAACATCAATATTCAGAGGTAAAAACAT
TCGTAATAGAGTTAGTT

AATCAAATGTCCAAAACACAAGAAAGCTTCACCGTCCAATACACAAGAAAGCTTCACCTTCTC
TTTGCCAAAAAAGATCT

TAGAATGTTTTGCTGAATTTGTGCAGGTCTTTCAACGGAGCAGATACAGTTCTGCTTTTGGAAA
GGTAAACGTTAACTTT

CGACCCAGAGAAATCCGGAAAATCTATTGCTTTGTTCTGATCAATACGTTAAACATATACACA
CACACTTTACACTTAGG

ACCAATACTGTTCTGATCTGTGATAGAAACTGGTAAACATCTAACAATTATGATTGCAGGATT
CGTATGTGTCCGTGGAT

TCGAACAGAAGACAAGAGCACCGCGTCCATTAATGGCAAGGTTGCATTTTCCTGCGAGCAAAT
TGAAGAACAACAAAACC

TAAAGATGACTGGAAGAAAGCAAACGCATTGCTTCTCTGCTCTCCTCTATTTAAAGCCAGGAA
AAGTCCCATTTAGACAT

AATAACAGGAATCCAAATAGGCTATTTTCTCTTTCTTTCTTATTTCATTCATAGAGCAGAAGCG
ACACAAAAAAGTTTTT

TGGGTTATTTATTTTCTCTCTAACAAATTTGTAGCGTTTTGGGTCTTTTTCTGGCTGTCACTAGC
GTGGCAAATCCAATG

TCCGCGCACACTTAGGCGCATTGTCAATAAATTCTCCGGCCACCGGAGTGTTACGATCTTFTTCC
AACGGCGGCTAATGCG

ATATTPCCGGTAACACATATTCCTTATTCTATGTTGGTTTTGTGTACGGCGTGGGCCTTACTAG
ACAATGATCATCAATA

AAACTAACACAAAGTTGAATGCTACAAAGTAGAAAGTGAAGAAAAAATAATATAGACATTGC
CGA
```

SEQ ID NO:2 DMT amino acid sequence

MQSIMDSSAVNATEATEQNDGSRQDVLEFDLNKTPQQKPSKRKRKFMPKVVVEGKPKRKPRKPA
ELPKVVVEGKPKRKPR

KAATQEKVKSKETGSAKKKNLKESATKKPANVGDMSNKSPEVTLKSCRKALNFDLENPGDARQG
DSESEIVQNSSGANSF

SEIRDAIGGTNGSFLDSVSQIDKTNGLGAMNQPLEVSMGNQPDKLSTGAKLARDQQPDLLTRNQQ
CQFPVATQNTQFPME

NQQAWLQMKNQLIGFPFGNQQPRMTIRNQQPCLAMGNQQPMYLIGTPRPALVSGNQQLGGPQGN
KRIPIFLNHQTCLPAGN

-continued

QLYGSPTDMHQLVMSTGGQQHGLLIKNQQPGSLIRGQQPCVPLIDQQPATPKGFTHLNQMVATSM
SSPGLRPHSQSQVPT

TYLHVESVSRILNGTTGTCQRSRAPAYDSLQQDIHQGNKYILSHEISNGNGCKKALPQNSSLPTPIM
AKLEEARGSKRQY

HRAMGQTEKHDLNLAQQIAQSQDVERHNSSTCVEYLDAAKKTKIQKVVQENLHGMPPEVIEIEDD
PTDGARKGKNTASIS

KGASKGNSSPVKKTAEKEKCIVPKTPAKKGRAGRXKSVPPPAHASEIQLWQPTPPKTPLSRSKPKG
KGRKSIQDSGKARG

PSGELLCQDSIIAEIIYRMQNLYLGDKEREQEQNAMVLYKGDGALVPYESKKRKPRPKVDIDDETTR
IWNLLMGKGDEKEG

DEEKDKKKEKWWEEERRVFRGRADSFIARMHLVQGDRRFSPWKGSVVDSVIGVFLTQNVSDHLS
SSAFMSLAARFPPKLS

SSREDERNVRSVVVEDPEGCILNLNEIPSWQEKVQHIPSDMEVSGVDSGSKEQLRDCSNSGIERFNFL
EKSIQNLEEEVLS

SQDSFDPALFQSCGRVGSCSCSKSDAEFPTTRCETKTVSGTSQSVQTGSPNLSDEICLQGNERPHLYE
GSGDVQKQETTN

VAQKKPDLEKTMNWKDSVCFGQPRINDTNWQTTPSSSYEQCATRQPHVLDIBDFGMQGEGLGYS
WMSISPRVDRVKNXNVP

RRFFRQGGSVPRLEFTGQIIPSTPHELPGMGLSGSSSAVQEHQDDTQHNQQDEMNKASHLQKTFLDL
LNSSEECLTRQSST

KQNITDGCLPRDRTAEDVVDPLSNNSSLQNILVESNSSNKEQTAVEYKETNATILREMKGTLADGK
KPTSQWDSLRKDVE

GNEGRQERNKNNMDSIDYEAIRRASISEISEAIKERGMNNMLAVRIKDFLERIVKDHGGIDLEWLRE
SPPDKAKDYLLSI

RGLGLKSVECVRLLTLHNLAFPVDTNVGPIAVRMGWVPLQPLPESLQLHLLELYPVLESIQKFLWP
RLCKLDQRTLYELH

YQLITFGKVFCTKSRPNCNACPMRGECRHFASAYASARLALPAPEERSLTSATIPVPPESFPPVAIPM
IELPLPLEKSLA

SGAPSNRBNCEPIIEEPASPGQECTEITESDIEDAYYNEDPDEIPTIKLNIEQFGMTLREHMERNMELQ
EGDMSKALVAL

HPTTTSIPTPKLKNISRLRTEHQVYELPDSHRLLDGMDKREPDDPSPYLLAIWTPGETANSAQPPEQ
KCGGKASGKMCFD

ETCSECNSLREANSQTVRGTLLIPCRTAMRGSFPLNGTYFQVNELFADHESSLKPIDVPRDWIWDLP
RRTVYFGTSVTSI

FRGLSTEQIQFCFWKGFVCVRGFEQKTRAPRLPLMARLHFPASKLKNNKT

SEQ ID NO:3 DMT 5' flanking sequence

AAGCTTAAAGCTACCAACATCGAATTTAGTAAAAGACCCATGATTTGAAATTGGAATTGTCGG
CAAAATCGAGAAGATAT

AGAGCCGACACGGGAACAGTGAAAACCACAAAGCGCGTAAGAATGAAACAGTGGGAGAAGG
AAGAGAGAATCTTACCGAT

CATTCGAGGGAAAAGATGGGAATCAGAGAAAAATCTGGAAAAAAAGAAATTAAGAGAAAGA
GAGAGAAGAAAGTGAGGAG

GAAGATGCAGTGAAGACTGCTATAGCCACATCCCACATGGTGTGATGAGAGAGAGAGAGAGA
GAGGTTAAAGCAGCAAAT

TGTGGAGAGATAAAGAGAGAGAGACTGAGCGAGTCAAGTTCGTCGTCGTGTTTAAAAGAA
AGAATCCTATATTTGCCT

TTTTCTTTACTACTTTATTTTCAGACTATTTGCTTATTTTGCCTCAAACTTTTTTGATTGTCACTT
TTCGATCCTAAAGT

-continued

GTTTGACAATTTACCTGCCTTTTTCTCCAAGAAAAATCAGAACAGACCACAGCAAATTTATGTA
TTTTCTATTAAAAAAG

AAAGAAAGAATTCATATTACTTATAGAATTAAAAGCTAAGCAGTTGAAAACGTGAAAGCAGA
ATTTCTAAAAAAAATAGT

AAACTGCTACAAACTTATTTATGTGTATATAACATATCTATAAAGAAACTCAAATATATGATA
AATCATTTTAACAAAAT

TTCTATGAAATTATAATAAAAAAAGTCACTTTTGACACTTAAAAGGTTGACAATAACCGTCTCT
CCAAAAAAAAATCAAA

ACATTTATAATTTCTAAAACTATGGTGTAATTTTGCTGAAATCAAAAAGAAAAGAAGGATTTC
TATATCATAAGTTTCAT

TATTGTATCAAACTTTCAAATTTCATGTAATTTGAAAGGAAAAAAATTAAGATATAATGTTGTT
TTTGTTTCTTATGTTA

CATTTTCATGGAATATATATTCATAACAAAAAATGTATTTTAATATGATGAGAGATTACCATCC
AAAAGGTCGAACTTAT

ATAAAACAAGTTAATAACTAAACAATACATGTGATCACAATCAATGACAGTTTTGATCTTAAA
ATAGAAATGATTGAGCA

AACCTCAAAAATGTCTTCTTAGGATCACAAAATCTTTCCTTTAGCTTATTAAAGCCGGGAGTTC
AACTCTCTCTCCCTTG

TAGACTTTTTGTTTTCAAATCTTTTTCTTTCAAAAAATCAATAATTAGTTAATGGGCATAATATT
TGGTTTTAATTAAGT

CCATAGATTTTTTAGGACCATCTCTAATCACGACAAATATCCTAAATTGTAACACATTTAAAAC
TTAAAAGTATTGCATT

CACAATCCTTAAAATATATATATATATATATATATATATATATATATATATATATATGAAAGTTAT
ATAGAAACGATAACTC

CTTACTCAACAATTAGCCCAAAAAAACATCCATAATGCATTTAAACTAGGAATTTTAACAAAC
TCAAATAGGTTGGTAGT

TAAAAAAAACAAATAGTAGATGTACATACGTACCTTTAAAAATATATACTCATATCGAAAGT
TTTAAATTTTGCGAAAT

TAAATACATTTATCTATCAATTAAAATACATTTAATAATGCATAATTCTGTAATATCTATCTTT
AATTTCCATATAGAAC

CAAAACAAAATAAACATATCAAATAGTTTTAACTTAACAAAAACGTTAGGGAAAAGTTGACCT
AACTAGCTTGATTGACG

TTGAACTTGTGAATGCGAAAGCGATATTTCCAATATATACTACATGTAGTATTATTTATATGGA
AGTTTCTAAAAAGGTG

TTGAGTGGATTGTTACTTGTTGGAGGATGCTATTTTTTCCTTCTTGCCATAATATTTTACGAGTA
TGGGATAACTACATA

CTCATGATTATGAAACGCTCACTTTATTTGAAAAACCTCCTAATACACCAAATATGTCACTAGA
TTCCAAAACGTAGACC

AATTGTATCTAATCTCAAATTCTCAATCAAAGTATTAATTTACCGATGGTAAGAAAAGTTAACC
GATATAATTATCAAAA

GAAAGAATAAGTCAACAGATTCTTAATCTCTTTATTTTGGTATATGAACATTTGTACAAAAATC
TCAAAAGATATGTAAC

TGTTTAAAATATAAATTCACTGAGATTAATTCTTCAGACTCGTGTTAGCTATAATAATGTCAAG
AGTTCTTCTTGTTTCA

AGGAAAAACCTTAAAGATATGTATATTTTGTAATTATGATGATATAATTTGCTATTCATTGT
CACAAACATTACTTTA

AAAAATCGTATTTTCATTACTACAATGTTGACTAAGAACAAAAATACATTGATTATTGATATAT
CGTCAACTGAATTTTC

TTCCGAGGGATATAATTCTCAAACATAGCAAGAATCTCATAATAATGTTTCGTGACTACCTTTA
GACGAAATTTTTTAA

GATTCGTAACGTGACTTATGGTCTCTTGCTGTGGGGGTCAATGCGAATAAATCTAAATGTATG
GGAGTCAAATAAAATAC

CAAGAAAAATAAAGGAGCAGCACCCAATAAACTATATGGGACCAGAAATCCTTTCATTGGTTT
AAAATAGGATTATCCCG

-continued

AAAGATGAAGGACTAAATTGAAACTGATTGGGGGTAGGAAGAGATCCGTCACAATCATTAAT
GGCTTCCACGCGGAAACT

TGTCGTTTATACAATTTCATTAACTTTCGGGTCGGGTTTATATTCCAAATGGGTCAAATAATAT
TAGTTTAATACACTAA

CGGAGTAATTAATTGGTGACTACAATTTTATCAGTTTGGTGCAATTAGAAACGAACATAGTCG
TAAAATACGAGTTCGGT

GTTATACCTTTATTTACGTTAAAAAAATACGAGAATTTTGTGTCAAATTTCAAATTAATTTCAT
GAATATATGGAAATTA

TTAGATACTCTAGCGAAAATAGTGATTATGAGCGTTTTACAAAAATACGATTTTAGCATTGAA
CTTCCTTTATGTAATTC

GGTCAAATGTTGGCATGAAGAAGCAAGTTTGCAACATTAAATTTCATTTAAAAATCGTGTTGA
CATACTTTAAAATCTAA

ATATAGGAAGAAGACCAAAACATTAAATTTAGTAAGATTCTAATGAACATTTATAAGTTATAA
CTTATAACCAACAAAAG

TTGGGTTTAGCGTTGTTGCTTTATCTGAAAACTTGCAAACTAAACCATTTTAATAGGACTAATG
ACAATTAACAACAAAA

TACACTTAAGCAACAACGTCCTCGTGAATATAATTTGGGCCTCAGGCCCATATTGCTAACGCC
AACTGATATTTCACTTT

ATTCCTTCTTCATCTCACCACACTCTCTCTCTATCTCTATCTCTAACGGCATAGCTGACTCAGT

SEQ ID NO:4 DMT 3' flanking sequence

AGATGACTGGAAGAAAGCAAACGCATTGCTTCTCTGCTCTCCTCTATTTAAAGCCAGGAAAAG
TCCCATTTAGACATAAT

AACAGGAATCCAAATAGGCTATTTTCTCTTTCTTTCTTATTTCATTCATAGAGCAGAAGCGACA
CAAAAAAGTTTTTTGG

GTTATTTATTTTCTCTCTAACAAAAAAAAAAAAAAAAAAACTCGAG

SEQ TD NO:5 DMT cDNA sequence

GTTCTCCGGCATTGACTCGCCTGAGAATCAGAAAGCTTAGATCGGTGAGCTTTTAGCTCCATTT
TCTGTTTATTTACATA

TTATTTCCTTTTTTCTCTCTCCCTTTTTTATCTGGAATTTGTTCTGCTAAATTTTCCAGCTGTTA
CATTTTCCGATCAC

GAGAAGAATCACTGGGTTTTTATGTTAATCAATACATGTTCCTGTTTTCTGATCATAAATCTCA
GCTATTAACACCTGAT

TTTGATTCTGCGTAATAAAAACCTCTGATTTGCTTTTATCTTCACTTTCCCCATAAACATTGCTT
ACTTTATTCGCTCTT

CTTTTACCGTTTCCAGCTAAAAAATTCTTCGCTATTCAATGTGTTTCTCGTTTTGTTGATGAGAA
AAATATCTGACAAAA

AATCATTTATTGCATTTTATGGTGCAGATTCTTAGTTAATGTCGCCTTCTCTAACCAAGTCAGA
TTAAAAAGGAGTGTTC

GTCCATGTTGCTTTGTTTTGGTGTTTGGAGAGAGTTTTCGGAGAGTTAGGTGAGTGTTATTTGG
GGTGAGGTAGTGATAA

GGTTTGAAGGGGAGTGATTCATCAAGTGTGTTATGAATTCGAGGGCTGATCCGGGGATAGA
TATTTTCGAGTTCCTTT

GGAGAATCAAACTCAACAAGAGTTCATGGGTTCTTGGATTCCATTTACACCCAAAAAACCTAG
ATCAAGTCTGATGGTAG

-continued

```
ATGAGAGAGTGATAAACCAGGATCTAAATGGGTTTCCAGGTGGTGAATTTGTAGACAGGGGA
TTCTGCAACACTGGTGTG

GATCATAATGGGGTTTTTGATCATGGTGCTCATCAGGGCGTTACCAACTTAAGTATGATGATCA
ATAGCTTAGCGGGATC

ACATGCACAAGCYYGGAGTAATAGTGAGAGAGATCTTTTGGGCAGGAGTGAGGTGACTTCTCC
TTTAGCACCAGTTATCA

GAAACACCACCGGTAATGTAGAGCCGGTCAATGGAAATTTTACTTCAGATGTGGGTATGGTAA
ATGGTCCTTTCACCCAG

AGTGGCACTTCTCAAGCTGGCTATAATGAGTTTGAATTGGATGACTTGTTGAATCCTGATCAGA
TGCCCTTCTCCTTCAC

AAGCTTGCTGAGTGGTGGGGATAGCTTATTCAAGGTTCGTCAATGTGAGTGATCAAATCTATTT
TCAGTTTTTTTTTTC

CCTTTCTTCCGTTCTTGCAGTACTTAGAGTAGAACATGAATTAGAATATCTTAAGAAAGTCATG
GTTTTGAACAGATGGA

CCTCCAGCGTGTAACAAGCCTCTTTACAATTTGAATTCACCAATTAGAAGAGAAGCAGTTGGG
TCAGTCTGTGAAAGTTC

GTTTCAATATGTACCGTCAACGCCCAGTCTGTTCAGAACAGGTGAAAAGACTGGATTCCTTGA
ACAGATAGTTACAACTA

CTGGACATGAAATCCCAGAGCCGAAATCTGACAAAAGTATGCAGAGCATTATGGACTCGTCTG
CTGTTAATGCOACGGAA

GCTACTGAACAAAATGATGGCAGCAGACAAGATGTTCTGGAGTTCGACCTTAACAAAACTCCT
CAGCAGAAACCCTCCAA

AAGGAAAAGGAAGTTCATGCCCAAGGTGGTCGTGGAAGGCAAACCTAAAAGAAAGCCACGCA
AACCTGCAGAACCCTCCCA

AAGTGGTCGTGGAAGGCAAACCTAAAAGGAAGCCACGCAAAGCTGCAACTCAGGAAAAAGTG
AAATCTAAAGAAACCGGG

AGTGCCAAAAAGAAAAATTTGAAAGAATCAGCAACTAAAAAGCCAGCCAATGTTGGAGATAT
GAGCAACAAAAGCCCTGA

AGTCACACTCAAAAGTTGCAGAAAAGCTTTGAATTTTGACTTGGAGAATCCTGGAGATGCGAG
GCAAGGTGACTCTGAGT

CTGAAATTGTCCAGAACAGTAGTGGCGCAAACTCGTTTTCTGAGATCAGAGATGCCATTGGTG
GAACTAATGGTAGTTTC

CTGGATTCAGTGTCACAAATAGACAAGACCAATGGATTGGGGCTATGAACCAGCCACTTGAA
GTGTCAATGGGAAACCA

GCCAGATAAACTATCTACAGGAGCGAAACTGGCCAGAGACCAACAACCTGATTTATTGACTAG
AAACCAGCAATGCCAGT

TCCCAGTGGCAACCCAGAACACCCAGTTCCCAATGGAAAACCAACAAGCTTGGCTTCAGATGA
AAAACCAACTTATTGGC

TTTCCATTTGGTAACCAGCAACCTCGCATGACCATAAGAAACCAGCAGCCTTGCTTGGCCATG
GGTAATCAACAACCTAT

GTATCTGATAGGAACTCCACGGCCTGCATTAGTAAGTGGAAACCAGCAACTAGGAGGTCCCCA
AGGAAACAAGCGGCCTA

TATTTTTGAATCACCAGACTTGTTTACCTGCTGGAAATCAGCTATATGGATCACCTACAGACAT
GCATCAACTTGTTATG

TCAACCGGAGGGCAACAACATGGACTACTGATAAAAAACCAGCAACCTGGATCATTAATAAG
AGGCCAGCAGCCTTGCGT

ACCTTTGATTGACCAGCAACCTGCAACTCCAAAAGGTTTTACTCACTTGAATCAGATGGTAGCT
ACCAGCATGTCATCGC

CTGGGCTTCGACCTCATTCTCAGTCACAAGTTCCTACAACATATCTACATGTGGAATCTGTTTC
CAGGATTTTGAATGGG

ACTACAGGTACATGCCAGAGAAGCAGGGCTCCTGCATACGATTCTTTACAGCAAGATATCCAT
CAAGGAAATAAGTACAT

ACTTTCTCATGAGATATCCAATGGTAATGGGTGCAAGAAAGCGTTACCTCAAAACTCTTCTCTG
CCAACTCCAATTATGG
```

-continued

CTAAACTTGAGGAAGCCAGGGGCTCGAAGAGACAGTATCATCGTGCAATGGGACAGACGGAA
AAGCATGATCTAAACTTA

GCTCAACAGATTGCTCAATCACAAGATGTGGAGAGACATAACAGCAGCACGTGTGTGGAATA
TTTAGATGCTGCAAAGAA

AACGAAAATCCAGAAAGTAGTCCAAGAAAATTTGCATGGCATGCCACCTGAGGTTATAGAAA
TCGAGGATGATCCAACTG

ATGGGGCAAGAAAAGGTAAAAATACTGCCAGCATCAGTAAAGGTGCATCTAAAGGAAACTCG
TCTCCAGTTAAAAAGACA

GCAGAAAAGGAGAAATGTATTGTCCCAAAAACGCCTGCAAAAAAGGGTCGAGCAGGTAGAAA
AAAATCAGTACCTCCGCC

TGCTCATGCCTCAGAGATCCAGCTTTGGCAACCTACTCCTCCAAAGACACCTTTATCAAGAAG
CAAGCCTAAAGGAAAAG

GGAGAAAGTCCATACAAGATTCAGGAAAAGCAAGAGGTCCATCAGGAGAACTTCTGTGTCAG
GATTCTATTGCGGAAATA

ATTTACAGGATGCAAAATCTGTATCTAGGAGACAAAGAAAGAGAACAAGAGCAAAATGCAAT
GGTCTTGTACAAAGGAGA

TGGTGCACTTGTTCCCTATGAGAGCAAGAAGCGAAAACCAAGACCCAAAGTTGACATTGACG
ATGAAACAACTCGCATAT

GGAACTTACTGATGGGGAAAGGAGATGAAAAAGAAGGGGATGAAGAGAAGGATAAAAAGAA
AGAGAAGTGGTGGGAAGAA

GAAAGAAGAGTCTTCCGAGGAAGGGCTGATTCCTTCATCGCTCGCATGCACCTGGTACAAGGA
GATAGACGTTTTTCGCC

ATGGAAGGGATCGGTGGTTGATTCGGTCATTGGAGTTTTCCTTACACAGAATGTCTCGGATCA
CCTTTCAAGCTCTGCGT

TCATGTCTCTAGCTGCTCGATTCCCTCCAAAATTAAGCAGCAGCCGAGAAGATGAAAGGAATG
TTAGAAGCGTAGTTGTT

GAAGATCCAGAAGGATGCATTCTGAACTTAAATGAAATTCCTTCGTGGCAGGAAAAGGTTCAA
CATCCATCTGACATGGA

AGTTTCTGGGGTTGATAGTGGATCAAAAGAGCAGCTAAGGGACTGTTCAAACTCTGGAATTGA
AAGATTTAATTTCTTAG

AGAAGAGTATTCAAAATTTAGAAGAGGAAGTATTATCATCACAAGATTCTTTTGATCCGGCGA
TATTTCAGTCGTGTGGG

AGAGTTGGATCCTGTTCATGTTCCAAATCAGACGCAGAGTTTCCTACAACCAGGTGTGAAACA
AAAACTGTCAGTGGAAC

ATCACAATCAGTGCAAACTGGGAGCCCAAACTTGTCTGATGAAATTTGTCTTCAAGGGAATGA
GAGACCGCATCTATATG

AAGGATCTGGTGATGTTCAGAAACAAGAAACTACAAATGTCGCTCAGAAGAAACCTGATCTTG
AAAAAACAATGAATTGG

AAAGACTCTGTCTGTTTTGGTCAGCCAAGAAATGATACTAATTGGCAAACAACTCCTTCCAGC
AGCTATGAGCAGTGTGC

GACTCGACAGCCACATGTACTAGACATAGAGGATTTTGGAATGCAAGGTGAAGGCCTTGGTTA
TTCTTGGATGTCCATCT

CACCAAGAGTTGACAGAGTAAAGAACAAAAATGTACCACGCAGGTTTTTCAGACAAGGTGGA
AGTGTTCCAAGAGAATTC

ACAGGTCAGATCATACCATCAACGCCTCATGAATTACCAGGAATGGGATTGTCCGGTTCCTCA
AGCGCCGTCCAAGAACA

CCAGGACGATACCCAACATAATCAACAAGATGAGATGAATAAAGCATCCCATTTACAAAAAA
CATTTTTGGATCTGCTCA

ACTCCTCTGAAGAATGCCTTACAAGACAGTCCAGTACCAAACAGAACATCACGGATGGCTGTC
TACCGAGAGATAGAACT

GCTGAAGACGTGGTTGATCCGCTCAGTAACAATTCAAGCTTACAGAACATATTGGTCGAATCA
AATTCCAGCAATAAAGA

-continued

```
GCAGACGGCAGTTGAATACAAGGAGACAAATGCCACTATTTTACGAGAGATGAAAGGGACGC
TTGCTGATGGGAAAAAGC

CTACAAGCCAGTGGGATAGTCTCAGAAAAGATGTGGAGGGGAATGAAGGGAGACAGGAACG
AAACAAAAACAATATGGAT

TCCATAGACTATGAAGCAATAAGACGTGCTAGTATCAGCGAGATTTCTGAGGCTATCAAGGAA
AGAGGGATGAATAACAT

GTTGGCCGTACGAATTAAGGATTTCCTAGAACGGATAGTTAAAGATCATGGTGGTATCGACCT
TGAATGGTTGAGAGAAT

CTCCTCCTGATAAAGCCAAGGACTATCTCTTGAGCATAAGAGGTCTGGGTTTGAAAAGTGTTG
AATGCGTGCGACTCTTA

ACACTCCACAATCTTGCTTTCCCTGTTGACACGAATGTTGGAAGGATAGCAGTTAGGATGGGA
TGGGTGCCTCTACAACC

CCTACCTGAATCACTTCAGTTACACCTCCTGGAGCTATACCCAGTGCTCGAGTCCATCCAAAAA
TTTCTTTGGCCAAGAC

TTTGCAAACTCGATCAACGAACACTGTATGAATTACACTACCAACTGATTACGTTTGGAAAGG
TATTTTGCACAAAGAGT

AGACCAAATTGTAATGCATGTCCAATGAGAGGAGAGTGCAGACACTTTGCCAGTGCTTATGCT
AGTGCAAGACTTGCTTT

ACCGGCACCAGAGGAGAGGAGCTTAACAAGTGCAACTATTCCGGTCCCTCCCGAGTCCTTTCC
TCCTGTAGCCATCCCGA

TGATAGAACTACCTCTTCCGTTGGAGAAATCCCTAGCAAGTGGAGCACCATCGAATAGAGAAA
ACTGTGAACCAATAATT

GAAGAGCCGGCCTCGCCCGGGCAAGAGTGCACTGAAATAACCGAGAGTGATATTGAAGATGC
TTACTACAATGAGGACCC

TGACGAGATCCCAACAATAAAACTCAACATTGAACAGTTTGGAATGACTCTACGGGAACACAT
GGAAAGAAACATGGAGC

TCCAAGAAGGTGACATGTCCAAGGCTTTGGTTGCTTTGCATCCAACAACTACTTCTATTCCAAC
TCCCAAACTAAAGAAC

ATTAGCCGTCTCAGGACAGAGCACCAAGTGTACGAGCTCCCAGATTCACATCGTCTCCTTGAT
GGTATGGATAAAAGAGA

ACCAGATGATCCAAGTCCTTATCTCTTAGCTATATGGACACCAGGTGAAACAGCGAATTCGGC
ACAACCGCCTGAACAGA

AGTGTGGAGGGAAAGCGTCTGGCAAAATGTGCTTTGACGAGACTTGTTCTGAGTGTAACAGTC
TGAGGGAAGCAAACTCA

CAGACAGTICGAGGAACTCTTCTGATACCTTGTCGGACTGCCATGAGAGGAAGTTTTCCGCTC
AACGGGACATATTTCCA

AGTCAACGAGTTATTTGCAGACCACGAGTCCAGTCTCAAACCCATCGATGTTTCCTAGAGATTG
GATATGGGATCTCCCAA

GAAGGACTGTTTACTTCGGAACATCAGTAACATCAATATTCAGAGGTCTTTCAACGGAGCAGA
TACAGTTCTGCTTTTGG

AAAGGATTCGTATGTGTCCGTGGATTCGAACAGAAGACAAGAGCACCGCGTCCATTAATGGCA
AGGTTGCATTTTCCTGC

GAGCAAATTGAAGAACAACAAAACCTAAAGATGACTGGAAGAAAGCAAACGCATTGCTTCTC
TGCTCTCCTCTATTTAAA

GCCAGGAAAAGTCCCATTTAGACATAATAACAGGAATCCAAATAGGCTATTTTTCTCTTTCTTTC
TTATTTCATTCATAGA

GCAGAAGCGACACAAAAAAGTTTTTTGGGTTATTTATTTTCTCTCTAACAAAAAAAAAAAAAA
AAAACTCGAG
```

SEQ ID NO:6 5' untranslated region of DMT

GTTCTCCGGCATTGACTCGCCTGAGAATCAGAAAGCTTAGATCGGTGAGCTTTTAGCTCCATTT
TCTGTTTATTTACATA

TTATTTCCTTTTTTTCTCTCTCCCTTTTTTATCTGGAATTTGTTCTGCTAAATTTTCCAGCTGTTA
CATTTTCCGATCAC

GAGAAGAATCACTGGGTTTTTATGTTAATCAATACATGTTCCTGTTTTCTGATCATAAATCTCA
GCTATTAACACCTGAT

TTTGATTCTGCGTAATAAAAACCTCTGATTTGCTTTTATCTTCACTTTCCCCATAAACATTGCTT
ACTTTATTCGCTCTT

CTTTTACCGTTTCCAGCTAAAAAATTCTTCGCTATTCAATGTGTTTCTCGTTTTGTTGATGAGAA
AAATATCTGACAAAA

AATCATTTATTGCATTTTATGGTGCAGATTCTTAGTTAATGTCGCCTTCTCTAACCAAGTCAGA
TTAAAAAGGAGTGTTC

GTCCATGTTGCTTTGTTTTGGTGTTTGGAGAGAGTTTTCGGAGAGTTAGGTGAGTGTTATTTGG
GGTGAGGTAGTGATAA

GGTTTGAAGGGGAGTGATTCATCAAGTGTGTTATGAATTCGAGGGCTGATCCGGGGATAGA
TATTTTCGAGTTCCTTT

GGAGAATCAAACTCAACAAGAGTTCATGGGTTCTTGGATTCCATTTACACCCAAAAAACCTAG
ATCAAGTCTGATGGTAG

ATGAGAGAGTGATAAACCAGGATCTAAATGGGTTTCCAGGTGGTGAATTTGTAGACAGGGGA
TTCTGCAACACTGGTGTG

GATCATAATGGGGTTTTTGATCATGGTGCTCATCAGGGCGTTACCAACTTAAGTATGATGATCA
ATAGCTTAGCGGGATC

ACATGCACAAGCTTGGAGTAATAGTGAGAGAGATCTTTTGGGCAGGAGTGAGGTGACTTCTCC
TTTAGCACCAGTTATCA

GAAACACCACCGGTAATGTAGAGCCGGTCAATGGAAATTTTACTTCAGATGTGGGTATGGTAA
ATGGTCCTTTCACCCAG

AGTGGCACTTCTCAAGCTGGCTATAATGAGTTTGAATTGGATGACTTGTTGAATCCTGATCAGA
TGCCCTTCTCCTTCAC

AAGCTTGCTGAGTGGTGGGGATAGCTTATTCAAGGTTCGTCAATGTGAGTGATCAAATCTATTT
TCAGTTTTTTTTTTTC

CCTTTTCTTCCGTTCTTGCAGTACTTAGAGTAGAACATGAATTAGAATATCTTAAGAAAGTCATG
GTTTTGAACAGATGGA

CCTCCAGCGTGTAACAAGCCTCTTTACAATTTGAATTCACCAATTAGAAGAGAAGCAGTTGGG
TCAGTCTGTGAAAGTTC

GTTTCAATATGTACCGTCAACGCCCAGTCTGTTCAGAACAGGTGAAAAGACTGGATTCCTTGA
ACAGATAGTTACAACTA

CTGGACATGAAATCCCAGAGCCGAAATCTGACAAAAGT

SEQ ID NO:7 >Arabidopsis thaliana DMT1(1DMT5) gene sequence from
BAC T32M21 (gi 7406444);

64441 tcactagatt ccaaaacgta gaccaattgt atctaatctc aaattctcaa tcaaagtatt 64501 aatttaccga tggtaagaaa agttaaccga tataattatc aaaagaaaga ataagtcaac 64561 agattcttaa tctctttatt ttggtatatg aacatttgta caaaatctc aaaagatatg 64621 taactgttta aaatataaat tcactgagat taattcttca gactcgtgtt agctataata 64681 atgtcaagag ttcttcttgt ttcaaggaaa aaccttaaag atatgtatat tttctgtaat 64741 tatgatgata taatttgcta ttcattgtca caaacattac tttaaaaaat cgtattttca 64801 ttactacaat gttgactaag aacaaaaata cattgattat tgatatatcg tcaactgaat -continued

```
64861 tttcttccga gggatataat tctcaaacat agcaagaatc tcataataat gtttcgtgac
64921 tacctttaga cgaaattttt ttaagattcg taacgtgact tatggtctct tgctgtgggg
64981 gtcaatgcga ataaatctaa atgtatggga gtcaaataaa ataccaagaa aaataaagga
65041 gcagcaccca ataaactata tgggaccaga aatcctttca ttggtttaaa ataggattat
65101 cccgaaagat gaaggactaa attgaaactg attggggta ggaagagatc cgtcacaatc
65161 attaatggct tccacgcgga aacttgtcgt ttatacaatt tcattaactt tcgggtcggg
65221 tttatattcc aaatgggtca ataatatta gtttaataca ctaacggagt aattaattgg
65281 tgactacaat tttatcagtt tggtgcaatt agaaacgaac atagtcgtaa aatacgagtt
65341 cggtgttata cctttattta cgttaaaaaa atacgagaat tttgtgtcaa atttcaaatt
65401 aatttcatga atatatggaa attattagat actctagcga aaatagtgat tatgagcgtt
65461 ttacaaaaat acgattttag cattgaactt cctttatgta attcggtcaa atgttggcat
65521 gaagaagcaa gtttgcaaca ttaaatttca tttaaaaatc gtgttgacat actttaaaat
65581 ctaaatatag gaagaagacc aaaacattaa atttagtaag attctaatga acatttataa
65641 gttataactt ataaccaaca aaagttgggt ttagcgttgt tgctttatct gaaaacttgc
65701 aaactaaacc attttaatag gactaatgac aattaacaac aaaatacact taagcaacaa
65761 cgtcctcgtg aatataattt gggcctcagg cccatattgc taacgccaac tgatatttca
65821 ctttattcct tcttcatctc accacactct ctctctatct ctatctctaa cggcatagct
65881 gactcagtgt tctccggcat tgactcgcct gagaatcaga aagcttagat cggtgagctt
65941 ttagctccat tttctgttta tttacatatt atttccttttt tttctctctc cctttttttat
66001 ctggaatttg ttctgctaaa ttttccagct gttacatttt ccgatcacga gaagaatcac
66061 tgggttttta tgttaatcaa tacatgttcc tgttttctga tcataaatct cagctattaa
66121 cacctgattt tgattctgcg taataaaaac ctctgatttg cttttatctt cactttcccc
66181 ataaacattg cttactttat tcgctcttct tttaccgttt ccagctaaaa aattcttcgc
66241 tattcaatgt gtttctcgtt ttgttgatga gaaaaatatc tgacaaaaaa tcatttattg
66301 cattttatgg tgcagattct tagttaatgt cgccttctct aaccaagtca gattaaaaag
66361 gagtgttcgt ccatgttgct ttgttttggt gtttggagag agttttcgga gagttaggtg
66421 agtgttattt ggggtgaggt agtgataagg tttgaagggg gagtgattca tcaagtgtgt
66481 tatgaattcg agggctgatc cgggggatag atattttcga gttcctttgg agaatcaaac
66541 tcaacaagag ttcatggggtt cttggattcc atttacaccc aaaaaaccta gatcaagtct
66601 gatggtagat gagagagtga taaaccagga tctaaatggg tttccaggtg gtgaatttgt
66661 agacaggyga ttctgcaaca ctggtgtgga tcataatggg gttttttgatc atggtgctca
66721 tcagggcgtt accaacttaa gtatgatgat caatagctta gcgggatcac atgcacaagc
66781 ttggagtaat agtgagagag atcttttggg caggagtgag gtgacttctc ctttagcacc
66841 agttatcaga aacaccaccg gtaatgtaga gccggtcaat ggaaatttta cttcagatgt
66901 gggtatggta aatggtcctt tcacccagag tggcacttct caagctggct ataatgagtt
66961 tgaattggat gacttgttga atcctgatca gatgcccttc tccttcacaa gcttgctgag
67021 tggtgggat agcttattca aggttcgtca atgtgagtga tcaaatctat tttcagtttt
67081 ttttttttccc tttcttccgt tcttgcagta cttagagtag aacatgaatt agaatatctt
67141 aagaaagtca tggttttgaa cagatggacc tccagcgtgt aacaagcctc tttacaattt
67201 gaattcacca attagaagag aagcagttgg gtcagtctgt gaaagttcgt ttcaatatgt
```

```
-continued
67261 accgtcaacg cccagtctgt tcagaacagg tgaaaagact ggattccttg aacagatagt
67321 tacaactact ggacatgaaa tcccagagcc gaaatctgac aaaagtATGc agagcattat
67381 ggactcgtct gctgttaatg cgacggaagc tactgaacaa aatgatggca gcagacaaga
67441 tgttctggag ttcgacctta acaaaactcc tcagcagaaa ccctccaaaa ggaaaaggaa
67501 gttcatgccc aaggtgytcg tggaaggcaa acctaaaaga aagccacgca aacctgcaga
67561 acttcccaaa gtggtcgtgg aaggcaaacc taaaaggaag ccacgcaaag ctgcaactca
67621 ggaaaaagtg aaatctaaag aaaccgggag tgccaaaaag aaaaatttga agaatcagc
67681 aactaaaaag ccagccaatg ttggagatat gagcaacaaa agccctgaag tcacactcaa
67741 aagttgcaga aaagctttga attttgactt ggagaatcct ggagatgcga ggcaaggtga
67801 ctctgagtct gaaattgtcc agaacagtag tggcgcaaac tcgttttctg agatcagaga
67861 tgccattggt ggaactaatg gtagtttcct ggattcagtg tcacaaatag acaagaccaa
67921 tggattgggg gctatgaacc agccacttga agtgtcaatg ggaaaccagc cagataaact
67981 atctacagga gcgaaactgg ccagagacca caacctgat ttattgacta gaaaccagca
68041 atgccagttc ccagtggcaa cccagaacac ccagttccca atggaaaacc aacaagcttg
68101 gcttcagatg aaaaaccaac ttattggctt tccatttggt aaccagcaac ctcgcatgac
68161 cataagaaac cagcagcctt gcttggccat gggtaatcaa caacctatgt atctgatagg
68221 aactccacgg cctgcattag taagtggaaa ccagcaacta ggaggtcccc aaggaaacaa
68281 gcggcctata tttttgaatc accagacttg tttacctgct ggaaatcagc tatatggatc
68341 acatacagac atgcatcaac ttgttatgtc aaccggaggg caacaacatg gactactgat
68401 aaaaaaccag caacctggat cattaataag aggccagcag ccttgcgtac ctttgattga
68461 ccagcaacct gcaactccaa aaggttttac tcacttgaat cagatggtag ctaccagcat
68521 gtcatcgcct gggcttcgac ctcattctca gtcacaagtt cctacaacat atctacatgt
68581 ggaatctgtt tccaggattt tgaatgggac tacaggtaca tgccagagaa gcagggctcc
68641 tgcatacgat tctttacagc aagatatcca tcaaggaaat aagtacatac tttctcatga
68701 gatatccaat ggtaatgggt gcaagaaagc gttacctcaa aactcttctc tgccaactcc
68761 aattatggct aaacttgagg aagccagggg ctcgaagaga cagtatcatc gtgcaatggg
68821 acagacggaa aagcatgatc taaacttagc tcaacagatt gctcaatcac aagatgtgga
68881 gagacataac agcagcacgt gtgtggaata tttagatgct gcaaagaaaa cgaaaatcca
68941 gaaagtagtc caagaaaatt tgcatggcat gccacctgag gttatagaaa tcgaggatga
69001 tccaactgat ggggcaagaa aaggtaaaaa tactgccagc atcagtaaag gtgcatctaa
69061 aggaaactcg tctccagtta aaaagacagc agaaaaggag aaatgtattg tcccaaaaac
69121 gcctgcaaaa aagggtcgag caggtagaaa aaaatcagta cctccgcctg ctcatgcctc
69181 agagatccag cttttggcaac ctactcctcc aaagacacct ttatcaagaa gcaagcctaa
69241 aggaaagggg agaaagtcca tacaagattc aggaaaagca agaggtaact aatgtattct
69301 acaatctctg tgatataatt ttgagatttt agtaactgat gtgtccaaac cagctcctta
69361 tcactgttgg tgcgttgtat aggtccatca ggagaacttc tgtgtcagga ttctattgcg
69421 gaaataattt acaggatgca aaatctgtat ctaggagaca agaaagaga acaagagcaa
69481 aatgcaatgg tcttgtacaa aggagatggt gcacttgttc cctatgagag caagaagcga
69541 aaaccaagac ccaaagttga cattgacgat gaaacaactc gcatatggaa cttactgatg
69601 gggaaaggag atgaaaaaga agggatgaa gagaaggata aaaagaaaga gaagtggtgg
```

-continued

```
69661 gaagaagaaa gaagagtctt ccgaggaagg gctgattcct tcatcgctcg catgcacctg
69721 gtacaaggtg aagatccact tctcttctca actccatttt tattcacaca aattagtaga
69781 atactcaaaa atgatgtttt gtttgcaaaa ttttaaaatt cactagttaa ccatgtcaaa
69841 taatattcat aatgcatctt gtgaagaaca ggtgtgcatt tatggtgaca gctgaatggt
69901 ttatgtgcct attatttctt ttactgctat agatgaccaa ttgaacttaa acgtttacag
69961 gagatagacg tttttcgcca tggaagggat cggtggttga ttcggtcatt ggagttttcc
70021 ttacacagaa tgtctcggat cacctttcaa ggtatatgag ttgccttaat aaattgagtt
70081 ccaaaacata gaaattaacc catggtggtt ttacaatgca gctctgcgtt catgtctcta
70141 gctgctcgat tccctccaaa attaagcagc agccgagaag atgaaaggaa tgttagaagc
70201 gtagttgttg aagatccaga aggatgcatt ctgaacttaa atgaaattcc ttcgtggcag
70261 gaaaaggttc aacatccatc tgacatggaa gtttctgggg ttgatagtgg atcaaaagag
70321 cagctaaggg actgttcaaa ctctggaatt gaaagattta atttcttaga gaagagtatt
70381 caaaatttag aagaggaagt attatcatca caagattctt ttgatccggc gatatttcag
70441 tcgtgtggga gagttggatc ctyttcatgt tccaaatcag acgcagagtt cctacaacc
70501 aggtgtgaaa caaaaactgt cagtggaaca tcacaatcag tgcaaactgg gagcccaaac
70561 ttgtctgatg aaatttgtct tcaagggaat gagagaccgc atctatatga aggatctggt
70621 gatgttcaga acaagaaac tacaaatgtc gctcagaaga aacctgatct tgaaaaaaca
70681 atgaattgga aagactctgt ctgttttggt cagccaagaa atgatactaa ttggcaaaca
70741 actccttcca gcagctatga gcagtgtgcg actcgacagc cacatgtact agacatagag
70801 gattttggaa tgcaaggtga aggccttggt tattcttgga tgtccatctc aacaagagtt
70861 gacagagtaa agaacaaaaa tgtaccacgc aggttttca gacaaggtgg aagtgttcca
70921 agagaattca caggtcagat cataccatca acgcctcatg aattaccagg aatgggattg
70981 tccggttcct caagcgccgt ccaagaacac caggacgata cccaacataa tcaacaagat
71041 gagatgaata agcatcccca tttacaaaaa acattttggg atctgctcaa ctcctctgaa
71101 gaatgcctta caagacagtc cagtaccaaa cagaacatca cggatggctg tctaccgaga
71161 gatagaactg ctgaagacgt ggttgatccg ctcagtaaca attcaagctc acagaacata
71221 ttggtcgaat caaattccag caataaagag cagacggcag ttgaatacaa ggagacaaat
71281 gccactattt tacgagagat gaaagggacg cttgctgatg ggaaaaagcc tacaagccag
71341 tgggatagtc tcagaaaaga tgtggagggg aatgaaggga gacaggaacg aaacaaaaac
71401 aatatggatt ccatagacta tgaagcaata agacgtgcta gtatcagcga gatttctgag
71461 gctatcaagg aaagagggat gaataacatg ttggccgtac gaattaaggt aaatctacta
71521 atttcagttg agaccctcat caaatctgtc agaaggcttg aacatcagta aattatgtaa
71581 ccatatttac aacattgcag gatttcctag aacggatagt taaagatcat ggtggtatcg
71641 accttgaatg gttgagagaa tctcctcctg ataaagccaa gtgggtaaat cacatttta
71701 gtgactgcaa cactagcacg atcgatttac tcaacaatta cgtcaaactg agtattaaca
71761 agttgctcat gaacatttca cagggactat ctcttgagca taagaggtct gggtttgaaa
71821 agtgttgaat gcgtgcgact cttaaCaCtc cacaatcttg ctttccctgt gagtcagact
71881 attccattat ctactaaaaa cttagaataa ctccggctaa ctaagctgga acttgtattg
71941 atgatatgaa ggttgacacg aatgttggaa ggatagcagt taggatggga tgggtgcctc
72001 tacaaccccct acctgaatca cttcagttac acctcctgga gctgtaagtt tcttttttgtt
```

-continued

```
72061 tgtcatctaa acaacgaaat ttttatgcaa gtcataacca tgctgtgttt tcacagataC
72121 ccagtgctcg agtccatcca aaaatttctt tggccaagac tttgcaaact cgatcaacga
72181 acactgtatg ctcataaact ctaacaaatc atctgtctga aaaaccaata tttctttggt
72241 agaattctat tgtcattact cattactaac agcgaaatta attaacgttc tttttcttac
72301 tcaggtatga attacactac caactgatta cgtttggaaa ggtattattg ctctaagctt
72361 tgaatttatc atatggtaat ttcaagcatt gtaggcacct gatcaattat gtgtctaaat
72421 catgtgaatt catgtcaggt attttgcaca aagagtagac caaattgtaa tgcatgtcca
72481 atgagaggag agtgcagaca ctttgccagt gcttatgcta ggtaagcaag ctttcatgta
72541 cttatatgca ataattaaag ataaaattta ggattatggg taagtaacaa aaaattaggc
72601 tcagtttcat ggtagctagc tggaaatagt attacaagaa caacataaag atcaaagaca
72661 gaatcatgga tccatatgca ctatcatttt agctcttgta atacatacat gaacactata
72721 tgccaaagta gggatttcaa atatgagatt cgatgactga tgccattgta acagtgcaag
72781 acttgcttta ccggcaccag aggagaggag cttaacaagt gcaactattc cggtccctcc
72841 cgagtcctat cctcctgtag ccatcccgat gatagaacta cctcttccgt tggagaaatc
72901 cctagcaagt ggagcaccat cgaatagaga aaactgtgaa ccataattg aagagccggc
72961 ctcgcccggg caagagtgca ctgaaataac cgagagtgat attgaagatg cttactacaa
73021 tgaggaccct gacgagatcc caacaataaa actcaacatt gaacagtttg gaatgactct
73081 acgggaacac atggaaagaa acatggagct ccaagaaggt gacatgtcca aggctttggt
73141 tgctttgcat ccaacaacta cttctattcc aactcccaaa ctaaagaaca ttagccgtct
73201 caggacagag caccaagtgt aagctaatat ctcctcctat attttatctt ccatataaat
73261 tttggggaaa aaatcgctct ccatctggtt ttagaacatg cgggtcagcc agggttatgg
73321 catttttata tatttcaccg atcggcccga gctggctctg gttgactcgt atgccaccct
73381 gcattgaaca aaccagtagg agacaagcaa gcaaaacgtt ttaagataag gtctatggta
73441 aaatgacaag gtaactgata aatgtgtcgt ctatttgcag gtacgagctc ccagattcac
73501 atcgtctcct tgatggtgta agtcaatttt taactctctc tatactcgag ttgtttcact
73561 tgagcaacac tgtttaaaag tcctcatttg ataaaataac agatggataa aagagaacca
73621 gatgatccaa gtccttatct cttagctata tggacaccag gtgagaataa aactgcaatg
73681 tttcattcat gtgtctacag tatcaaagaa agtacagcta gagctaaaaa 9catttgaaa
73741 tagagtcggt taaatatgaa agtttgaatc tgtaaatgaa agccggaacg tagcattggt
73801 ggatgttata tgtaaattag ttttgagat tggtctaatg tagttgtttg actgccaggt
73861 gaaacagcga attcggcaca accgcctgaa cagaagtgtg gagggaaagc gtctggcaaa
73921 atgtgctttg acgagacttg ttctgagtgt aacagtctga gggaagcaaa ctcacagaca
73981 gttcgaggaa ctcttctggt gagattatct tgatcttttg tgttgctcat gaaaaggaga
74041 agtgagaata caagtttgct aatatcattt tttcgtcatt cacagatacc ttgtcggact
74101 gccatgagag gaagttttcc gctcaacggg acatatttcc aagtcaacga ggttagatga
74161 aataaaactc aaacagacag acgaaacatt atttctgttt agtgttggtt ctttatcctc
74221 cttgccattt tttatcttgc agttatttgc agaccacgag tccagtctca aacccatcga
74281 tgttcctaga gattggatat gggatctccc aagaaggact gtttacttcg gaacatcagt
74341 aacatcaata ttcagaggta aaaacattcg taatagagtt agttaatcaa atgtccaaaa
74401 cacaagaaag cttcaccgtc caatacacaa gaaagcttca ccttctcttt gccaaaaaag
```

```
-continued
74461 atcttagaat gttttgctga atttgtgcag gtctttcaac ggagcagata cagttctgct 74521 tttggaaagg taaacgttaa ctttcgaccc agagaaatcc ggaaaatcta ttgctttgtt 74581 ctgatcaata cgttaaacat atacacacac actttacact taggaccaat actgttctga 74641 tctgtgatag aaactggtaa acatctaaca attatgattg caggattcgt atgtgtccgt 74701 ggattcgaac agaagacaag agcaccgcgt ccattaatgg caaggttgca ttttcctgcg 74761 agcaaattga agaacaacaa aaccTAAaga tgactggaag aaagcaaacg cattgcttct 74821 ctgctctcct ctatttaaag ccaggaaaag tcccatttag acataataac aggaatccaa 74881 ataggctatt ttctctttct ttcttatttc attcatagag cagaagcgac acaaaaaagt 74941 tttttgggtt atttattttC tctctaacaa atttgtagcg ttttgggtct ttttctggct 75001 gtcactagcg tggcaaatcc aatgtctgcg cacacttagg cgcattgtca ataaaatttc
```

SEQ ID NO:8
*ARABIDOPSIS THALIANA* DMT2
>DMT2 (1DMT2);

MEKQRREESSFQQPPWIPQTPMKPFSPICPYTVEDQYHSSQLEERRFVGNKDMSGLDHLS

FGDLLALANTASLTFSGQTPTPTRNTEVMQKGTEEVESLSSVSNNVAEQILKTPEKPKRK

KHRPKVRREAKPKREPKPPAPRKSVVTDGQESKTPKRKYVRKKVEVSKDQDATRVESSkA

VETSTRPKRLCRRVLDFEAENGENQTNGDTREAGEMESALQEKQLDSGNQELKDCLLSAP

STPKRKRSQGKRKGVQPKKNGSNLEEVDISMAQAAKRRQGPTCCDMNLSGIQYDEQCDYQ

KMHWLYSPNLQQGGMRYDAICSKVFSGQQHNYVSAFHATCYSSTSQLSANRVLTVEERRE

GIFQGRQESELNVLSDKIDTPIKKKTTGHARFRNLSSMNKLVEVPEHLTSGYCSKPQQNK

KILVDTRVTVSKKKPTKSEKSQTKQKNLLPNLCRFPPSFTGLSPDELWKRRNSIETTSEL

LRLLDTNREHSETALVPYTMNSQIVLFGGGAGAIVPVTPVKKPRPRPKVDLDDETDRVWK

LLLENINSEGVDGSDEQKAKWWEEERNVFRGRADSFTARMHLVQGDRRFTPWKGSVVDSV

VGVFLTQNVSDHLSSSAFMSLASQFPVPFVPSSNFDAGTSSMPSTQITYLDSEETMSSPP

DHNHSSVTLKNTQPDEEKDYVPSNETSRSSSEIAISAHESVDKTTDSKEYVDSDRKGSSV

EVDKTDEKCRVLNLFPSEDSALTCQHSMVSDAPQNTERAGSSSEIDLEGEYRTSFMKLLQ

GVQVSLEDSNQVSPNMSPGDCSSEIKGFQSMKEPTKSSVDSSEPGCCSQQDGDVLSCQKP

TLKEKGKKVLKEEKKAFDWDCLRREAQARAGTREKTRSTMDTVDWKAIPAADVKEVAETI

KSRGMNHKLAERIQYLTLNMKIMQGFLDRLVNDHGSIDLEWLRDVPPDKAKEYLLSFNGL

GLKSVECVRLLTLHHLAFPVDTNVGRIAVRLGWVPLQPLPESLQLHLLEMYPMLESIQKY

LWPRLCKLDQKTLYELHYQMTTFGKVFCTKSKPNCNACPMKGECRHFASAFARKFSNIHL

FYSARLALPSTEKGMGTPDKNPLPLHLPEPFQREQGSEVVQHSEPAKKVTCCEPIIEEPA

SPEPEPETAEVSIADIEEAFFEDPEEIPTTRLNMDAFTSNLKKIMEHNKELQDGNMSSALVA

LTAETASLPMPKLKNISQLRTEHRVYELPDEHPLLAQLEKREPDDPCSYLLAIWTPGETA

DSIQPSVSTCTFQANGMLCDEETCFSCNSIKETRSQIVRGTILIPCRTANRGSFPLNGTY

FQVNEVFADHASSLNPINVPRELTWELPRRTVYFGTSVPTIFKGLSTEKIQACFWKGYVC

VRGFDRKTRGPKPLIARLHFPASKLKGQQANLA

SEQ ID NO:9
>DMT2(1DMT2) novel 480 amino acid amino terminus;

MEKQRREESSFQQPPWTPQTPMKPFSPTCPYTVEDQYHSSQLEERRFVGNKDMSGLDHLS

PGDLLALANTASLIFSGQTPIPTRNTEVMQKGTEEVESLSSVSNNVAEQTLKTPEKPKRK

KHRPKVRREAKPKREPKPRAPRKSVVTDGQESKTPKRKYVRKKVEVSKDQDATPVESSAA

VETSTRPKRLCRRVLDFEAENGENQTNGDIREAGEMESALQEKQLDSGNQELKDCLLSAP

STPKRKRSQGKRKGVQPKKNGSNLEEVDTSMAQAAKRRQGPTCCDMNLSGIQYDEQCDYQ

KMHWLYSPNLQQGGMRYDATCSKVFSGQQHNYVSAFHATCYSSTSQLSANRVLTVEERRE

GIFQGRQESELNVLSDKIDTPIKKKTTGHARFRNLSSMNKLVEVPEHLTSGYCSKPQQNN

KILVDTRVTVSKKKPTKSEKSQTKQKNLLPNLCRFPPSFTGLSPDELWKRPNSIETISEL

SEQ ID NO:10
>DMT2 (1DMT2) Nucleotide sequence from BAC F1011 (gi 6598632);

```
60001 tcgctgagcc tgggtttctt catcggacct ggatctctgg atctatcaaa cggtctacga
60061 ggattctcca ttccaaagaa ctatacaata caagaggtac gcaaataatg ccctaaatta
60121 aacctaatcg gcaaaaatcg attgcagtga caacaaatcc tcgttagagg gaattcaga
60181 gcattacaac aatcagtaac cctaagttac aatctaaaaa ttgagatgca taacgcgatt
60241 ctgcgaagaa gacggagaag atagaaggaa tgcttcgaat tcggcaaaaa tgtcagagag
60301 tttggacaat ctccgatcaa ttagggttgt gaattgggga ttttatggag acgagacaaa
60361 aaaagttga agatcggagc tggttccaaa aatatttagg cccatttaat gacccacatt
60421 ccatgtataa taggcccatc atctaatatt tgcaacaat agaattcttt ggtccggttg
60481 aactatctga tttaaaccaa gttaagtgag atcctccaca tatcgaacca gatcttgatt
60541 caggtaacca aaagctaacc gtaaattcag atataaacca aacgaaggga acagagagtt
60601 tacacagcta cgggtctgtt ttttgtgaca agtgtttgat acaaatttaa gacgaaacta
60661 aaatgggatt tagaaacctt gtacaactct aggactgtta actttacgtt ttcactttct
60721 tacattaact agattggaac agtgtgctct ctcactctta accataagct tgtatttgtt
60781 tgcttgccaa cggaTTAggc gaggttagct tgttgtccct tcagtttgct cgccgggaag
60841 tgcaatcttg caatcaaagg cttcggtccc ctcgtctttc gatcaaatcc acgtacacat
60901 acgtacccta cataatatca aaagataagt tatgtttcag aacaagaaga aactgcttaa
60961 tacaaaatgt acctttccaa aagcaagcct gtatcttctc agttgataaa cctgagaaaa
61021 atagagctca agtggttaga acaactttct tttatataaa caatcgcatc acaatccaat
61081 aaagaaaatc ttatacccttt gaatatcgta ggaacagagg taccaaaata gaccgttctt
61141 cgaggtaatt cccatatcaa ttcccttggg acattgattg gtttaggct ggatgcatga
61201 tccgcaaaca cctgtatcaa tagaatacat cacaagtttc aatgcaaata attaaaatga
61261 aagagttgga gttattggag ttcaagtctt acctcattta cttgaaagta cgttccattt
61321 agaggaaaac taccctcat cgctgttcta caaggaatct gtacaattta caacatatta
61381 atctgtagaa aacataagtg tagtaagccg cataaggaga ttgatgcaac tacttaccaa
61441 aattgtccct ctcacaattt gagatctagt ctccttgatg ctgttgcagg agaaacaagt
61501 ctcctcgtca caaagcatac catttgcttg aatatgcac gtactaacag acggttgaat
```

```
-continued
61561 agaatcagcc gtctcacctg ttgaataaca catcgattaa agataccgat ttgatttcat
61621 gattaaaaga tatgcaaatc attaaattac ctggcgtcca tatagcaagc aaataagaac
61681 atggatcatc aggttctctc ttttccaact gccacaagaa atcacaaaca gctagtcaga
61741 ttttacaata tagacagcac tctatacggc atgtgtcctt atccagttag ctcacatacc
61801 tgagctagaa gaggatgctc gtctggaagt tcgtaactgc aagatacggg aaaagaaaca
61861 agttatggca tagcctgtaa ttattgggaa gtttgtctgc tttccaactt acgagttcat
61921 gcttggtcaa tcacttaaat attctactct gttcaagctt taataatttt gaaaaatgtg
61981 tttctgattt catttttaac ctaagaacga agaaaaacag agaaaaatgg attcttacac
62041 tcggtgttct gtccttaact ggctgatatt cttgagctta ggcattggaa gagaagcagt
62101 ttcagcagta agtgcaacta aagcgctgga catgttttcg tcttgaagtt ccttgttgtg
62161 ttccattatc ttcttcaagt tactggtaaa tgcatccatg tttagcctga tggtaggaat
62221 ttcttctgga tcctcaaaaa acgcctcctc tatgtcagct attgatactt ctgcggtttc
62281 tggctccggt gaagcaggct cttcgatgat tggttcacaa catgtgacct tttttgctgg
62341 ttctgagtgc tgtactactt cagacccttg ctctctctgg aatggctctg gcaggtgtag
62401 aggcaaaggg tttttatcag gtgtccccat acctttctct gtacttggta aagcaagcct
62461 tgcactgtaa aacaaatgaa tgttactaaa ttttctgtaa tgatgattca gagcttcgtt
62521 tagatacaga ccaattctca tttaactggg ttatatttta acaaggactt tcctcataga
62581 gtcatagtgg tactaaaggt ttaagagaac atgttgtagc accttgcaaa cgcactggca
62641 aaatgtctgc attctccttt catcggacat gcattgcaat taggtttgct ctttgtgcaa
62701 aagacctgat acaataatca agcagattac aaacctcatc atgtgagctg attttgacat
62761 acgtatatat gtatttcttt aatacatacc tttccaaaag taatcatctg gtagtgcaac
62821 tcatacctgt gagataatag ggtattaaac taatgaataa gtgtattaga ctgaggcatg
62881 aaaaaaaaaa agttagtgat aaacatcatt cttacaatgt tttttggtcg agtttgcaga
62941 gacggggcca agatacttt tgaatagatt caagcatagg atacctagac aaaccaaacc
63001 tcagatgtat taagtaacaa attacaattt ccaagtagga ccatttgaa aagtgcttac
63061 atttccagaa gatgcaactg aagtgactct gggagcggct gaaggggcac ccatccaagt
63121 ctgacggcta tgcgcccaac atttgtatca acctgtcaat aaattaagtt catgcatcat
63181 ataattcact ttttataggg acagaaacaa aagtttgatc cttgcttact ggaaaggcaa
63241 gatggtgaag tgttagaagc cgcacacact ccacactttt cagtcccaat ccgttaaagc
63301 tcagaagata ttctctgcag ggttttgtaa tatacgagag tacataattc attattaagt
63361 cactaaaact gccaaagtag taatctttgt ataggttaat aaagaagaaa taaaatgctt
63421 cgtctttcaa acttactttg ctttatctgg tggaacatct ctcaaccatt caagatcgat
63481 acttccatgg tcatttacca gtcgatcaag gaagccctgc atgattttca tgttcagagt
63541 caaatactta aaatgaatgt tatcacgaaa tttagccact aaattttac ctgtatacgt
63601 tctgcaagtt tatggttcat cccgcgactc ttgattgttt cagcaacttc cttaacatct
63661 gctgctcgta ttgccttcca atccacggtg tccattgtac ttcttgtttt ttctctaatt
63721 cctgctctag cttgggcttc tcttcttaaa caatcccagt caaacgcttt ttttttcctcc
63781 ttcaaaacct ttttcccttt tcttttaag gtaggtttct gacaactcaa aacatcccca
63841 tcttgctgag agcaacaacc aggttcacta ctatcaacag aggattttgt gggctctttc
63901 attgactgga aacccttaat ttctgagcta caatcacccg gagacatatt tggtgatact
```

```
63961 tgattggaat cttctagaga gacttgtacc ccctgtagga gcttcataaa ggaagtacga
64021 tactctcctt ctaagtcgat ctctgagctt gatcctgctc tctctgtatt tgaggagca
64081 tcagacacca tcgaatgttg acatgtaagt gcagaatctt cagatggaaa caggttcagg
64141 acacgacact tctcatccgt cttatcaacc tctacacttg agccttttcg atctgaatca
64201 acatactact ttgaatccgt ggtttttgtca actgattcat gggctgagat ggcaatctca
64261 ctactgcttc tggaggtttc attgctaggt acataatcct tctcctcatc aggctgtgta
64321 tttttcaaag taacagaact gtgattgtga tcgggtgggc ttgacatcgt ttcctctgag
64381 tccaagtacg ttatttgaat agaaggcatc gagcttgttc cagcgtcaaa gttactgctc
64441 ggtacaaaag ggacagggaa ctgggaagcc aacgacatga agccgaact acaaggagta
64501 aaaaacatca agcaagtta gttttgtgac tttttgctgt cttggattta gtttgacata
64561 gaattatgta agagcttgta ccttgagaga tggtctgaaa cattttgagt gagaaatact
64621 ccaacaacag aatccacgac ggatcccttc caaggcgtaa aacgtcgatc ccctgttaga
64681 aaccaaagac cataacaaga agcagtagct gagacatact aattgaaacc atgtggttag
64741 aacagaaaca cataaaagga caagtgtggt gtataacctt gtacaaggtg catccttgca
64801 ataaatgagt cagctcgtcc tcgaaacaca ttacgttctt cctcccacca tttcgccttc
64861 tgctcgtctg atccgtcaac accttcgcta ttaatattct ccaatagcag tttccacact
64921 ctgtctgtct catcgtctag atcaaccttt ggtcgtgggc gtggtttttt aacaggagtt
64981 acaggcacaa ttgctccagc gccaccacca aagagtacaa tctggctatt cattgtgtaa
65041 ggaacgagag cagtttcaga atgctccctg ttgatgtcta atagacgcaa tagctcactg
65101 attgtttcga tcgagttacg tcgtttccaa agttcatctg gagaaagacc tgcaggaatc
65161 aaacatcatc attatcaaga atagtctgc atttaacaga ttcaaaaaaa caaagaaata
65221 tagttctgta tctattcatt accagtaaat gaaggtggaa aacggcaaag attcggaaga
65281 agatttttct gtttggtttg tgatttctca gacttggttg gcttcttttt gctcacagtc
65341 acccgcgtat caacaagaat cttattattt tgctgtggct tgctacaata tcctgaggtt
65401 aaatgctcag gaacttccac aagtttattc attgaagaca aattccggaa tcgagcatgg
65461 cctgttgttt tcttcttgat cggcgtgtct atcttatccg agagaacatt tagctcagac
65521 tcttgccttc cttgaaagat accttctcgt ctttcttcaa cggttaggac tctattagca
65581 ctgagctgag atgtggaact gtagcacgta gcgtgaaagg cagaaacata attgtgctgt
65641 tgtccagaga atactttgct gcaaatggca tcatatctca tccctccctg ttgcaagttt
65701 ggggaataca accaatgcat tttctggtag tcacattgct catcatactg aatccctgat
65761 agattcatgt cgcaacaagt tggtccttgt cttctctttg cagcttgcgc catcgaaata
65821 tcgacttctt ctagattact gccattttc tttggttgaa ctccctttct tttaccttgg
65881 ctgcgctttc tcttgggcgt gctaggagcc gaaagaaggc aatcttttaa ctcttgattc
65941 ccagaatcta actgcttctc ttgaagagct gattccatct cacctgcttc tctaatgtca
66001 ccgttggtct ggttttctcc attttcggct tcaaaatcca agactcgtct acagagcctc
66061 ttaggacgag ttgaagtttc aacagctgct gatgattcaa ccggagtagc gtcttgatcc
66121 ttactgactt caaccttctt ccgcacatat ttcctctttg gtgttttgct tccttgacca
66181 tcggtgacaa cagacttcct cggagctcgt ggtttaggct ccctcttggg tttagcttct
66241 ctacgaacct ttggccgatg cttcttcctc ttaggttttt caggagtctt gaggatctgt
66301 tcagcaacat tgttactcac tgagctcaaa ctctccactt cttcagtacc tttttgcata
```

```
-continued
66361 acctctgtgt tcctacatt gagaatcaca tctttctcag tccaactcaa acagaatcaa
66421 aatttgacaa agcgatttca tttctcatga gaccagaatc aaaatcccct cttacttgta
66481 ggtattggag tctgaccaga gaatatgagg gatgcagtgt tagctagagc aagcaaatcc
66541 ccaaaagaca agtgatcaag accactcata tccttgttcc caacaaatct cctgcatgca
66601 tcaataccct acttaaccaa ttacccatca ctactctttg aaatttctca actttagaac
66661 aaaaaagcac aaacctttcc tccaattgac tgctatgata ttgatcctCc accgtgtatg
66721 ggcagatcgg tgaaaatggc ttcatgggtg tctgaggaat ccatggaggt tgttgaaagc
66781 tgctttcttc tctcctctgt ttctcCATtt ctgactctat ttttactttt cttcactctt
66841 acttaaatca gaaccatttg agaaaaagct tggaacttct atttttttcc actgcaaaaa
66901 gttcaataat ttcttcaata aagagatca ccaattttt ttaaaaatca cgattttata
66961 aaatgatcag atccactttt ttctggggtt ttagagaaag agagatctcc ggaagtcatt
67021 gattttgggt gagtggcgac atgaacgatt aatccgttcg ttaggtgaaa gagagacttt
67081 ttagattcac aacaaaatgt aaaaaaaagt aagaaaaaaa caaaattcat taccagtaga
67141 atcaatggtt atggtggtga tggagagagt tagttcggtg gtagctatga gaggataaga
67201 tcactgatgc ttcgtttctt ctcttggaat cgatgaagtt aaagagtaat atagaaaaag
67261 ctttttggc ctaacgtata aagaagagga tataacatgt gttgttgtgt gtttcactat
67321 ttttcataac cgtttgttta tgtagggcga aagttcgttt ggttggcggg aaaagtttta
67381 cggaatttta ttttaaaaat aatgattctt ttctacaaaa tctcctagac tatgggaaag
67441 atgatttaaa aagttaataa tattgtcgtt gttatcgtca tcgtcatcat cgtctttct
67501 gttatctttt tctctttaaa atttcgtatt ttttctcgtt tacgtaacta tttaaaatta
67561 tatgaactaa ctaatttat aattaataga aattataaaa taatcttaat tttgctttag
67621 atataaaata attagaactt tatttataaa tttatcatca aattatgatt taaacaaata
67681 acatgttatg taatccacgt ttataatttt gatcaataat atattattt gctaatttt
67741 acgtaatctc ataaatttac acgttttcgt ttacatatgc agaagttaaa tgattcgttt
67801 tagaattatt attttccact gatatgggag ctagtgtagt agagtgatta ttaggctagt
67861 tgcccaacga gtctttcgtt tttgatcatt ccaaatgttt tagtctagta cgataggagt
67921 caaaatactg caccatatgt gtgaaactgt gaatgtgtgt gaaaaaaaga gtaattagtg
67981 tgctaacctt tgatttcctg tcatgcaaga aaccttcaaa gagacgtaca tgagaaatga
68041 gtattgtaaa tcatttattt catggacttg gttggaatct tagtgaatcg ttgttgtcaa
68101 tcttaacaac ttgttggatt ggttatgagc ctatgactta tgacttatga gtgagtcaat
68161 ggtggtcata acctaatgat tgggttatga gcaaagaaat ttggaatttg taaaaaaaaa
68221 aaaaaaatc aagagctttt ttgtgtggac atatctatcc tagaaactga gacgaataat
68281 agtggataaa aagttgggaa cggattattc gaatgtttaa aactattatt gaaaacaata
68341 caactaaata tggtacaaaa gtaaacgaat tcgtatagct aaacctaatt caaattacga
68401 agctaatcca tacttggatc ctaaacgctt ttacttttac ttacggtttc tttttcaaaa
68461 aagtttttac aaatttgggt ttgtcttatg aagattatgg cagaagagac tgatcaaaag
68521 tgaatgccta attcggttta atccattcaa gtttatctta aacaatgaaa ctgaccatga
68581 aagtgaattc aaagaccaaa tcaaagaaaa attaaactga tttagttgta atattggtat
68641 tgaattaaac tataaataga aataaccaaa catataacca caaaagaaga ctatttatat
68701 aaatatatga gttggaagtc attttttggac tattatataa gatctaatta tcacacgacg
```

-continued

```
68761 tgtggatgta tggttagcag agttgtgttc agagagttcg ataaagccat cactccaaac
68821 atacaaaata tccatacatt gatccaccaa tataaccggc tgtgtgccaa gcaaagtgaa
```

SEQ ID NO:11
*ARABIDOPSIS THALIANA* DMT3
>DMT3 (1DMT3);

MEVEGEVREKEARVKGRQPETEVLHGLPQEQSIFNNMQHNHQPDSDRRRLSLENLPGLYN

MSCTQLLALANATVATGSSIGASSSSLSSQHPTDSWINSWKMDSNPWTLSKMQKQQYDVS

TPQKFLCDLNLTPEELVSTSTQRTEPESPQITLKTPGKSLSETDHEPHDRIKKSVLGTGS

PAAVKKRKIARNDEKSQLETPTLKRKKIRPKVVREGKTKKASSKAGIKKSSIAATATKTS

EESNYVRPKRLTRRSIRFDFDLQEEDEEFCGIDFTSAGHVEGSSGEENLTDTTLGMFGHV

PKGRRGQRRSNGFKKTDNDCLSSMLSLVNTGPGSFMESEEDRPSDSQISLGRQRSIMATR

PRNFRSLKKLLQRIIPSKRDRKGCKLPRGLPKLTVASKLQLKVFRKKRSQRNRVASQFNA

RILDLQWRRQNPTGTSLADIWERSLTIDAITKLFEELDINKEGLCLPHNRETALILYKKS

YEEQKAIVKYSKKQKPKVQLDPETSRVWKLLMSSIDCDGVDGSDEEKRKWWEEERNMFHG

RANSFIARMRVVQGNRTFSPWKGSVVDSVVGVFLTQNVADHSSSSAYMDLAAEFPVEWNF

NKGSCHEEWGSSVTQETILNLDPRTGVSTPRIRNPTRVIIEEIDDDENDIDAVCSQESSK

TSDSSITSADQSKTMLLDPFNTVLMNEQVDSQMVKGKGHIPYTDDLNDLSQGISMVSSAS

THCELNLNEVPPEVELCSHQQDPESTIQTQDQQESTRTEDVKKNRKKPTTSKPKKKSKES

AKSTQKKSVDWDSLRKEAESGGRKRERTERTMDTVDWDALRCTDVHKIANTIIKRGMNNM

LAERIKAFLNRLVKKHGSIDLEWLRDVPPDKAKEYLLSINGLGLKSVECVRLLSLHQIAF

PVDTNVGRIAVRLGWVPLQPLPDELQMHLLELYPVLESVQKYLWPRLCKLDQKTLYELHY

HMITFGKVFCTKVKPNCNACPMKAECRHYSSARASARLALPEPEESDRTSVMIHERRSKR

KPVVVNFRPSLFLYQEKEQEAQRSQNCEPIIEEPASPEPEYIEHDIEDYPRDKNNVGTSE

DPWENKDVIPTIILNKEAGTSHDLVVNKEAGTSHDLVVLSTYAAAIPRRKLKIKEKLRTE

HHVFELPDHHSILEGFERREAEDIVPYLLAIWTPGETVNSIQPPKQRCALFESNNTLCNE

NKCFQCNKTREEESQTVRGTILIPCRTAMRGGFPLNGTYFQTNEVFADHDSSINPIDVPT

ELIWDLKRRVAYLGSSVSSICKGLSVEAIKYNFQEGYVCVRGFDRENRKPKSLVKRLHCS

HVAIRTKEKTEE

50

SEQ ID NO:12
>DMT3(1DMT3) novel 375 amino acid amino terminus;

MEVEGEVREKEARVKGRQPETEVLHGLPQEQSIFNNMQHNHQPDSDRRRLSLENLPGLYN

MSCTQLLALANATVATGSSIGASSSSLSSQHPTDSWINSWKMDSNPWTLSKMQKQQYDVS

TPQKFLCDLNLTPEELVSTSTQRTEPESPQITLKTPGKSLSETDHEPHDRIKKSVLGTGS

PAAVKKRKIARNDEKSQLETPTLKRKKIRPKVVREGKTKKASSKAGIKKSSIAATATKTS

EESNYVRPKRLTRRSIRFDFDLQEEDEEFCGIDFTSAGHVEGSSGEENLTDTTLGMFGHV

-continued

PKGRRGQRRSNGFKKTDNDCLSSMLSLVNTGPGSFMESEEDRPSDSQISLGRQRSIMATR

PRNFRSLKKLLQRII

SEQ ID NO:13
>DMT3(1DMT3) nucleotide sequence from BAC T22K18 (gi 12408726);

```
53341 aatcaagtac taatgcagat ttaaggggggg tgtattgacg gcgttaaaac ggtttctcaa
53401 cggaatcgta cgtagtcaca cgtgatttta ttgtttaccc cggattggtc atgcgttcct
53461 tcttttccac ttgcgcggac cactcaatga cactctcttc ttttgtagca gtggcccgac
53521 accagaatgc agcatttaat ctctcaaatt accattttgc tcctacctct tttacccctt
53581 ttggtatttt gtgtcttttt tctttctatt tcgtgtgaaa aaggatctct tccttaatcg
53641 tattatttct tccgatatct acttttattc tgttttctat ttttggtagg ttacatcttt
53701 tttataaaga aaatatgagc taacacgaca ttagtgttgt taaccaaaga attggaaaaa
53761 agttataaga gagataataa gattctctta cagagactca cttcagtgaa aaaggaagaa
53821 gcaagtggtt cccttaaggg aaaaaaaagt cacgtacgtt catatacaac tttaatacgt
53881 actgtgtaac tcaatagatc gtgcagtaat attcagtcgt attagtaaga aggaatttat
53941 ttgctaagta aactcaagcc tccttttttct cttttttttc ttttttagtaa aaattaggct
54001 agtgttttttt ttgactcagc aacactctgc ttaaatttag gagtaatttg acctattcct
54061 acgagtttct aagtgaattc tgttggggtc aaagaagcaa ctagttgaat tagtggaaaa
54121 tcgtttcctt tctttacgca tagttcacgt tggacactca gtctcaatgc tttcacgttt
54181 cacgtagcaa caacatatat tcatcagttt gtgatcgtgc catcgtggat aagttgcaat
54241 tcagtgaaac tctgcaccac tttgtgcaat tatttggccg tctaatctat ttgtgagaat
54301 tttacaatct aattgttcta ttatttcatt tacttgtcat caatttatta tatttgtagc
54361 caatgaacgt tgtaattaaa gaaccaaaat aaattaatat cttgaaattt gtaacagtca
54421 ctagaagctg atttcttatt aattgtatca ctaaagtatt attaaaaacg gttacaaatt
54481 atgataatta tatatttaat aaatttcgtg tgtcacattt cttttaaact acaattatga
54541 atatctaaaa ctcattcatg catatcttaa aatttgaatt caaaactttc ttatcttatc
54601 tttaggttct taattaacag tcactaaaaa tagtcaaagt tttgaagttt atgaaaaaag
54661 ataagagtat aattaatgga tacgcctcgt aacaaattct tgtaaagtat agataaatata
54721 catttgttaa atatgacacg tgtttatttt ttttttaaat atgatcaaaa tatattttaa
54781 ctaccagat ggtatgtatg tctccaattt tgaataacaa gtcaattgtt attagaaatg
54841 tcataatata aagaagggaa ttaaatttgc aaagaaaaag tgaaaaacaa aggatttgta
54901 ttttggagaa aattaaggac tggatttgca aaaacgaaaa agtaacttca tgtatattgt
54961 cttccttata gtctctataa actattatct caaattttgt ctggactctg aaactcacaa
55021 gacttgactc tggcttactt ggcttcatct ttttctctct ggtaatctct cctgcaactt
55081 caagctttca ttttcaaata aatgtaatca aatctgttat tttcactcaa gaactaattg
55141 agttctctat cccttttcaat tgaaattgac attaaaatga aagattttg aggaggttttc
55201 acctaccaca accgaatcac ttcttttctcc aaatattgtt tcttttcagtg gccaagaatc
55261 acaatcaatt tttgtatctt ccacaggtaa attaattgtg attgaacaga gaagaggaca
```

-continued

```
55321 agtgatcttg gttcaaaaga aATGgaagtg gaaggtgaag tgagagagaa agaagctagg 55381 gttaaaggga gacaaccaga gacagaagtt ctacatggtc tgccacaaga acagtcaata 55441 tttaataaca tgcaacacaa ccatcagcct gactcagaca ggttttgtga ctcaaccgaa 55501 tttactctgt tcttctcccg gaatttccat attttctggt gattctgttt tgttaaattc 55561 tgcaaaagga agaaaataaa tcaaacattt ttcacttctt caaaacatga gtaaatgcaa 55621 aaactgagat atgtaaacac acagcaattt tttgatgaac tggttttggc tgtgtgatct 55681 ttgtgtctat gcaattacgt tttagttatt ttctacttta taaggagaga tgttaactga 55741 aactgttatt gatcatacag gaggaggctt agtcttgaaa acttacctgg actatacaac 55801 atgtcttgta cacaactctt ggctctggcc aatgccacag tcgccacagg ttcatcaatt 55861 ggtgcatcat catcatcgtt aagctctcag catccaacgg attcttggat taatagctgg 55921 aagatggact ctaatccgtg gactttgagt aaaatgcaaa acaacaatg tgagtaaaat 55981 ttgttcctga atttgtagga tcttttaaga gaaagtaagc gtttatgtgt agattaagtc 56041 agactgaaat cgattatctc ataataagtt ctcagtgatc tctcaaatca tgaattttat 56101 gtttacctga tatcaacttc ttgtcttggt gaaccacaga tgatgtgtca actccgcaga 56161 agtttctttg tgaccttaat cttacacctg aagagttggt gagcaccagt acgcaacgaa 56221 cagaacctga gtctcctcaa ataactttaa agacaccagg aaaaagtctg tctgaaactg 56281 atcatgagcc tcacgaccgt atcaagaagt ctgttcttgg aactggatct cctgcagcag 56341 taaagaaaag aaagatagca agaaatgatg agaaatctca gctggaaaca ccaacactaa 56401 agagaaaaaa gatcaggcca aaggttgtcc gtgaaggcaa aacaaaaaaa gcatcatcta 56461 aagcagggat taaaaaatcc tctattgctg ctactgctac taaaacttct gaagagagca 56521 attatgttcg gccaaaaaga ttaacgagaa gatctatacg attcgacttt gaccttcaag 56581 aagaagatga ggaattttgt ggaatcgatt tcacatcagc aggtcacgta gagggttctt 56641 caggtgaaga aaatctaacc gatacaacac tgggaatgtt tggtcacgtc ccaaagggaa 56701 gaagagggca aagaagatcc aatggctttta aaaaaaccga caatgattgc ctcagttcta 56761 tgttgtctct tgtcaatacc ggaccaggaa gtttcatgga atcagaagaa gatcgtccga 56821 gtgattcaca aatttctctg ggaagacaga gatccattat ggcaaccaga ccgcgtaact 56881 tccgatcgtt aaagaaactt ttacaaagga ttataccaag caaacgtgat agaaaaggat 56941 gtaagcttcc tcgtggactt ccgaagctta ccgtcgcatc caagttgcaa ctaaaagtgt 57001 ttagaaagaa gcggagtcaa agaaaccgtg tagcaagcca gttcaatgca aggatattgg 57061 acttgcagtg gcgacgccaa aatccaacag gtgataaaca cacaagcaac tttcatctat 57121 aatattttc ttagatttct atcttttgaa ttaatactag ttttacaaaa tgcaggtaca 57181 tcgctagctg atatatggga agaagtttg actattgatg ctatcactaa gttgtttgaa 57241 gaattagaca tcaacaaaga gggtctttgc cttccacata atagagaaac tgcacttatt 57301 ctatacaaaa agtcgtatga agagcaaaag gcaatagtga agtatagcaa gaagcagaaa 57361 ccgaaagtac aattggatcc tgaaacgagt cgagtgtgga aactcttaat gtcaagtatc 57421 gactgtgacg gtgttgatgg atcagatgag gaaaaacgta atggtggga agaggagagg 57481 aacatgttcc atggacgtgc aaactcgttc attgcgcgaa tgcgtgttgt ccaaggtatt 57541 atttattgct ttagttatga cattgttgtg tggctttata ccttagatct ttctttcttt 57601 ctttttgta tccaaagcaa catggtctta aatcaagctt atcactgcag gcaatagaac 57661 tttctcacct tggaaagggt cagtagtgga ttcagtagtg ggagttttcc taacccagaa
```

```
57721 tgtcgcagac cattcatcaa ggtatatgca ttcaagagat ttctaataag tagaagatat
57781 atgcaacaga gtggtttaga aattataact tgttcacttt tgcagttctg catatatgga
57841 tttagctgct gagtttcctg tcgagtggaa cttcaacaag ggatcatgtc atgaagagtg
57901 gggaagttca gtaactcaag aaacaatact gaatttggat ccaagaactg gagtttcaac
57961 tccaagaatt cgcaatccaa ctcgcgtcat catagaggag attgatgatg atgagaacga
58021 cattgatgct gtttgtagtc aggaatcctc taaaacaagt gacagttcca taacttctgc
58081 agaccaatca aaacgatgc tgctggatcc atttaacaca gttttgatga acgagcaagt
58141 tgattcccaa atggtaaaag gcaaaggtca tataccatac acggatgatc ttaatgactt
58201 gtcccagggg atttcgatgg tctcatctgc ttctactcat tgtgagttga acctaaatga
58261 agtaccacct gaagtagagt tgtgcagcca tcaacaagac ccggagagta ccattcagac
58321 acaagaccag caagagagca caagaacgga ggatgtgaag aagaatagga aaaaccaac
58381 tacctccaaa ccaaagaaaa agtcaaagga atcagcaaag agcacgcaaa agaaaagcgt
58441 tgactgggat agtttgagaa aggaagcaga aagtggtggc cgaaagagag agagaacaga
58501 aagaacaatg gacacagttg attgggatgc acttcgatgt acagacgtac acaagatcgc
58561 taatataatc atcaaacgag ggatgaacaa catgcttgcc gaaagaatca aggtttgact
58621 aatcacagtg ctatatatac ctcatttata cattctaaca aggtgaattt ttttgactct
58681 ggaaattgga caggccttct taaacagact agttaaaaaa catgaaagca ttgacttaga
58741 gtggctaaga gatgttcctc ctgataaagc caagtaagaa aattatttac aaatcttgag
58801 attatatgta gcctctggtt aaagaatata tctcagtaaa tggaatcgat agtaattgag
58861 atacatataa atgagagata cttgatagtg actactaatg gttgcaggga gtatctacta
58921 agcataaacg gattaggatt gaagagtgtg gagtgtgtta gacttttgtc actacatcag
58981 attgcattcc ctgtaagtca atgaaggata ctgaatactc agaccctaat gaatgtggaa
59041 cagatacatt aatagttacg tattttttaca aatgcaggtt gacacgaatg tcggacgcat
59101 agctgtaaga ctaggatggg ttcccttaca gccattgccc gacgagctgc aaatgcatct
59161 tttagagttg taagaaaaaa aaattaaaga tcattcttca atcatgaaag ggaacatgag
59221 aaatttacag tagttccctt taattctatt caggtaccca gttctagagt cagttcaaaa
59281 gtacctctgg ccacgcctct gcaagcttga ccaaaaaacc ttgtaagtaa attacattag
59341 catcaaccat tactctagac ccttaaactt ctctaactaa ctctaactgt atcatacaat
59401 tctaggtacg agctgcatta ccacatgata acatttggaa aggtacctca aacaaatttc
59461 aagtgtttgt ggaatgaaaa catcttaaag tggcttttcc tattttgcag gtcttttgca
59521 caaaagtaaa acccaattgc aatgcatgtc caatgaaggc ggagtgtcga cattactcta
59581 gtgcacgtgc aaggttaaac cccacaaaat tctttgttat tgccattaac atgaaaaaaa
59641 aaacactagc ttaaagagaa agagatctgc tcaaaatagt cattttaatg gttgtatgtt
59701 ctaaatgctt gtgttatatc gcagcgcacg gcttgcttta ccagaaccag aggagagtga
59761 cagaacaagt gtaatgatcc atgagaggag atctaaacgc aagcctgttg tggttaattt
59821 tcgaccatcc ttatttcttt atcaagaaaa agagcaagaa gcacaaagat cccaaaactg
59881 tgaaccaatc attgaggaac cagcatcacc agaaccagag tatatagaac atgatattga
59941 agactatcct cgggacaaaa acaacgttgg aacatcagag gatccttggg aaaataagga
60001 cgtaattcct accatcatcc tcaacaagga agctggtaca tcacatgatt tggtggtcaa
60061 caaggaagct ggtacgtcac atgatttggt ggtactaagc acatatgcag cagcaatacc
```

-continued

```
60121 tagacgtaaa ctcaagatca aggaaaagct acgcacagag caccacgtgt gagttgccac
60181 tttcaatttt ttcttctatt ataccctaaa ccgtaaaatt tgagactttc ctcagcattt
60241 atctcatact aattctcttt tacagatttg agctccctga tcaccattcc attctagaag
60301 gggttagtaa ctcttgcaaa atgatttagc aagaattttt ctacttattc ccgccttaaa
60361 aactgtttga ttatctttt ttacagtttg agaggcgaga agctgaggat atagtccctt
60421 acttgttagc catttggacg ccaggtaaga agaaataggc acacaataaa atctgattat
60481 gattttcctt ttcaagaata ccgctatatt tttacgagtt ttcatcctta gatgtatatg
60541 actaatgtct aacaagtgat tgtaatattt ttccatacca ggtgaaaccg tgaattccat
60601 tcaaccgcca aaacaaagat gtgctttatt tgaaagcaat aatacattat gcaacgaaaa
60661 caaatgtttt caatgcaaca agacacggga agaggaatca cagactgtac gaggaactat
60721 attggtaaga ttctggtgga caattttcaa gagaatatct ctaagtagaa atataaggaa
60781 ggtataaaaa tgactaattt gtttgttaac agataccttg cagaacagca atgagaggtg
60841 gattccctt gaatggcaca tacttccaaa ctaatgaggt aattttccca aaaatgaatt
60901 taacttaaac aaatgatcaa aagcaacatt ctcgtcaaag ctcgatttgg actatacttg
60961 tgcaggtttt tgctgaccat gactctagca taaaccctat cgacgtccca acagaactga
61021 tatgggatct aaaaagaaga gtcgcatact taggatcctc tgtatcctcg atttgtaaag
61081 gtaaattttc aaaacaaaac tgtcgattta tgcatgtgtt tggatatata atccaaggt
61141 cttgtctcaa tatgttttc tcattttt aggtttatca gtggaagcca taaaatacaa
61201 tttccaggaa ggtatgctaa tatgtcttac actgaaaaca cctttagtat caaacattga
61261 attcatgaaa agaacaaaca atagtatcaa aatcagtcac gatgttttg ctttggcgat
61321 gtaagatgtt gataggaaag tatagaagat atagcttaag ttggttaata ctgtttttat
61381 agagctttga ggtgggttt gactagcatt gtaatatata tgcaggatat gtctgtgtaa
61441 ggggattcga cagggagaat cgtaagccaa agagtctagt gaaaagactg cattgttctc
61501 acgtagcaat cagaactaaa gagaagacag aggaatgaaa ccttccagat tgcattaaca
61561 tgttagacat atttgattca ttggtttagg gtttacatca ccaaggtcat agaggatctt
61621 agcttttcat taactttaa attcatgcaa ctctttttag gtgtttcttt ttgttccttg
61681 ccatagtttt gggcaatgga tggatgttct ttgcaaactc aggttttttg tagtcattaa
61741 cagaaatttg cagcactaat tcatctttcc tattatctat caaagctctc agtgtttctc
61801 cataacttga tgagatttag tcactctcaa gctaattcag tctggtccta atttcaatca
61861 gatttggtaa aggaacaact gcaattgcta agtacaaatc gatccagatt tcaaacaagt
61921 tccaggttta atccaaatca tcacattcaa tcaaagacca aactagaatt caaaacatat
61981 aatctctgat tcagattcaa gaaagacaaa gcatgagaca tcattctgca agttaaccaa
62041 ttccggttat tctcgaatcc tactgaatta agcatcaatc atctaaagga acttcataag
```

55

SEQ ID NO:14
*Arabidopsis thaliana* DMT4
>DMT4 (1DMT4);

MEFSIDRDKNLLMVVPETRIKTKQFEKVYVRRKSIKLPQNSMVHNTLIKMARQRIQKSMK

ESVMNQHIFKNFDSYLSVIYHPCCFVINNSQTTHKKKEKKNSKEKHGIKHSESEHLQDDI

-continued

SQRVTGKGRRRNSKGTPKKLRFNRPRILEDGKKPRNPATTRLRTISNKRRKKDIDSEDEV

IPELATPTKESFPKRRKNEKIKRSVARTLNFKQEIVLSCLEFDKICGPIFPRGKKRTTTR

RRYDFLCFLLPMPVWKKQSRRSKRRKMMVRWARIASSSKLLEETLPLIVSHPTINGQADA

SLHIDDTLVRHVVSKQTKKSANNVIEHLNRQITYQKDHGLSSLADVPLHIEDTLIKSASS

VLSERPIKKTKDIAKLIKDMGRLKINKKVTTMIKADKKLVTAKVNLDPETIKEWDVLMVN

DSPSRSYDDKETEAKWKKEREIFQTRIDLFINRMHRLQGNRKFKQWKGSVVDSVVGVFLT

QNTTDYLSSNAFMSVAAKFPVDAREGLSYYTEEPQDAKSSECIILSDESISKVEDHENTA

KRKNEKTGIIEDEIVDWNNLRRMYTKEGSRPEMHMDSVNWSDVRLSGQNVLETTIKKRGQ

FRILSERILKFLNDEVNQNGNIDLEWLRNAPSHLVKRYLLEIEGIGLKSAECVRLLGLKH

HAFPVDTNVGRIAVRLGLVPLEPLPNGVQMHQLFEYPSMDSIQKYLWPRLCKLPQETLYE

LHYQMITFGKVFCTKTIPNCNACPMKSECKYFASAYVSSKVLLESPEEKMHEPNTFMNAH

SQDVAVDMTSNINLVEECVSSGCSDQAICYKPLVEFPSSPRAEIPESTDIEDVPFMNLYQ

SYASVPKIDFDLDALKKSVEDALVISGRMSSSDEEISKALVIPTPENACIPIKPPRKMKY

YNRLRTEHVVYVLPDNHELLHDFERRKLDDPSPYLLAIWQPGETSSSFVPPKKKCSSDGS

KLCKIKNCSYCWTIREQNSNIFRGTILVFADHETSLNPIVFRRELCKGLEKRALYCGSTV

TSIFKLLDTRRIELCFWTGFLCLRAFDRKQRDPKELVRRLHTPPDERGPNGFHIVVVDEK

EESPRVGLMVMPGFWIGGSVIQNRVYVSGVKVLE

SEQ ID NO:15
>DMT4 novel 372 amino acid NH2 terminus;

MEFSIDRDKNLLMVVPETRIKTKQFEKVYVRRKSIKLPQNSMVHNTLIKMARQRIQKSMK

ESVMNQHIFKNFDSYLSVIYHPCCFVINNSQTTHKKKEKKNSKEKHGIKHSESEHLQDDI

SQRVTGKGRRRNSKGTPKKLRFNRPRILEDGKKPRNPATTRLRTISNKRRKKDIDSEDEV

IPELATPTKESFPKRRKNEKIKRSVARTLNFKQEIVLSCLEFDKICGPIFPRGKKRTTTR

RRYDFLCFLLPMPVWKKQSRRSKRRKNMVRWARIASSSKLLEETLPLIVSHPTINGQADA

SLHIDDTLVRHVVSKQTKKSANNVIEHLNRQITYQKDHGLSSLADVPLHIEDTLIKSASS

VLSERPIKKTKD

SEQ ID NO:16
>DMT4 nucleotide sequence BAC F28A23 (gi 7228244);

14881 gctatggatg tcaacagaga gaattacgaa ttgggtttac cgatcattga gaaagccggc 14941 gttgctcaca agatcgactt cagggaaggc cctgctcttc ccgttcttga tgaaatcgtt 15001 gctgacgtaa gcattcttct ttctgacgta attaacaaaa aagatgatga agataatgaa 15061 ataattaaaa actcatggcc taattaggtt gatttaatat cttgatgaga atttctgtat 15121 acgcaaattt gtttcctttt tcatagaaga aagtgtggta actgattatt gtgtgtggtt 15181 gggtgcagga gaagaaccat ggaacatatg actttatatt cgttgatgct gacaaagaca 15241 actacatcaa ctaccacaag cgtttgatcg atcttgtgaa aattggagga gtgattggct 15301 acgacaacac tctgtggaat ggttctgtcg tggctcctcc tgatgcacca atgaggaagt -continued

```
15361 acgttcgtta ctacagagac tttgttcttg agcttaacaa ggctcttgct gctgaccctc
15421 ggatcgagat ctgtatgctc cctgttggtg atggaatcac tatctgccgt cggatcagtt
15481 gatttgactc ctccctactc tgagtttgtc cacagtggat tactttccat cttcttatac
15541 ctttcaatcg cattttcacc aaccactaaa atggaccttt ttatgtattt gtgttaagta
15601 atatctccat tgtccttgtt ttgctttctt ctgaacaaag aaataatatg taccttactt
15661 ttcttcttgg tctcgttctt ttgttttttct ccatgataca acatctaaag aaattatttg
15721 tgtcacagca acgtaagtcg ataaaattag ttgaacatat tgagaaaaag ttatcataga
15781 ccttcaattg ttgaaagtcg atgttggtat ttgtcaattg atattagatt accaaataaa
15841 tattagacag taagaaacga acaaagtagg aagatgtagg tcaccggtct ttgaaaattt
15901 atcagataga attcataata cacagttagg tagtttcagt tgagagttaa aagggaaaaa
15961 tatgtaattg tgtgtgataa atacgtcaaa aattagttga tgagcaaaat cgtaaacaaa
16021 aatactttt tgcattagtt ttgttggatt ccctataaat acgggttccc atatctaact
16081 cgtagttagc ataattataa gcaacaaata aacacaaaat actgaattta gaaattttcc
16141 agaaaattaa ttagagtttt tacattattt ttacaaactt tagtgaatta tttcttaaac
16201 gtatgttagt tatttattaa ctgaagtttc acatatttga tagaataaca tttaaataaa
16261 aaaatttgaa gtaaggttag aatgttctta taatacttta taactttttt aaaaggtaca
16321 agccaaaatt atcgcaaatg taaataataa atcattgtaa aaatcttaaa ctaattaaaa
16381 gatctaacgc aatctaaaca aagatttggt atcatcgccc atttatgttt tgatataatc
16441 aaaactggtt aataattaaa ttaaattatc aatttcttaa ttagttagaa ttcttgttaa
16501 tgtaatcaac tcaccattat tttaattatt taaaatatgg gttaatatct cttaatcata
16561 tctaagatga tattttcttc catttatgaa agaaaaata tgttaattaa gcattaaaaa
16621 gaaggaaaaa ataatttaaa taatattaaa tatatataca tcgtttttag agttcgagtt
16681 cttccgtatt tacagtttct cttttttcca aagcagggtt tggattggta gttttctgg
16741 attaattttg tctcaaattc tttcttcttt ttattttttt ttgtgaaatt ctttgtttta
16801 attggtgtga catcgtttcc aaaatatttt caaatttgat tgcttttgaa gtttttttt
16861 tttttctatg ttttggaatt cattatacta gcgttgttgt ttttctttct gcaagagtaA
16921 TGgagttttc aatagatcga gacaaaaatc ttctcatggt tgttccgyag acacgtatca
16981 aaacaaaaca atttgaaaaa gtttatgtga aagaaaatc tattaagctt ccacaaaatt
17041 cggtaatttt tccacatgaa atcaaagatc gtggtgaaga agagagtaag gagaaggaat
17101 ttttccatca aggtaaacaa aatctctaat accttaatta cttccgttta gtaattctcc
17161 ttttacttgt ttttttttta atgagagtat gtgacaattt cataaagaaa ttagttgttt
17221 gacatacgag atggtttttt gactaattat attttttgtt ttgaaagatt tccaagctaa
17281 ttttaatgag catattttg atttattga ttgaggaaat tttcagaatt tcgacattta
17341 agttttttt ttgttttaaa tacttttg attcgatgat aagagattgg gaaagcagac
17401 taatgatgtt ttgttgtcac gttcattgat tagagatctc ttatattcat atttgtctac
17461 aatatatcat gcatgtgttg atttgttcg ttaattcaat tttttttttt tcatgttgac
17521 agatggttca caacacactt atcaaaatgg cgagacaaag aattcaaaag agcatgaaag
17581 aaagtgtgat gaatcagcac atcttcaagg taaataattt taaattcatt cttaaaaaag
17641 ttagcttatt ggtaagttca ttacaattta tatttaacca tcgtcacttt ttatttaacg
17701 agtttgataa gcatttttcaa aacctgtcct tcatctgccg atgcagatgt ggttatgttc
```

-continued

```
17761 atctttgatt ttattgattg aggattttt cagaatttcg attcatactt gtctgtaata
17821 tatcatccat gttgttttgt aatcagttaa ttcacttatt ttatttttaa cttttattgt
17881 aacagataat tcacaaacca cccataaaaa aaggagaag aagaattcaa aagaaaagca
17941 tggaataaag cattctgaat cagaacatct tcaaggtaaa tacttttgaa ttcattcatt
18001 aaaaaaacag tttatttgta agttcattac agtttatata tatttaaatt gttatgata
18061 atgtattttt gcacaatcga ctaatcatta cccactcatt catttatatt ttatttatg
18121 gtgaaagatg atatttcgca acgtgttacc ggaaaaggaa ggagaaggaa ttcaaagggg
18181 acaccaaaaa aactgaggtt taataggcct cggatcttgg aagacggaaa gaaaccaaga
18241 aatcccgcca ccactcgact gagaactata tccaacaaga ggaggaaaaa ggacatagac
18301 agtgaagatg aagttatacc agagcttgca actccaacaa aggaaagctt tccaaagaga
18361 agaaagaacg agaagattaa gagatccgtg gctcggactt taaattttaa gcaagaaatt
18421 gttctgagtt gtcttgagtt cgacaagatt tgtggaccaa ttttccaag agggaaaaag
18481 aggaccacca cacgacgcag atatgatttC ctttgttttt tacttccgat gcctgtttgg
18541 aaaaaacaat caagaaggtc taagcgtagg aaaaatatgg tcagatgggc tagaattgct
18601 tcttcttcaa aactgctaga agaaactttg cctttaatag taagtcatcc gactattaat
18661 ggacaagcag atgcttcttt acacattgat ggtaatcgag ttttttttt gttaatttat
18721 ctgttacatc aaaattgttt atgcttatat ctaaagtatc attgtgtatt atttttgca
18781 gacacactcg tgagacatgt agtctcaaag caaaccaaga aaagtgctaa caatgtcatt
18841 gagcatttaa atcgacaaat aacttatcag aaagatcacg gtctctcatc tctggcagat
18901 gttcctttgc acattgaagg taatctagtc ttattttgt tctttttaa tatattgatt
18961 aaaagattg tgatatattt atttaatata ttttgttat attatatcta tattttattg
19021 tttgtacttt ttttttgtag atacactaat aaaatcggct agttctgtac tttcagaacg
19081 acccatcaag aaaactaagg atattgctaa gttaatcaaa gatatgggaa gattaaagat
19141 caataaaaag gtaacaacga tgatcaaagc tgacaagaaa ctcgttacgg caaggttaa
19201 tcttgatcca gagaccatta aagagtggga tgtcttaatg gtgaatgatt caccaagccg
19261 atcatatgac gataaggaga cggaggccaa atggaaaaaa gaaagagaga ttttcaaac
19321 ccggatagat ctttcatta accggatgca tcgcttacaa ggtacattat tgttattatc
19381 attattgtta ttatgatcta tttatacttg tattctaaat tagcttacat atatatataa
19441 ggaatccaag tataagtgag tatgctaagt atatgatcat tttttgaaat tatgtttcct
19501 tccatgatgt ttaaatgatt gtcttgcagg caatagaaag tttaaacagt ggaaaggctc
19561 agttgttgac tcagtggttg gagttttttt gacacaaaat actaccgact atctttcaag
19621 gtaaaatctt tgtttaaatt gttaagaaat ttgaaaaact aattcatata atagatgatc
19681 actttgattg tgagtttcta cagcaacgcg tttatgagcg tggctgcaaa atttcctgtt
19741 gatgcaagag aaggtctatc atactatatt gaggaacctc aagatgctaa aagttctgaa
19801 tgtatcattt tatctgatga gtcaatatca aaggtggaag atcatgagaa tactgcaaaa
19861 aggaaaaacg agaaaaccgg tattatagaa gatgagatag ttgactggaa caatcttaga
19921 aggatgtaca cgaaagaagg atctcgtccc gaaatgcata tggactctgt taattggagt
19981 gacgtgagat tatctggcca aaatgttttg gaaaccacca ttaaaaaacg tggacaattc
20041 aggattcttt cagaaagaat attggtaaga aaaacaaaac ttctaatgaa ctttgtgaat
20101 aatttattca aatgatttaa gactaacact tttttttttt tccttgtttt ctcaagaaat
```

-continued

```
20161 ttcttaacga tgaagttaac caaaatggaa atattgatct ggaatggctt cgaaatgctc
20221 catcacattt agtgaagtat gtttatgttg gtttttatgt tctcatagat ctcattatta
20281 gtaagcgatc ataaactctt tctattattt tatcaggaga tatctgttgg aaatcgaagg
20341 gatagggctg aaaagtgctg agtgcgtacg actgttagga cttaaacatc atgcgtttcc
20401 ggtatgaaaa tattattatg atttttcatt taacatatat tattaatttt tactgataaa
20461 acccatgtgt taatgtgtag gttgacacaa atgttggtcg tatagcagtt cgactaggtc
20521 tggttcctct tgaaccttta ccaaatggag ttcaaatgca tcaactattc gagttatgtt
20581 ttctcattaa tttgattaag aaaatacatt acaagttact aacaactatc tcctatcgat
20641 aaacatgaac tcgtttcagg tacccttcaa tggattcgat tcaaaagtac ctttggccac
20701 gattgtgtaa acttccccaa gaaactttgt aagttcaaat gttttcctc aatttaagaa
20761 gccaactatt tttacgccat ttgaacacat attacctaat tttatttcta aatattttta
20821 cagatatgaa ctacattatc aaatgataac atttggaaag gtgtgcgtta cttttttctt
20881 ttttatatta atgaataaaa taatattgtt ggtttaatca aattttgtca acttttaggtt
20941 ttctgcacaa aaactattcc taattgtaat gcatgtccaa tgaagtcaga atgcaaatat
21001 tttgcaagtg catatgtcag gtacaatctt ttttctcttt cctactttga tacttagata
21061 taacttaatt tgttaattcc ataaatatta aagaaaaatc ttagaataat cataaaaaat
21121 aattgctaaa cgtctcagct attttatata ataaattttc taaatattga gagtgaattt
21181 gagtttttaat aattacatta tatatataaa tatataatgt tagaattgac aaattgtgtt
21241 ttttttttaat agttctaaag ttcttctcga gagtccagaa gaaaagatgc atgagcctaa
21301 tacttttatg aatgcacatt ctcaagacgt tgctgtagat atgacatcaa atataaattt
21361 ggtagaagaa tgtgtttctt ctggatgtag cgatcaagct atatgttata agccactagt
21421 tgagtttcct tcgtccccaa gagcggaaat tcccgagtca acagacattg aagatgttcc
21481 attcatgaat ctttatcagt catatgctag tgttcctaaa attgattttg acttggatgc
21541 attgaagaaa agtgtagaag atgcacttgt aataagtggc aggatgagca gttctgatga
21601 agaaatatca aaagcattag tgattcccac tcctgaaaat gcatgcattc ctatcaaacc
21661 acctcggaaa atgaagtatt ataatcgact aagaactgaa catgtggtgt aagtatcttt
21721 atgtaaatac tgattatacc atataaatta tatgcatttt ttgggaatat ataatctaat
21781 acttgttttt tttgcagtta tgtgcttcct gataatcatg agctgctaca cgatgtaagt
21841 atacacatac tttaagctac aaaaaaatgc aactcttttg tataattaat tagaaaatgc
21901 ttttggtttt ttacatatat tatatagttt gagagaagaa aacttgatga tccaagtcct
21961 taccttcttg cgatttggca accaggtata atacaagcat aatttatcat tgttcacata
22021 actataaact aaattttca ttcgaataat ttttaggtga aacatcatcc tcgttcgttc
22081 caccaaagaa aaagtgtagt tctgatggat caaagctttg caagataaag aattgttcat
22141 attgttggac tatacgagaa caaaactcca acatttttcg cggaacaatt ttggtaaaca
22201 aaatttacaa tttgatattt taacattggt gacttgaaac tcacataaat tcaattgatc
22261 agattccatg tagaacagca atgcgagggg cctttccact taatggaaca tacttccaaa
22321 ccaatgaggc aagcattttt tcttataatt ttttgtctga gttttttactt aatggtttta
22381 aagagaacac aatggtttat ttttccaggt ttttgctgat catgagacaa gcttaaaccc
22441 cattgtcttt cgtagggagt tgtgtaaggg actagaaaaa cgtgcactat attgtggttc
22501 aacagtgaca tctatttta aactttaga cacaagacgg attgaacttt gcttttggac
```

-continued

```
22561 aggtaacaaa cataaatata tattaaattt tttgttgaat tatgaaytta aaataactgt
22621 ggaatgttgt gtggtgctgt gcagggtttt tatgtttgag agcatttgat cgaaagcaac
22681 gagatccaaa agagcttgtc cgacgtctac acactccacc tgatgagaga gggccaaagt
22741 ttatgagtga tgatgatata TAGtttcatt ttattctttt tggtctagtt agcaaattat
22801 ttaaacgaac gaatcttttc ttataataac aagcgattca acgattgagt aaatgcacgt
22861 acgtattgtt tcttgattta aatgcatgta cattataatt atttcacaag tggttttcat
22921 atagtagttg tggatgaaaa agaagagagc ccaagagttg gtcttatggt tatgcctggg
22981 ttttggattg gtggcagtgt cattcaaaac cgagtttatg tttctggtgt gaaggtcctt
23041 gagTGAagga tttcaggaac tgtcttaatg cttcttccca ctttgttgtg caactttat
23101 tttctctttg ttataagcaa gcctatatgt atcaatgata cagtatcatc tattgttcaa
23161 aaaaattgga attaatatct tcttcgtctc aacatctttg ggtcgatcgt tattcgatga
23221 cagtagcaac tagcgagtct cttgtgatat atcctagcca agcgacctca aaactttttt
23281 tacttcgatt gttgtcagta tttctgtttc agacgttttt agcaaaaaag ttctcatggt
23341 gataaaatta ggcttaaaac agtatgactc tgtctttaag actcagtttc agatagtaat
23401 aataaaatta cataaacaaa gagtggtcat agacgtgtat ctgtaagtgt tgtcagagat
```

SEQ ID NO:17
RICE(*Oryza sativa*) DMT1
>DMTRICE (1DMTRICE);

MQDFGQWLPQSQTTADLYFSSIPIPSQFDTSIETQTRTSAVVSSEKES
ANSFVPHNGTGLVERISNDAGLTEVVGSSAGPTECIDLNKTPARKPKKKKHRPKV
LKDDKPSKTPKSATPIPSTEKVEKPSGKRKYVRKKTKTSPGQPPAEQAASSHCRSELK
SVKRSLDFGGEVLQESTQSGSQVPVAEICTGPKRQSIPSTIQRDSQSQLACHVVSST
SSIHTSASQMVNAHLFPPDNMPNGVLLDLNNSTSQLQNEHAKFVDSPARLFGSRI
RQTSGKNSLLEIYAGMSDRNVPDLNSSISQTHSMSTDFAQYLLSSSQASVRETQM
ANQMLNGHRMPENPITPSHCIERAALKEHLNHVPHAKAAVMNGQMPHSYRLAQ
NPILPPNHIEGYQVMENLSELVTTNDYLTASPFSQTGAANRQHNIGDSMHIHALD
PRRSNASSGSWISLGVNFNQQNNGWASAGAADAASSHAPYFSEPHKRMRTAYL
NNYPNGVVGHFSTSSTDLSNNENENVASAINSNVFTLADAQRLIAREKSRASQRM
ISFRSSKNDMVNRSEMVHQHGRPAPHGSACRESIEVPDKQFGLMTEELTQLPSMP
NNPQREKYIPQTGSCQLQSLEHDMVKGHNLAGELHKQVTSPQVVIQSNFCVTPP
DVLGRRTSGEHLRTLIAPTHASTCKDTLKALSCQLESSRDIIRPPVNPIGPSSADVP
RTDNHQVKVSEETVTAKLPEKRKVGRPRKELKPGEKPKPRGRPRKGKVVGGELA
SKDSHTNIPLQNESTSCSYGPYAGEASVGRAVKANRVGENISGAMVSLLDSLDIVI
QKIKVLDINKSEDPVTAEPHGALVPYNGEFGPIVPFEGKVKRKRSRAKVDLDPVT
ALMWKLLMGPDMSDCAEGMDKDKEKWLNEERKIFQGRVDSFIARMHLVQGDR
RFSPWKGSVVDSVVGVFLTQNVSDHLSSSAFMALAAKFPVKPEASEKPANVMFH
TISENGDCSGLFGNSVKLQGEILVQEASNTAASFITTEDKEGSNSVELLGSSFGDG
VDGAAGVYSNIYENLPARLHATRRPVVQTGNAVEAEDGSLEGVVSSENSTISSQN

-continued

SSDYLFHMSDHMFSSMLLNFTAEDIGSRMPKATRTTYTELLRMQELKNKSNETI

ESSEYHGVPVSCSNNIQVLNGIQNIGSKHQPLHSSISYHQTGQVHLPDIVHASDLE

QSVYTGLNRVLDSNVTQTSYYPSPHPGIACNNKETQKADSLSNMLYGIDRSDKTTS

LSEPTPRIDNCFQPLSSEKMSFAREQSSSENYLSRNEAEAAFVKQHGTSNVQGDN

TVRTEQNGGENSQSGYSQQDDNVGFQTATTSNLYSSNLCQNQKANSEVLHGVSS

NLIENSKDDKKTSPKVPVDGSKAKRPRVGAGKKKTYDWDMLRKEVLYSHGNKE

RSQNAKDSIDWETIRQAEVKEISDTIRERGMNNMLAERIKDFLNRLVRDHGSIDLE

WLRYVDSDKAKDYLLSIRGLGLKSVECVRLLTLHHMAFPVDTNVGRICVRLGW

VPLQPLPESLQLHLLEMYPMLENIQKYLWPRLCKLDQRTLYELHYQMITFGKVFC

TKSKPNCNACPMRAECKHFASAFASARLALPGPEEKSLVTSGTPIAAETFHQTYIS

SRPVVSQLEWNSNTCHHGMNKRQPIIEEPASPEPEHETEEMKECAIEDSFVDDPEE

IPTIKLNFEEFTQNLKSYMQANNIEIEDADMSKALVAITPEVASIPTPKLKNVSRLR

TEHQVYELPDSHPLLEGFNQREPDDPCPYLLSIWTPGETAQSTDAPKSVCNSQEN

GELCASNTCFSCNSIREAQAQKVRGTLLIPCRTAMRGSFPLNGTYFQVNEVFADH

DSSRNPIDVPRSWIWNLPRRTVYFGTSIPTIFKGLTTEEIQHCFWRGFVCVRGFDRT

SRAPRPLYARLHFPASKITRNKKSAGSAPGRDDE

SEQ ID NO:18
>DMTRICE novel 723 amino acid NH2 terminus;

MQDFGQWLPQSQTTADLYFSSIPIPSQFDTSIETQTRTSAVVSSEKESANSFVPHNGTGLVERISNDAGLTEVVGSSAGP

TECIDLNKTPARKPKKKKHRPKVLKDDKPSKTPKSATPIPSTEKVEKPSGKRKYVRKKTSPGQPPAEQAASSHCRSELKS

VKRSLDFGGEVLQESTQSGSQVPVAEICTGPKRQSIPSTIQRDSQSQLACHVVSSTSSIHTSASQMVNAHLFPPDNMPNG

VLLDLNNSTSQLQNEHAKFVDSPARLFGSRIRQTSGKNSLLEIYAGMSDRNVPDLNSSISQTHSMSTDFAQYLLSSSQAS

VRETQMANQMLNGHRMPENPITPSHCIERAALKEHLNHVPHAKAAVMNGQMPHSYRLAQNPILPPNHIEGYQVMENLSEL

VTTNDYLTASPFSQTGAANRQHNIGDSMHIHALDPRRESNASSGSWISLGVNFNQQNNGWASAGAADAASSHAPYFSEPH

KRMRTAYLNNYPNGVVGHFSTSSTDLSNNENENVASAINSNVFTLADAQRLIAREKSRASQRMISFRSSKNDMVNRSEMV

HQHGRPAPHGSACRESIEVPDKQFGLMTEELTQLPSMPNNPQREKYIPQTGSCQLQSLEHDMVKGHNLAGELHKQVTSPQ

VVIQSNFCVTPPDVLGRRTSGEHLRTLIAPTHASTCKDTLKALSCQLESSRDIIRPPVNPIGPSSADVPRTDNHQVKVSE

ETV

SEQ ID NO:19
>DMTRICE nucleotide sequence from PAC P0489G09;
10261 aaatattgct taatggata taaagttgaa aaatgtactt gagggaagtt gtaggtgcac 10321 gtggggtccc acaatttttc ttcactagtg cacctttagt tatatatttt ttgcgcaaga 10381 ggacaaaggc gctccgtgta attttgagta agggccggcg ggatatttat ttgtgtaaag 10441 gacctagcca agaaaagcat gatagtgcat atgtatcctt tcttttctt ttcttttgtt 10501 ttcataactg tcttacagaa tttcatgttg gctggtgaca cttgtctcac tcattatttg 10561 gtatattttg actaaatgca acgtgttggt gctcggtagt ttatatttgt ttttacgcat -continued

```
10621 tcttcattga ctgtatgtat ttgatgttga taccctgggc tgtcttattt tataggtgga
10681 tgctgggagg ccacatagga ggcctgtgtg atccaagtgt gctgctcctg agttgaaatt
10741 gcatagccat atagcaacta ctggtgtaaa cttgagagat gaagtagtga aaggaaatat
10801 gcaggatttt ggacaatggc tgcctcaatc tcagaccact gccgatctat atttctccag
10861 tattccaata ccatcacagt tcgatacttc catagagacg cagactagaa cttctgcagt
10921 tgtatcgtca gagaaagaat ctgctaattc gttcgtccct cataatggta ctgggcttgt
10981 tgaacgcatt agcaatgatg ctgggctaac tgaagtagtt ggaagtagtg ctggaccaac
11041 tgaatgtatt gacttgaaca agacaccagc acggaaaccc aagaagaaaa agcacaggcc
11101 aaaggtgcta aaggacgata aaccatcgaa gacacctaaa tctgctactc caataccttc
11161 aacagaaaag gtagaaaaac catctggaaa gagaaaatat gtccgcaaga agacatctcc
11221 aggccaacct cctgcagaac aggcagctag ctcacactgc agatctgagc tgaagtcagt
11281 taaacgaagt ttggactttg gtggagaagt actgcaagag agtacacaat ctggatctca
11341 agttccggtg gcagaaatat gtactggtcc caagcgtcaa tcaatacctt ctaccatcca
11401 aagagattcg caaagccagt tggcttgcca cgtggtttct agcaccagct caattcacac
11461 ttcagctagt cagatggtta atgcacattt gtttcctcct gataacatgc caaatggagt
11521 attgcttgac ctcaataatt ctactagtca gttacaaaac gaacatgcta aatttgtgga
11581 cagtccggca cgtcttttg gttccagaat aagacagaca tcaggtaaaa attctttgct
11641 agaaatctat gctggcatgt cagatagaaa tgtacctgat ctcaacagtt caatcagtca
11701 gacgcatagc atgtctactg attttgctca atacttgctt tcatcctcac aagcttctgt
11761 aagggaaaca caaatggcca atcagatgct taatggtcat aggatgccag aaaatccaat
11821 tacacctagt cattgtattg aaagggctgc attgaaggaa catttgaatc atgttcctca
11881 cgcaaaagcc gcagtgatga atggccaaat gccccatagt tacaggttgg cgcaaaatCc
11941 catcctacct ccaaatcata ttgaagggta tcaagtgatg gaaaatttga gtgaacttgt
12001 cacgacaaat gactatctaa ctgctagtcc tttcagtcaa actggagctg caaataggca
12061 gcataatatt ggtgactcca tgcatataca tgcattggat cctagaagag agagtaatgc
12121 ttcaagtggt tcttggatat cattaggtgt gaactttaac caacaaaata atggatgggc
12181 atctgcaggt gctgccgatg ctgcgagctc acatgcccca tattttcag aacctcacaa
12241 aagaATGagg acagcttatc ttaacaatta tccaaatgga gtcgtgggac attttctaa
12301 ctcatctacg gatttgtcaa ataatgagaa tgaaaatgtg gcctcagcaa tcaactcaaa
12361 cgtttttacc cttgctgatg cacaaagatt gatagcccgt gagaaatcac gagcttccca
12421 aagaatgatc agttttagat catctaaaaa tgatatggtt aacagatcag aaatggtcca
12481 tcaacatggc agacctgctc cgcatggctc tgcatgcagg gagtctattg aagtacctga
12541 caaacagttc gggctcatga cagaagaact cacacaatta cctagtatgc aaataaccc
12601 acaaagggaa aaatatattc cgcaaactgg aagttgccaa cttcagtctt tggaacatga
12661 catggttaaa gggcataact tggcaggtga attgcataag caagtaactt cacctcaagt
12721 tgttattcag agcaatttct gtgttacccc tcctgatgtg ctcggcagaa gaaccagtgg
12781 ggagcattta agaaccctta tagctccaac acatgcatcg acatgtaagg acactctgaa
12841 agctttaagt tgtcaactgg agagttctag agacattatt aggcctcctg tcaatcctat
12901 aggyccatcc tctgccgatg ttccaagaac tgataaccat caagtcaagg tttctgaaga
12961 aaccgttaca gccaaactcc ctgagaagcg aaaagtagga cgtcccagaa aagagttaaa
```

-continued

```
13021 acctggtgag aaaccaaaac ctagaggccg tccaaggaag ggaaaagttg ttggtggaga
13081 acttgcatca aaggatagtc acactaatcc attgcaaaat gagagtactt catgttctta
13141 tggtccttat gcaggggagg cttctgttgg aagagcagtt aaagcaaata gagttggaga
13201 aaacatttct ggagctatgg tatccctact ggattcttta gatattgtta ttcaaaagat
13261 aaaggtcttg gacataaaca aatcagaaga ccctgtgaca gctgaacctc atggtgctct
13321 tgtcccttac aatggagaat ttggtcctat tgttcctttt gaggggaaag tgaaaagaaa
13381 acgctctcga gccaaagtgg atcttgaccc tgtaactgct ttaatgtgga agttactaat
13441 gggaccagat atgagtgatt gtgctgaagg tatggataag gataaagaga atggctaaa
13501 tgaagaaaga aaatattcc aagggcgtgt tgattcattt attgctcgaa tgcatctagt
13561 tcaaggtatt tctatcattt taaaattgtt ttcctaacat gaacatgatg gcttccatct
13621 tgtgattgct gccctcacat tagtgaatgg tctcaaatct tcaatattta ctgtgtaccc
13681 aaatcctatt tcttcatccc aatatattca tgtttgtact cgtactgtcc cattagactt
13741 gcattgtgct gtgaagatca acacctttac ttttaggatt acctctatgt ttgcaggaga
13801 tcggcgtttt tctccttgga aaggatcagt tgtagattct gtagtgggag tatttcttac
13861 acagaatgtt tcggaccatc tttccaggtg aataatgcct agagcctatt tgaaaactgt
13921 gacttgactt gcattgtgag gttatgttgt ttttctgtct gactatttcc ttttttttca
13981 gctctgcatt tatggctctt gctgcaaaat ttcctgtaaa gccagaagcc tctgaaaaac
14041 ccgcaaatgt gatgtttcat acaatttcag aaaatggtga ttgttctggg ttgtttggta
14101 attctgtcaa gctacagggt gagatccttg ttcaggaggc cagcaacaca gcagcctctt
14161 ttatcacaac cgaggataag gaaggaagta acgtgtggaa attgcttgga agttcttttg
14221 gggatggagt ggatggtgca gcaggagttt attctaatat ttatgagaat ctgccagcta
14281 gactgcatgc tactaggcgt ccagtCgttc aaactggaaa cgctgtcgaa gcggaagatg
14341 ggtcactgga gggtgttgtt tcatcagaaa actccactat ttcatctcaa aattcatcag
14401 attatctatt tcacatgtct gatcatatgt tttcgagcat gttactaaat ttcactgccg
14461 aagacattgg cagcagaaat atgcccaaag caacaagaac cacatataca gaacttctac
14521 gaatgcagga gctgaagaac aagtctaatg aaaccattga atcatcagag tatcatgggg
14581 ttccagtctc atgtagtaac aacattcaag tgctcaatgg aatacaaaat atcggcagta
14641 aacatcagcc tttacattcc tctatttcat atcaccagac tggccaagtt cacctcccag
14701 acatagtaca tgcgagtgat ttggagcaat cagtatacac tggccttaat agagtgcttg
14761 attctaatgt tacacaaacc agttattatc cttcacctca tcctggaatt gcctgtaaca
14821 atgaaacaca aaaggctgac tctttaagca acatgttata tggtatagat agatcagata
14881 agactacttc cctgtctgag cctacaccaa gaatcgataa ctgttttcaa ccattaagtt
14941 cagagaaaat gtcatttgct agggaacagt cctcttctga aaattatctt tcaaggaatg
15001 aagctgaagc tgcatttgtt aaacagcatg gaacatcaaa tgtgcaaggt gataatactg
15061 tcaggacaga gcaaaatgga ggtgaaaatt ctcaatcagg atacagccaa caggatgata
15121 atgttggatt tcaaacagcg acaaccagta atctttattc ttcaaactta tgccaaaacc
15181 agaaagcaaa ttctgaagta ctacacggag tttcttccaa cttgatagag aattctaaag
15241 atgacaaaaa gacttccccC aaagttccag tcgatggatc aaaagcaaag aggccaagag
15301 ttggggctgg taaaaagaaa acatatgatt gggatatgtt gagaaaagaa gttcttttaca
15361 gtcatggtaa taagaaaaga tcccagaatg ctaaggactc aattgattgg gaaacaataa
```

-continued

```
15421 gacaagcaga ggtgaaggaa atatctgaca caattagaga gcgaggaatg aataacatgc
15481 tggcagaacg gataaaagta agtatggcat aaaacagttt acattgaaag ttgacataac
15541 tctagtcata tgtgcatgca tgctattcca tatagatttg cttatttgtt ggaattccaa
15601 gttttggatc aaccatactc atctttagca attcatgttg caggacttcc taaaccgatt
15661 ggtgagagac catgggagca tcgatcttga gtggttgcgc tatgtcgatt cagataaagc
15721 gaagtaagct aactaaattt attttgagca aacattcata atgcaattgg cccttgggca
15781 ttctataatt tgtcattttg acctctgcat tgcttagcaa tgacaattgg atgtagtgag
15841 catgggtaat aatgtaagca atgacaattg gatgtagtgg gcatggttaa taattgaaca
15901 tgtctgtgtt tgcgggataa taatgcctat cacctgtgag cctgtgacat gcaaaccttg
15961 aacgttgaac cttgaacccc ctacctcgca ctgtgtgctc tcaaccaact gagcaagtga
16021 gggaccttgt tgtatggaaa aaataatttt aaataaccct tgattcaacc aaagcttcat
16081 aaaagaatat attttctatt attcatttga accagcggtt gaaccagtga accgatggtc
16141 ttgctggtcc ggatttaata ataactatgg ctagaacaga ttagagcacc gaatacttgc
16201 gcgatgctaa atatttcaat ggggacacac ctgctcgtgt gttgcatcaa ctacctaagc
16261 cacacaggca tggcaatcaa atcagcttgc ccatgtaaca tcaactatct gatcgcgaga
16321 aggccggagc tctcacttga tgtttgtcat tcaaaaaata gttattcacc aatgcaatgt
16381 caagctcccg taaagaccat gaatgtagtt tatccttctt tgatcaagtt tttatttata
16441 ttaaagtgtt taccaatgta atcctacatt atttgtacct ggttttttaca tataaataca
16501 ttgtaccttt tgtgtttctt ccagggacta tctcttaagc attagaggac ttggacttaa
16561 aagtgttgag tgtgtgcgtc ttttgacact ccatcacatg gcttttcctg tatgtttcct
16621 ttcacaaata attttcaaga atcttcgttt ctttatttct ggagaagtgg agattttatc
16681 tgtatctgtt gatgatgtag gtggatacaa atgttggtag aatatgtgtg aggcttggat
16741 gggtgccact tcagcccta cccgagtctc ttcagttgca cctgttggag atgtaagtat
16801 cttaaatcca ctggttggct tcactaatgc tggagagtga taggagtttg atcatctgct
16861 attgaaggta tccaatgctg gagaacatac agaaatacct ctggccgagg ttatgcaagc
16921 ttgatcaacg gacattgtga gttttagaaa tgcagttaaa aactatatat ataagagcat
16981 gtcattatct gagagtgtaT AAcaggttct tgatgatatg taggtatgag cttcactatc
17041 aaatgataac ttttggaaag gtatgagaca caactttga taaagtgaat tcaacccaat
17101 tactgtgttt tgatggacca tctgtgttac tttccttcta ggtattttgt acaaaaagta
17161 agcccaattg caacgcatgc ccaatgagag ctgagtgcaa gcactttgca agtgcatttg
17221 ccaggtaatt ctcaagatgt acatatttta tatacattct gtgaaatcac ggtgatgatt
17281 gttaggtatg aacaattggc tgagatcccc cccctccccc ctcccatcct tttcctggtc
17341 ctacaagttc tcctaggcta atttaactgg tgcataccac atttatgtta ttttgataca
17401 tcaaagatta tgtttgtggt tgtgaggcta tattagtgtg ttgtatgtaa ctcagttttg
17461 caattgtagt tttagttaga acacgttgtt ctctacattt taataaatac tttttgactg
17521 gacatcaatg actggtgtat ttccgatata aaaggttga ttgttgccga gggatttcaa
17581 ttcggtccga ataggttcga caaatgcagt gggcctatta gtttaagagt gaaagttcta
17641 tcagctgttt gactccactg tgacctttac actttgtact tttgaagaaa cagactaacc
17701 tgctcatatt aaagtcttgg aatgactcca ttgcgacctt tacgctttgt attttagaag
17761 aaacagacta acctgttcat attagagtct tggaactgtg tgtgtgtgtg tttttttttt
```

-continued

```
17821 ttttgggggg ggggggggcat ggagatttaa tccaacattc ctggatgacc ttatattggt
17881 aatgatatgg ttttttttatg atatagtgca aggctcgctc ttcctggacc tgaagagaag
17941 agtttagtta catctggaac cccaatagct gcagaaacct tccaccagac atatataagt
18001 tctaggcctg tagtaagtca gcttgagtgg aattcaaaca cctgtcacca tggtatgaac
18061 aatcgccagc caatcattga ggagccagca agcccagaac ctgaacatga gacagaagag
18121 atgaaagagt gtgcaataga ggatagtttt gtcgatgatc cagaagaaat ccctactatc
18181 aagcttaatt ttgaggagtt tacacagaac ctgaagagtt atatgcaagc aaataacatt
18241 gagattgaag atgctgatat gtcaaaggct ttggtcgcta taactcctga agttgcttct
18301 atcccaactc ctaagctcaa gaatgtcagt cgcctaagga cagagcacca agtgtatgat
18361 cttgtccctc ttgcaaaacc aatctcatga atatttacta ttgactatca tgtgttttgc
18421 tgcattgctt acttctctgt tttcaacata tatgtagcta tgaactgcca gattcacatc
18481 cacttcttga aggagtaagt tcataaaaca ttatagaatt ctgtactttc cttatcacca
18541 actgagaata tattgatgct tattttctta caatacacag ttcaaccaaa gagaaccaga
18601 tgatccttgc ccatacctac tctctatatg acccccaggt aagaagtgca taaacagaac
18661 acaatatcat gggaaccaaa cttttttcaa tggttactta taattgttga aatatgcaac
18721 aggtgaaaca gctcaatcaa ctgatgcacc taagtcggtc tgcaattcac aagagaatgg
18781 tgaactatgt gcaagcaata catgctttag ttgcaacagt ataagagaag cgcaggacca
18841 aaaagttcga gggacactgc tggtaagtag ttgtttctgt aacatatgct cagttgccct
18901 tggttcaaga tgtgctattc aagtttatca tgttcacgaa tagtgataaa gctgctatct
18961 gtcctagcta ttgtccaagc tataacagtt ctgattcact ggttgggcac cagctaggga
19021 ataggatgta aaaaacttat cccgcagttt gttgacaatc tgttttttctt tgttgaaaat
19081 taaaaataga taccatgccg aacagcaatg agaggaagct ttccacttaa tgggacatat
19141 tttcaagtca atgaggtgaa acagaaaagt tcttaaagtt gatcttagtt taattattat
19201 aataccatta aaatatatgc aagtttctac tttctagtat ctctttttatt agtgttcaaa
19261 tgttatgcgg caggtatttg ctgatcatga ctcaagccgg aacccgattg atgttccaag
19321 gagttggata tggaatctcc ctaggagaac tgtttacttt ggaacttcaa ttccgacaat
19381 atttaaaggt atttcactaa taaattttga ccaagaatag gattttttggc agcgccaaat
19441 gtgccactat ctttattgtg tgaagtccat tatgtgattg taataatttg aatcaccaag
19501 aggactaagg cctgctttgg gacatattac gagcagcttt tgcttgcaaa gaaaccagat
19561 tctggtgccg caccttctcc gctcttctgc cacccaagtc cgtccaatac ccctcattga
19621 gcgcttggat cctaacccca tctgccatca tgcatcatcc tgctaacaac tgcttccacc
19681 attgcctgtt tctgttgttg ggaggcactc acgctgcttg ctatagttta ggttttcttt
19741 gtgtcctgat ttagatgaaa tttccagctg ctgtcttta cataactagc taaatgtccg
19801 cgctttgcta tggataaatag aaaatatatt ataatattgt caaataaatt aaatatgttt
19861 tatacgaaat gtgttaacaa tccttttgct atagggaata ttgaccttaa tttgatttta
19921 tatgtggcta tccatttaga tttgtttgtt tttctaataa taataagttc aagggctaat
19981 gtacaaaatt gacaatggga gtaggtgggg tggcagattc actgccacca ccactacctt
20041 cttttaaagg ggtatataga tttgcagcag tggttgcttg atctgtgatt tgaaatgtca
20101 agtacacgct catgcatcag caccatatgt ctacgctcct gacccaacat gcaaccaatg
20161 caattgaggg ttggctctga tacaattact aatgtcctat atccaaaaca actataggcc
```

-continued

```
20221 tatgaccaaa cataattaat aacctcgctt gcgcttttgt cctcacttgc tccatgtaaa 20281 agggttaacc cgaggttact atgttaggaa tagctggktt tatgaaacgg ttcaactctc 20341 aactcctcat atagcactaa ttcatgtatt gctgtcagca gtgatttgag ttccagatca 20401 tgctcataag ataggaccaa attgtcctta ctatctactc cctccgtccc aaaatataag 20461 gtatttccgg tcaaaatatc ttatattttg ggatggaggg agtactatac tacggaccca 20521 ccaccaaata gtgccgcaga agagagagag agagagagaa gagggggtgg gggtgggggt 20581 gtatgggtga aataagaata gtgccaagta tttgccaaca aatgaggcgc tcaaatgtgt 20641 cacatcaatt gggaagtatg tcagatcaac tgaaaatttg attgggaaat tattattcat 20701 gcaacaaagc tgtacaactg atcccatgtt tctatcgcag gtttgacaac tgaagaaata 20761 caacattgct tttggagagg taatcatttt tttttgtatg tacgttttgg tttccataac 20821 aaagagagat gaagtgtata ggtactatgt ttactgacaa ggataataat agtagcaagt 20881 ataggcag aggagcatgt ctctattcta ccagtattat tactcataat aactagtata 20941 tccttttttt tgccatttca gctgatagct actctccagt caaaatattt gccatctcta 21001 ttgaacttt cattgtcttc tgaatgtatc ttactcttgg atcattaata tttcattttg 21061 tcacgatata gtggtatagg acaataaaat catgggaagt atttattttc atcaccaatc 21121 tactcatata attttcaaat gacaattata aatatcttaa aaatatattg ttagttgtcc 21181 tgtataaaat aattgtcaca ccctagtcca cagcgacaag aatttgtgtc tacaggctag 21241 agtgagtact ctagaagtat cttcatagga atcggaataa aatgccaatg tgaatgaaca 21301 aggatatcaa gtataccctc aaaatctcta gagaggattg cgtaaatatg taggtgtaat 21361 taaacaattg tttcatatgg agggttttct taaggaggt acaagactta tcaatatggg 21421 taaagtagtt tttatccata ggcattgttg gcagaaagct gcttagggta gaatgctact 21481 ccctccgtcc cacaatataa gagattttga gtttttgctt gcaacgtttg accactcggc 21541 ttattcaaaa atttttgaaa ttattattta ttttatttgt gacttacttt attattcaca 21601 gtactttaag tacaacttt cgttttttat atttgcaaaa aaaattgtat aagacgagtg 21661 gtcaaacgtt gtacgcaaaa actcaaaatc ccttatattg tgggacggag ggagtactta 21721 tggatgcctt ttttgtccaa gatgtcagta acatttttct tcagggatgt ggattttac 21781 ttctttttc cctaacttt tcaggatttg tgtgcgtgag aggctttgat aggacatcaa 21841 gagcacccag accactgtat gcaagactcc actttccagc aagcaaaatt accaggaata 21901 aaaaatctgc aggttctgct ccaggaagag atgatgaata ggccatctgg aaaaccagaa 21961 aggaaataaa gaggaggtac atatgatctg ccagaagatc actgacctga aatggatcgc 22021 tgaccaataa gttgccgtag gcaattcaat tatttctggc catatacatc tgctgaaagt 22081 tatgaactcc agccactgac gaattcgtgg tgctggtatt cttcggcaac atgatccatc 22141 atacagattc tatgcttggt tgttgcaagc aattcttatg cggtgacagt tgctgctgat 22201 agggagaaaa ggcatgtccg gcggctcagc ggctctaact gtactttcat atgagtggaa 22261 ccgattgttg tacatgtgaa aagtttgcca ttcaaaatgg tcattcatgt tgttaggtca 22321 ttcatgtagt cgatgtcaaa ttaatcatca attatttgat ttgattcatt cacaagttta
```

SEQ ID NO:20
CORN(*ZEA MAYS*)DMT.1
>Corn DMT.1 660990 (688512 selclone ID);

EPDDPCPYLLSIWTPGETAQSIDAPKTFCDSGETGRLCGSSTCFSCNNIREMQAQKVRGT

LLIPCRTAMRGSFPLNGTYFQVNEVFADHCSSQNPIDVPRSWIWDLPRRTVYFGTSVRTI

FRGLTTEEIQRCFWRGFVCVRGFDRTVRAPRPLYARLHFPVSKVVRGKKPGAARAEE

SEQ ID NO:21
>Corn DMT.1 cDNA 660990 (668512 selcone ID);

gaaccagatgatccttgtccatatcttctttccatatggaccccaggtgaaactgcacaa
tcgatcgatgcccccaagac attctgtgattcaggggagacgggtagactatgtggaagttcaacatgctttagttgcaa
caatatacgagaaatgcagg ctcagaaagtcagaggaacacttttgataccatgccgaacagcaatgagaggaagcttcc
cacttaatgggacgtatttt caagttaatgaggtatttgctgaccattgctcaagtcaaaatccaattgatgtcccacga
agttggatttgggacctccc aagacgaactgtttactttggaacctcagttcctacaatattcagaggtttaacgactga
agagatacaacgatgctttt ggagaggatttgtttgcgtgaggggctttgataggacagtgcgggcaccaaggcccttt
atgcaaggttgcattttcct gtcagcaaggttgttagaggcaaaaagcctggagcagcaagagcagaagaataatagaac
attgaagaaatatagggtg ctaaccagatgaggatggatagcccgaaatgagatgctgacccaataggtcgccaaatca
cctccaaattctaacccaat gacttccatctgtaatgaatggcaataccttgaaaacctgtgatggagatgttttgtggc
gacatgatctcttaaattag attccgtctttggtaacagcctagctgttcttgttgagtcgcatattctttattctgaag
atcaatatagcaaatggg SEQ ID NO:22
CORN(*ZEA MAYS*)DMT.2
>Corn DMT.2 371537 (441428 selclone ID);

MITFGKVFCTKRQPNCNACPMRSECKHFASAFASARLALPAPQEESLVKLSNPFAFQNSS

MHAMNSTHLPRLEGSIHSREFLPKNSEPIIEEPASPREERPPXTMENDIEDFYEDGEIPT

IKLNMEAFAQNLENCIKESNNELQSDDIAKALVAIXTEXASIPXPK

SEQ ID NO:23
>Corn DMT.2 cDNA 371537 (441428 selcone ID)

tatcagatgattacatttggaaaggtcttttgtaccaaaagacagccaaattgcaatgca
tgcccaatgaggagtgagtg caagcattttgcaagtgcatttgcaagtgcaaggcttgcacttcctgctccccaggaga
aagcttagtgaagttgagca atccatttgctttccagaatagcagcatgcatgctatgaattcgactcacctacctcgcc
ttgaggggagtatccattca

```
agggagtttcttcctaagaactcagagccaataatcgaggagcctgcaagtccaagagag
gaaagacctccakaaaccat ggaaaatgatattgaagattttatgaagatggtgaaatcccaacaataaagcttaacat
ggaagcttttgcacaaaact tggagaattgcattaaagaaagcaataacgaactccagtctgatgatattgcaaaagcat
tggttgctattarcactgaa rcagcttcsattcctgkaccgaaact
```

SEQ ID NO:24
Corn(*Zea mays*)DMT.3
>Corn DMT.3 218853;

MPRKPKRKAPASPARHDPSPEPYPSHASPCSAQCLVVRDALLAFHGFPEEFAAFRVLRLG

GLSPNRDPRPSSPTVLDGLVTTLLSQNTTDAISRRAFASLKAAFPSWDQVVDEEGKRLED

AIRCGGLAATKAARIRSMLRDVRERRGKICLEYLRELSVDEVKKELSRFKGIGPKTVACV

LMFYLQKDDFPVDTHVLRITKAMGWVPATASREKAYIHLNNKIPDDLKFDLNCLFVTHGK

LCQSCTKKVGSDKRKSSNSACPLAGYCCIGEKLQQL

SEQ ID NO:25
WHEAT DMT.1
>Wheat DMT.1 614028 (887053 selclone ID);

MRAECKHFASAFASARLALPGPEEKSLVTSGNPIASGSCQQPYISSMRLNQLDWNANAHD

HILDNRQPIIEEPASPEPEPETAEMRESAIEDIFLDDPEEIPTIKLNFEEFAQNLKNYMQ

VNNIEMEDADMSSALVAITPEAASIPTPRLKNVSRLRTEHQVYELPDSHPLLEGYDQREP

DDP

SEQ ID NO:26
>Wheat DMT.1 614028 (887053 selclone ID);

```
          tgcccaatgagagctgaatgcaagcactttgcaagtgcatttgcaagtgctagacttgctcttcctggacctg aagagaagagtttggttacgtcaggaaacccaattgcttcagggagctgccagcagccatacataagttctatgcgtttaaatcaa cttgactggaatgcaaatgcccatgaccatattctggacaatcgccagccaatcattgaggagccagcaagtccggaaccagaa ccagagactgcagagatgagagagagtgccatagaggatattttcttgatgatcctgaagaaattcctacaatcaagcttaatttc gaggagtttgcacagaatctcaagaattatatgcaagtcaataacattgaaatggaagatgctgatatgtcaagtgccttggttgcc ataactccggaagctgcatctatcccgactcctaggctcaagaatgttagtcgcctaagaacagagcatcaagtctatgaactgcc ggactcacatccacttctggaaggatacgaccaaagagagcctgatgatccttg
```

SEQ ID NO:27
Wheat DMT.2

>Wheat DMT.2 568842 (908118 selclone ID);

NRVDESTVGGADKAASPKKTRTTRKKNTENFDWDKFRRQACADGHMKERKSERRDSVDWE

AVRCADVQRISQAIRERGMNNVLSERIQEFLNRLVRDHGSIDLEWLRDIPPDSAKDYLLS

IRGLGLKSVECVRLLTLHHLAFPVD

SEQ ID NO:28
>Wheat DMT.2 568842 (selclone ID 908118);

caaacagggtggatgaatctactgtcggaggagcagataaagcagcaagtccaaagaaaacaagaaccacaagaaaaaaa aatactgaaaacttcgactgggacaaatttcgaagacaggcctgtgctgatggccacatgaaagaaaggaagtctgaaag aagagactctgttgattgggaagcagtacgatgtgcagatgtacaaagaatttctcaggccatccgggaacgaggaatga ataatgtttatcagaacgaatccaggaattcctgaatcgcttggttagagatcatggaagcattgatcttgaatggtta agagatatccccccctgactcagcaaaggactacttgcttagcatacgtggactgggctcaaaagtgttgaatgtgttcg tctactgacattacatcatctcgctttccctgtwgacac SEQ ID NO:29
WHEAT DMT.3
>Wheat DMT.3 611792 (838515 selclone ID);

NRKQVNEVFADHKSSYDPIYVAREQLWKLERRMVYFGTSVPSIFKGLTTEEIQQCFWKGF

VCVRGFERETGAPRPLCQHLHVAASKVPRSRNAAAAGLNSDSAKASAP

SEQ ID NO:30
>Wheat DMT.3 611792(838515 selclone ID);

aatcgaaaacaagttaatgaggtatttgcagaccacaaatctagctacgatcccatatacgtgcaaggga gcagttatggaagttggaaagacgaatggtctactttggaacttcagtgccctccatattcaaaggtctaacaactgaagaaataca gcagtgcttctggaaaggatttgtctgtgtgcggggattcgagagggaaaccggggcaccaaggcctctatgccaacatctgca cgtcgcggctagcaaagtgccgagatcacgcaacgcggcagcagctgggctgaactcggattcagcaaaggcatcggctcca tgagtatcatcacaccggctatcgacctgtgcatgggtacgctagtgttggttcctgccgggcwacagccgttyttgtaggaaata aaccsctgcgcaaragaattatcatccagttggtytgagtgtatacttytgctgtagkaccttttttTaaatccctgtgagctytattg taccttgaatttactttccgaccagtttatccgcttgcaaaraggcctttgttatgkaccggcatcttgttgtatatacatcatggttcctc traaaaacttgtcttgccakacgaccttacgt SEQ ID NO:31
Wheat DMT.4

>Wheat DMT.4 615131 (861906 selclone ID);

MRSECRHFASAFASARLALPAPQEKSLVMSSNQFSFQSGGMPTPYSTVLPQLEGSAQGQD

FCTNNSEPIIEEPASPAREECPETLENDTEDYDPDTGEIPLTKLNLQAFAQNLENCTKES

NMDLGSDDTAKALVAVSTGSASIPV

SEQ ID NO:32
>Wheat DMT.4 615131 (861906 selclone ID);

tacttttggaaaggtgttctgtacaaaaaacaagccaaattgcaatgcttgtccaatgag aagcgaatgcaggcatttcgcaagtgccttcgcaagtgcacggcttgcacttcctgcacc tcaggagaaaagtttggtgatgtcgagcaatcaattcagtttccagagtggtggcatgcc aactccatactcaactgtgcttcctcagcttgagggaagtgcccagggacaggattttg cactaacaattcagagccaattattgaggagccagcaagtccagcacgggaagaatgtcc agaaactcttgaaaatgata ttgaagattacgatccagatactggtgaaatcccactaattaagcttaacttgcaagctt ttgctcagaacttggaaaactgcattaaagaaagcaatatggatcttggtctgatgata tcgcgaaagcacttgttgctgttagcactggatcagcttcaattcctgtccc SEQ ID NO:33
Soybean(Glycine max)DMT.1

>Soy DMT.1 449122 (557119 selclone ID);

MDSLDWDAVRCADVSETAETIKERGMNNRLADRIKNFLNRLVEEHGSIDLEWLRDVPPDK

AKEYLLSTRGLGLKSVECVRLLTLHHLAFPVDTNVGRIAVRLGWVPLQPLPESLQLHLLE

LYPVLESIQKYLWPRLCKLDQETLYELHYQMTTFGKXFCTKSKRNCNACPMRXECRHFAS

AFASARFALPGPEQKSIVSTTGNSVINQNPSEIISQLHLPPPENTAQEDEIQLTEVSRQL

ESKFEINICQPIIEEPRTPEPECLQESQTDIEDAFYEDSSEIPTINLNIEEFTLNLQN

SEQ ID NO:34
>Soy DMT.1 449122 (557119 selclone ID);
          ataaaatttaakagcaaggaacaagaaaaagagaaaaaggatgayttgactgggatagtttaagaattg aagcacaggctaaggctgggaaaagagaaaagacagataacaccatggattctttggactgggatgctgtgagatgtgcagat gtcagtgaaatcgctgagaccatcaaagaaggggcatgaacaacaggcttgcagatcgtattaagaatttcttaaatcgattggt tgaagaacatggaagcattgaccttgaatggcttagagacgttccacctgacaaagcaaaagaatacttgctcagcataagagga ttgggactaaaaagtgtggaatgtgtgcggcttttaacactgcaccatcttgccttcccggtagacacaaatgtcggacgtatagca gtacgactgggatgggtccctctacagccactgcctgagtcactgcagttgcatctcctagaattgtacccagtgttggagtcaata caaaatatctctggcctcgactatgcaagctagatcaggaaacactatatgagctacattaccagatgattacatttggaaaggkc ttctgtacaaaaagcaaaccaaattgtaatgcatgcccaatgagaggagaat SEQ ID NO:35
SOYBEAN(GLYCINE MAX)DMT.2
>Soy DMT.2 387990 (473695 selclone ID);

MRMTTDLVSQQSLTARLQLSTLKDKLKIQCRKARGLDFGRNESSKIDSSPVKLRSREHGK

EKKNNFDWDSLRTQAEAKAGKREKTENTMDSLDWDAVRRADVSETANATKERGMNNMLAE

RTQSFLNLLVDKHGGTDLEWLRDVPPDQAKEFLLSIRGLGLKSVECVRLLTLHHLAFPVD

TNVGRTAVRLGWVPLQPLPESLQLHLLELYPVLESTQKYLWPRLCKLDQRTLYELHYQLI

TFGKVFCTKSK

SEQ ID NO:36
>Soy DMT.2 387990 (473695 selclone ID);
gaaaagataggatcattctcagatagcaactcagaaatagaagacctgtctagcgctgcc
aagtacaatagttattataa tagaatttctttcagtgagcttttagaaatggcaagttcaaccat9ttgcatgaagttaa
cagtcaaagaagcaaatcaa ctgagaacttaggagatacatgtgatcagtctatagacatgaagcatgacaacctggcag
aaaacttggaaaaatcggat gttactcaaggctccgcagaagcacccatcaccaatggatatacttttaaaataacccca
aactcaggagtacttgaggt taactgttatgatcctctcaaaatagaagtcccatcaagtggctcctcaaagggtaaaga
tgagaatgacaatagatcta gtttcccaacagagtctgactgccaggctgcaattgtccattctcaaggacaaactgaag
atccaatgcaggaaagcaag gggactagattttggtaggaatgaaagcagtaagatagattcttccctgtaaaattaag
gagcagggagcatggaaaag agaaaaagaataactttgattgggatagtttaagaatacaagcagaagctaaggcaggga
aaagagaaaagacagagaac accatggactccttggactgggatgctgttagacgcgcagatgtcagtgaaattgccaat
gcaatcaaagaaagggcat gaacaacatgcttgctgaacgtattcagagtttcctgaatctattggttgacaagcatgg
gggcatcgatcttgagtggc tgagagatgttccacctgatcaagcaaaagaattcttgctcagcataagggattgggat
tgaaaagtgtggagtgtgta cgactcttaacactacaccatcttgcctttccggtggacacaaatgttggacgtatagca
gtaagattgggatgggtgcc tctccagccactgccagagtcactacagttgcatcttctagaattgtacccagtgttgga
gtccatacaaaaatatctct ggccccggctctgcaagctagaccaaagaacattgtatgagctgcattaccagctgatta
catttggaaaggtcttctgt actaaaagcaagcc SEQ ID NO:37
SOYBEAN(GLYCINE MAX)DMT.3
>Soy DMT.3 657152 (546665 selclone ID);

INQAELQQTEVIRQLEAKSEINISQPITEEPATPEPECSQVSBNDIEDTFNEESCEIPTI

KLDIEEFTLNLQNYMQENMELQEGEMSKALVAHPGAACIPTPKLKNVSRLRTEHYVYEL

PDSHPLLNGWNKREPDDPGKYLLATWTPGETABSTQPPESKCSSQEECGXLCNENECFSC

NSFREAXFXDSXRDTPDTMSNSXXXGAFH

SEQ ID NO:38
>Soy DMT.3 657152 (546665 selclone ID);

tataaaccaagcagaacttcaacaaacagaagtgatcaggcaactagaagcaaaatctga
aatcaacatcagccaaccta ttattgaagagccagcaactccagagccagaatgctcccaagtatccgaaaatgatatag
aggatacctttcaatgaggaa tcatgtgaaattcccaccatcaaactagacatagaagagttcactttgaacttacaaaac
tatatgcaagaaaacatgga acttcaagaaggtgaaatgtcaaggccttggttgctctacatccaggtgctgcatgcat
tcctacacccaagctgaaga atgtgagccggttgcgaacagagcattatgtttatgaactccctgattcacatccccttc
tgaatgggtggaacaagcga gaacctgatgatccaggcaaataccttctagctatatggactccaggggagacagcagat
tctatacagccaccagaaag caaatgcagctctcaggaatgtggccggctctgtaatgagaatgaatgttttctcatgcaa
cagtttccgtgaagcaaggt tcacagatagttcgagggacactcctgataccatgtcgaacagctwtgaragggag SEQ ID NO:39
SOYBEAN(GLYCINE MAX)DMT.4
>Soy DMT.4 432980 (663678 selclone ID);

EAASIPMPKLKNVSRLRTEHCVYELPDTHPLLQGWDTREPDDRGKYLLAIWTPGETANSI

QPPESKCSSQEECGQLCNENECFSCNSFREANSQTVRGTLLV

SEQ ID NO:40
>Soybean DMT.4 432980 (663678 selclone ID);

agaagctgcttccattcctatgcccaagctaaagaatgtgagccgattacgaacagagca
ttgtgtttatgaactcccag atacgcatcctcttctccaagggtgggacacacgagagcctgatgatccaggcaaatatc
ttcttgctatatggactcca ggtgagacagcaaattctatacagccaccagaaagcaaatgcagctctcaagaagaatgt
ggccaactctgtaatgagaa tgaatgtttctcgtgcaacagtttccgtgaagcaaattctcagatagttagagggacact
cctggtctgaatgcttatca aaatcattgttttaaccatatgtagcttactaattcttatacattatgggaacaggggag
ggaatacatctccatagaaa ttcaagcattataatagactgacttgaatttatgataaatatgagcagataccatgt SEQ ID NO:41
>Medicago 6654943;

MELQEGEMSKALVALNQEASYTPTTKLKNVSRLRTEHSVYELPDSHPLLEGWEKRBPDDP

GKYLLAIWTPGETANSIQPPDRRCSAQDCGQLCNEEECFSCNSFREANSQIVRGTTLTPC

RTAMRGSFPLNGTYFQVNEVFADHESSLNPTSVPRSLIWNLDRRTVHFGTSVTSIFKGLA

TPEIQQCFWRGFVCVRSFERSTPAPRPLMARLHFPAS

SEQ ID NO:42
>Medicago 6654943 EST306265

GAGAACATGGAACTTCAAGAAGGTGAAATGTCAAAGGCCTTGGTTGCTCTAAATCAAGAA

GCTTCTTACATTCCTACAACGAAGCTGAAGAACGTGAGTCGGTTGCGCACAGAGCATTCT

GTTTATGAACTCCCAGATTCTCATCCTCTTCTGGAAGGGTGGGAAAAGCGAGAACCTGAT

GATCCAGGAAAATACCTTCTAGCTATATGGACGCCAGGTGAGACTGCAAATTCTATACAG

CCACCAGACAGAAGATGCAGCGCTCAACATTGTGGCCAACTCTGTAATGAGGAGGAATGT

TTTTCGTGCAACAGCTTCCGTGAAGCAAATTCACAGATAGTTCGAGGGACAATCCTGATA

CCATGTCGAACAGCTATGAGAGGGAGCTTTCCGCTAAACGGAACCTATTTTCAAGTCAAT

GAGGTTTTTGCAGACCATGAATCAAGTCTTAATCCGATTAGCGTTCCCAGAAGTTTCATA

TGGAACCTTGATAGGAGGACAGTGCATTTTGGAACCTCCGTAACAAGCATATTCAAAGGT

TTAGCAACACCAGAAATTCAACAGTGCTTCTGGAGAGGGTTTGTCTGTGTGCGGAGCTTT

GAAAGGTCAACGAGAGCACCCCGTCCTTTAATGGCCAGACTGCATTTCCCAGCAAGC

SEQ ID NO:43
>Tomato 12624037;

MELQEGEMSKALVALNQEASYIPTTKLKNVSRLRTEHSVYELPDSHPLLEGWEKREPDDP

GKYLLATWTPGETANSIQPPDRRCSAQDCGQLCNEEECFSCNSFREANSQIVRGTILIPC

RTAMRGSFPLNGTYFQVNEVFADHESSLNPISVPRSLIWNLDRRTVHFGTSVTSIFKGLA

TPEIQQCFWRGFVCVRSFERSTPAPRPLMA

SEQ ID NO:44
>Tomato 12624037 EST469495

GCTTGAGAAAGGAAGTCCAATCAAAGAGTGGGAAAAAAGAAAGAAGCAAGGATGCAATGG

ACTCATTGAACTACGAAGCAGTCAGAAGTGCAGCAGTTAAAGAAATTTCTGATGCTATTA

AGGAACGAGGGATGAACAACATGCTGGCAGAGCGAATTAAGGACTTCCTCGATAGACTGG

TGAGGGATCATGGAAGTATTGACCTAGAATGGTTGAGAGATGTGGCCCCAGACAAAGCGA

AAGAGTATCTTTTGAGTATTCGTGGACTGGGTCTGAAAAGTGTAGAATGTGTGCGGCTAT

TAACACTTCATAACCTTGCTTTTCCAGTTGACACAAATGTTGGACGAATAGCTGTGAGAT

TAGGATGGGTTCCTCTCCAACCACTTCCTGAGTCCCTGCAGTTGCATCTTCTTGAACTGT

ATCCAATTCTGGAGTCAATTCAGAAGTATCTCTGGCCACGACTCTGCAAGCTCGATCAGA

GAACACTGTATGAGTTGCACTACCACATGATTACCTTTGGAAAGGTTTTCTGCACCAAAA

GTAAGCCTAACTGTAATGCATGCCCACTGAGAGCTGAATGCAGACACTTTGCTAGTGCTT

ACGCAAGTGCAAGACTTGCCCTTCCTGGCCCAGAGGAGAAGAGTATAGTGAGTTCAGCAG

TTCCGATCCCTAGTGAGGGAAATGCAGCTGCCGCATTCAAGCCCATGCTATTACCCCCAG

AGCTGAAGTAGGGATGGCGTACCCATATGCTCCAATTG

SEQ ID NO:45
>Barley 13256964;

MASETETFAFQAEINQLLSLIINTFYSNKEIFLRELISNASDALDKTRFESLTDKSKLDA

QPELFIHIIPDKATNTLTLIDSGIGMTKSDLVNNLGTIARSGTKDFMEALAAGADVSMIG

QFGVGFYSAYPCAERVXVTSKHNDDEQYGGEXQAGWLLYCGHVTLLESPFGGVLRSPSTS

RTNSWSTLERPAFKDLGKNTPSS

SEQ ID NO:46
>Barley 13256964 HVSMEI0014B12F

CGAGAACCCCGCTCCAAAGCCCTAACCCTAGGCCATCCCCTCTCCCTCCCCTCAACCCTC

GTCGACTCCGCGCGCGCCTGCGTTCCAGGAGCTTCCGCTGCCGGCGGCGCCATGGCCTCA

GAGACCGAGACCTTCGCCTTCCAGGCGGAGATCAACCAGCTGCTCTCGCTCATCATCAAC

ACCTTCTACTCCAACAAGGAGATCTTCCTCCGCGAGCTCATCTCCAACGCCTCCGATGCG

TTGGATAAGATCAGGTTTGAGAGCCTCACTGACAAGAGCAAGCTGGATGCTCAGCCAGAG

CTGTTCATCCACATTATCCCTGACAAGGCCACCAACACACTCACCCTTATCGACAGTGGC

ATTGGTATGACCAAGTCAGACCTCGTGAACAACCTTGGTACCATTGCAAGGTCTGGCACC

AAGGATTTCATGGAGGCATTGGCTGCTGGTGCCGATGTGTCCATGATTGGTCAGTTTGGT

GTTGGTTTCTACTCTGCTTACCCTTGTGCTGAGAGAGTCGNTGTGACCAGCAAGCACAAC

GATGACGAGCAGTATGGGGGGGAGTNCCAGGCTGGGTGGCTTCTTTACTGTGGACACGTG

ATACTCTTGGAGAGCCCCTTTGGAGGGGTACTAAGATCCCCCTCTACCTCAAGGACGAAC

AGTTGGAGTACCTTGGAGAGGCGCGCCTTTAAGGATTTGGGGAAAAACACTCCGAGTTCA

TAACTTTTTCATCTCCTCTGGACGGGGAAAACCCCTGAAAAGGAATTTTTGCGCTGGAAA

GTGGGTGGAAAAATGGGTTCCTGGGGGGCCCGGTTGAGGGATTGTTGGTCACATAAACA

ACTATCGTCTTCTATCTTAGCACCTAATAGTCCTTCACATGAG

SEQ ID NO:47
>Corn 1BE511860;

LLEGFEQREPDDPCPYLLSTWTPGETAQSTDAPKTFCDSGETGRLCGSSTCFSCNNIREM

QAQKVRGTLLIPCRTAMRGSFPLNGTYFQVNEVFADHCSSQNPIDVPRSWTWDLPRRTVY

FGTSVPTTFRGLTTEEIQRCFWRGFVCVRGFDRTVPAPRALYAR

SEQ ID NO:48
>Corn 1BE511860 946063H01.Y1 946

TATGAACTGCCAGATTCACACCCTCTTCTGGAAGGATTCGAACAGAGAGAACCAGATGA

TCCCTCTCCATATCTTCTTTCCATATGGACCCCAGGTGAAACTGCACAATCGATCGATGC

CCCCAAGACATTCTGTGATTCAGGGGAGACGGGTAGACTATGTGGAAGTTCAACATCCTT

TAGTTGCAACAATATACGAGAAATGCAGGCTCAGAAAGTCAGAGGAACACTTTTGATACC

ATGCCGAACAGCAATGAGAGGAAGCTTCCCACTTAATGGGACGTATTTTCAAGTTAATGA

GGTATTTGCTGACCATTGCTCAAGTCAAAATCCAATTGATGTCCCACGAAGTTGGATTTG

-continued

GGACCTCCCAAGACGAACTGTTTACTTTGGAACCTCAGTTCCTACAATATTCAGAGGTTT

AACGACTGAAGAGATACAACGATGCTTTTGGAGAGGATTTGTTTGCGTGAGGGGCTTTCA

TAGGACAGTGCGGGCACCAAGGGCCCTTTATGCAAGG

SEQ ID NO:49
>Cotton 11206330;

MQGNMELQEGDLSKALVALNPDAASIPTPKLKNVSRLRTEHYVYELPDKHPLLKQMEKRE

PDDPSPYLLATWTPGETANSIQPPEQSCGSQEPGRLCNEKTCFACNSVREANTETVRGTI

LIPCRNAMRGSFSLNGT

SEQ ID NO:50
>Cotton 11206330 GA_EB0023J04F

CTCCGCCAGTGCATAACTTGCTTAAAGTAGGGCCTAATGTTGGCAACAATGAACCTATCA

TTGAGGAGCCTGCAACACCTGAACCAGAGCATGCAGAAGGATCAGAGAGTGATATTGAAG

ATGCAAGCTATGATGATCCAGATGAAATTCCCACAATAAAACTCAACATTGAAGAGTTCA

CAGCAAACCTACAGCATTACATGCAGGGCAATATGGAACTCCAAGAAGGGGACTTGTCAA

AGGCTTTAGTAGCTTTGAATCCTGATGCTGCTTCTATCCCTACTCCAAAATTGAAGAATG

TAAGCAGGCTACGAACAGAGCACTATGTATATCAGCTTCCAGATAAACATCCTCTCTTGA

AACAGATGGAAAAGCGGGAACCTGATGATCCTAGCCCCTATCTTCTTGCAATATGGACAC

CAGGTGAAACTGCAAACTCAATTCAACCACCAGAACAAAGTTGTGGGTCCCAAGAACCAG

GAAGACTGTGCAATGAGAAGACCTGCTTTGCTTGCAACAGTGTAAGAGAAGCTAACACTG

AGACAGTCCGAGGAACCATCTTGATACCTTGTAGAAATGCAATGAGAGGAAGCTTTTCCC

TTAATGGGACTTAATTTTCAAGTTAATGAGGTCTTTTGCAGATCATGAATCAAGCCTCAA

CCCAATCGACCTTCCAAGGGGAATGGATTGGGAATTTAACAAGAACGAACTGTATACTTC

GAACATCCTGCTTCATCAATATTTAAAGGACTTTTCGACGAGGGAA

SEQ ID NO:51
>Soybean 5606759

MGWVPLQPLPESLQLHLLELYPVLESIQKYLWPRLCKLDQETLYELHYQMITFGKVFCTK

SKPNCNACPMPAECRHFASAFASARFALPGPEQKSIVSTTGNSVINQNPSEIISQLHLPP

PENTAQBDEIQLTEVSRQLESKFEIYTCQPIIEEPRTPEPECLQESXTDIEDAVYEDSS

SEQ ID NO:52
>Soybean 5606759 SB95C12.

ACGAGCTTCCCGGTAGACACAAATGTCGGACGTATTGCCGTACGACTGGGATGGGTGCCT

CTGCAGCCACTGCCTGAGTCACTGCAGTTGCATCTCCTAGAATTGTACCCGGTGTTGGAG

TCAATACAAAAATATCTCTGGCCTCGACTGTGCAAGCTAGATCAGGAAACACTATATGAG

CTACATTACCAGATGATTACATTTGGAAAGGTCTTCTGTACAAAAAGCAAACCAAATTGT

AATGCATGCCCAATGAGAGCAGAATGTAGACACTTTGCTAGTGCATTTGCAAGTGCAAGG

TTTGCACTGCCTGGACCAGAGCAGAAGAGTATAGTTAGCACAACTGGAAATAGTGTGATT

AACCAGAACCCATCTGAAATCATCAGTCAGTTGCACTTGCCTCCACCTGAGAACACAGCC

CAAGAAGATGAAATTCAACTAACAGAAGTGAGCAGACAATTGGAATCAAAATTTGAAATA

TATATTTGCCAACCTATCATTGAAGAGCCCAGAACTCCAGAGCCAGAATGCTTGCAAGAA

TCACANACTGATATAGAGGATGCTGTCTATGAGGATTCAAGTG

SEQ ID NO:53
>Wheat 12019155

MFHCHGTRGSDLGFDLNKTPEQKAPQRRKHRPKVIKEAKPKSTRKPATQKTQMKENPHKK

RKYVRKTAATPQTNVTEESVDSIVATKKSCRRALNFDLEHNKYASQSTISCQQETDHRNE

KAFNTTSDHKAKEPKNTDDNTLLLHEKQANNFQSE

SEQ ID NO:54
>Wheat 12019155

AACAGTCAGGACAAAGGCAACAAGATCAGCAGTCAGGACAAGGGCAGCAACCGGGACAAA

GGCAGCCAGGGTACTACTCAACTTCTCCGCAACAATTAGGACAAGGCCAACCAAGGTACT

ACCCAACTTCTCCGCAGCAGCCAGGACAAGAGCAGCAGCCAAGACAATTGCAACAACCAG

AACAAGGGCAACAAGGTCACCAGCCAGAACAAGGGCAGCAAGGTCAGCAGCAAAGACAAG

GGGAGCAAGGTCAGCAGCCAGGACAAGGGCAACAAGGGCAGCAACCGGGACAAGGGCAGC

CAGGGTACTACCCAACTTCTCCGCAGCAGTCAGGACAAGGGCAACCAGGGTACTACCCAA

CTTCTCCACAGCAGTCAGGACAATTGCAACAACCAGCACAAGGGCAGCAACCAGGACAAG

AGCAACAAGGTCAACAGCCAGGACAAGGGCAGCAACCGGGACAAGGGCAAGCCACGGTAC

TACCCAACTTCTCCGCAGCAGTCAGGACAAGACCAACAGCTAGAACAATGGCAACAGTCA

GGACAGGGCAACCAGGGCACTACCCAACTTCTCCGTTGCAAGCCAGGACAAGGGCAACC

AGGGTACTACCCAACTTCTCACAACAGATAGGACAAGGGCAGCAGCCAAGAACAATTTGC

ACAACCAACACAAGGGCAACAANGGGCAGCAACCAAGGACAANGGGCAACAAGGTCAACA

GCCCANGAAAAAGGCAACAAAGGTCAAGCAACCAAGNACAAGGGGCAGCAANCCAGGAC

AAGGGCAGCCANGGTCCTACCCAACTTNTTTTGAGCAAGTCANGGAAAAGGGGCACCANC

CNAGGANAAATGGGNACCACCCAGNACAAGGACAACCCCGGGTCTTCCCCAAANTTTTTN

CN

SEQ ID NO:55
>Tomato 8106032

MSLAAHPPLKTDSTQKHEGNTGIIIEEPEECATDPNVSIRWYEDQPNQSTHCQDSSGVYN

TDSNEEKPAVNDSESSENSTECIKSAECSVILQSDSSREGSDLYHGSTVTSSQDRKELND

LPSSPSSVVSSEISAVIQASEGTDSSNFCSSTSFLKLLQMAGTSGAQGTRCTEHLHNQHK

GNXGQQPRTXGNKVNSPXKKATKVKQPXTRGSXPGQGQPXSYPTXFEQVXEKGHXPRXNG

XHPXQGQPRVFPKXF

SEQ ID NO:56
>Tomato 8106032 EST356474

CTCGTGCCGGTTGGGGTATATCTTACACAGAATGTTTCAGATCACCTTTCTAGTTCTGCA

TTCATGTCACTCGCTGCCCACTTTCCTCTGAAAACAGACAGTACTCAGAAGCATGAAGGA

AATACAGGTATTATAATTGAAGAACCTGAAGAGTGTGCAACAGACCCCAATGTTTCCATC

AGATGGTATGAAGATCAACCAAATCAGTCAACCCATTGTCAGGATTCTTCAGGAGTCTAT

AATACAGATTCAAATGAAGAAAAACCAGCTGTCAATGACTCTGAATCAAGTGAAAATAGC

ACAGAATGCATAAAAATCAGCAGAATGTTCTGTAATTCTGCAATCAGATTCTTCTACAGAA

GGCTCAGATCTGTATCATGGATCAACAGTTACAAGTTCCCAAGATCGAAAAGAGTTGAAT

GATTTGCCTTCTTCTCCGAGTTCTGTTGTTTCTTCTGAGATCTCTGCTGTTATTCAAGCT

TCAGAAGGAACTGACTCAAGCAACTTTTGCAGCTCCACTTCTTTTTTGAAGCTATTACAG

ATGGCAGGAACTTCAGGAGCACAAGGAACCAGGTGCACTGAACATCTAC

SEQ ID NO:57
>Corn 1AW042334;

DAHPLLQQLGLDQREHDDPTPYLLAIWTPDGTKEITKTPKPCCDPQMGGDLCNNEMCHNC

TAEKENQSRYVRGTILVPCRTANRGSFPLNGTYFQVNEVFADHRSSHNPTHVEREMLWNL

QRRMVFFGTSVPTIFKGLRTEETQQCFWRGFVCVRGFDMETPAPRPLCPHLHNTEARPKA

SEQ ID NO:58
>Corn 1AW042334 614027C01.y1 614

GAATTCGGCACCAGCAGATGCACATCCACTTTTACAACAGCTAGGACTTGACCAACGGGA

ACATGATGATCCTACCCCATACTTATTGGCCATATGGACACCAGATGGAATAAAGGAAAT

AACTAAGACACCAAAACCATGCTGTGACCCTCAAATGGGAGGCGATTTATGCAATAATGA

AATCTGCCACAATTGTACTGCAGAGAAAGAAAACCAATCTAGATATGTCAGAGGCACAAT

TCTGGTTCCTTGTCGAACAGCTATGAGGGGTAGTTTCCCACTTAATGGCACTTACTTTCA

AGTCAATGAGGTATTTCCTGACCACAGATCTAGCCACAACCGAATCCATGTGGAAAGGGA

GATGCTATGGAACTTGCAAAGGCGCATGGTCTTTTTCGGGACTTCAGTACCCACCATATT

CAAAGGTCTAAGAACAGAAGAAATACAACAATGCTTCTGGAGGGGATTTGTCTGTGTGCG

-continued

AGGATTCGACATGGAGACTAGAGCACCAAGGCCTCTGTGCCCCCATTTGCACGTTATAGC

AAGCCCGAAAGCCCGCAAGACAGCAGCAACTCAGCAAGTACTCTAATCAGCAAAG

SEQ ID NO:59
>Corn AW076298

PCRTAMRCSFPLNGTYFQVNEVFADHCSSQNPIDVPRSWIWDLPRRTVYFGTSVPTIFRG

LSTEQIQFCFWKGFVCVRGFEQKTRAPRPLMARLHFPASKLKNNKLTTEEIQQCFWRGFV

CVRGFDRTVRAPRPLYARLHFPASKVVRGK

SEQ ID NO:60
>Corn AW076298 614065C03.Y1 614 -
CGGCCCCAGACCATGCCGGACAGCAATGAGAGGAAGCTTCCCACTTAATGGGACATATTT

TCAAGTTAATGAGGTATTTGCTGACCATTGTTCAAGCCAAAATCCAATTGATGTCCCACG

AAGTTGGATATGGGACCTCCCAAGACGAACTGTTTACTTTGGAACCTCAGTTCCTACAAT

ATTTAGAGGTTTAACGACTGAAGAGATACAACAATGCTTTTGGAGAGGATTCGTTTCTGT

GAGGGGCTTTGATAGGACAGTAAGGGCACCAAGGCCCCTTTATGCAAGGTTGCATTTTCC

TGCCAGCAAGGTTGTTAGAGGCAAAAAGCCTGGAGCGGCAAGCGTCGAAGAATAATAGGT

ACATCGAAGAAATATAGAGGAGCTAACAAAACGGATGGATAGCCCTAAATGAGATGCTGA

CCCAATAAGTCGCCGAATCACCTCCAAGTTCTAACCCAATTTTTGAGGCGACATGACCTG

TTAAATTATGTTCCATCTATGGTAACAGCTTAGATGTTCTTGTGAGTCGCATATTCTTTA

CTCTGAAATTCAATATAGCAAATGAAAAAAAACACAGTGCATAGTCTAGTTCTAATTGTA

CCTGTGAGTGGAATCAGTTGTTGTACAACATGAAGATGGG

SEQ ID NO:61
>Corn BE639158;
KNSEPIIEEPASPREERPPETMENDIEDFYEDGEIPTIKLNMEAFAQNLENCIKESNNEL

QSDDIAKALVAISTEAASIPVPKLKNVLRLRTEHYVYELPDAHPLLQQLGLDQREHDDPT

PYLLAIWTPDGIKEITKTPK

SEQ ID NO:62
>Corn BE639158 946021E09.Y1 946 -
TGAGCTGCATTATCAGATGATTACATTTGGAAAGGTCTTTTGTACCAAAAGACAGCCAAA

TTGCAATGCATGCTATGAATTCGACTCACCTACCTCGCCTTGAGGGGAGTATCCATTCAA

GGGAGTTTCTTCCTAAGAATTCAGAGCCAATAATCGAGGAGCCTGCAAGTCCAAGAGAGG

AAAGACCTCCAGAAACCATGGAAAATGATATTGAAGATTTTTATGAAGATGGTGAAATCC

CAACAATAAAGCTTAACATGGAAGCTTTTGCACAAAACTTGGAGAATTGCATTAAAGAAA

GCAATAACGAACTCCAGTCTGATGATATTGCAPAAGCATTGGTTGCTATTAGCACTGAAG

CAGCTTCGATTCCTGTACCGAAACTAAAGAATGTGCTTAGGCTTCGAACAGAACACTATG

TGTATGAGCTTCCAGATGCACATCCACTTTTACAACAGCTAGGACTTGACCAACGGGAAC

-continued

ATGATGATCCTACCCCATACTTATTGGCCATATGGACACCAGATGGAATAAAGGAAATAA

CTAAGACACCAAAACCATGCT

SEQ ID NO:63
>Corn T25243;
NHQPIIEEPLSPECETENIEAHEGAIEDFFCEESDEIPTINLNIEEFTQNLKDYMQANNV

EIXYADMSKALVAITPDAASIPTPKLKNVNRLRTEHQVYELPDSHPLLEGFEQXEPDDPC

PYLLSIWTPGELHNRSMP

SEQ ID NO:64
>Corn T25243;
CTGGTAATCATCAGCCAATCATCGAGGAACCACTGAGCCCAGAATGTGAAACTGAAAATA

TAGAGGCACATGAGGGTGCAATTGAGGATTTCTTTTGTGAAGAATCTGATGAAATTCCTA

CCATTAATCTTAATATCGAGGAGTTCACACAAAACTTGAAGGACTATATGCAASCAAACA

ATGTTGAGATTGANTATGCTGACATGTCAAAGGCATTGGTTGCCATCACGCCTGATGCTG

CTTCCATTCCAACTCCAAAGCTCAAGAATGTCAATCGTCTGAGGACAGAACACCAAGTTT

ATGAACTGCCAGATTCACACCCTCTTCTGGAAGGATTCGAACAGNGNGAACCAGATGATC

CCTGTCCATATCTTCTTTCCATATGGACCCCAGGTGAACTGCACAATCGATCGATGCCCC

AA

SEQ ID NO:65
>Corn AW453174;
FQGNEVFADHCSRQNPIDGPRSWIWDLPRRTGYFGTSGPTIFRGLTTEEIQRCFWRGFVC

VRGPDRTVRAPRPLYARLHFPVSKVVRGK

SEQ ID NO:66
>Corn AW453174 660032D01.Y1 660 -;
CATGCCGAACAGCAATGAGAGGAAGCTTCCCACTTAATGGGACGATTTTCAAGGTAATGA

GGTATTTGCTGACCATTGCTCAAGGCAAAATCCAATTGATGGCCCACGAAGTTGGATTTG

GGACCTTCCAAGACGAACTGGTTACTTTGGAACCTCAGGTCCTACAATATTCAGAGGGTT

AACGACTGAAGAGATACAACGATGCTTTTGGAGAGGATTTGTTTGCGTGAGGGGCTTTGA

TAGGACAGTGCGGGCACCAAGGCCCCTTTATGCAAGGTTGCATTTTCCTGTCAGCAAGGT

TGTTAGAGGCAAAAAGCCTGGAGCAGCAAGAGCAGAAGAATAATAGAACATTGAAGAAAT

ATAGGGGTGCTAACCAGATGAGGATGGATAGCCCGAAATGAGATGCTGACCCAATAGGTC

CCCAAATCACCTCCAAATTCTAACCCAATGACTTCCATCTGTAATGAATGGCAATACCTT

GAAAACCT

SEQ ID NO:67
>Corn BE509759;
NGTYFQVNEVFADHRSSHNPIHVEREMLWNLQRRMVFFGTSVPTIFKGLRTEEIQQCFWR

GFVCVRGFDMETRAPRPLCPHLHIIARPKARKT

SEQ ID NO:68
>Corn BE509759 946021E09.X1 946 -
TGGCATCTTACATGGACTAACAGCTAGATGCTAATTTACATACAGTAGATCTGAAACAAAAAAGTGAAAATTATTGGTGC

TTCCTGATGCTTCATTAGTCCTCTCGTCTCAGAAACTAACAGTCTCGGACCCCATCCATGGCTTAAATTTCCTAAACAAT

GGCTCTTTTTTAGGCAGGAAGTAATATGATTCCATGCATAGGTCGAGAGCTATTGATGTCATATCACAATAAACATGATG

TTCATAAAACTGATATCTTTGCTGATTAGAGTACTTGCTCAGTTGCTGCTGTCTTGCGGGCCTTCGGCCTTGCTATAATG

TGCAAATGGGGCACAGAGGCCTTGGTGCTCTAGTCTCCATGTCGAATCCTCGCACACAGACAAATCCCCTCCAGAAGCA

TTGTTGTATTTCTTCTGTTCTTAGACCTTTGAATATGGTGGGTACTGAAGTCCCGAAAAAGACCATGCGCCTTTGCAAGT

TCCATAGCATCTCCCTTTCCACATGGATTGGGTTGTGGCTAGATCTGTGGTCAGCAAATACCTCATTGACTTGAAAGTAA

GTGCCATTAA

SEQ ID NO:69
>Corn 1AW017984;
VPRSWIWDLPRRTVYFGTSVPTIFRGLTTEEIQQCFWRGFVCVRGFDRTVRAPRPLYARL

HFPASKVVRGK

SEQ ID NO:70

>Corn    1AW017984;

CCTGAAACAATCAAATAACGGCCGATGAGGTTACATTGTTTATAGTATATGATCAAAGAA

CATGTATCACCATTGTACAAATAGGCCCATCTTCATGTTGTACAACAACTGATTCCACTC

ACAGGTACAATTAGAACTAGACTATGCACTGTGTTTTTTTCATTTGCTATATTGAATTT

CAGAGTAAAGAATATGCGACTCACAAGAACATCTAAGCTGTTACCATAGATGGAACATAA

TTTAACAGGTCATGTCGCCTCAAAAATTGGGTTAGAACTTGGAGGTGATTCGGCGACTTA

TTGGGTCAGCATCTCATTTAGGGCTATCCATCCGTTTTGTTAGCTCCTCTATATTTCTTC

GATGTACCTATTATTCTTCGACGCTTGCCGCTCCAGGCTTTTTGCCTCTAACAACCTTGC

TGGCAGGAAAATGCAACCTTGCATAAAGGCGCCTTGGTGCCCTTACTGTCCTATCAAAGC

CCCTCACACAAACGAATCCTCTCCAAAAGCATTGTTGTATCTCTTCAGTCGTTAAACCTC

TAAATATTGTAGGAACTGAGGTTCCAAAGTAAACAGTTCGTCTTGGGAGGTCCCATATCC

AACTTCGTGGGAC

What is claimed is:

1. A method of modulating development in a plant, the method comprising:
   introducing into a plant an expression, cassette comprising a promoter operably linked to an expression-inhibiting polynucleotide, wherein the expression-inhibiting polynucleotide comprises SEO ID NO:1 or SEO ID NO:5, thereby producing a plant that exhibits:
   (a) modulated floral organ identity;
   (b) modulated floral organ number;
   (c) increased meristem size; or
   (d) increased endosperm size.

2. The method of claim 1, wherein the promoter is a constitutive promoter.

3. The method of claim 1, wherein the promoter is a tissue-specific promoter.

4. A method of delaying flowering in a plant, the method comprising:
   introducing into a plant an expression cassette comprising a promoter operably linked to a DMT polynucleotide encoding a polypeptide comprising SEQ ID NO:2, thereby delaying flowering of the plant compared to a plant lacking the expression cassette.

5. The method of claim 4, wherein the polynucleotide comprises SEQ ID NO:5.

6. The method of claim 4, wherein the polynucleotide comprises SEQ ID NO:1.

7. The method of claim 4, wherein the promoter is a constitutive promoter.

8. The method of claim 4, wherein the promoter is a tissue-specific promoter.

* * * * *